(12) United States Patent
Rademacher et al.

(10) Patent No.: US 12,290,535 B2
(45) Date of Patent: May 6, 2025

(54) LANGERIN+ CELL TARGETING

(71) Applicants: Max-Planck-Gesellschaft zur Förderung der Wissenschaften e.V., Munich (DE); Humboldt-Universität zu Berlin, Berlin (DE)

(72) Inventors: Christoph Rademacher, Potsdam (DE); Eike-Christian Wamhoff, Roxbury, MA (US); Jessica Schulze, Potsdam (DE); Robert Carsten Willi Wawrzinek, Berlin (DE); Oliver Seitz, Berlin (DE); Gunnar Bachem, Berlin (DE)

(73) Assignees: Max-Planck-Gesellschaft zur Förderung der Wissenschaften e.V., Munich (DE); Humboldt-Universität zu Berlin, Berlin (DE)

( * ) Notice: Subject to any disclaimer, the term of this patent is extended or adjusted under 35 U.S.C. 154(b) by 1285 days.

(21) Appl. No.: 16/963,107

(22) PCT Filed: Jan. 16, 2019

(86) PCT No.: PCT/EP2019/051055
§ 371 (c)(1),
(2) Date: Jul. 17, 2020

(87) PCT Pub. No.: WO2019/141731
PCT Pub. Date: Jul. 25, 2019

(65) Prior Publication Data
US 2021/0047620 A1    Feb. 18, 2021

(30) Foreign Application Priority Data

Jan. 18, 2018   (EP) .................................... 18152362
Mar. 20, 2018   (EP) .................................... 18162955

(51) Int. Cl.
*A61K 35/36* (2015.01)
*A61K 39/00* (2006.01)
*A61K 47/54* (2017.01)
*C12N 5/0784* (2010.01)

(52) U.S. Cl.
CPC .......... *A61K 35/36* (2013.01); *A61K 39/4615* (2023.05); *A61K 39/4622* (2023.05); *A61K 39/4644* (2023.05); *A61K 39/464838* (2023.05); *A61K 47/549* (2017.08); *C12N 5/0639* (2013.01)

(58) Field of Classification Search
CPC ................................................... C12N 5/0639
See application file for complete search history.

(56) References Cited

U.S. PATENT DOCUMENTS

2007/0292494 A1   12/2007   Gieseler et al.
2012/0231023 A1   9/2012    Zurawski et al.

FOREIGN PATENT DOCUMENTS

| CN | 102711824 A | 10/2012 |
| EP | 0372777 A2 | 6/1990 |
| WO | 2005092288 A1 | 10/2005 |
| WO | 2011032161 A2 | 3/2011 |

OTHER PUBLICATIONS

Flacher et al., "Epidermal Langerhans Cells rapidly capture and present antigens from C-Type Lectin-Targeting Antibodies Deposited in the Dermis", Journal of Investigative Dermatology, vol. 130, Mar. 1, 2010 (Year: 2010).*

Chabrol et al., "Rational-Differential Design of Highly Specific Glycomimetric Ligands", American Chemical Society, Dec. 22, 2017 (Year: 2017).*

Gammon et al., "Conjugates of plumbagin and phenyl-2-amino-1-thioglucaoside inhibit MshB, a deacetylase involved in the biosynthesis of mycothiol", Bioorganic and Medicinal Chemistry, Mar. 1, 2010 (Year: 2010).*

Li et al., "Donor substrate promiscuity of bacterial B1-3-N-acetyglycoasminyltransferases and acceptor substrate flexibility of B1-4-galactosyltrasnferases", Elsevier, Bioorganic and Medicinal Chemistry, Mar. 3, 2016 (Year: 2016).*

Porkolab et al., "Rational-Differential Design of Highly Specific Glycomimetic Ligands: Targeting DC-SIGN and Excluding Langerin Recognition", ACS Chem Biol, Dec. 22, 2017 (Year: 2017).*

Meiboom et al., "Modified Spin-Echo Method for Measuring Nuclear Relaxation Times", The Review of Scientific Instruments, 1958, pp. 688-691, vol. 29, No. 8.

Molinero et al., "Epidermal Langerhans Cells Promote Skin Allograft Rejection in Mice With NF-K-B-impaired T Cells", American Journal of Transplantation, 2008, pp. 21-31, vol. 8.

Morales et al., "Buccal delivery of small molecules and biologics: of mucoadhesive polymers, films, and nanoparticles", Current Opinion in Pharmacology, 2017, pp. 22-28, vol. 36.

Muñoz et al., "Synthesis of giant globular multivalent glycofullerenes as potent inhibitors in a model Ebola virus infection", Nature Chemistry, 2016, pp. 50-57, col. 8, No. 1.

Muñoz-García et al., "Langerin-Heparin Interaction: Two Binding Sites for Small and Large Ligands As Revealed by a Combination of NMR Spectroscopy and Cross-Linking Mapping Experiments", Journal of the American Chemical Society, 2015, pp. 4100-4110, vol. 137, No. 12.

Obhrai et al., "Langerhans Cells Are Not Required for Efficient Skin Graft Rejection", Journal of Investigative Dermatology, 2008, pp. 1950-1955, vol. 128, No. 8.

Ortner et al., "Langerhans cells and NK cells cooperate in the inhibition of chemical skin carcinogenesis", Oncoimmunology, 2017, 12 pages, vol. 6, No. 2, Article e1260215.

(Continued)

*Primary Examiner* — Andrew D Kosar
*Assistant Examiner* — Gillian A Hutter
(74) *Attorney, Agent, or Firm* — The Webb Law Firm

(57) ABSTRACT

The present invention relates to the use of a vehicle for specific molecular targeting of Langerin+ cells, wherein the vehicle is capable of specifically binding to a Langerin+ cell, said vehicle comprising (a) at least one carrier and (b) at least one saccharide moiety-based conjugate for a targeted cargo delivery into a Langerin+ cell, as well as pharmaceutical compositions and uses comprising the inventive vehicle.

22 Claims, 50 Drawing Sheets

Specification includes a Sequence Listing.

(56) References Cited

OTHER PUBLICATIONS

Panyam et al., "Biodegradable nanoparticles for drug and gene delivery to cells and tissue", Advanced Drug Delivery Reviews, 2003, pp. 329-347, vol. 55, No. 3.
Pavlopoulou et al., "Human cancer databases (Review)", Oncology Reports, 2015, pp. 3-18, vol. 33, No. 1.
Pederson et al., "Structural Characterization of the DC-SIGN-LewisX Complex", Biochemistry, 2014, pp. 5700-5709, vol. 53, No. 35.
Porkolab et al., "Rational-Differential Design of Highly Specific Glycomimetic Ligand Targeting DC-SIGN and Excluding Langerin Recognition", ACS Chemical Biology, 2018, pp. 600-608, vol. 13, No. 3.
Reyon et al., "FLASH Assembly of TALENs Enables High-Throughput Genome Editing", Nature Biotechnology, 2011, pp. 460-465, vol. 30, No. 5.
Rosental et al., "Proliferating Cell Nuclear Antigen Is a Novel Inhibitory Ligand for the Natural Cytotoxicity Receptor NKp44", The Journal of Immunology, 2011, pp. 5693-5702, vol. 187, No. 11.
Ryder et al., "The DrosDel Collection: A Set of P-Element Insertions for Generating Custom Chromosomal Aberrations in *Drosphila melanogaster*", Genetics, 2004, pp. 797-813, vol. 167, No. 2.
Sala et al., "Lipid nanocarriers as skin drug delivery systems: Properties, mechanisms of skin interactions and medical applications", International Journal of Pharmaceutics, 2018, pp. 1-17, vol. 535, Issues 1-2.
Sela et al., "Dendritic cells induce antigen-specific regulatory T cells that prevent graft versus host disease and persist in mice", Journal of Experimental Medicine, 2011, pp. 2489-2496, vol. 208, No. 12.
Sharabi et al., "Regulatory T Cells in the treatment of disease", Nature Reviews Drug Discovery, 2018, pp. 823-844, vol. 17, No. 11.
Soussan et al., "Drug Delivery by Soft Matter: Matrix and Vesicular Carriers", Angewandte Chemie International Edition, 2009, pp. 274-288, vol. 48, No. 2.
Stary et al., "Glucocorticosteroids Modify Langerhans Cells to Produce TGF-β and Expand Regulatory T Cells", The Journal of Immunology, 2011, pp. 103-112, vol. 186, No. 1.
Stepniewski et al., "Study of PEGylated Lipid Layers as a Model for PEGylated Liposome Surfaces: Molecular Dynamics Simulation and Langmuir Monolayer Studies", Langmuir, 2011, pp. 7788-7798, vol. 27, No. 12.
Stetefeld et al., "Dynamic light scattering: a practical guide and applications in biomedical sciences", Biophysical Reviews, 2016, pp. 409-427, vol. 8, No. 4.
Tagliamonte et al., "Antigen-specific vaccines for cancer treatment", Human Vaccines & Immunotherapeutics, 2014, pp. 3332-3346, vol. 10, No. 11.
Tarleton, "New approaches in vaccine development for parasitic infections", Cellular Microbiology, 2005, pp. 1379-1386, vol. 7, No. 10.
Hirabayashi et al., "Lectin-based structural glycomics: A practical approach to complex glycans", Electrophorasis, 2011, pp. 1118-1128, vol. 32, No. 10.
Valladeau et al., "Langerin, a Novel C-Type Lectin Specific to Langerhans Cells, Is an Endocytic Receptor that Induces the Formation of Birbeck Granules", Immunity, 2000, pp. 71-81, vol. 12, No. 1.
Verdijk et al., "Sensitivity of magnetic resonance imaging of dendritic cells for in vivo tracking of cellular cancer vaccines", International Journal of Cancer, 2006, pp. 978-984, vol. 120, No. 5.
Vranken et al., "The CCPN Data Model for NMR Spectroscopy: Development of a Software Pipeline", Proteins: Structure, Function, and Bioinformatics, 2005, pp. 687-696, vol. 59, No. 4.
Walzer et al., "Natural-killer cells and dendritic cells: "l'union fait la force"", Blood, 2006, pp. 2252-2258, vol. 106, No. 7.
Wamhoff et al., "A specific, glycomimetic Langerin ligand for human Langerhans cell targeting", Supplementary Material, 60 pages.
Wamhoff et al., "F NMR-Guided Design of Glycomimetic Langerin Ligands", ACS Chemical Biology, 2016, pp. 2407-2413, vol. 11, No. 9.
Wamhoff et al., "A Specific, Glycomimetic Langerin Ligand for Human Langerhans Cell Targeting", ACS Central Science, 2019, pp. 808-820, vol. 5, No. 5.
Wang et al., "AAgAtlas 1.0: a human autoantigen database", Nucleic Acids Research, 2016, pp. D769-D776, vol. 4, No. 45(D1).
Ward et al., "Polymorphisms in Human Langerin Affect Stability and Sugar Binding Activity", The Journal of Biological Chemistry, 2006, pp. 15450-15456, vol. 281, No. 22.
Watt et al., "IFN-γ-Dependent Recruitment of Mature CD27high NK Cells to Lymph Nodes Primed by Dendritic Cells", The Journal of Immunology, 2008, pp. 5323-5330, vol. 181, No. 8.
Williamson, "Using chemical shift perturbation to characterise ligand binding", Progress in Nuclear Magnetic Resonance Spectroscopy, 2013, pp. 1-16, vol. 73.
Wright et al., "Standardized reagents and protocols for engineering zinc finger nucleases by modular assembly", Nature Protocols, 2006, pp. 1637-1652, vol. 1, No. 3.
Yamano et al., "Ex vivo-expanded DCs induce donor-specific central and peripheral tolerance and prolong the acceptance of donor skin grafts", Blood, 2011, pp. 2640-2648, vol. 117, No. 9.
Yamazaki et al., "Dendritic cells in the periphery control antigen-specific natural and induced regulatory T cells", Frontiers in Immunology, 2013, 13 pages, vol. 4, Article 151.
Zell et al., "A Paradigm Shift in the Mechanisms of Graft Rejection", Journal of Investigative Dermatology, 2008, p. 1874, vol. 128, No. 8.
Zhang et al., "Efficient construction of sequence-specific TAL effectors for modulating mammalian transcription", Nature Biotechnology, 2011, pp. 149-153, vol. 29, No. 2.
Zhao et al., "Kinetic and Structural Studies of Interaction between Glycosaminoglycans and Langerin", Biochemistry, 2016, pp. 4552-4559, vol. 55, No. 32.
Liu et al., "Improved Watergate Pulse Sequences for Solvent Suppression in NMR Spectroscopy", Journal of Magnetic Resonance, 1998, pp. 125-129, vol. 132, Issue 1.
Needham et al., "PEG-covered lipid surfaces: bilayers and monolayers", Colloids and Surfaces B: Biointerfaces, 2000, pp. 183-195, vol. 18, Nos. 3-4.
"Opinion of the Scientific Panel on Dietetic Products, Nutrition and Allergies on a request from the Commission relating to the evaluation of allergenic foods for labelling purposes", The EFSA Journal, 2004, pp. 1-197, vol. 32.
"Solid-in-Oil (S/O)", Drug Delivery System 32-3, 2017, pp. 176-183.
Adhikary et al., "In Vivo Depletion of Dividing Donor Cells Using Post-Transplant Cyclophosphamide can Reduce the Development of Graft-Versus-Host Disease in a Humanised Mouse Model", Transplantation, 2018, p. S235, vol. 102, Supplement 7.
Angulo et al., "STD-NMR: application to transient interactions between biomolecules—a quantitative approach", European Biophysics Journal, 2011, pp. 1357-1369, vol. 40, No. 12.
Ansari et al., "AntigenDB: an immunoinformatics database of pathogen antigens", Nucleic Acids Research, 2010, pp. D847-D853, vol. 38, Database Issue.
Aretz et al., "Computational and experimental prediction of human C-type lectin receptor druggability", Frontiers in Immunology, 2014, 12 pages, vol. 5, Article No. 323.
Aretz et al., "Allosteric Inhibition of a Mammalian Lectin", Journal of the American Chemical Society, 2018, pp. 14915-14925, vol. 140, No. 44.
Bae et al., "Human zinc fingers as building blocks in the construction of artificial transcription factors", Nature Biotechnology, 2003, pp. 275-280, vol. 21, No. 3.
Bartneck, PhD et al., "Liposomal encapsulation of dexamethasone modulates cytotoxicity, inflammatory cytokine response, and migra-

(56) References Cited

OTHER PUBLICATIONS tory properties of primary human macrophages", Nanomedicine: Nanotechnology, Biology, and Medicine, 2014, pp. 1209-1220, vol. 10, No. 6.
Barwell et al., "Overexpression, Purification, and Crystallization of the DNA Binding and Dimerization Domains of the Epstein-Barr Virus Nuclear Antigen 1", The Journal of Biological Chemistry, 1995, pp. 20556-20559, vol. 270, No. 35.
Benson, "Elastic Liposomes for Topical and Transdermal Drug Delivery", Liposomes: Methods in Molecular Biology, 2017, pp. 107-117, vol. 1522, Springer Science+Business Media, New York, USA.
Bodenhausen et al., "Natural Abundance Nitrogen-15 NMR by Enhanced Heteronuclear Spectroscopy", Chemical Physics Letters, 1980, pp. 185-189, vol. 69, No. 1.
Boyd et al., "Predicting Vaccine Responsiveness", Cell Host & Microbe Minireview, 2015, pp. 301-307, vol. 17, No. 3.
Carr et al., "Effects of Diffusion on Free Precession in Nuclear Magnetic Resonance Experiments", Physical Review, 1954, pp. 630-638, vol. 94, No. 3.
Chabrol et al., "Glycosaminoglycans Are Interactants of Langerin: Comparison with gp120 Highlights an Unexpected Calcium-Independent Binding Mode", PLoS One, 2012, 12 pages, vol. 7, Issue 11, Article e50722.
Chen et al., "In vivo targeting of B-cell lymphoma with glycan ligands of CD22", Blood, 2010, pp. 4778-4786, vol. 115, No. 23.
Clausen et al., "Functional specialization of skin dendritic cell subsets in regulating T cell responses", Frontiers in Immunology, 2015, 19 pages, vol. 6, Article 534.
Cohen, M.D., "Epstein-Barr Virus Infection", The New England Journal of Medicine, 2000, pp. 481-492, vol. 343, No. 7.
Cong et al., "Multiplex Genome Engineering Using CRISPR/Cas Systems", Science, 2013, pp. 819-823, vol. 339, No. 6121.
Connolly, "The molecular surface package", Journal of Molecular Graphics, 1993, pp. 139-141, vol. 11, Issue 2.
Corbeil et al., "Variability in docking success rates due to dataset preparation", Journal of Computer-Aided Molecular Design, 2012, pp. 775-786, vol. 26, No. 6.
Dai et al., "Thermo-responsive magnetic liposomes for hyperthermia-triggered local drug delivery", Journal of Microencapsulation, 2015, pp. 408-415, vol. 34, No. 4.
Delaglio et al., "NMRPipe: A multidimensional spectral processing system based on UNIX pipes", Journal of Biomolecular NMR, 195, pp. 277-293, vol. 6, No. 3.
Desai et al., "The Mechanism of Uptake of Biodegradable Microparticles in Caco-2 Cells Is Size Dependent", Pharmaceutical Research, 1997, pp. 1568-1573, vol. 14, No. 11.
Detmer et al., "Live bacterial vaccines—a review and identification of potential hazards", Microbial Cell Factories, 2006, 12 pages, vol. 5, No. 23.
Doebel et al., "Langerhans Cells—The Macrophage in Dendritic Cell Clothing", Trends in Immunology, 2017, pp. 817-828, vol. 38, No. 11.
Ernst et al., "From carbohydrate leads to glycomimetic drugs", Nature Reviews Drug Discovery, 2009, pp. 661-677, vol. 8, No. 8.
Fehres et al., "Cross-presentation through langerin and DC-SIGN targeting requires different formulations of glycan-modified antigens", Journal of Controlled Release, 2015, pp. 67-76, vol. 203.
Feinberg et al., "Structural Basis for Langerin Recognition of Diverse Pathogen and Mammalian Glycans through a Single Binding Site", Journal of Molecular Biology, 2011, pp. 1027-1039, vol. 405, No. 4.
Feinberg et al., "Common Polymorphisms in Human Langerin Change Specificity for Glycan Ligands", The Journal of Biological Chemistry, 2013, pp. 36762-36771, vol. 288, No. 52.
Fillon et al., "Cell Penetrating Agents Based on a Polyproline Helix Scaffold", Journal of the American Chemical Society, 2006, pp. 11798-11803, vol. 127, No. 33.
Flacher et al., "Epidermal Langerhans Cells Rapidly Capture and Present Antigens from C-Type Lectin-Targeting Antibodies Deposited in the Dermis", Journal of Investigative Dermatology, 2010, pp. 755-762, vol. 130, No. 3.
Fujii et al., "Characterizing PEG Chains Tethered onto Micelles and Liposomes Applied as Drug Delivery Vehicles Using Scattering Techniques", ACS Symposium Series: Control of Amphiphile Self-Assembling at the Molecular Level: Supra-Molecular Assemblies with Tuned Physicochemical Properties for Delivery Applications, 2017, pp. 115-129, vol. 1271.
Gao et al., "Heritable targeted mutagenesis in maize using a designed endonuclease", The Plant Journal, 2010, pp. 176-187, vol. 61, No. 1.
Gerber et al., "MAB, a generally applicable molecular force field for structure modelling in medicinal chemistry", Journal of Computer-Aided Molecular Design, 1995, pp. 251-268, vol. 9, No. 3.
Güven et al., "Rapid and efficient method for the size separation of homogeneous fluorescein-encapsulating liposomes", Journal of Liposome Research, 2009, pp. 148-154, vol. 19, No. 2.
Halgren, "Merck Molecular Force Field. I. Basis, Form, Scope, Parameterization, and Performance of MMFF94", Journal of Computational Chemistry, 1996, pp. 490-519, vol. 17, Nos. 5 & 6.
Hanske et al., "Intradomain Allosteric Network Modulates Calcium Affinity of the C-Type Lectin Receptor Langerin", Journal of the American Chemical Society, 2016, pp. 12176-12186, vol. 138, No. 37.
Hanske et al., "Bacterial Polysaccharide Specificity of the Pattern Recognition Receptor Langerin is Highly Species-dependent", The Journal of Biological Chemistry, 2017, pp. 862-871, vol. 292, No. 3.
Hanske et al., "Calcium-Independent Activation of an Allosteric Network in Langerin by Heparin Oligosaccharides", ChemBioChem, 2017, pp. 1183-1187, vol. 18, No. 13.
Harayama et al., "Understanding the diversity of membrane lipid composition", Nature Reviews Molecular Cell Biology, 2018, pp. 281-296, vol. 19, No. 5.
Higashi, "Vaccines for Parasitic Diseases", Annual Reviews Public Health, pp. 483-501, vol. 9.
Holla et al., "Comparative analysis reveals selective recognition of glycans by the dendritic cell receptors DC-SIGN and Langerin", Protein Engineering, Design & Selection, 2011, pp. 659-669, vol. 24, No. 9.
Hwang et al., "Water Suppression That Works. Excitation Sculpting Using Arbitrary Waveforms and Pulsed Field Gradients", Journal of Magnetic Resonance Series A, 1995, pp. 275-279, vol. 112, No. 2.
Immordino et al., "Stealth liposomes: review of the basic science, rationale, and clinical applications, existing and potential", International Journal of Nanomedicine, 2006, pp. 297-315, vol. 1, No. 3.
Ito et al., "The *Drosophila* mushroom body is a quadruple structure of clonal units each of which contains a virtually identical set of neurones and glial cells", Development, 1997, pp. 761-771, vol. 124.
Jones, "Use of Liposomes to Deliver Bactericides to Bacterial Biofilms", Methods of Enzymology, 2005, pp. 211-228, vol. 391.
Koymans et al., "Staphylococcal Superantigen-Like Protein 1 and 5 (SSL1 & SSL5) Limit Neutrophil Chemotaxis and Migration through MMP-Inhibition", International Journal of Molecular Sciences, 2016, 16 pages, vol. 17, No. 1072.
Lion et al., "NK Cells: Key to Success of DC-Based Cancer Vaccines?", The Oncologist, 2012, pp. 1256-1270, vol. 17, No. 10.
Mayer et al., "Characterization of Ligand Binding by Saturation Transfer Difference NMR Spectroscopy", Angewandte Chemie International Edition, 1999, pp. 1784-1788, vol. 38, No. 12.
Mayer et al., "Group Epitope Mapping by Saturation Transfer Difference NMR To Identify Segments of a Ligand in Direct Contact with a Protein Receptor", Journal of the American Chemical Society, 2001, pp. 6108-6117, vol. 123, No. 25.
De Witte et al., "Langerin is a natural barrier to HIV-1 transmission by Langerhans cells", Nature Medicine, 2007, pp. 367-371, vol. 13, No. 3.

(56) References Cited

OTHER PUBLICATIONS

O'Reilly et al., "CD22 Is a Recycling Receptor That Can Shuttle Cargo between the Cell Surface and Endosomal Compartments of B Cells", The Journal of Immunology, 2011, pp. 1554-1563, vol. 186.

* cited by examiner

FIGURE 15
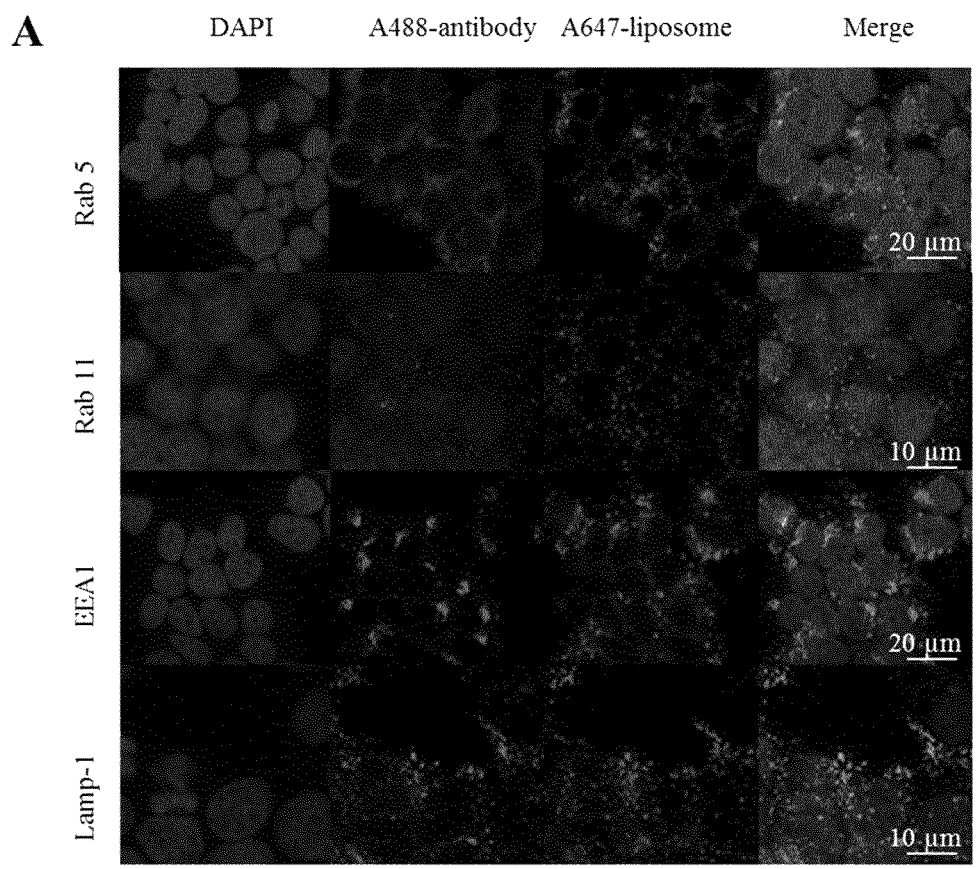
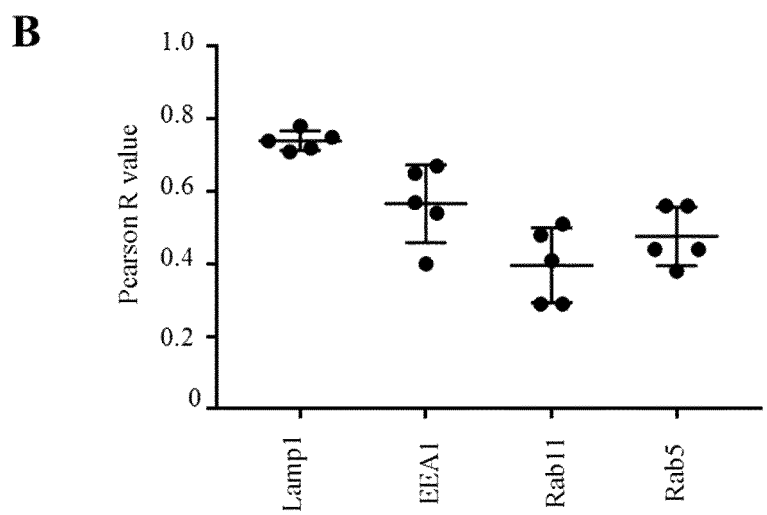

FIGURE 19A-C
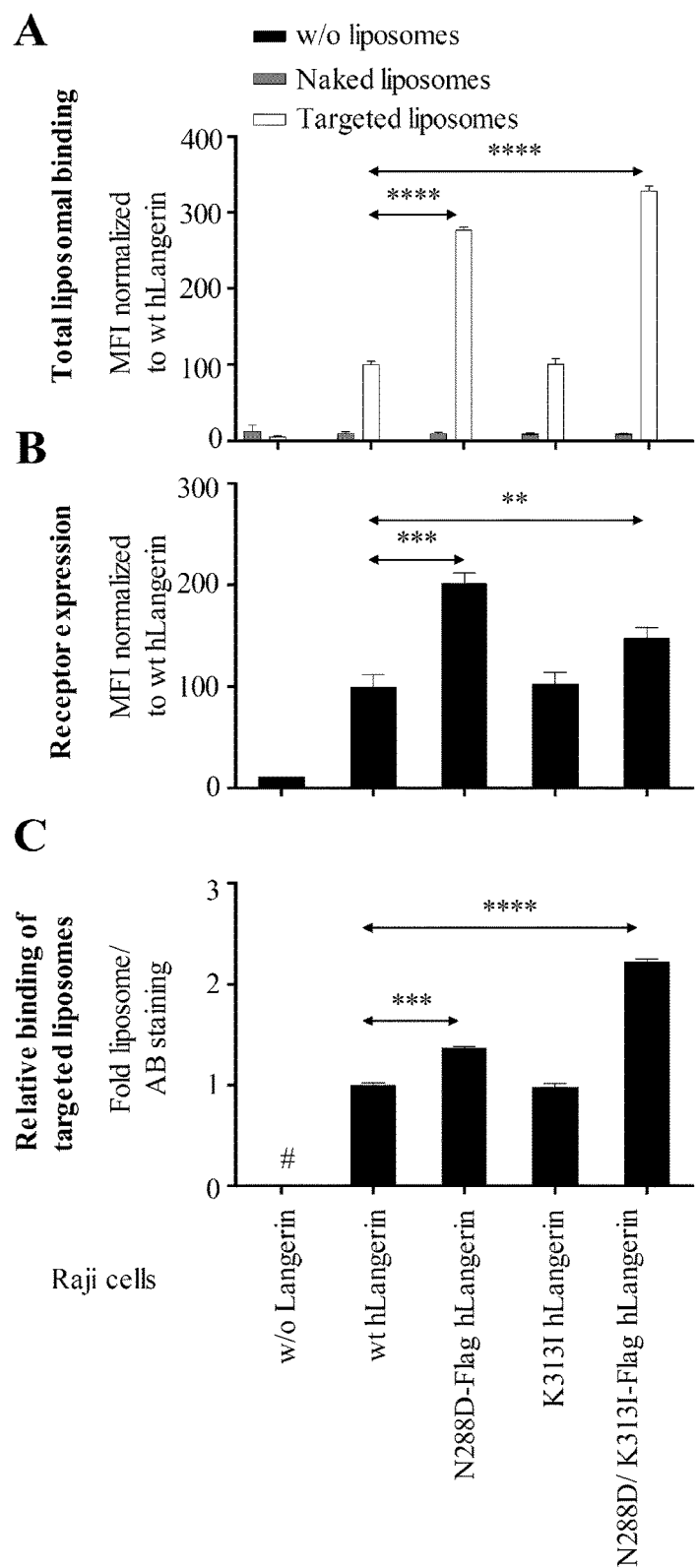

FIGURE 27a+b
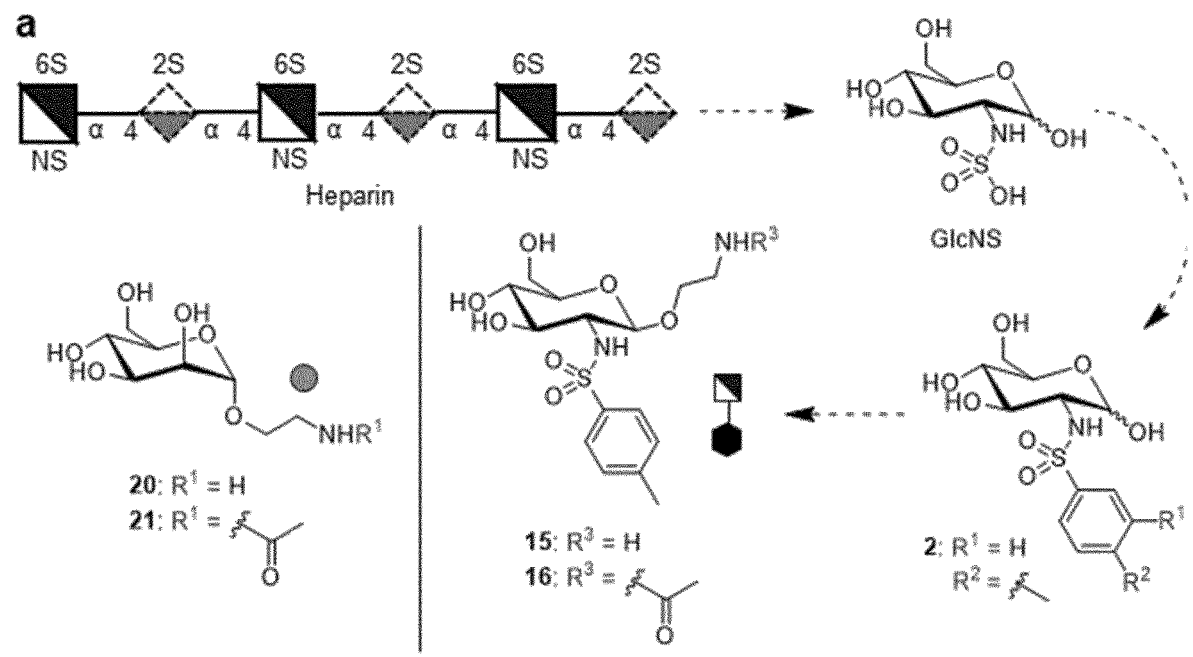
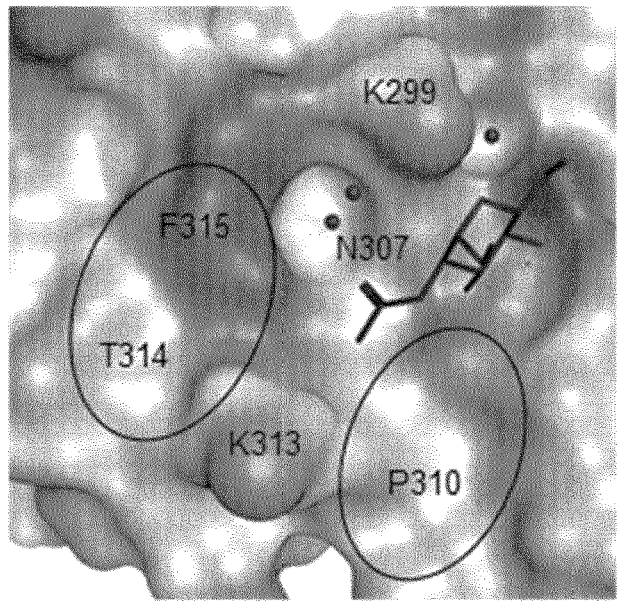

FIGURE 27c+d
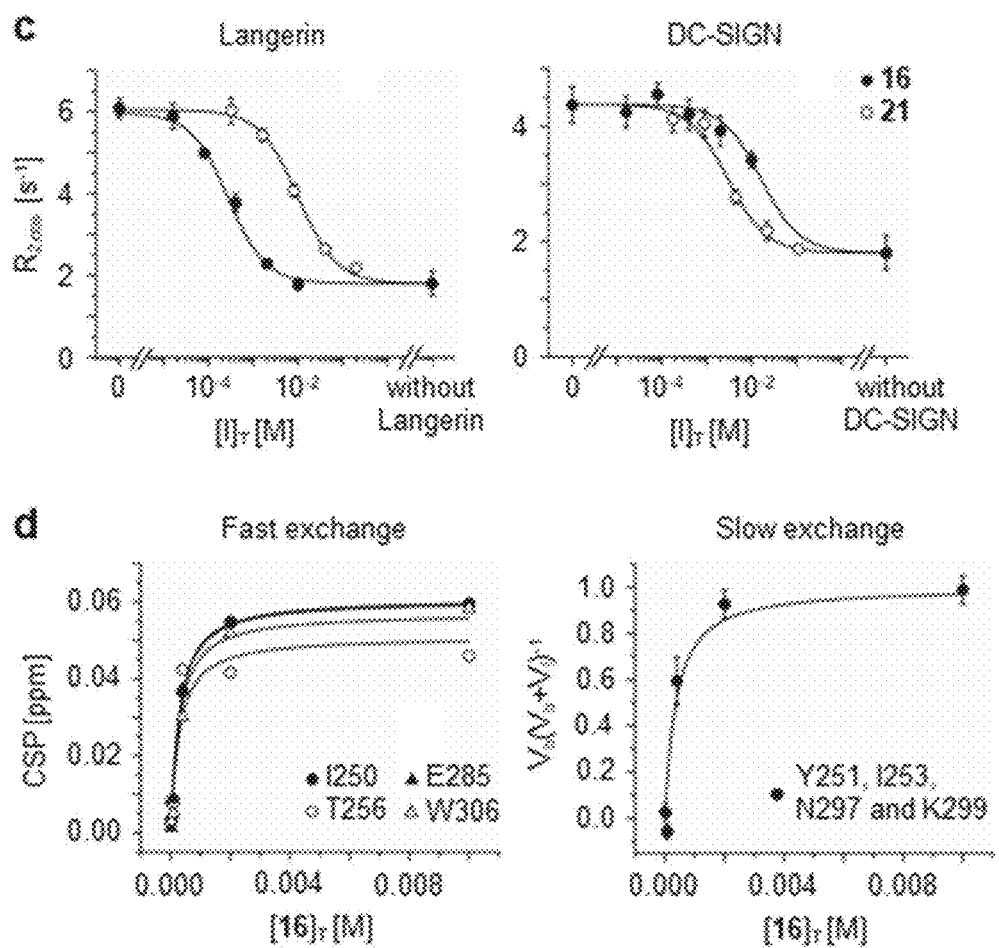

FIGURE 28a+b
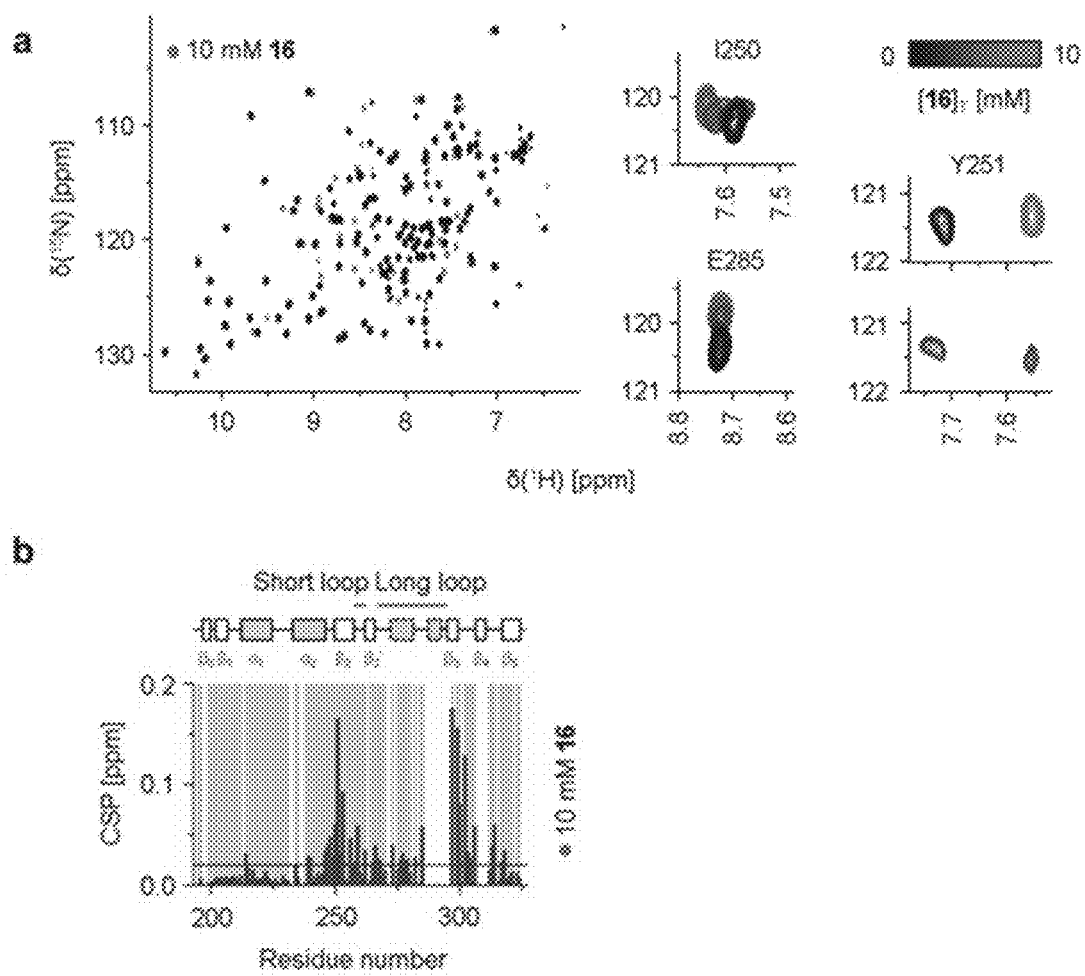

FIGURE 28d+e
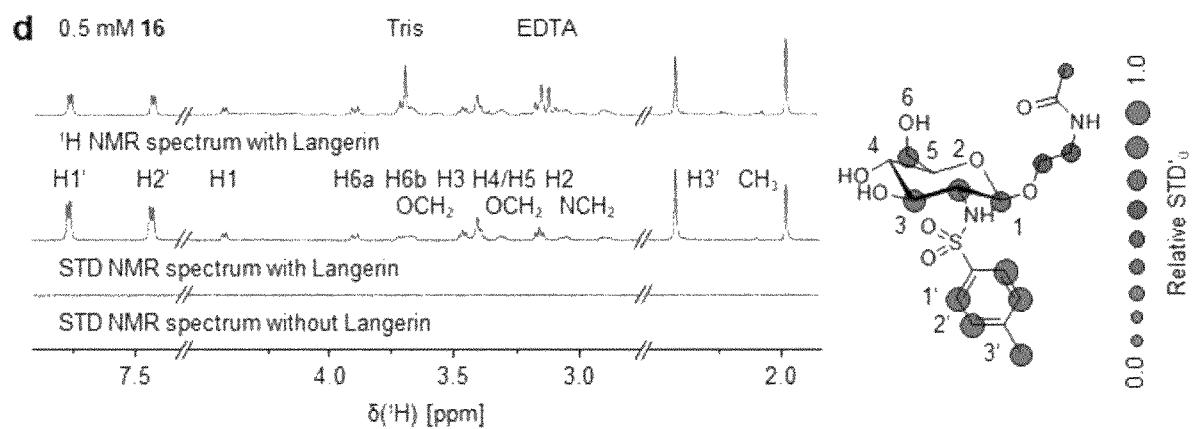
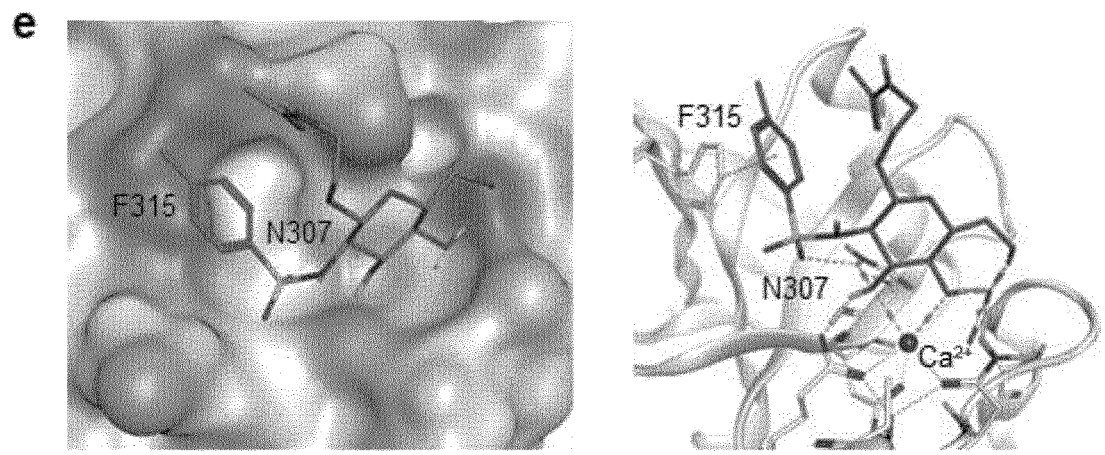

FIGURE 29

Structure-activity relationship and specificity against DC-SIGN.

| Structure | Langerin | | | DC-SIGN | |
| --- | --- | --- | --- | --- | --- |
| | $K_I$ [mM] | $K_D$ [mM] | Relative potency[a] | $K_I$ [mM] | Specificity |
| 2 | 0.32±0.05 | 0.46±0.04<br>0.5±0.2[b] | 31 | 17±1 | 53 |
| 16 | 0.24±0.03 | 0.23±0.07<br>0.3±0.1[b] | 42 | 15±3 | 63 |
| Man | 4.5±0.5[c] | 6.5±0.2[c] | 2.2 | 3.0±0.3 | 0.67 |
| 21 | 10±1 | 12±1 | 1.0 | 2.7±0.3 | 0.27 |

[a] The relative potency was calculated utilizing the $K_I$ value determined for 21.
[b] The value was determined from integrals V of resonances observed to be in slow exchange.
[c] The value was previously published[50].

FIGURE 33a+b
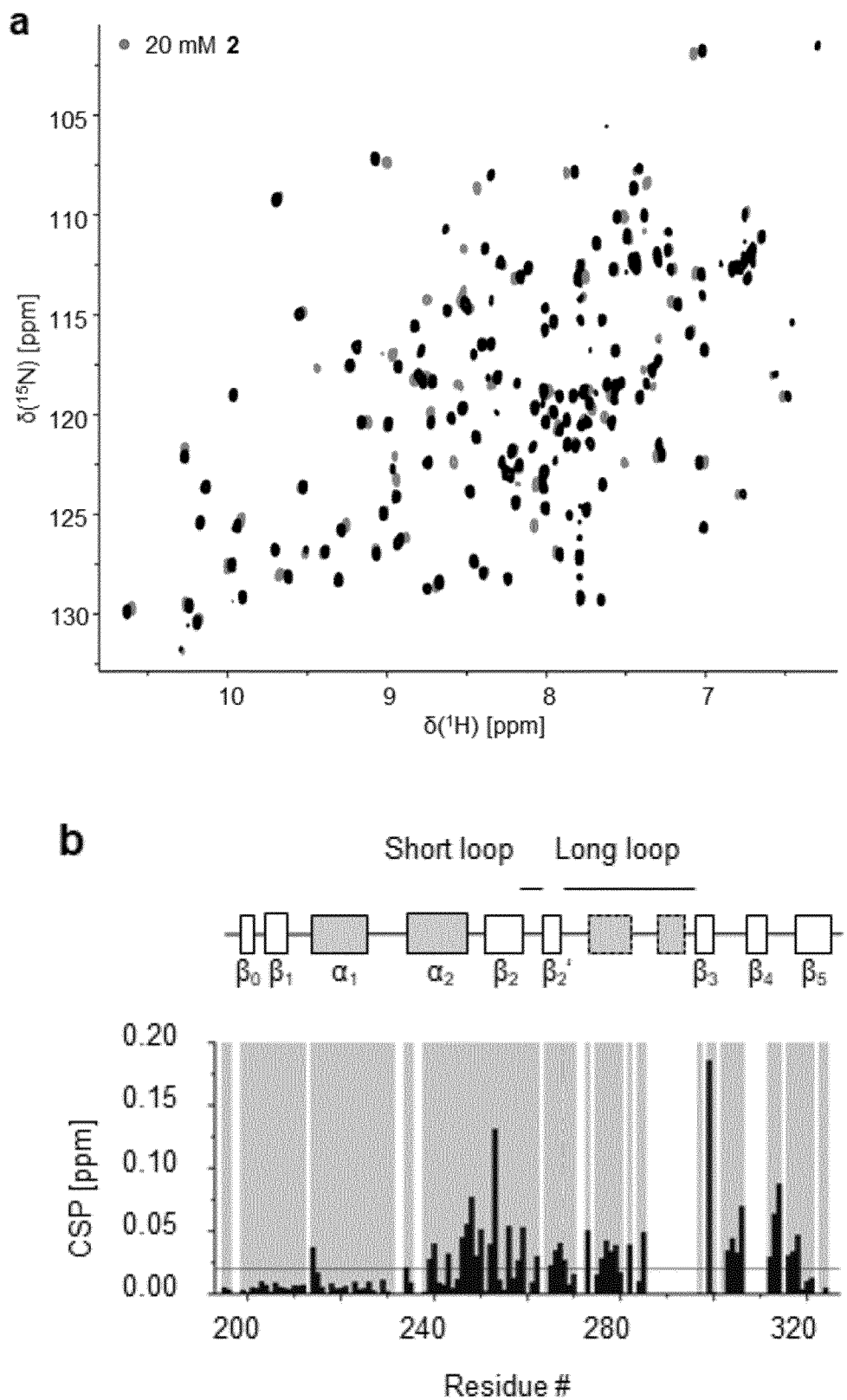

FIGURE 33c+d
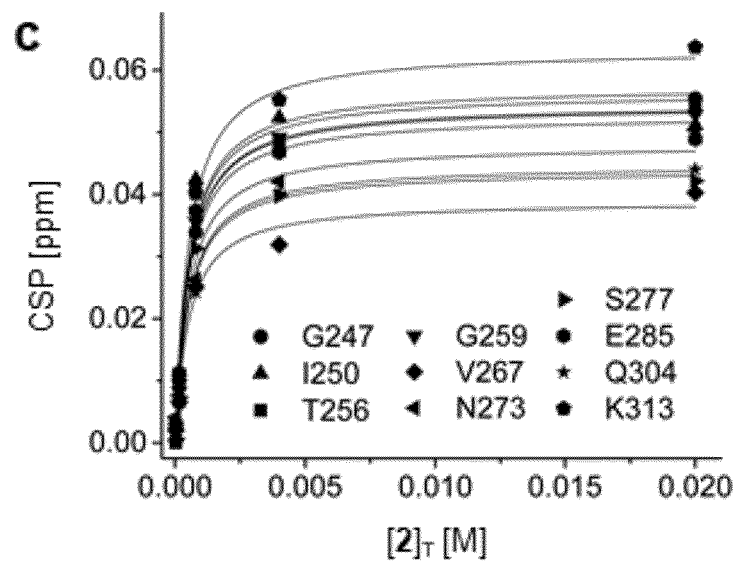
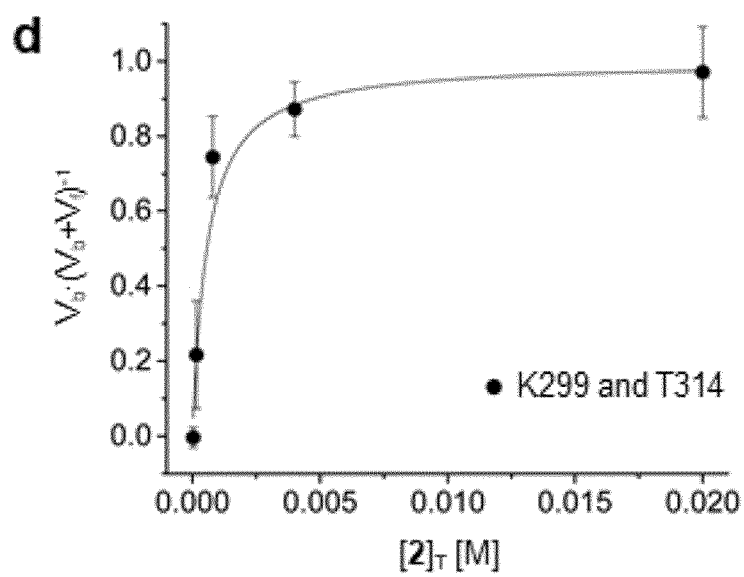

FIGURE 37-2
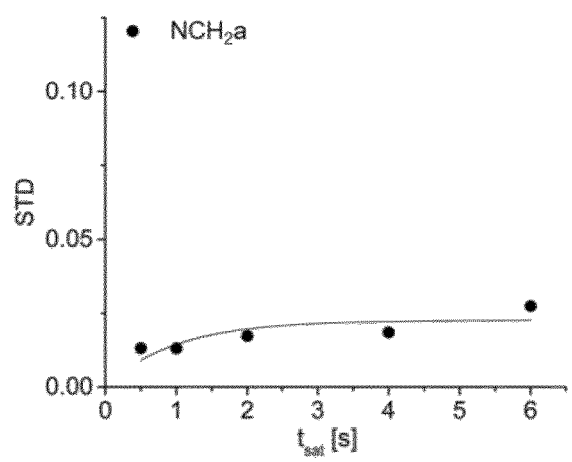
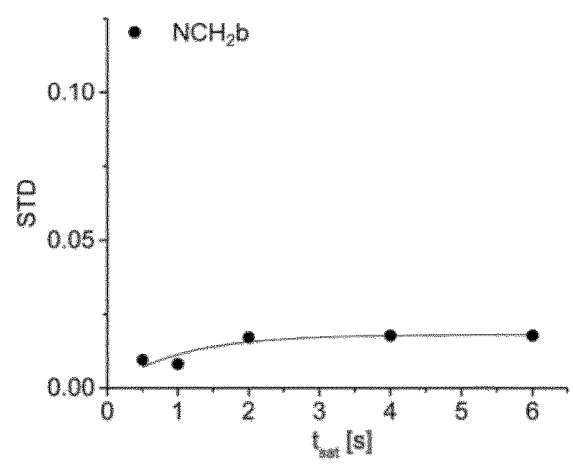
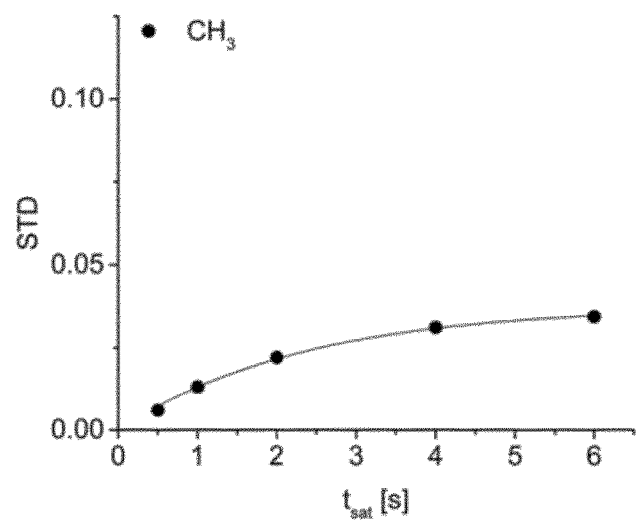

FIGURE 39

LANGERIN+ CELL TARGETING

CROSS-REFERENCE TO RELATED APPLICATIONS

This application is the United States national phase of International Application No. PCT/EP2019/051055 filed Jan. 16, 2019, and claims priority to European Patent Application Nos. 18152362.2 filed Jan. 18, 2018 and 18162955.1 filed Mar. 20, 2018, the disclosures of which are hereby incorporated by reference in their entirety.

REFERENCE TO A SEQUENCE LISTING SUBMITTED VIA EFS-WEB

The content of the ASCII text file of the sequence listing named "2004102_ST25.txt" which is 53,581 bytes in size was created on Jul. 16, 2020 and electronically submitted herewith via EFS-Web, and is hereby incorporated by reference in its entirety.

FIELD OF THE INVENTION

The present invention relates to the use of a vehicle for specific molecular targeting of Langerin$^+$ cells, wherein the vehicle is capable of specifically binding to a Langerin$^+$ cell, said vehicle comprising (a) at least one carrier and (b) at least one saccharide moiety based conjugate for a targeted cargo delivery into a Langerin$^+$ cell. The present invention also relatives to corresponding pharmaceutical and diagnostic compositions, as well as uses comprising the inventive vehicle and methods involving said vehicle.

BACKGROUND OF THE INVENTION

The skin is the soft tissue covering vertebrate animals. In mammals the skin is an organ of integumentary systems comprising multiple layers of ectodermal tissue including the epidermis, which provides waterproofing and works as barrier against infections; and the dermis, which is a cell-poor layer consisting of fibroblasts that produce the extracellular matrix containing proteoglycans and entwined collagen and elastic fibers, both layers being separated by the basement membrane, a sheet of fibers, which controls the traffic of cells and molecules between dermis and epidermis and provides necessary factors for remodeling or repair processes. The skin, hence, interfaces with the outside world and is therefore not only exposed to physical stress but also to a variety of environmental antigens, including chemicals, bacteria, and pathogens.

Accordingly, the skin immune system must be prepared to detect and discriminate between diverse antigens and must be capable of inducing appropriate reactions such as tolerogenic or protective immune responses. In order to fulfil this function, the skin contains a heterogeneous population of dendritic cells (DCs) that represent key regulators of immune responses. Dendritic cells are generally defined as population of antigen presenting cells coordinating the interplay between innate and adaptive immunity and are the only cells, which are able to induce primary immune responses. Therefore, DCs are an interesting target in immunotherapy strategies. Several DC types have been described in humans and can be classified according to their tissue distribution. Some of these DC types have been recognized for their capacity to cross-present exogenous tumor-associated antigens via MHC-I and efficiently prime naïve CD8$^+$ T cells. The skin dendritic cells play a critical role in guarding the host against invading pathogens, but also limit collateral tissue damage. Furthermore, they are associated with the breakdown of peripheral tolerance leading to chronic immune-mediated inflammatory diseases such as allergic contact dermatitis and psoriasis (Clausen and Stoitzner, 2015, Frontiers in Immunology, 6, Article 534).

DCs can be subdivided into conventional DCs and plasmacytoid DCs (pDCs). Healthy skin contains no or very few pDCs which only enter inflamed skin to promote wound healing through type-I interferons or mediate a proinflammatory reaction that develops after TLR7 stimulation, for example, during psoriasis. In the steady state, conventional DCs residing in the skin are typically not inactive, but—as immature cells—constantly probe their environment for invading pathogens and continuously sample self- and environmental antigens. Upon maturation, the DCs migrate to the skin-draining lymph nodes and detach from the surrounding keratinocytes. During their migration to the T cell areas of local lymph nodes, the cells upregulate surface expression of MHC/peptide complexes for recognition of and interaction with antigen-specific naïve T cells. Upon encounter with potentially autoreactive T cells that have escaped central tolerance or with T cells recognizing peptides derived from innocuous foreign antigens, these DCs induce T cell anergy or deletional T cell tolerance (tolerizing function).

In addition, the frequent T cell-DC contacts during T cell scanning of DCs in lymphoid organs, i.e., in the absence of cognate antigen, induce a basal activation level in T cells required for rapid responsiveness to subsequent encounters with foreign antigen during inflammation. Pathogen invasion together with proinflammatory signals typically drive a full functional maturation of skin dendritic cells. Beyond the homeostatic differentiation program, the cells now also upregulate the expression of costimulatory molecules and, in particular, proinflammatory cytokines. Together these promote clonal expansion of naïve antigen-specific T cells and instruct the T cells to acquire appropriate effector functions specifically tailored to eliminate the invading pathogen (sensitizing function). Thus, immature DCs in the periphery have a sentinel function and are capable of antigen capture, antigen processing and peptide-MHC association. They also have a migratory function and provide for the antigen transport to the lymph nodes. There, the DC-T cell interaction leads to high surface MHC I and II/peptide complexes, which finally result in Th1/Th2/Th17 instruction, or T cell deletion and anergy or cytotoxic T-lymphocyte (CTL, T-killer cell) activation.

According to current reports (Doebel et al., 2017, Trends Immunol, 38, 11, 817-828) the groups of dendritic cells in the skin can be subdivided into several DC subsets. The dendritic cells can either be epidermal Langerhans cells (LCs) and dermal DCs. Dermal DCs constitute Langerin$^+$ and Langerin$^-$ subtypes, i.e. cells which express the C-type lectin Langerin (also known as CD207) on their surface, or do not express it. Langerin$^+$ dermal DCs are further be subdivided into CD103$^+$ and CD103$^-$ groups (Yamazaki and Morita, 2013, Frontiers in Immunology, 4, Article 151) according to the expression of CD103, i.e. integrin alpha E (ITGAE). A further division into subsets defines the DCs as Langerin$^+$ CD11blow, Langerin$^-$ CD11b$^-$, and Langerin$^-$ CD11b$^+$ populations (Yamazaki and Morita, 2013, Frontiers in Immunology, 4, Article 151).

Langerin is known to be involved in the Ca$^{2+}$-dependent recognition of both pathogen- and self-associated glycans as well as heparin like oligosaccharides (Munoz-Gracia et al., J. Am. Chem. Soc. 2015, 137, 12, 4100-10). Moreover, Langerin binds to glycans, such as glactose-6-sulfated oligosaccharides, including keratan sulfate (Tateno et al., Journal of Biological Chemistry, 2010, 283, 9, 6390-6400). Since Langerin displays an expression profile highly restricted to specific DC subtypes, mostly in the skin, it represents an attractive target for vaccine development or the establishment of novel immunotherapies.

The skin is hence a particularly attractive entry point for vaccines or other immunotherapies due to the Langerin expressing DCs residing in the uppermost layer which enable local application of a vaccine or drug with potential systemic responses—and without the use of needles. The strategies, which can potentially be followed include the provision of cancer vaccines, prophylactic vaccines against viral or bacterial infections, immunotherapies against allergies, the treatment of autoimmune diseases such as lupus or the use of regenerative approaches in the context of skin transplantations.

However, it is difficult to specifically target Langerin$^+$ DCs since the carbohydrate binding sites of C-type lectins are highly solvent exposed and hydrophilic. Consequently, interactions with mono- and oligosaccharides are typically characterized by low affinities in the millimolar range. Furthermore, the recognition process is highly promiscuous as individual C-type lectins bind several mono- or oligosaccharides and vice versa. In this context, Aretz et al., 2014 notes that the structure-based in silico analysis of 21 X-ray structures corroborated the classification of C-type lectins as undruggable or challenging targets. Druggable secondary binding pockets adjacent to the carbohydrate binding site were exclusively identified for C-type lectins of limited therapeutic relevance (Aretz et al., 2014, Front Immunol, 5, Article 323). There are, on the other hand, successful approaches which are based on an ex vivo method in which progenitor dendritic cells have been isolated from the patient, differentiated ex vivo and were subsequently loaded with SPIO particles (Verdijk et al., 2006, Int. J. Cancer, 120, 978-984). This setup, however, suffers from high costs and low efficacy, owing, in particular, to the lack of cell migration from the site of injection into the target tissue and poor cell differentiation. Further alternative methods are based on the use of antibodies. For example, in Flacher et al., 2010, Journal of Investigative Dermatology, 130, 755-762 the capture of presentation of antigens from Langerin-targeting antibodies in epidermal Langerhans cells is described. Yet, antibodies do not dissolve per se from the receptor after endocytosis and thus may limit the absorption capacity of the cells. Moreover, due to the high affinity of the antibody it may also bind to cells with very low expression of the receptor.

There is hence a need for an approach which allows to effectively target Langerin$^+$ dendritic cells, in particular in the skin, and which further provides for an operative and reliable entry and subsequent processing of substances, e.g. antigens, into the cell.

OBJECTS AND SUMMARY OF THE INVENTION

The present invention addresses these needs and provides the use of a vehicle for specific molecular targeting of Langerin$^+$ cells, wherein the vehicle is capable of specifically binding to a Langerin$^+$ cell, said vehicle comprising (a) at least one carrier and (b) at least one conjugate of the general formula (I)

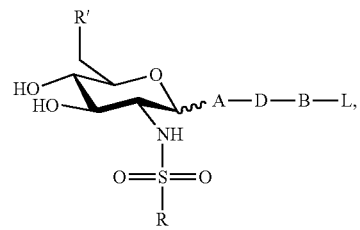

wherein
(i) R is independently selected from the group consisting of substituted or non-substituted alkyl, alkenyl, alkynyl, cycloalkyl, $C_1$-$C_8$ alkyl cycloalkyl, aryl, $C_1$-$C_8$ alkyl aryl, heteroaryl, $C_1$-$C_8$ alkyl heteroaryl, biaryl, and $C_1$-$C_8$ alkyl biaryl;
wherein the substituents are independently selected from the group consisting of
—N($R^a$)($R^b$), —O$R^a$, —S$R^a$, —C(O)$R^a$, —C(O)O$R^a$, —C(O)N($R^a$)($R^b$), —N($R^a$)C(O)$R^b$, —N($R^a$)S(O)$_2$$R^b$, —OS(O)$_2$$R^a$, halogen, —NO$_2$, —CN, —NC, —N$_3$, —NCO, —OCN, —NCS, —SCN, substituted or non-substituted alkyl, alkenyl, alkynyl, aryl and heteroaryl;
wherein $R^a$ and $R^b$ are independently selected from the group consisting of hydrogen, substituted or non-substituted $C_{1-8}$ alkyl, $C_{2-8}$ alkenyl, $C_{2-8}$ alkynyl, $C_{3-6}$ cycloalkyl, aryl-$C_{1-5}$ alkyl, heteroaryl-$C_{1-5}$ alkyl, aryl, heteroary;
(ii) R' is independently selected from the group consisting of
—O$R^a$, and —NHS(O)$_2$$R^a$,
wherein $R^a$ is defined as above; and wherein
(iii) A-D-B-L is a linker group binding the glucose derivative of formula (I) covalently to the carrier or to a part of the carrier,
for a targeted cargo delivery into a Langerin$^+$ cell.

The inventors surprisingly found that the vehicle as described above binds specifically to Langerin$^+$ cells and effectively delivers the cargo, i.e. substances of different size and nature, into a Langerin$^+$ cell, which in turn may present internalized substances, e.g. antigens, on its surface. Langerin is particularly suitable for the receptor-mediated uptake of particles into endosomal compartments, which enables the CD8$^+$ T-cell immune response suitable for cancer and antiviral therapy due to the cross-presentation of antigens via MHC I molecules on the surface of the targeted cells. A major challenge of the current invention was in fact the development of a ligand structure which suitably binds the C-type lectin Langerin. In fact, the addressing of the binding site of the Langerhans cell-specific marker, Langerin, which is a sugar-binding protein, has so far failed mostly due to the complex architecture and low accessibility of drug-like compounds as reported for carbohydrate binding proteins in general in Ernst and Magnani, 2009, Nat Rev Drug Disc, 8(8), 661-77. The right choice of the binding pocket and the associated mechanism for the release of the cargo in the endosomal compartment of the cells were the essential factors of success. The inventors further found that when the cargo is released under the influence of acidity and calcium concentration in the cell, the receptor can advantageously bring more particles into the cell. The presently provided Langerin ligand, as part of the above described vehicle, emerged from a rational ligand design to meet the criteria of durability, scalability, synthetic accessibility, sufficient affinity and specificity for the target receptor, as well as sufficient hydrophilicity to avoid unwanted interaction, such as surface aggregation, with the carrier. Computer-assisted methods, as well as innovative methods of fragment-based drug design were used to arrive at the herein described ligand structure.

Using the above described advantageous ligand in a cargo-delivery approach into Langerin$^+$ cells allows for the first time the employment of targeted transdermal and intradermal dosage forms which significantly increases the compliance of the patient (due to needle free applicability) and at the same time allows cheaper vaccines. By specifically targeting specialized dendritic cells, it is now possible to initiate an immune response in vivo to the cargo introduced, e.g. as therapeutic or prophylactic vaccines, or to reduce the immune response, e.g. due to peripheral or central tolerance induction. Another advantageous application is the direct modulation of a deregulated Langerhans cell function as manifested in some autoimmune diseases and in Langerhans cell histocytosis, i.e. a cancerous change in Langerhans cells. Thus, the hitherto problematic environment of the skin, typically comprising several competing groups of cells, whose complexity has often reduced the efficacy of vaccination approaches since, for example, active ingredients have not reached the intended dendritic cells and may even have produced unwanted side effects by unintended inclusion in immune cells, becomes now a first-rate and very attractive area of immunologic and medical operation.

In addition, due to the versatile cargo-carrier concept of the present invention, which is implemented on the basis of the coupling of the innovative ligand-comprising conjugate and the carrier, the introduction of a diverse group of different substances (cargos) into Langerin$^+$ cells becomes possible. Thus, not only proteins coupled to antibodies, as described in the prior art, can be introduced into the cell, but also substances such as nucleic acids, e.g. DNA or RNA, glycosylated elements, stimulants, independent peptides, or any low-molecular compound. This allows for a greatly increased variability in terms of cellular and immunologic modulation and elicitation of immune responses. Furthermore, it is the only system that allows simultaneous delivery of different molecules and thus may modulate different arms of the adaptive immune system, i.e. antibodies and cytotoxic T-lymphocytes at the same time.

Moreover, the cargo-carrier concept of the present invention entails a high flexibility and adaptability of the vehicle (ligand-conjugate plus carrier) and the cargo. This results in fast and cost-effective adaptation and optimization options during product development. Other systems, such as antibody-based systems are less flexible and, due to long development and production times, generate high costs. The targeted delivery in combination with dermal administration thus not only increase efficiency and safety by reducing the drug load, but also enables better dosing and the avoidance of systemic drug administration. Furthermore, the subject-matter of the present invention allows for the provision of treatment options without induction of adverse antibody responses. Also the co-administration of adjuvants and antigens as envisaged by the present invention allows to avoid the systemic activation of the immune system.

Moreover, the present invention allows for the combination of different cargos for the same or for different targets, which can amplify the modulation of immune responses through different pathways.

In a preferred embodiment of the present invention, the vehicle of the invention as defined herein above comprises the general formula (I), wherein R' is R' is —OH, —$OCH_3$, —$OCH_2CH_3$, or —$NHS(O)_2R^a$.

In another preferred embodiment, said vehicle as described above comprises the general formula (I), wherein R' is —OH or —$NHS(O)_2R^a$.

In a further preferred embodiment, said vehicle as described above comprises the general formula (I), wherein R' is —OH, —$NHS(O)_2CH_3$ or N-tosyl.

In yet another preferred embodiment, said vehicle as described above comprises the general formula (I), wherein R' is —OH.

In a still further preferred embodiment, the vehicle as described above comprises said general formula (I), wherein R is independently selected from the group consisting of:

substituted or non-substituted alkyl, cycloalkyl, $C_1$-$C_8$ alkyl cycloalkyl, aryl, $C_1$-$C_8$ alkyl aryl, heteroaryl, $C_1$-$C_8$ alkyl heteroaryl, biaryl, and $C_1$-$C_8$ alkyl biaryl.

In another preferred embodiment, said vehicle as described above comprises the general formula (I), wherein R is independently selected from the group consisting of:

substituted or non-substituted $C_1$-$C_6$ alkyl, $C_3$-$C_6$ cycloalkyl, $C_1$-$C_3$ alkyl $C_3$-$C_6$ cycloalkyl, $C_6$-$C_{14}$ aryl, $C_1$-$C_3$ alkyl $C_6$-$C_{14}$ aryl, heteroaryl, $C_1$-$C_3$ alkyl heteroaryl, biaryl, and $C_1$-$C_3$ alkyl biaryl.

In a particularly preferred embodiment, said vehicle as described above comprises the general formula (I), wherein R is independently selected from the group consisting of:

substituted or non-substituted cyclohexyl, phenyl, benzyl, biphenyl, pyridyl, and oxazolyl.

In yet another preferred embodiment, said vehicle as described above comprises said general formula (I), wherein R is a substituted or non-substituted phenyl.

In a particularly preferred embodiment, the vehicle as described above comprises the general formula (I), wherein the substituents of R are independently selected from the group consisting of:

—$N(R^a)(R^b)$, —$OR^a$, —$SR^a$, —$C(O)R^a$, —$C(O)OR^a$, —$C(O)N(R^a)(R^b)$, —$N(R^a)C(O)R^b$, —$N(R^a)S(O)_2R^b$, —$OS(O)_2R^a$, halogen, —$NO_2$, —CN, —NC, —$N_3$, —NCO, —OCN, —NCS, —SCN, substituted or non-substituted alkyl, alkenyl, alkynyl, aryl and heteroaryl, wherein $R^a$ and $R^b$ are independently selected from the group consisting of hydrogen and $C_{1-2}$ alkyl.

In another preferred embodiment, said vehicle as described above comprises the general formula (I), wherein the substituents of R are independently selected from the group consisting of:

—$NH_2$, —OH, —$OCH_3$, —$C(O)CH_3$, —$NHC(O)CH_3$, —F, —Cl, —Br, —$NO_2$, —CN, $C_1$-$C_4$ alkyl and phenyl.

In a further preferred embodiment, said vehicle as described above comprises said general formula (I), wherein said phenyl is mono-, di- or trisubstituted and substituents of the phenyl are independently selected from the group consisting of:

—$NH_2$, —OH, —$OCH_3$, —$C(O)CH_3$, —$C(O)NH_2$, —$C(O)NHCH_3$, —$CH_2OH$ —$NHC(O)CH_3$, —F, —Cl, —Br, —$NO_2$, —CN, $C_1$-$C_4$ alkyl, naphtyl and phenyl.

In another preferred embodiment, said vehicle as described above comprises the general formula (I), wherein said phenyl is monosubstituted in para position and substituents of the phenyl are independently selected from the group consisting of —$NHC(O)CH_3$, —CN, —$CH_3$ and phenyl.

In yet another preferred embodiment, the conjugate as mentioned above is a conjugate of the following formula (I-1) or (I-2):

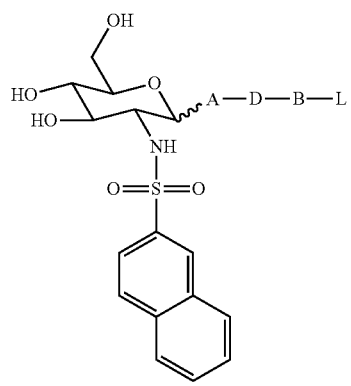
(I-1)
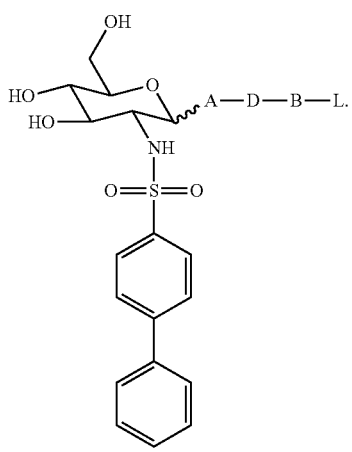
(I-2)
In a still further preferred embodiment, the conjugate as mentioned above is a conjugate of any one of the following formulas (I-3) to (I-15):
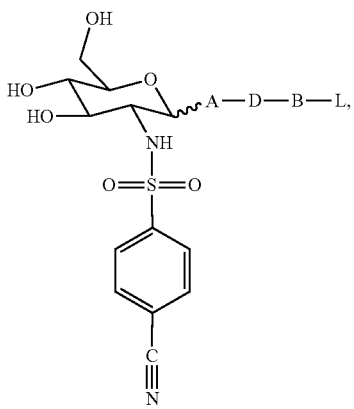
(I-3)
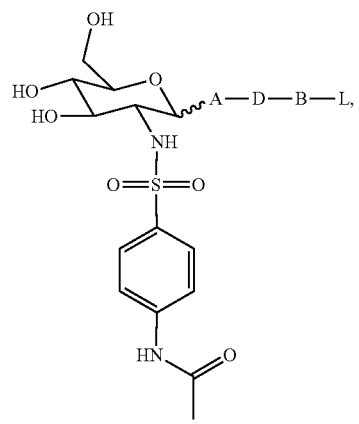
(I-4)
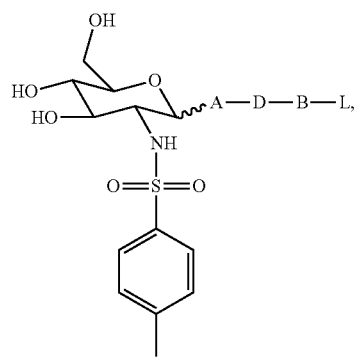
(I-5)
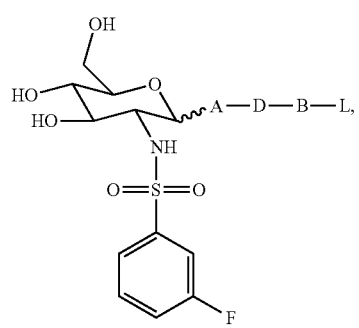
(I-6)
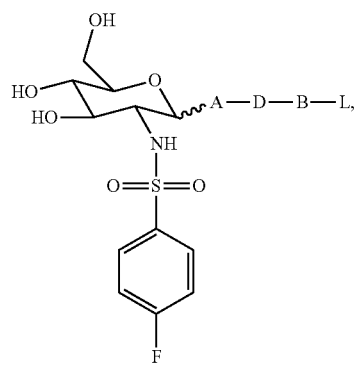
(I-7)

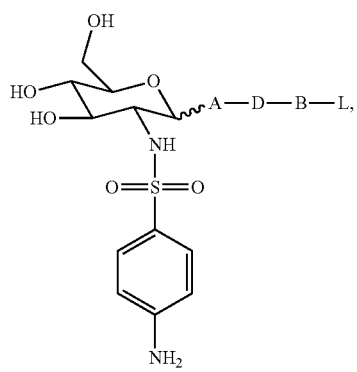

(I-8)

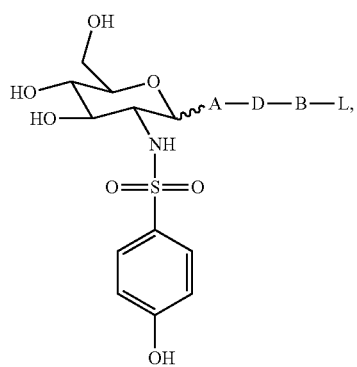

(I-9)

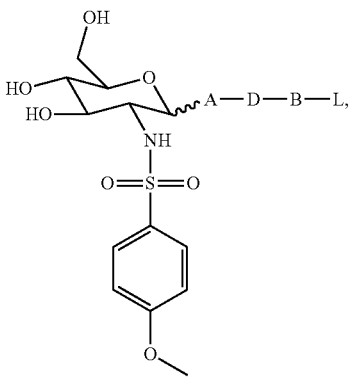

(I-10)

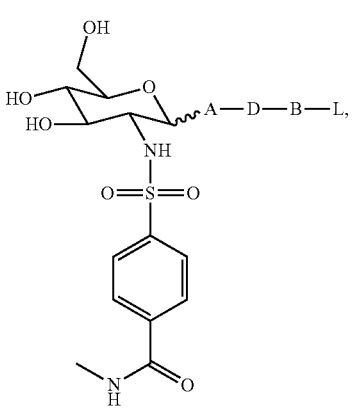

(I-11)

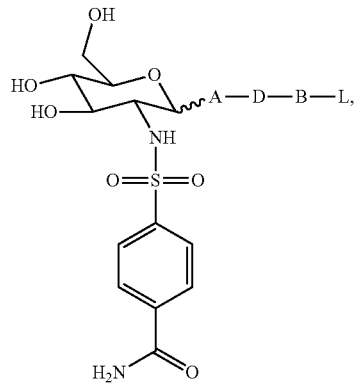

(I-12)

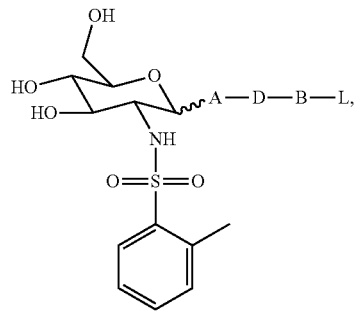

(I-13)

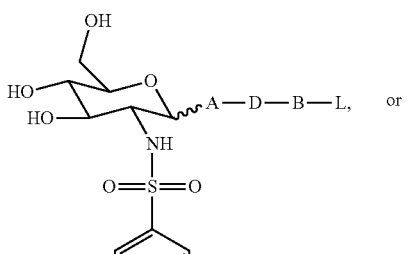

(I-14) or

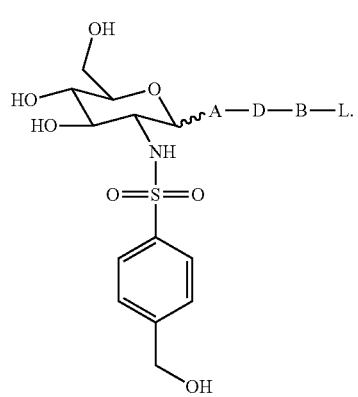

(I-15)

In a particularly preferred embodiment, said A-D-B-L linker group as mentioned above is a group consisting of a spacer A-D-B and a linker L connecting the glucose derivative with the carrier. It is particularly preferred that said linker L comprises one or more of synthetic polymers or natural polymers or one or more single units of those polymers or a combination thereof.

According to further preferred embodiments of the present invention said synthetic polymer as mentioned above is selected from a group consisting of saturated and unsaturated hydrocarbon polymer; polyamines; polyamide; polyester; polyether, polyethylene glycol, polypropylene glycol; block copolymers, and poloxamers.

According to another group of preferred embodiments of the present invention said natural polymer as mentioned above is selected from a group consisting of carbohydrates, modified carbohydrates, peptides, modified peptides, lipids and modified lipids.

In a particularly preferred embodiment, the vehicle of the present invention as described above comprises the general formula (I), wherein D is a spacer connected with A and B of the general formula (D-1)

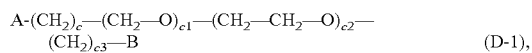
(D-1), wherein D is connected to the linker L via B, wherein B is selected from the group consisting of:
—O—, —S—, —C($R^{c1}$)($R^{c2}$), —S—S—, —N($R^{c1}$)—, —C(O)—, —C($R^{c1}$)=N—, —N=N—, —OC(O)—, —C(O)O—, —C(O)N($R^{c1}$)—, —N($R^{c1}$)C(O)—, —N($R^{c1}$)C(O)N($R^{c2}$)—, —N($R^{c1}$)C(S)N($R^{c2}$)—, —N($R^{c1}$)C(O)O—, —OC(O)N($R^{c1}$)—, -cyclohexene- and -triazoles-;

wherein $R^{c1}$ and $R^{c2}$ are independently selected from the group consisting of hydrogen, substituted or non-substituted alkyl, alkenyl, cycloalkyl, $C_1$-$C_8$ alkyl cycloalkyl, aryl, $C_1$-$C_8$ alkyl aryl, heteroaryl, and $C_1$-$C_8$ alkyl heteroaryl;

D is connected to the glucose derivative via A, wherein A is selected from the group consisting of —O $CH_2$—, —S—, —NH—, —NHC(O)—, —OC(O)—, -cyclohexene- and -triazoles-; and c is an integer selected from 0 to 20, c1 is an integer selected from 0 to 20, and c2 is an integer selected from 0 to 20, c3 is an integer selected from 1 to 20, if A is —$CH_2$— c3 is an integer selected from 0 to 20.

In a further preferred embodiment, said vehicle as described above comprises the general formula (I), wherein linker L is a linker of the following general formula (L-1)

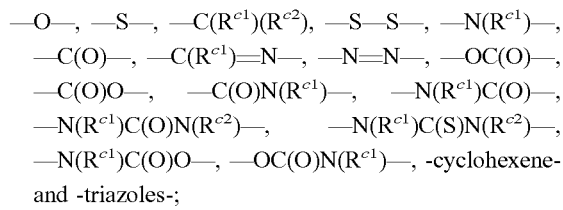

wherein $U^1$ is a group connected via B with the spacer D, wherein $U^1$ is selected from the group consisting of, —$CH_2$—, —CH=CH—, or —C≡C—;

$Z^1$ is a moiety binding the linker to the carrier selected from the group consisting of —O—, —S—, —N($R^d$)—, —C($R^d$)($R^e$)—, —$R^d$C=C$R^e$—, —C(O)—, —C(O)O—, —OC(O)—, —C(O)S—, —C(O)N($R^d$)—, —N($R^d$)C(O)—, —N($R^d$)C(O)N($R^e$)—, —N($R^d$)C(S)N($R^e$)—, —N($R^d$)C(O)O—, —OC(O)N($R^d$)—, -cyclohexene-, -triazoles-, —NHS(O)$_2$—, —S(O)$_2$—, —OP(O)(H)O—, or —OP(O)(OH)O wherein $R^d$ and $R^e$ are independently selected from the group consisting of hydrogen, substituted or non-substituted $C_{1-32}$ alkyl, $C_{2-32}$ alkenyl, $C_{3-8}$ cycloalkyl, aryl, $C_1$-$C_5$ alkyl aryl, heteroaryl, $C_1$-$C_5$ alkyl heteroaryl; and d1 to d5 is each an integer from 0 to 50, d6 an integer from 1 to 50.

In a still further preferred embodiment, said A-D-B-L linker group as mentioned above is a molecular chain having a total number of carbon atoms, nitrogen atoms and oxygen atoms contained in the main chain of at least 4.

In a further embodiment of the present invention, said A-D-B-L linker group as mentioned above is a molecular chain having a total number of carbon atoms, nitrogen atoms and oxygen atoms contained in the main chain of between 4 atoms to 600 atoms.

In yet another further preferred embodiment, said A-D-B-L linker group is a molecular chain having a length of the main chain of between about 0.4 nm to about 400 nm.

In a further preferred embodiment, said vehicle as described herein above comprises at least one carrier, wherein said at least one carrier is a soft particle.

In another preferred embodiment, said soft particle is selected from the group consisting of a liposome, a noisome, a micelle, a Sequessome™ and a transferosome and wherein the conjugate is directly bound via Z' to one part of said soft particle, wherein said one part of the soft particle is a lipid, a modified lipid, such as a phospholipid, 1,2-distearoyl-sn-glycero-3-phosphoethanolamine (DSPE), a membrane lipid, or a modified phosphatidylcholine.

In a further embodiment, the soft particle may be a soft particle, such as a liposome, which contains one or more types of lipids. In one embodiment, the conjugate may be bound to a part of the soft particle, such as any types of lipid, which forms a part of the liposome.

In another embodiment the lipids bound to a conjugate and the lipid which are not bound to a conjugate have a specific ratio of about 1:15, 1:20, 1:25, 1:50, 1:100, 1:150, 1:200, preferably 1:20.

In a particularly preferred embodiment, said conjugate of the present invention as defined herein above is bound to one part of a soft particle carrier resulting in the following formula (II):

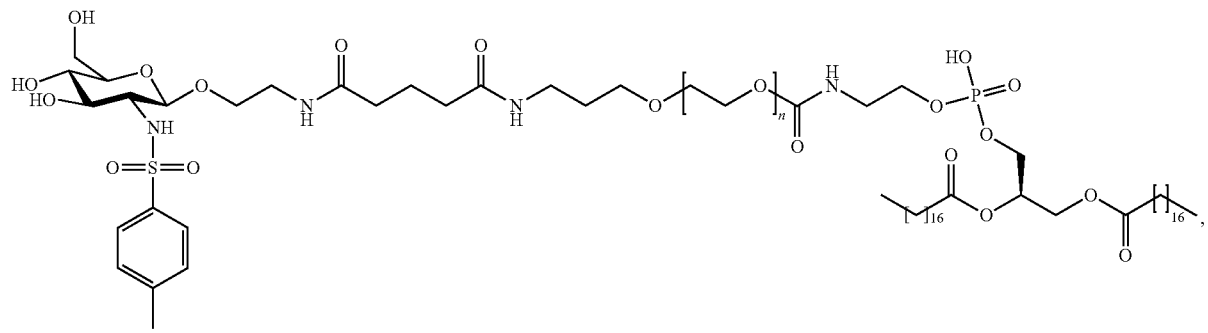

(II)

wherein n is an integer from 0 to 150.

In a further preferred embodiment, said at least one carrier is selected from the group consisting of a nanoparticle, peptide, protein, toxin, dendrimer, fullerene and carbon nanotube, wherein the conjugate is directly bound via Z1 to the carrier, or wherein the conjugate is bound via Z1 to an additional spacing element of the carrier.

In another preferred embodiment, said additional spacing element is a natural or synthetic polymer, e.g. as defined herein above.

In yet another preferred embodiment, said liposome is a bilayer phospholipid liposome. In a particularly preferred embodiment said liposome has a size of 30 to 250 nm.

In a further preferred embodiment, said liposome comprises or is associated with an additional component. It is particularly preferred that said additional component is cholesterol. In certain embodiments, the amount of the additional component, e.g. cholesterol, may vary, preferably in an amount of about 20 to 50 mol %. More preferably, the amount of said additional component is about 40 mol %.

In a further preferred embodiment, said nanoparticle as mentioned above is a gold, silver or iron nanoparticle. It is particularly preferred that said nanoparticle has a size of 5 to 1000 nm.

In a still further preferred embodiment, said carrier comprises, or is associated to, a cargo.

In a particularly preferred embodiment, said cargo is located within the carrier and/or is linked to the outside of the carrier and/or is integrated into a mono- or bilayer structure of the carrier.

In yet another preferred embodiment, said specific molecular targeting as mentioned above comprises an interaction between said conjugate and a receptor present on a Langerin$^+$ cell.

In a particularly preferred embodiment, said receptor present on a dendritic cell is C-type lectin receptor (CLR) Langerin (CD207).

In a preferred embodiment, said specific binding of said vehicle to a dendritic cell is based on a binding to C-type lectin receptor (CLR) Langerin (CD207) with a specificity which is at least 2-, 4-, 8- or 16-fold higher than a control in a cell-based assay comprising the introduction of liposomes under identical conditions into Raji B cells presenting recombinant Langerin, Raji B cells presenting recombinant DC-SIGN (control 1) and Raji wildtype B cells presenting no C-type lectin receptor (WT, control 2).

In a further preferred embodiment, the average size of the vehicle is from 2 to 1000 nm measured by Dynamic Light Scattering (DLS).

In another aspect, the present invention relates to the use of a composition, comprising at least one vehicle for specific molecular targeting of Langerin$^+$ cells as defined above comprising or associated to a cargo as defined herein and an additive, for a targeted cargo delivery into a Langerin$^+$ cell.

In a preferred embodiment, said additive is a divalent ion, an adjuvant, or a factor which promotes the binding to C-type lectin receptor (CLR) Langerin. It is particularly preferred that said divalent ion is $Ca^{2+}$ or $Zn^{2+}$.

In another preferred embodiment, said composition as mentioned above further comprises a solvent or a combination of a solvent with a further compound. Preferred examples of solvent are $H_2O$, aqueous sucrose solution, phosphate buffered saline, tricine buffer, HEPES buffer. In specific embodiments combinations of solvents with further compounds are any of the before mentioned, with DMSO. In one specific embodiment the concentration of DMSO is 10%.

In yet another preferred embodiment, said composition comprises the vehicle as defined above in an amount of about 1 to 10 mol %, preferably of about 4 to 6 mol %, more preferably 4.75 to 5 mol %.

In a further aspect, the present invention relates to a method for targeted cargo delivery into a Langerin$^+$ cell, comprising contacting the vehicle for specific molecular targeting of Langerin$^+$ cells as defined above comprising or associated to a cargo as defined herein, or the composition as defined above with a Langerin$^+$ dendritic cell.

In a preferred embodiment, said cargo is selected from the group consisting of a small molecule, a peptide, a protein, a cytotoxic substance, a nucleic acid, a pigment, a dye, a metal, a radionuclide, a virus, a modified virus, a viral vector, an inoculant, a plasmid and/or a multicomponent system. The multicomponent system is preferably a system for genomic editing comprising different components. It is particularly preferred that said genomic editing system is a CRISPR/Cas system.

In another preferred embodiment of the use or the method as described above, said cargo is a pharmaceutically or immunologically active compound, which is (i) capable of eliciting an immunological reaction in the body, (ii) an immunomodulator, (iii) an immunological tolerance inducer or an (iv) inhibitor of cellular function, such as an inhibitor of apoptosis.

In a further preferred embodiment of the use or the method as described above, said cargo comprises, essentially consists of or consists of (i) a cancer antigen or epitope or comprises a cancer antigen or epitope, (ii) an autoimmune disease antigen or epitope or comprises an autoimmune disease antigen or epitope, (iii) a bacterial antigen or comprises a bacterial antigen or epitope, (iv) a viral antigen or comprises a viral antigen or epitope, (v) a parasitic antigen or comprises a parasitic antigen or epitope, or (vi) an allergen, or an epitope of an allergen, or comprises an allergen or an epitope of an allergen.

In another aspect, the present invention relates to a pharmaceutical composition comprising the vehicle as defined above, or the composition as defined above, wherein the carrier comprises or is associated to a pharmaceutically active cargo and optionally a pharmaceutically acceptable carrier substance or a pharmaceutical adjuvant.

In a preferred embodiment, said pharmaceutical composition is suitable for oral, intravenous, topical, corneal, nasal, subcutaneous, intradermal, transdermal administration, for vaccination or for administration via hair follicles.

In another preferred embodiment, said pharmaceutical composition is provided as patch, as liquid, cream, ointment, paste, gel, lotion, tape, film, sublingual, buccal, tablet, spray, suppository, vaccine, or in the form of a microneedle. A particularly preferred form of a patch is a nanopatch or a hydrogel patch.

In a still further preferred embodiment, said pharmaceutical composition is to be administered with a medical device, such as a needle, a vaccination gun, a plaster, or an inhaler.

In a particularly preferred embodiment, said pharmaceutical composition is for use in the treatment or prevention of cancer, of an autoimmune disease, of a bacterial infection, of a viral infection, or of a graft-vs. host disease, of a local or systemic inflammation, of allergy, or for hyposensitization.

In a further aspect, the present invention relates to a diagnostic composition comprising the vehicle as defined above, or the composition as above, wherein the carrier comprises or is associated to a pharmaceutically active cargo and optionally a pharmaceutically acceptable carrier substance or a pharmaceutical adjuvant.

In a preferred embodiment, said diagnostic composition is for use in diagnosing, detecting, monitoring or prognosticating cancer, an autoimmune disease, a bacterial infection, a viral infection, a parasitic infection or a graft-vs. host disease local or systemic inflammation, or allergy.

In a further aspect, the invention relates to a method of identifying a suitable dose for a Langerin+ dendritic cell-targeting therapy of a disease comprising: (a) contacting a population of Langerin+ cells with a compound capable of being introduced into the cells (b) determining the number of cells which incorporated said compound; (c) determining a suitable dose of the compound by comparing the number of cells with incorporated compound and the starting population, preferably after a period of 1-3 days, optionally by additionally correlating the number of cells with incorporated compound or their status with observed literature results.

In another aspect, the invention relates to a medical kit comprising at least one element selected from the vehicle as defined above and/or the composition as defined above, wherein the carrier comprises or is associated to a pharmaceutically active cargo, and optionally a leaflet with instructions.

In a still further aspect, the invention relates to a vaccine comprising the vehicle as defined above, or the composition as defined above, wherein the carrier comprises or is associated to an inoculant cargo.

In a preferred embodiment, the vaccine is for use in the treatment or prevention of cancer, of an autoimmune disease, of a bacterial infection, of a viral infection, of a parasitic infection or of a graft-vs. host disease.

In a further aspect, the invention relates to a method of inducing an immune response against cancer, a bacterial infection, a viral infection, a parasitic infection in a subject comprising administering to said subject a therapeutically effective amount of the vehicle as defined above, wherein the carrier comprises or is associated to a pharmaceutically active cargo, the composition as defined above, wherein the carrier comprises or is associated to a pharmaceutically active cargo, the pharmaceutical composition as defined above, or the vaccine as defined above.

In a final aspect, the invention relates to a method of treatment or prevention of cancer, of an autoimmune disease, of a bacterial infection, of a viral infection, of a parasitic infection or of a graft-vs. host disease, of a local or systemic inflammation, of allergy, or for hyposensitization comprising administering to a subject a therapeutically effective amount of the vehicle as defined above, wherein the carrier comprises or is associated to a pharmaceutically active cargo, of the composition as defined above, wherein the carrier comprises or is associated to a pharmaceutically active cargo, of the pharmaceutical composition as defined above, or of the vaccine as defined above.

In a preferred embodiment, said administration is an oral, corneal, nasal, intravenous, topical, subcutaneous, intradermal, transdermal administration, a vaccination or an administration via hair follicles.

BRIEF DESCRIPTION OF THE DRAWINGS

FIG. 3 (A) shows results from size exclusion and ultracentrifugation methods to remove free antigen from encapsulated antigen. FITC-BSA fluorescence was measured with a plate reader. It also shows FITC-BSA encapsulated liposomes which were utilized in a cell-based assay. Liposomes were incubated for 2 h at 37° C. and MFI values of FITC and Alexa647 were measured by flow cytometry (FIG. 3 (B). FIG. 3 (C) illustrates how quality of liposomes was measured by DLS after different purification methods. Size and zeta potential (ZP) were analyzed. FIG. 3 (D) shows FITC-encapsulated liposomes which were incubated with Langerin+ Hek293 cells for 6 h at 37° C. The nucleus was stained with DAPI and cells were analyzed by microscopy.

In FIG. 5 (A) the initial FITC-BSA concentration that was used to rehydrate the thin lipid film and in FIG. 5 (B) the initial liposome concentration of the rehydrated lipid film were varied to detect optimized encapsulation efficiencies. In FIG. 5 (C) a quality report is provided, including size and zeta potential (ZP), which were analyzed by DLS. The encapsulation efficiency was calculated after ultracentrifugation with a plate reader. Encapsulated FITC-BSA antigen (AG) was calculated per 1 mM liposome.

In FIG. 6 (A) dose-dependent internalization of FITC-BSA encapsulated liposomes is shown. Alexa647 co-formulated liposomal dye was compared to the fluorescein signal of FITC-BSA. In FIG. 6 (B) a kinetic study of FITC-BSA encapsulated liposomes is shown. Alexa647 co-formulated liposomal dye was compared to the fluorescein signal of FITC-BSA.

In FIG. 7 (A) an FPLC chromatogram of His-tag purified PCNA and EBNA protein is shown. In FIG. 7 (B) SDS-PAGE gel of PCNA and EBNA purified proteins as well as a loading control, a flow through control and a washing control are depicted. The protein size was determined with a protein ladder. In FIG. 7 (C) quality reports are provided, including size and zeta potential (ZP), of formulated liposomes which were analyzed by DLS. The encapsulation efficiency was calculated after ultracentrifugation with a plate reader. Encapsulated antigen (AG) was calculated per 1 mM liposome.

FIG. 9 (A) shows that for liposomal binding, 16 μM non-functionalized and functionalized liposomes were incubated with stable expressing Raji cells at 4° C. for 1 h. After washing, cells were directly analyzed by flow cytometry. Liposomal binding was analyzed with the co-formulated Alexa 647 dye. MFI values of one representative experiment is shown and values were compared to background signal by a t-test (**p<0.0001, n=3). In FIG. 9 (B) liposomal binding to Langerin+ and DC-SIGN+ cells was competed with 10 mM EDTA or 50 μg/ml mannan. MFI values of one representative example were plotted (*p<0.001, ****p<0.0001, n=3, t-test, one of two representative experiments).

In FIG. 11 (A) Binding and in FIG. 11 (B) internalization of Langerin targeting liposomes were analyzed after various incubation periods at 4° C. or 37° C. respectively. FIG. 11 (C) shows various concentrations of Langerin targeting liposomes which were incubated with Langerin+ cells for 24 h at 37° C.

In FIG. 14 (A) binding and in FIG. 14 (B) internalization of Langerin targeting liposomes were analyzed after various incubation periods at 4° C. or 37° C., respectively. FIG. 14 (C) shows that various concentrations of Langerin targeting liposomes were incubated with Langerin+ cells for 24 h at 37° C.

FIG. 15 shows liposomal routing into endosomal compartments. In FIG. 15 (A) human Langerin expressing Hek293 cells were incubated with 16 μM targeted liposomes for 2 h at 37° C. After incubation, cells were immunefluorescently stained with endosomal markers, including Rab5, Rab11, EEA1 and Lamp-1. Primary antibodies were then labeled with an Alexa488 conjugated secondary antibody. The cell nucleus was stained with DAPI and cells were analyzed by microscopy. FIG. 15 (B) shows the correlation between colocalization of targeted liposomes and different endsosomal compartments expressed by Pearson R values.

In FIG. 17 (A) the gating strategy is exemplarily shown for untreated, DMSO treated and liposome treated cells. Cells were incubated for 72 h at 37° C. DMSO treated cells were incubated with 50% DMSO for 3 min after the 72 h incubation. Viable and dead cells were distinguished from cell debris in the FSC-A/SSC-A plot. Doublets were discriminated in a FSC-A/FSC-H plot. Single cells were then analyzed in a dot plot showing Annexin-V-FITC staining on the x-axis and 7-AAD on the y-axis to determine early and late apoptotic effects. Untreated cells were used as a negative control and DMSO treated cells represent the positive control. In FIG. 17 (B) the frequent of parent (FoP) of several incubation time points was analyzed for each quadrant and plotted in a grouped column bar. In FIG. 17 (C) A647 MFIs of targeted and naked liposomes incubated with Langerin+ cells were analyzed to detect liposome internalization.

In FIG. 18 (A) the gating strategy is exemplarily shown for untreated, DMSO treated and liposome treated cells. Cells were incubated for 24 h at 37° C. DMSO treated cells were incubated with 50% DMSO for 3 min after the 24 h incubation Viable and dead cells were distinguished from cell debris in the FSC-A/SSC-A plot. Doublets were discriminated in a FSC-A/FSC-H plot. Single cells were then analyzed in a dot plot showing Annexin-V-FITC staining on the x-axis and 7-AAD on the y-axis to determine early and late apoptotic effects. Untreated cells were used as a negative control and DMSO treated cells represent the positive control. In FIG. 18 (B) several concentrations of liposomes up to 1 mM were analyzed. The Frequent of parent (FoP) was determined for each quadrant and plotted in a grouped column bar. In FIG. 18 (C) A647 MFIs of targeted and naked liposomes incubated with Langerin$^+$ cells were analyzed to detect liposome internalization.

In FIG. 19 (A) naked and targeted liposomes were tested for their binding to Raji wt cells, Raji cells expressing the wt human Langerin$^+$, the N288D mutant, the K313I mutant or the N288D/K313I double mutant. 16 μM liposomes were incubated for 1 h at 4° C. Binding was analyzed by the MFI of the A647 co-formulated dye. Data was normalized to wt Langerin$^+$ cells (*p<0.001, p<0.0001, n=3, t-test, one of two representative experiments). FIG. 19 (B) Raji expressing cells were tested for their extracellular receptor expression with a PE conjugated anti-human Langerin antibody (clone DCGM4). The MFI was normalized to wt Langerin expression (p<0.01, *p<0.001, n=3, t-test, one of two representative experiments). FIG. 19 (C) the relative liposomal binding was plotted by calculating the fold of liposome binding (A) to antibody staining (B) (*p<0.001, ****p<0.0001, n=3, t-test; # Data of wt Raji cells was excluded, one of two representative experiments). FIG. 19 (D) in addition to liposomal binding, liposomal internalization was tracked over 24 h at 37° C. The MFI of the co-formulated A647 dye was directly plotted.

In FIG. 21 (A) the binding and uptake of functionalized GFP at 4° C. and 37° C. was dose-dependently measured by flow cytometry with Raji and Langerin$^+$ Raji cells. In FIG. 21 (B) GFP and liposomes were incubated for various time points with Langerin$^+$ Raji cells. Here, FITC-BSA encapsulated liposomes were utilized to compare the FITC fluorescence with the GFP fluorescence.

In FIG. 22 (A) binding of ligand functionalized liposomes or GFP was competed with mannan. Ligand carriers were incubated with Langerin$^+$ Raji cells for 4 h at 37° C. Mannan was added directly at 37° C. to compete binding and internalization or added after the 4 h incubation step (after washing at 4° C.) to remove extracellular bound carriers. (One representative experiment of three, n=3). In FIG. 22 (B) functionalized liposomes or GFP were incubated with Langerin$^+$ Raji cells for 30 min at 37° C. After washing, mannan or DPBS (with Ca$^{2+}$/Mg$^{2+}$) was added for different time periods. (One representative experiment of four, n=3).

In FIG. 24 (A) epidermal cell suspensions were prepared from human skin samples. Cells were subsequently incubated with liposomes at a concentration of 16 μM for 1 h at 37° C. As a control, 10 mM EDTA was added to the cell media. After liposome incubation, cells were stained with Langerhans cell markers, including CD45, HLA-DR, CD1a and Langerin. In addition, cells were stained with a viability dye eFluor 780 for live/dead (LID) determination. Epidermal cell suspensions were analyzed by flow cytometry and Langerhans cells were evaluated for liposome staining. FIG. 24 (B): based on the gating strategy of (A) the MFI of naked and targeted liposomes was analyzed of different cell subsets, including CD45$^-$; CD1a$^-$, HLR-DR$^-$; and CD1a$^+$, HLR-DR$^+$ expressing cells. FIG. 24 (C): to analyze liposome internalization, EDTA was added after or during the incubation step. EDTA added after incubation removes extracellular bound liposomes and therefore, reflects liposomal internalization. Whereas EDTA added during the incubation step prevents liposomal binding and serves as a control. To prevent receptor internalization, cells were incubated at 4° C. In FIG. 24 (D) epidermal cell suspensions were stained with a FITC conjugated anti-CD1a antibody and incubated with targeted liposomes for 1 h at 37° C. Cells were subsequently analyzed by microscopy.

In FIG. 27 (A) the heparin-derived monosaccharide GlcNS was identified as a favorable scaffold for glycomimetic ligand design. The design of GlcNS analogs lead to the discovery of glycomimetic targeting ligand 15. 15 bears an ethylamino linker in β-orientation of C1 for conjugation to the delivery platform. 20 served as a Man-based reference molecule throughout this study. FIG. 27 (B): Based on the binding mode of GlcNAc (PDB code: 4N32), the small aromatic substituents in C2 were hypothesized to increase the affinity by the formation of cation-π interactions with K299 and K313 or π-π and H-π interactions with F315 and P310. The receptor surface is contrasted according to its lipophilicity (lipophilic: dark grey, hydrophilic: light grey). FIG. 27 (C): $^{19}$F R2-filtered NMR experiments revealed a 42-fold affinity increase for model ligand 16 ($K_i$=0.24±0.03 mM) over Man-based reference molecule 21 ($K_i$=10±1 mM). Additionally, 16 displayed an encouraging specificity against DC-SIGN ($K_{i,DC-SIGN}$=15±3 mM). FIG. 27 (D): The affinity of 16 for Langerin was validated in $^{15}$N HSQC NMR experiments analyzing resonances in the fast ($K_{D,fast}$=0.23±0.07 mM) and the slow ($K_{D,slow}$=0.3±0.1 mM) exchange regime.

FIGS. 28 (A) and (B): $^{15}$N HSQC NMR experiments revealed the chemical shift perturbation (CSP) pattern for 16. Upon titration, fast exchanging resonances such as I250 and E285 as well as slow exchanging resonances including Y251 were observed. FIG. 28 (C): Mapping the CSPs on the X-ray structure of Langerin in complex with GlcNAc (PDB code: 4N32) validated a Ca$^{2+}$-dependent binding mode as indicated by CSPs observed for E285 and K299. Compared to titrations with 21, Y251, I250 and T314 displayed a relative CSP increase, while a decrease was observed for K313. Overall, the majority of residues displaying increased CSPs can be associated with N307 and F315, which could not be assigned. FIG. 28 (D): STD NMR experiments served to further validate the interaction formed between 16 and Langerin. STD NMR spectra were recorded at saturation times $t_{sat}$ of 0.4 s and are magnified 8-fold. Epitopes determined from build-up curves suggest strong interactions formed by the phenyl substituent. By contrast, low relative STD'$_0$ values were observed for the acetylated ethylamino linker, consistent with a solvent exposed orientation. FIG. 28 (E): 16 was docked into the carbohydrate binding site to rationalize the observations from $^{15}$N HSQC and STD NMR experiments. The selected docking pose predicted the formation of π-π interactions between the phenyl ring and F315 as well as the formation of a hydrogen bond between the sulfonamide group and N307. The linker displays high solvent exposure. The receptor surface is contrasted according to its lipophilicity (lipophilic: dark grey, hydrophilic: light grey).

FIG. 29 shows the structure-activity relationship and specificity of selected compounds against DC-SIGN.

FIGS. 32 (A) and (B): $^{15}$N HSQC NMR experiments served to validate the obtained $K_i$ value for 2. Assigned resonances detected in the reference spectrum are highlighted (grey). FIG. 32 (C): Assigned resonances displaying fast chemical exchange and CSPs larger than 0.06 ppm were selected for the determination of $K_D$ values. The obtained $K_D$ value is given in FIG. 29.

FIG. 33 shows the $K_D$ determination for GlcNS analog 2. FIGS. 33 (A) and (B): $^{15}$N HSQC NMR experiments served to validate the obtained $K_i$ value for 2. Assigned resonances detected in the reference spectrum are highlighted (grey) FIG. 33 (C): Assigned resonances displaying fast chemical exchange and CSPs larger than 0.04 ppm were selected for the determination of $K_D$ values. FIG. 33 (D): Additionally, a set of residues including K299 and T314 displayed slow exchange phenomena. For these residues, integrals $V_f$ and $V_b$ of resonances corresponding to the free and the bound state of the Langerin were utilized to determine $K_D$ values. Obtained $K_D$ values are given in FIG. 29.

FIG. 34 (A) to (C): The mapping of CSP values on the X-ray structure of Langerin (PDB code: 4N32 or 35PF) validated a Ca$^+$-dependent binding mode for 2 and 16 as indicated by CSPs observed for E285 and K2999, 10. Additionally, CSPs were observed for N297, A300 and S302 residues also affected upon recognition of Man or 21. By contrast, Y251 and I250 displayed considerably increased CSP values compared to 21, while a relative decrease was observed for K313. This decrease was accompanied by a relative increase for the proximal T314. Notably, residues that display considerably increased CSP values can predominantly associated with F315 and N307 which were not assigned. This also hold true for W252 and W306 that displayed smaller relative increases. Accordingly, the observed CSP pattern might be induced by interactions formed between 2 or 16 and F315 rather than K313. Similar to Man and 21, CSPs were also observed in remote regions of the C-type lectin-like domain fold, particularly for K257 and G259 in the short loop region. This might indicate a modulation of the previously reported allosteric network. FIG. 33 (D): A comparison of titrations with 16 and 21 revealed distinct CSP trajectories for residues associated with the carbohydrate binding site such as E285 or W252 while trajectories of residues located in remote regions of the C-type lectin-like fold such as K257 were conserved.

FIG. 36 (A): STD NMR experiments served to investigate the interaction of 21 with Langerin. STD NMR spectra were recorded at saturation times $t_{sat}$ of 0.4 s and are magnified 8-fold. FIG. 36 (B): The epitope for 21 was determined from build-up curves and suggests a solvent exposed orientation for acetylated ethylamino linker (see also FIG. 37).

FIG. 38 (A): A pharmacophore model was defined to guide the initial placement of 16 in the carbohydrate binding site of Langerin (PDB code: 4N32) and to constrain the orientation of the Glc scaffold during the force field-based refinement of docking poses. All features displayed require an oxygen atom within the indicated spheres. FIG. 38 (B): Four out of ten generated docking poses resemble the depicted conformation of 16. The selected docking pose predicted the formation of π-π interactions between the phenyl ring and F315 as well as the formation of a hydrogen bond between the sulfonamide group and N307. The acetylated ethylamino linker displays high solvent exposure. Accordingly, this docking pose is consistent with both $^{15}$N HSQC and STD NMR experiments. FIG. 38 (C): The depicted alternative conformation of 16 is representative for three out of ten generated docking poses. The selected docking pose predicts the formation of cation-π interaction between the phenyl ring and K313 as well as the formation of a hydrogen bond between the sulfonamide and E293. The acetylated ethylamino linker displays high solvent exposure. However, this docking pose was less consistent with the $^{15}$N HSQC NMR results, particularly the relative decrease of CSP values for K313. The molecular docking study afforded three additional unique docking poses for 16 that were excluded due unfavorable dihedral angles for the sulfonamide linker. The receptor surface is contrasted according to its lipophilicity (lipophilic: dark grey, hydrophilic: light grey).

FIG. 39 shows the structure activity relationship of a series of targeting ligands, analogs of GlcN in the 2'position and sulfated monosaccharides.

DETAILED DESCRIPTION OF THE EMBODIMENTS

Figure 1:
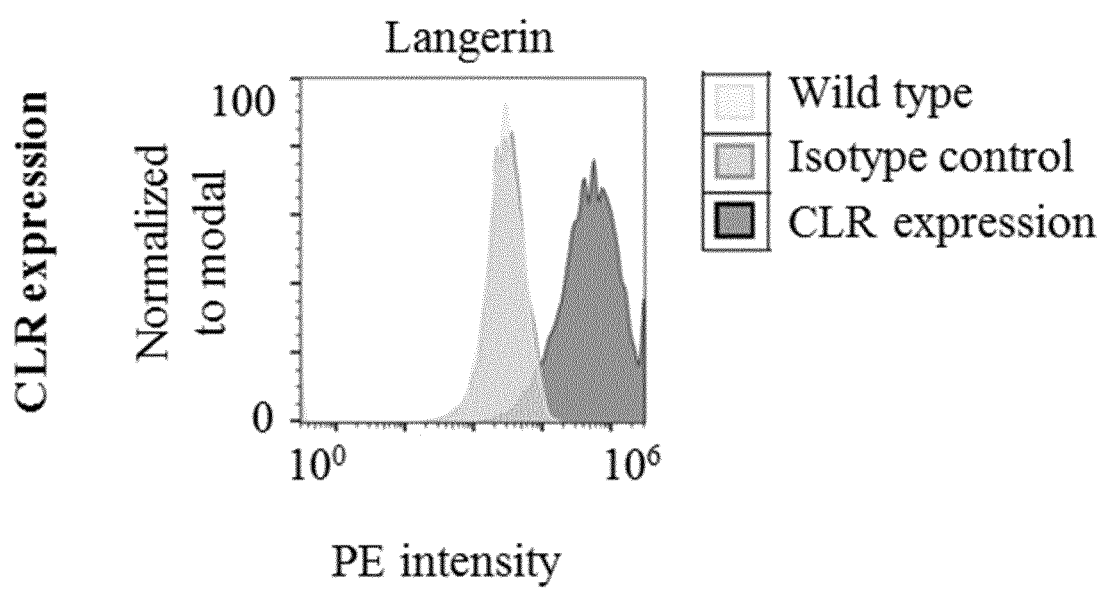
FIG. 1 shows stable human Langerin expression at the plasma membrane of Hek293 cells was detected via CLR specific antibodies. Isotype staining (grey) was applied as a negative control. Fluorescence intensities of Langerin staining (dark gray) was compared to background fluorescence from wild type cells (light grey) and plotted in a histogram plot.

Although the present invention will be described with respect to particular embodiments, this description is not to be construed in a limiting sense. In the following definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention, the term "consisting of" or "essentially consisting of" is considered to be a preferred embodiment of the term "comprising of". If hereinafter a group is defined to comprise at least a certain number of embodiments, this is meant to also encompass a group, which preferably consists of these embodiments only.

Furthermore, the terms "(i)", "(ii)", "(iii)" or "(a)", "(b)", "(c)", "(d)", or "first", "second", "third" etc. and the like in the description or in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. In case the terms relate to steps of a method or use there is no time or time interval coherence between the steps, i.e. the steps may be carried out simultaneously or there may be time intervals of seconds, minutes, hours, days, weeks etc. between such steps, unless otherwise indicated.

It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

As has been set out above, the present invention concerns in one aspect the use of a vehicle for specific molecular targeting of Langerin⁺ cells, wherein the vehicle is capable of specifically binding to a Langerin⁺ cell, said vehicle comprising (a) at least one carrier and (b) at least one conjugate of the general formula (I)

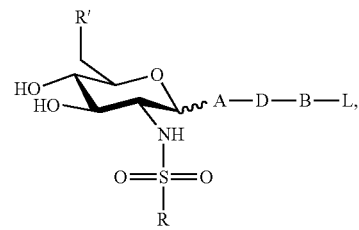

(I)

wherein
(i) R is independently selected from the group consisting of
substituted or non-substituted alkyl, alkenyl, alkynyl, cycloalkyl, $C_1$-$C_8$ alkyl cycloalkyl, aryl, $C_1$-$C_8$ alkyl aryl, heteroaryl, $C_1$-$C_8$ alkyl heteroaryl, biaryl, and $C_1$-$C_8$ alkyl biaryl;
wherein the substituents are independently selected from the group consisting of —N($R^a$)($R^b$), —$OR^a$, —$SR^a$, —C(O)$R^a$, —C(O)O$R^a$, —C(O)N($R^a$)($R^b$), —N($R^a$)C(O)$R^b$, —N($R^a$)S(O)$_2R^b$, —OS(O)$_2R^a$, halogen, —NO$_2$, —CN, —NC, —N$_3$, —NCO, —OCN, —NCS, —SCN, substituted or non-substituted alkyl, alkenyl, alkynyl, aryl and heteroaryl;
wherein $R^a$ and $R^b$ are independently selected from the group consisting of hydrogen, substituted or non-substituted $C_{1-8}$ alkyl, $C_{2-8}$ alkenyl, $C_{2-8}$ alkynyl, $C_{3-6}$ cycloalkyl, aryl-$C_{1-5}$ alkyl, heteroaryl-$C_{1-5}$ alkyl, aryl, heteroaryl;
(ii) R' is independently selected from the group consisting of
—$OR^a$, and —NHS(O)$_2R^a$,
wherein $R^a$ is defined as above; and wherein
(iii) A-D-B-L is a linker group binding the glucose derivative of formula (I) covalently to the carrier or to a part of the carrier,
for a targeted cargo delivery into a Langerin⁺ cell.

The use of a vehicle for specific molecular targeting of Langerin⁺ cells as described herein for a targeted cargo delivery into a Langerin⁺ cell may be either an in vivo use, e.g. in a therapeutic or diagnostic context, or an in vitro or ex vivo use.

The term "conjugate" as used herein relates to the combination of a glucose derivative as indicated in formula (I) which operates as a ligand for Langerin and a linker group of the form A-D-B-L wherein the elements A, D and B relate to or comprise a spacer functionality, as will be detailed further below, and wherein element L relates to a linker element, as will also be explained in more detail herein below.

Accordingly, a "conjugate" of the present invention is a part of a "vehicle" comprising the glucose derivative of formula (I)-ligand, the A-B-D-L linker group and a carrier, wherein said carrier is capable of carrying or transporting a cargo.

The term "ligand" as used herein refers to a molecule, peptide or protein that binds to a receptor protein, which alters the chemical conformation by affecting its three-dimensional shape orientation. The binding occurs by intermolecular forces, such as ionic bonds, hydrogen bonds and Van der Waals forces. The ligand as comprised in the vehicle of the invention is a ligand for Langerin also called "glucose derivative", wherein "Langerin" is a homotrimeric type II transmembrane receptor and a subtype of C-type lectin receptors located on the surfaces of Langerhans cells, which may also be called "CD207". The sequence of Langerin as used herein is represented by the wildtype version with the amino acid sequence of SEQ ID NO: 1, or being encoded by the nucleic acid having the nucleotide sequence of SEQ ID NO: 2. The present invention further envisages homologous variants thereof, e.g. amino acid sequence or nucleotide sequence variants having 90%, 91%, 92%, 93%, 94%, 95%, 96%, 97%, 98% or 99% or 99.5% homology with the sequence of SEQ ID NO: 1 or 2. Further envisaged are natural occurring SNP forms of of Langerin, for example, the SNP form V278A (rs741326, NCBI SNP database) with the amino acid sequence represented by SEQ ID NO: 3, encoded by the nucleic acid having the nucleotide sequence of SEQ ID NO: 4. Langerin containing the V278A SNP has a prevalence of 49.9% and has shown similar sugar binding as A278 (Ward et al., 2006. J Biol Chem, 281: 15450-6). Further information can be derived from the NCBI SNP database or a suitable literature source such as Feinberg et al., 2013, J. Biol Chem. 27, 288, 52, 36762-71. The present invention further envisages homologous variants thereof, e.g. amino acid sequence or nucleotide sequence variants having 90%, 91%, 92%, 93%, 94%, 95%, 96%, 97%, 98% or 99% or 99.5% homology with the sequence of SEQ ID NO: 3 or 4. Also envisaged are additional SNP variants such as N288D (rs13383830, NCBI SNP database) with the amino acid sequence represented by SEQ ID NO: 5, encoded by the nucleic acid having the nucleotide sequence of SEQ ID NO: 6; K313I (rs57302492, NCBI SNP database) with the amino acid sequence represented by SEQ ID NO: 7, encoded by the nucleic acid having the nucleotide sequence of SEQ ID NO: 8; and N288D/K313I with the amino acid sequence represented by SEQ ID NO: 9, encoded by the nucleic acid having the nucleotide sequence of SEQ ID NO: 10. The present invention further envisages homologous variants thereof, e.g. amino acid sequence or nucleotide sequence variants having 90%, 91%, 92%, 93%, 94%, 95%, 96%, 97%, 98% or 99% or 99.5% homology with the sequence of any one of SEQ ID NOs: 5 to 10. Further encompassed are codon optimized variants of Langerin. These variants may be adapted to the expression context envisaged, e.g. the codon optimization may be provided for bacterial strains, e.g. E. coli strains, for mammalian cells etc., as would be known to the skilled person. In a specific embodiment, a codon optimized sequence for Langerin containing a StreptagII and TEV site at the C-terminus, which can be used for expression in E. coli, is represented by the nucleotide sequence of SEQ ID NO: 29.

In specific embodiments, the "Langerin" may also be a molecule derived from non-human mammals, e.g. mice, monkeys, cows, pigs etc. In a particular embodiment, the present invention thus envisages the use of a mouse Langerin variant with the amino acid sequence represented by SEQ ID NO: 13, encoded by the nucleic acid having the nucleotide sequence of SEQ ID NO: 14. The present invention further envisages homologous variants thereof, e.g. amino acid sequence or nucleotide sequence variants having 90%, 91%, 92%, 93%, 94%, 95%, 96%, 97%, 98% or 99% or 99.5% homology with the sequence of SEQ ID NO: 13 or 14.

Thus, if reference is made to "Langerin+", the presence of a Langerin receptor as defined herein above is contemplated. The term "Langerin+ cell" as used herein refers to a cell, preferably a dendritic cell (DC), e.g. a Langerhans cell, which displays at its surface the specific CLR Langerin. In certain embodiments, the cell may also be a cell of a different background.

Glycan-Langerin interactions as defined above have been found to be predominantly confined to a single monosaccharide and dominated by the coordination of the $Ca^{2+}$ ion by two vicinal, equatorial hydroxyl groups. These hydroxyl groups are part of an extended hydrogen bond network formed between the monosaccharide, the $Ca^{2+}$ ion and receptor residues including E285, E293, N297 and N307. Moreover, the equatorial acetamido group of N-acetyl glucosamine (GlcNAc) have been found to interact with the K299 via a structural $H_2O$ molecule and a weak hydrophobic contact of the methyl group with P310. Moreover, detailed analysis of glucosamine-2-sulfate (GlcNS) analogs via SAR have been conducted, which indicates that the introduction of the phenyl ring results in the aromatic interactions with K299, P310 or F315 resulting in increased affinities. Further design approaches showed favorable interactions, as is in detail described in the Examples section, herein. The introduction of a linker in C1 of the Glc scaffold via the formation of a beta-glucoside achieved potent targeting ligands. Due to these results, the vehicle may comprise a GlcNS-Structure, containing a linker structure in position C1, several substituent of the sulfate at position C2, equatorial hydroxyl groups in position C3 and C4 as well as a hydroxyl group or, a sulfonic acid or an uronic acid in position C6 of the GlcNS. Also envisaged are further functional groups.

The term "specific molecular targeting" as used herein comprises an interaction between the ligand as defined herein above, being part of a conjugate as defined herein, and the Langerin receptor present on a Langerin+ cell as defined herein. In a preferred embodiment the specific molecular targeting comprises an interaction between the ligand as defined herein above, being part of a vehicle as defined herein, and the Langerin receptor present on a Langerin+ cell as defined herein. In a further embodiment, the specific molecular targeting comprises interaction between said conjugate or vehicle and a receptor present on a Langerin+ cell.

The term "vehicle for specific molecular targeting of Langerin+ cells" as used herein thus relates to a vehicle, which is capable of a specific molecular targeting of Langerin+ cells.

This specific targeting as mentioned above is a specific binding of the vehicle as defined herein to a dendritic cell, in particular to a dendritic cell expressing Langerin. The specific binding takes place between the vehicle, namely the ligand part of the vehicle and the Langerin receptor on the surface of the cell. In specific embodiments, this binding shows a specificity which is at least 2-fold higher than a control in a cell-based assay comprising the introduction of liposomes under identical conditions into Raji B cells presenting recombinant Langerin, Raji B cells presenting recombinant DC-SIGN (control 1) and Raji wildtype B cells presenting no C-type lectin receptor (WT, control 2). In further, more preferred embodiments, the specificity is 4-, 5-, 6-, 7-, 8-, 9-, 10-, 11- or 12-fold higher than a control in a cell-based assay comprising the introduction of liposomes under identical conditions into Raji B cells presenting recombinant Langerin, Raji B cells presenting recombinant DC-SIGN (control 1) and Raji wildtype B cells presenting no C-type lectin receptor (WT, control 2). In particularly preferred embodiments, the specificity is 16-fold higher than a control in a cell-based assay comprising the introduction of liposomes under identical conditions into Raji B cells presenting recombinant Langerin, Raji B cells presenting recombinant DC-SIGN (control 1) and Raji wildtype B cells presenting no C-type lectin receptor (WT, control 2). The term "DC-SIGN" relates to a further dendritic cell-expressed receptor, which has the amino acid sequence of SEQ ID NO: 11 or is encoded by the nucleic acid having the nucleotide sequence of SEQ ID NO: 12. The present invention further envisages homologous variants thereof, e.g. amino acid sequence or nucleotide sequence variants having 90%, 91%, 92%, 93%, 94%, 95%, 96%, 97%, 98% or 99% or 99.5% homology with the sequence of SEQ ID NO: 11 or 12. Further encompassed are codon optimized variants of DC-SIGN. These variants may be adapted to the expression context envisaged, e.g. the codon optimization may be provided for bacterial strains, e.g. *E. coli* strains, for for mammalian cells etc., as would be known to the skilled person. In a specific embodiment, a codon optimized sequence for DC-SIGN containing a StreptagII and TEV site at the C-terminus, which can be used for expression in *E. coli*, is represented by the nucleotide sequence of SEQ ID NO: 52. In specific embodiments, the "DC-SIGN" may also be a molecule derived from non-human mammals, e.g. mice, monkeys, cows, pigs etc.

The assay to be performed in order to determine the specificity as mentioned above preferably comprises the steps as mentioned in Example 10.

Within the context of the present invention, a further Langerin related protein may be employed, e.g. for an assay format as described for DC-SIGN (see above). A preferred example of such a Langerin related protein is Dectin. It is particularly preferred that the Dection is mouse Dectin variant, or mDectin. The term "mDectin" relates to a C-type lectin domain family 7 member A, which has the amino acid sequence of SEQ ID NO: 15 or is encoded by the nucleic acid having the nucleotide sequence of SEQ ID NO: 16. The present invention further envisages homologous variants thereof, e.g. amino acid sequence or nucleotide sequence variants having 90%, 91%, 92%, 93%, 94%, 95%, 96%, 97%, 98% or 99% or 99.5% homology with the sequence of SEQ ID NO: 15 or 16. In specific embodiments, the "Dectin" may also be a molecule derived from humans, or other non-human mammals, e.g. monkeys, cows, pigs etc.

The term "targeted cargo delivery" as used herein relates to the transportation of a cargo, e.g. as defined herein below, to a targeted cell, e.g. a Langerin$^+$ cell as defined herein, preferably a cell displaying Langerin at its surface. The transportation may include the introduction of the cargo into the cell, or may include an unloading of the cargo in the vicinity, e.g. at the surface of the cell. The cargo delivery may in any case involve an interaction of the ligand as defined herein with its cognate receptor, i.e. the Langerin as mentioned herein. The cargo delivery may depend and/or be adjusted in accordance with the carrier used, in particular the carrier as defined herein below. Certain carriers may require an introduction of the cargo into the cell, whereas other carrier may be used to unload the cargo at the surface of the cell or in the vicinity of the cell. The term "delivery" may include an unloading process of the cargo, but may also include a linkage of the carrier and cargo even after the ligand has bound to its target, i.e. the Langerin. In certain embodiments, delivery may include release of the carrier in the early endosomal compartment or the late endosomal compartment or the lysosome for further processing of the cargo. This release may, for example, be triggered by acidification of the endosomal compartment, by enrichment or depletion of co-factors of the receptor/ligand interaction such as Ca$^+$, enzymatic digestion of the receptor, the targeting-ligand or the carrier. Further envisaged is a photoinduced drug release, which may, for example, be from thermosensitive AuNPs-liposome using an AuNPs-switch.

In an alternative embodiment, the delivery may be based on thermos-sensitive liposomes or thermo-responsive magnetic liposomes. These liposomes may, for example, be designed to combine features of magnetic targeting and thermo-responsive control release for hyperthermia-triggered local drug delivery. Further details may, for example, be derived from Dai et al., 2017, J Microencapsul. 34(4): 408-415 or from Kneidl et al., 2014, Int J Nanomedicine, 9: 4387-4398.

As used herein, the term "alkyl" refers to a straight-chained or branched hydrocarbon group. The hydrocarbon having the indicated number of carbon atoms (e.g., "C1-C8" alkyl refer to an alkyl group having from 1 to 8 carbon atoms). When the number of carbon atoms is not indicated, the alkyl group has from 1 to 100 carbon atoms. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 100 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 100 carbon atoms and at least one carbon-carbon triple bond. Alkynyl groups may be optionally substituted with one or more substituents.

A "substituted" group refers to any substitution of any pattern of that group. This group may be optionally substituted with one or more substituents, wherein the substituents may be of either the same type or different types. Substituents may be selected from the group comprising —N(R$^a$)(R$^b$), —OR$^a$, —SR$^a$, —C(O)R$^a$, —C(O)OR$^a$, —C(O)N(R$^a$)(R$^b$), —N(R$^a$)C(O)R$^b$, —N(R$^a$)S(O)$_2$R$^b$, —OS(O)$_2$R$^a$, halogen, —NO$_2$, —CN, —NC, —N$_3$, —NCO, —OCN, —NCS, —SCN, substituted or non-substituted alkyl, alkenyl, alkynyl, aryl and heteroaryl. Whereas the term "non-substituted" group refers to group, which is a hydrocarbon group.

As used herein, the term "halogen", "hal" or "halo" means F, Cl, Br or I.

The term "arylalkyl" as used herein refers to a saturated or unsaturated hydrocarbon chain that may be a straight chain or branched chain, containing 1 to 100 carbon atoms and may contain carbon-carbon triple bond and/or sp2 hybridized carbons of double bonds. The aryl and/or the alkyl groups may be optionally substituted with one or more substituents. The sp2 or sp carbons of an alkenyl group and an alkynyl group, respectively, may optionally be the point of attachment of the alkenyl or alkynyl groups.

The term "cycloalkyl" refers to a hydrocarbon 3-8 membered monocyclic or 7-14 membered bicyclic ring system or a larger ring system of more than 15 ring members having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "biaryl" refers to an aromatic ring system containing a substructure that is an assembly of two aromatic rings or aryl groups, if joined by a single bond. The aryl groups may be optionally substituted with one or more substituents. Examples of biaryl groups include biphenyl, binaphthyl and the like.

The term "heteroaryl" refers to a monocyclic, bicyclic or tricyclic aromatic ring system containing at least one heteroatom having carbon atoms (also referred to as ring members) and heteroatom ring members independently selected from N, O, P or S, and derived by removal of one carbon atom from a ring atom of a parent ring system. Examples of heteroaryl groups include furan, thiophene, pyrrole, thiazole, oxazole, pyridine, pyrazine, and the like.

The terms "alkyl cycloalkyl", "alkyl aryl", "alkyl biaryl", and "alkyl heteroaryl" as used herein refer to a an saturated or unsaturated hydrocarbon chain that may be a straight chain or branched chain, containing 1 to 8 carbon atoms and may contain carbon-carbon triple bond and/or sp2 hybridized carbons of double bonds bound to cycloalkyl, aryl, biaryl or heteroaryl. The different cyclic structures are defined as above. The cycloalkyl, aryl, biaryl or heteroaryl and/or the alkyl groups may be optionally substituted with one or more substituents. The sp2 or sp carbons of an alkenyl group and an alkynyl group, respectively, may optionally be the point of attachment of the alkenyl or alkynyl groups.

In preferred embodiments, the residue R is independently selected from the group consisting of substituted or non-substituted alkyl, alkenyl, alkynyl, cycloalkyl, $C_1$-$C_8$ alkyl cycloalkyl, aryl, $C_1$-$C_8$ alkyl aryl, heteroaryl, $C_1$-$C_8$ alkyl heteroaryl, biaryl and $C_1$-$C_8$ alkyl biaryl. In another embodiment, the residue R is independently selected from the group consisting of substituted or non-substituted alkyl, cycloalkyl, $C_1$-$C_8$ alkyl cycloalkyl, aryl, $C_1$-$C_8$ alkyl aryl, heteroaryl, $C_1$-$C_8$ alkyl heteroaryl, biaryl and $C_1$-$C_8$ alkyl biaryl. In a more preferred embodiment, the residue R is independently selected from the group consisting of substituted or non-substituted $C_1$-$C_6$ alkyl, $C_3$-$C_6$ cycloalkyl, $C_1$-$C_3$ alkyl $C_3$-$C_6$ cycloalkyl, $C_6$-$C_{14}$ aryl, $C_1$-$C_3$ alkyl $C_6$-$C_{14}$ aryl, heteroaryl, $C_1$-$C_3$ alkyl heteroaryl, biaryl and $C_1$-$C_3$ alkyl biaryl. In a more preferred embodiment, the residue R is independently selected from the group consisting of substituted or non-substituted cyclohexyl, phenyl, benzyl, biphenyl, pyridyl, or oxazolyl. In another preferred embodiment, the residue R is a substituted or non-substituted phenyl.

The substituents of the residue R may be any suitable substituent, which is not hindering the ligand in binding to Langerin. Moreover, the substituents can be one or more substituents of either the same type or different types. The substituents of R may have any substitution pattern. In one embodiment, the substituents of the residue R are independently selected from the group consisting of —N($R^a$)($R^b$), —O$R^a$, —S$R^a$, —C(O)$R^a$, —C(O)O$R^a$, —C(O)N($R^a$)($R^b$), —N($R^a$)C(O)$R^b$, —N($R^a$)S(O)$_2$$R^b$, —OS(O)$_2$$R^a$, halogen, —NO$_2$, —CN, —NC, —N$_3$, —NCO, —OCN, —NCS, —SCN, substituted or non-substituted alkyl, alkenyl, alkynyl, aryl and heteroaryl. $R^a$ and $R^b$ may be independently selected from the group consisting of hydrogen, substituted or non-substituted $C_{1-8}$ alkyl, $C_{2-8}$ alkenyl, $C_{2-8}$ alkynyl, $C_{3-6}$ cycloalkyl, aryl-$C_{1-5}$ alkyl, heteroaryl-$C_{1-5}$ alkyl, aryl, heteroaryl. In a preferred embodiment, $R^a$ and $R^b$ may be independently selected from the group consisting of hydrogen, methyl and ethyl.

More preferably, the substituents of the residue R are independently selected from the group consisting of NH$_2$, —OH, —OCH$_3$, —C(O)CH$_3$, —NHC(O)CH$_3$, —F, —Cl, —Br, —NO$_2$, —CN, $C_1$-$C_4$ alkyl and phenyl, biphenyl, and naphthyl. In a preferred embodiment, the residue R is a substituted phenyl residue. This phenyl residue may be substituted with 5 substituents. More preferably, the phenyl residue may be mono-, di- or trisubstituted. In a most preferred embodiment, the residue R is a monosubstituted phenyl residue, wherein the substituents are selected from the group consisting of —NH$_2$, —OH, —OCH$_3$, —C(O)CH$_3$, C(O)NH$_2$, —C(O)NHCH$_3$, —CH$_2$OH —NHC(O)CH$_3$, —F, —Cl, —Br, —NO$_2$, —CN, $C_1$-$C_4$ alkyl, naphthyl and phenyl. In a further preferred embodiment, the substituents are in para position to the ligand. In a further preferred embodiment, the substituents in para position and the substituents of the phenyl are independently selected from the group consisting of —NHC(O)CH$_3$, —CN, —CH$_3$, —F, —C(O)NH$_2$, —NH$_2$, —C(O)NHCH$_3$, —CH$_2$OH and phenyl. In a further preferred embodiment, the substituents are in meta position to the ligand.

In another embodiment, R' may be independently selected from the group consisting of —O$R^a$, and —NHS(O)$_2$$R^a$, wherein $R^a$ is defined as above. In a preferred embodiment, R' may be selected from the group consisting of —OH, —OCH$_3$, —OCH$_2$CH$_3$, or —NHS(O)$_2$$R^a$, wherein $R^a$ is defined as above. In a more preferred embodiment, —OH or —NHS(O)$_2$$R^a$, wherein $R^a$ is defined as above. In a more preferred embodiment, R' is —OH, —NHS(O)$_2$CH$_3$ or N-tosyl. In the most preferred embodiment, R' is —OH.

In yet another preferred embodiment, the conjugate as mentioned above is a conjugate of the following formula (I-1) or (I-2):

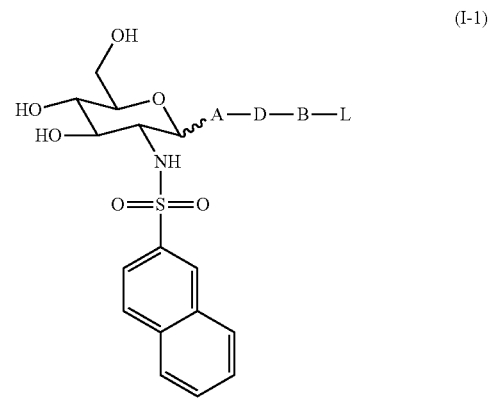

(I-1)

-continued
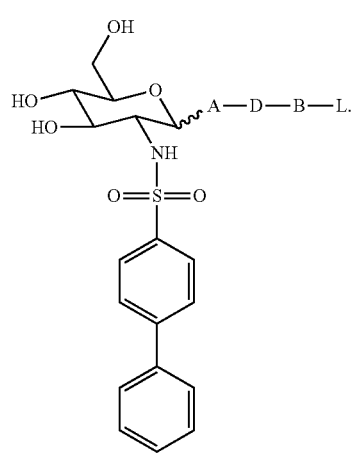
(I-2)
In a still further preferred embodiment, the conjugate as mentioned above is a conjugate of any one of the following formulas (I-3) to (I-15):
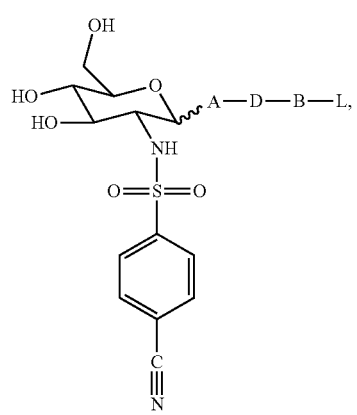
(I-3)
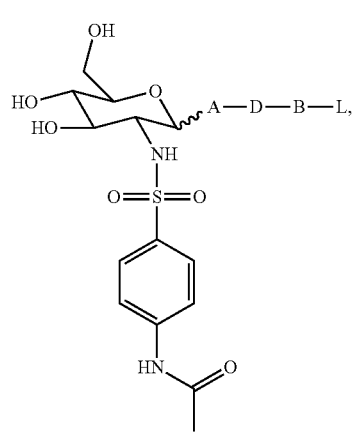
(I-4)
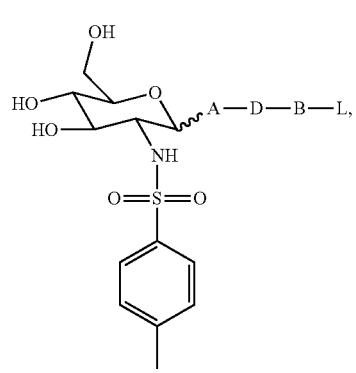
(I-5)
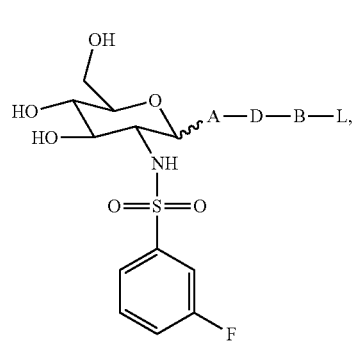
(I-6)
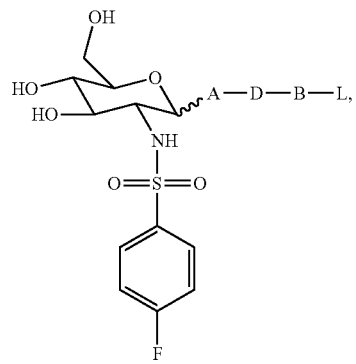
(I-7)
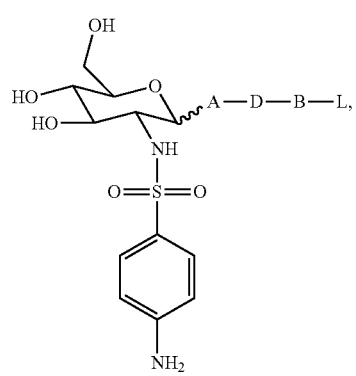
(I-8)

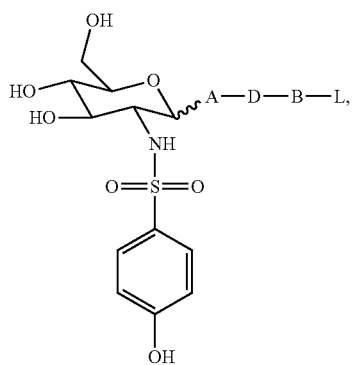 (I-9)

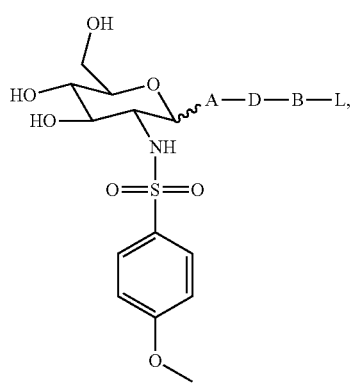 (I-10)

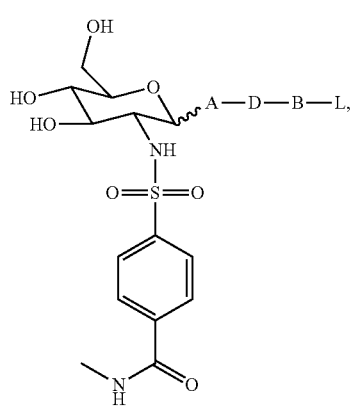 (I-11)

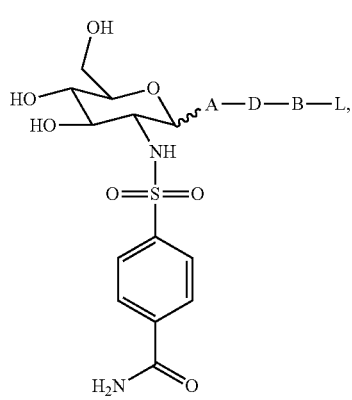 (I-12)

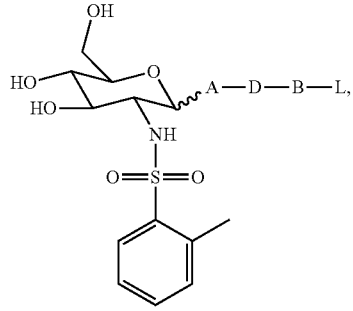 (I-13)

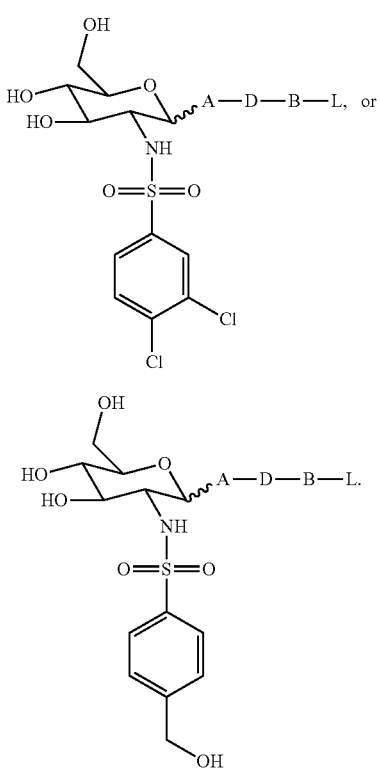

(I-14)

(I-15)

The wordings "A-D-B-L linker group", "A-D-B-L", or "linker group" refer to a group consisting of a spacer A-D-B and a linker L. The group connects the glucose derivative-ligand with the carrier. In a typical embodiment, on the one end the linker L of the general formula (I), as described above, is bound via a spacer A-D-B to the Langerin ligand structure as defined above, which comprises the glucose derivative of formula (I). The spacer A-D-B is covalently bound to position C1 of the mentioned glucose derivative. Also envisaged is that the spacer A-D-B is covalently bound to position C6 of the mentioned glucose derivative.

In certain embodiments, the A-D-B-L linker group between the ligand and the carrier is a molecular chain. In a preferred embodiment, said main chain may have a total number of carbon atoms, nitrogen atoms and oxygen atoms contained in the main chain of at least 4, preferably of between 4 atoms to 600 atom, more preferably of between 15 atoms to 400 atoms, and still more preferably of between 25 atoms to 200 atoms, e.g. 25, 30, 40, 50, 60, 70, 80, 90, 100, 110, 120, 130, 140, 150, 160, 170, 180, 190 and 200 atoms. In another embodiment, the length of main chain of the linker may be about 0.4 nm to about 400 nm, and more preferably about between 0.6 nm and 100 nm, e.g. 0.6, 0.8, 1, 2, 4, 8, 10, 20, 30, 40, 50, 60, 70, 80, 90 and 100 nm. The size or the length of the linker may be measured via analytical centrifugation measurements or SAXS measurements, e.g. as described in Fuji et al., ACS Symposium Series, 2017, 1271, "Control of Amphiphile Self-Assembling at the Molecular Level: Supra-Molecular Assemblies with Tuned Physicochemical Properties for Delivery Applications", Chapter 5, pages 115-129. An average chain length may be measured via suitable measurement techniques, e.g. as discussed in Needham and Kim, 2000, Colloids and Surfaces B: Biointerfaces, 18, 3-4, 183-195 or in Stepniwieski et al., 2011, Langmuir, 27(12), 7788-7798.

The term "linker L" or "L" as used herein further refer to a compound, which can be used to link the Langerin ligand of the invention as defined herein above and a carrier, either directly, or indirectly, e.g. via the spacer A-D-B. The provided linkage may be conveyed by any suitable chemical connection, preferably via covalent bonds.

In a preferred embodiment, said linker L may comprise one or more of synthetic polymers or natural polymers or one or more single units of those polymers or a combination thereof. The linker of the present invention is preferably biocompatible and/or biodegradable. The linker may, in certain embodiments, be a synthetic water-soluble polymer that dissolves, disperses or swells in water and, thus, modify the physical properties of aqueous systems in the form of gelation, thickening or emulsification/stabilization. In a preferred embodiment, the synthetic polymer may be a saturated or unsaturated hydrocarbon polymer; a polyamine; a polyamide; a polyester; a polyether, such as polyethylene glycol, polypropylene glycol; a block copolymer or a poloxamer. In particularly preferred embodiments, the linker is a polyethylene glycol. In corresponding, specific embodiments, the polyethylene glycol linker may have a length of about 0 to 150, more preferably 1 to 100, still more preferably 3 to 50 of the (—CH2-CH2-O—) repeating units. Further examples of suitable polymers are polyvinyl pyrrolidone, polyvinyl pyrrolidone-vinyl acetate copolymer, polyvinyl alcohol, polystyrene, polyacrylic acid, polyacylamides, N-(2-hydroxypropyl) methacrylamide and polyoxazoline.

In a preferred embodiment, natural polymers, which may be suitable linkers, are selected from a group consisting of carbohydrates, modified carbohydrates, peptides, modified peptides, lipids and modified lipids.

The term "carbohydrate" as used herein relates to any natural or synthetic carbohydrate. The term may further comprise trioses, tetroses, pentoses, hexoses and heptoses. Carbohydrates may be aldoses or ketoses. Carbohydrates may be in D- or in L-form. Carbohydrates may comprise one or more monosaccharides or disaccharides. The carbohydrate may form an oligosaccharide including 3 to 9 monosaccharides. The carbohydrate may also be a polysaccharide, which contains more than 9 monosaccharides. The term "monosaccharide" comprises, but is not limited to threose, ribulose, glucose, fructose, galactose, xylose, ribose, arabinose and mannose. Monosaccharides contained in disaccharides, oligosaccharides and polysaccharides may be linked to each other in any configuration. The term "disaccharide" comprises, but is not limited to sucrose, lactose, and maltose. The term "oligosaccharide" comprises, but is not limited to maltodextrins and cellodextrins. The term "polysaccharide" comprises, but is not limited to starch, cellulose, and chitin. Natural carbohydrates comprise natural monosaccharides. Synthetic carbohydrates may comprise D- and L-, modified, synthetic, unusual monosaccharides and monosaccharides derivatives. A "monosaccharide derivative" also called "modified carbohydrates" includes monosaccharides having substitutions or modifications by covalent attachment of a parent monosaccharides, such as, e.g., by alkylation, acetylation, phosphorylation, and the like. Further included within the definition of "monosaccharides derivative" are, for example, one or more analogs of a monosaccharide with substituted linkages, as well as other modifications known in the art. Preferred carbohydrates are mannose, glucose, fucose or xylose. In certain embodiments also inositols may be used.

The term "lipid" as used herein relates to any natural or synthetic lipid. It may accordingly comprise fatty acids and their derivatives including tri-, di-, monoglycerides, and phospholipids, glycerolipids, glycerophospholipids, sphingolipids, saccharolipids, polyketides, sterol lipids and prenol lipids, including DSPE (1,2-distearoyl-sn-glycero-3-phosphoethanolamine), DPPC (1,2-Dipalmitoyl-sn-glyceroyl-3-phosphocholine), DPPE (1,2-Dipalmitoyl-sn-glyceroyl-3-phosphoethanolamine), DMPC (1,2-Dimyristoyl-sn-glyceroyl-3-phosphocholine), DSPC (1,2-Distearoyl-sn-glyceroyl-3-phosphocholine), membrane lipids, and phosphatidylcholine as well as modified versions thereof. Preferred lipids are DPPC (1,2-Dipalmitoyl-sn-glyceroyl-3-phosphocholine), DPPE (1,2-Dipalmitoyl-sn-glyceroyl-3-phosphoethanolamine), DMPC (1,2-Dimyristoyl-sn-glyceroyl-3-phosphocholine), DSPC (1,2-Distearoyl-sn-glyceroyl-3-phosphocholine) or DSPE (1,2-distearoyl-sn-glycero-3-phosphoethanolamine). The term "modified lipids" is a lipid having one or more modifications. A modification of such a lipid may comprise an acetylation, glycosylation, alkylation, combination with a chelator or a further functionalization such as provision of pH sensitivity, addition of carbon acids, biotin, amines, thioethanol, azide groups etc. The lipids may further be combined with flexibility, elasticity and/or permeability enhancers. Further details are known to the skilled person or can be derived from suitable literature sources such as Benson, 2017, Methods Mol. Biol., 1522: 107-117, Sala et al., 2018, Int J. Pharm. 535 Molecular Cell Biology, 201(1-2), 1-17 or Harayama and Riezman, Nature Reviews, 2018 8, 19, 281-296.

The term "peptide" as used herein relates to any type of amino acid sequence comprising more than 2 amino acids or functional derivatives thereof. Furthermore, the peptide may be combined with further chemical moieties or functionalities, or may be a synthetic peptide. Natural peptides typically comprise natural amino acids. Synthetic peptides may comprise D- and L-, modified, synthetic, or not naturally occurring amino acids and amino acids derivatives. Natural peptides comprise natural amino acids. Synthetic peptides may comprise D- and L-, modified, synthetic, unusual amino acids and amino acids derivatives. An "amino acid derivative" includes an amino acid having substitutions or modifications by covalent attachment of a parent amino acid, such as, e.g., by alkylation, glycosylation, acetylation, phosphorylation, and the like. Further included within the definition of "amino acid derivative" is, for example, one or more analogs of an amino acid with substituted linkages, as well as other modifications known in the art. A "natural amino acid" refers to arginine, glutamine, phenylalanine, tyrosine, tryptophan, lysine, glycine, alanine, histidine, serine, proline, glutamic acid, aspartic acid, threonine, cysteine, methionine, leucine, asparagine, isoleucine, and valine, unless otherwise indicated by context. A preferred peptide according to the present invention may be oligo-L-glutamic acid or oligo-L-lysine. Other preferred peptides may be amphipathic peptides connecting to lipid-based carriers by insertion, e.g. of the sequence VLTTGLPALISWIKRKRQQ (SEQ ID NO: 81), with a short N-terminal di-L-glycine linker. Peptides may be distinguished from polypeptides. A "polypeptide" may, for example, have a length of more than 20 to 50 amino acids. In certain embodiments, the linker may also be a polypeptide linker. The term "protein" as used herein relates to an arrangement of one or more polypeptides. Accordingly, a protein may comprise or consist of one polypeptide and thus by synonymous to polypeptide. In other embodiments, a protein may comprise 2 or more polypeptides which may be organized in units or subunits of a higher order structure in the form of a protein.

Further examples of natural polymers, which are water soluble and may be suitably used as linkers in the context of the present invention are pectin, chitosan derivatives, xanthan gums, chitosan derivatives, dextran, cellulose ethers, hyaluronic acid, casein, carrageenan, starch and starch derivatives and the like.

In certain embodiments, the linker may merely be a covalent bond. In such a scenario, a carrier structure may be directly bound to the spacer A-D-B.

In a preferred embodiment, said linker L is a linker of the following general formula (L-1)

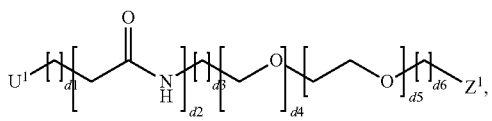

(L-1)

wherein
U$^1$ is a group connected via B with the spacer D, wherein U$^1$ is selected from the group consisting of, —CH$_2$—, —CH═CH—, or —C≡C—; U$^1$ may also be a single bond; preferably U1 is —CH2- or a covalent bond Z$^1$ is a moiety binding the linker to the carrier selected from the group consisting of —O—, —S—, —N(R$^d$)—, —C(R$^d$)(R$^e$)—, —R$^d$C═CR$^e$—, —C(O)—, —C(O)O—, —OC(O)—, —C(O)S—, —C(O)N(R$^d$)—, —N(R$^d$)C(O)—, —N(R$^d$)C(O)N(R$^e$)—, —N(R$^d$)C(S)N(R$^e$)—, —N(R$^d$)C(O)O—, —OC(O)N(R$^d$)—, -cyclohexene-, -triazoles-, —NHS(O)$_2$—, —S(O)$_2$—, —OP(O)(H)O—, or —OP(O)(OH)O; Z$^1$ may also be a single bond; preferably the Z$^1$ is a covalent bond, an amide or a carbonyl group;

wherein R$^d$ and R$^e$ are independently selected from the group consisting of hydrogen, substituted or non-substituted C$_{1-32}$ alkyl, C$_{2-32}$ alkenyl, C$_{3-8}$ cycloalkyl, aryl, C$_1$-C$_5$ alkyl aryl, heteroaryl, C$_1$-C$_5$ alkyl heteroaryl; and d1 to d5 is each an integer from 0 to 100, preferably an integer from 0 to 50, such as 0, 1, 2, 3, 4, 6, 8, 10, 12, 15, 20, 25, 30, 35, 40, 45, or 50; d6 an integer from 1 to 100, preferably an integer from 1 to 50, such as 1, 2, 3, 4, 6, 8, 10, 12, 15, 20, 25, 30, 35, 40, 45 or 50.

As described in more detail below the carrier or ligand can be prepared using a section of the linker L unit having a reactive site for binding to the ligand. To synthesize the conjugate, the linker may be provided as a bifunctional ligand or bifunctional unit. The linker L unit may accordingly have a reactive site, which has a nucleophilic group that is reactive with an electrophilic group present on a ligand unit or a carrier unit. Alternatively, the ligand unit or a carrier unit may accordingly have a reactive site, which has a nucleophilic group that is reactive with an electrophilic group present on the linker L unit. The electrophilic group on a ligand unit or a carrier unit provides a convenient site for attachment to a linker unit, or alternatively, the electrophilic group on the linker L unit provides a convenient site for attachment to a ligand unit or a carrier unit. Useful electrophilic groups on a ligand or linker unit include, but are not limited to, aldehyde and ketone carbonyl groups. The heteroatom of a nucleophilic group of a linker unit can react with an electrophilic group on a ligand and form a covalent bond to the ligand. Alternatively, the heteroatom of a nucleophilic group of a ligand unit can react with an electrophilic group on a linker and form a covalent bond to the linker. Useful nucleophilic groups on a linker unit or ligand unit include, but are not limited to, hydrazide, oxime, amino, hydrazine, thiosemicarbazone, hydrazine carboxylate, and acylhydrazide. In certain embodiments, a bifunctional linker may be used, which carries one OH group or which may, for example, be a general nucleophile, and an additional functional group. The second functional group can be any nucleophile carrying an orthogonal protecting group or a functional group compatible with glycosylation reactions and global deprotection methods. The bifunctional element may subsequently be reacted with the anomeric center of the monosaccharide via the OH group. Subsequently the monosaccharide and the second functional group are deprotected. The product may then be conjugated to a corresponding PEGylated lipid.

The term "spacer" as used herein refers to any structure covalently connecting the linker with the glucose derivative-ligand of the invention as defined herein above. In a preferred embodiment, said spacer group A-D-B comprises D as a spacer connected with A and B of the general formula (D-1)

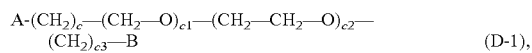

(D-1), wherein
D is connected to the linker L via B, wherein B is selected from the group consisting of —O—, —S—, —C(R$^{c1}$)(R$^{c2}$)—, —S—S—, —N(R$^{c1}$)—, —C(O)—, —C(R$^{c1}$)═N—, —N═N—, —OC(O)—, —C(O)O—, —C(O)N(R$^{c1}$)—, —N(R$^{c1}$)C(O)—, —N(R$^{c1}$)C(O)N(R$^{c2}$)—, —N(R$^{c1}$)C(S)N(R$^{c2}$)—, —N(R$^{c1}$)C(O)O—, —OC(O)N(R$^{c1}$)—, -cyclohexene- and -triazoles-; B may also be a single bond; preferably B is a covalent bond, an amide or a carbonyl group;

wherein R$^{c1}$ and R$^{c2}$ are independently selected from the group consisting of hydrogen, substituted or non-substituted alkyl, alkenyl, cycloalkyl, C$_1$-C$_8$ alkyl cycloalkyl, aryl, C$_1$-C$_8$ alkyl aryl, heteroaryl, and C$_1$-C$_8$ alkyl heteroaryl; preferably R$^{c1}$ and R$^{c2}$ are independently selected from the group consisting of hydrogen and methyl;

D is connected to the glucose derivative via A, wherein A is selected from the group consisting of —O—, —CH$_2$—, —S—, —NH—, —NHC(O)—, —OC(O)—, -cyclohexene- and -triazoles-; A may also be a single bond; preferably A is a covalent bond, an amide or a carbonyl group;

c is an integer selected from 0 to 20, preferably c is 0, 1, 2, or 3; c1 is an integer selected from 0 to 20, preferably c1 is 0, 1, 2, or 3; and c2 is an integer selected from 0 to 20, preferably c2 is 0, 1, 2, or 3; c3 is an integer selected from 1 to 20, preferably c3 is 1, 2, or 3; if A is —CH$_2$— c3 is an integer selected from 0 to 20. The spacer group D may be a single bond, one or more methylene glycol groups, one or more ethylene glycol groups or an hydrocarbon or a mixture thereof. The spacer is more preferably a group selected of a single bond, —CH$_2$—, —CH$_2$—CH$_2$—, or —CH$_2$—CH$_2$—O—. A and B may be therefore connected via a single bond.

The term "carrier" as used herein refers to any structure, which may be able to carry a cargo to a cell or group of cells. The cargo may accordingly be associated, i.e. bound to the carrier, or may be comprised, embraced or encompassed by the carrier. The carrier may, in particularly preferred embodiments, also be advantageously capable of introducing—upon previous interaction of the associated ligand, i.e. in the context of the above defined conjugate or vehicle, with the targeted cell—the transported cargo into said cell. The carrier may, in specific embodiments, comprise one or more types of cargo. These cargos may be connected to the carrier in an identical or different manner. For example, one cargo type may be bound to the carrier, e.g. at the outside, and a different cargo type may be embraced or encompassed by the carrier.

According to certain embodiments of the present invention, the carrier may be linked or associated to the conjugate as defined herein in a 1:1 ratio, i.e. one carrier is bound to one conjugate. In a further embodiment, the carrier may be bound to more than one conjugate. In a particular embodiment, the carrier is bound to less than 10 conjugates. In a more preferred embodiment, the carrier may be bound to less than 100 conjugates. In another preferred embodiment, the carrier may be bound to less than 200 conjugates. In further embodiments, the ratio between carrier and conjugate may be variable, e.g. adjusted to the carrier form, intended cargo, secondary binding intentions etc. For example, a ratio of 1:2, 1:3, 1:4, 1:5, 1:10, 1:15, 1:20, 1:25, 1:30, 1:35, 1:40, 1:50, 1:60, 1:70, 1:80, 1:90, 1:100 or 1:200 or more or any ratio (integer values) in between the mentioned ratios between the carrier and the conjugate may be provided. In further, alternative embodiments, also a ratio of one conjugate to more than one carrier may be provided. Accordingly, a ratio of 2:1, 3:1, 4:1, 5:1, 10:1, 15:1, 20:1, 25:1, 30:1 or more or any ratio in between the mentioned ratios between the carrier and the conjugate may be provided.

In specific embodiments, the carrier may be a soft particle. The term "soft particle" as used herein relates to particles, which are elastic, deformable and typically biodegradable or non-biopersistent. Preferred examples of soft particles are liposomes, niosomes, micelles, Sequessome™ and transfersomes. A soft particle as defined above may comprise or be composed of different types of constituents, e.g. lipids. A soft particle may, for example, comprise one or more types of phospholipids; in addition, a soft particle may comprise additional component which may, for example, have an influence on the stability, rigidity, binding capabilities, penetration capabilities for cells, secondary targeting capabilities etc. An example of components is cholesterol, which typically reduces the fluidity of a bilayer structure and increases the stability of a liposome. In a particularly preferred embodiment, the soft particle is a liposome. It is particularly preferred that the particle comprises 57% DSPC, 38% cholesterol and 5% DSPE-PEG.

A "liposome" is a spherical vesicle having at least one bilayer of lipids, e.g. as defined herein above. The liposomes may comprise phospholipids, e.g. phosphatidylcholine, or include other lipids such as phosphatidylethanolamine. The liposome may be provided in the form of a multilamellar vesicle (MLV), i.e. comprising several lamellar phase lipid bilayers, as a small unilamellar liposome vesicle (SUV), i.e. comprising one lipid bilayer, or a large unilamellar vesicle (LUV). The liposome typically has an aqueous solution core surrounded by a hydrophobic membrane. Accordingly, hydrophobic compounds dissolved in the core cannot pass through the bilayer, unless said bilayer is opened, e.g. by the introduction of a pore, or unless the bilayer fuses with a further bilayer structure, e.g. a cell membrane, and thereby delivers the liposome content to the core of the second bilayer, e.g. the cell. In turn, hydrophobic compounds typically associate with the lipid bilayer and may thus be loaded to said compartment of the liposome. Alternatively, the liposome may be delivered to a cell by the elicitation of an endocytosis or phagocytosis event. Liposomes may have different sizes, largely depending on the nature of the lipid, the lamellar structure and the presence of additional factors in the lipid bilayer, e.g. cholesterol. For example, the size of the liposome may range between a few nanometers and up to 2000 nm. The size of the liposomes may be measured with any suitable assay known to the skilled person, preferably with dynamic light scattering (DLS).

In a particularly preferred embodiment, the liposome is a bilayer phospholipid liposome. It is envisaged by the present invention that the size of said bilayer phospholipid liposome is between 10 to 500 nm. The size of the liposome may, for example, be 10, 20, 30, 40, 50, 60, 70, 80, 90, 100, 120, 140, 150, 160, 180, 200, 220, 240, 250, 260, 280, 300, 350, 400, 450 or 500 nm. Preferably, the size is between 30 and 250 nm, e.g. 40, 50, 60, 70, 80, 90, 100, 120, 140, 150, 160, 180, 200, 220, 240, or 250 nm. Also envisaged are further sized in between the mentioned sizes.

The preferred size of approximately 140 nm of liposomes was found to give a reproducible liposome stability over several months.

Liposomes including the bilayer phospholipid liposome may contain one or more additional components. One example of these additional components is cholesterol. In a preferred embodiment, cholesterol may be comprised in the liposome preferably in an amount of about 20 to 50 mol %, e.g. in an amount of about 20 mol %, 25 mol %, 30 mol %, 35 mol %, 40 mol %, 45 mol % or 50 mol %, or any suitable value in between the mentioned values. More preferably, it may be present in an amount of about 40%.

Liposomes may further preferably be composed of phospholipids, more preferably of phosphatidylcholines, but may also include other lipids, such as egg phosphatidylethanolamine, as long as they are compatible with lipid bilayer structure. Particularly envisaged examples of phospholipids include POPC (1-Palmitoyl-2-oleoyl-sn-glycero-3-phosphocholine), DPPG (1,2-Dipalmitoyl-sn-glycero-3[Phospho-rac-(1-glycerol), DSPC (1,2-Distearoyl-sn-glycero-3-phosphocholine), DOPC (1,2-Dioleoyl-sn-glycero-3-phosphocholine), DSPE (1,2-Distearoyl-sn-glycero-3-phosphoethanolamine), DMPC (1,2-Dimyristoyl-sn-glycero-3-phosphocholine), DPPC (1,2-Dipalmitoyl-sn-glycero-3-phosphocholine), DMPE (1,2-Dimyristoyl-sn-glycero-3-phosphoethanolamine), DPPE (1,2-Dipalmitoyl-sn-glycero-3-phosphoethanolamine), DMPA·Na (1,2-Dimyristoyl-sn-glycero-3-phosphate (sodium salt)), DPPA·Na (1,2-Dipalmitoyl-sn-glycero-3-phosphate (sodium salt)), DOPA·Na (1,2-Dioleoyl-sn-glycero-3[Phospho-rac-(1-glycerol) (sodium salt),) DMPG·Na (1,2-Dimyristoyl-sn-glycero-3[Phospho-rac-(1-glycerol) (sodium salt)), DPPG·Na (1,2-Dipalmitoyl-sn-glycero-3[Phospho-rac-(1- glycerol) (sodium salt)), DMPS·Na (1,2-Dimyristoyl-sn-glycero-3-phosphoserine (sodium salt)), DPPS·Na (1,2-Dipalmitoyl-sn-glycero-3-phosphoserine (sodium salt)), and DOPS·Na (1,2-Dioleoyl-sn-glycero-3-phosphoserine (sodium salt)).

The term "niosome" as used herein refers to a non-ionic surfactant-based vesicle. Typically, a noisome is formed by non-ionic surfactant of the alkyl or dialkyl polyglycerol ether class and cholesterol with subsequent hydration in aqueous media. Niosomes are structurally similar to liposomes in having a bilayer, but are more stable due to their composition. These are small unilamellar vesicles (SUV, size=0.025-0.05 µm), multilamellar vesicles (MLV, size=>0.05 µm), and large unilamellar vesicles (LUV, size=>0.10 µm). Examples of surfactants used for the preparation of niosomes include sorbitan monostearate (Span-60), polyoxyethylene alkyl ether, and Span 40 (C16 G2).

A "micelle" as used in the context of the present invention means an aggregate of surfactant molecules, e.g. phospholipids, block copolymers or triblock copolymers, dispersed in a liquid. A typical micelle in aqueous solution forms an aggregate with the hydrophilic head regions in contact with surrounding solvent, sequestering the hydrophobic single-tail regions in the micelle centre. The micelle has hence a monolayer structure. Micelles form beyond the critical micelle concentration and typically display a diameter between 1 and 100 nm. Polymeric micelles are generally more stable and typically monodisperse with diameters between 20 and 50 nm. Further details may be derived from suitable literature sources such as Soussan et al., 2009, Angew Chem Int Ed Engl. 48(2), 274-88. Besides these normal-phase micelles, there is a further group of differently shaped inverse micelles where the hydrophilic head groups are at the centre of the micelle with the tails extending out. The shape and size of a micelle are a function of the molecular geometry of its surfactant molecules and solution conditions such as surfactant or polymer concentration, temperature, pH, and ionic strength. Examples of envisaged surfactants include cationic surfactants such as DeTAB, DTAB, TTAB, or CTAB; anionic surfactants such as SDS or SDC; Zwitter-ionic surfactants such as SB-14 or CHAPS; or non-ionic surfactants such as NOG, Tween 20, Tween 80 or Triton X. Due to their increased stability, polymeric micelles are a preferred embodiment of the present invention. According to particularly preferred embodiments, these polymeric micelles comprise polyethyleneoxide- or biodegradable carbohydrate- and glycerol-base polymers, which may be used for the hydrophilic moiety. The hydrophobic moiety may preferably be composed of biodegradable lactate-based polymers. In another preferred embodiment micelles composed of pH-sensitive block copolymers are provided. Such micelles may be generated by inclusion of basic or acidic functional groups, which advantageously may change the solubility of the polymers and therefore the stability of the micelles at varying pH values.

The term "sequessomes" ™ as used herein relates to ultra-deformable, hydrophilic spheres made from phospholipid and surfactant molecules arranged as a bilayer. The inclusion of surfactants softens the bilayer membrane making sequessome vesicles flexible, but also stable, allowing them to pass through the skin intact and penetrate deep into the body without requiring injection or skin permeation enhancers. Further details may be derived, for example, from Benson, 2017, Methods Mol. Biol., 1522: 107-117, or Sala et al., 2018, Int J. Pharm. 535 (1-2), 1-17.

The term "transferosome" as used herein relates to a carrier aggregate composed of at least one amphipath, which in aqueous solvents self-assembles into a lipid bilayer that closes into a simple lipid vesicle. Typically, the amphipath is phosphatidylcholine. By addition of at least one bilayer softening component, e.g. a biocompatible surfactant or an amphiphile drug, the lipid bilayer flexibility and permeability may be increased. The resulting transfersome is optimized for flexibility and permeability, and can therefore adapt its shape to ambient conditions easily and rapidly by adjusting local concentration of each bilayer component to the local stress experienced at the bilayer. The transferosome typically differs from more conventional vesicles or liposomes primarily by its softer, more deformable, and better adjustable artificial membrane. The transferosome further typically has an increased affinity to bind and retain water. Without wishing to be bound by theory, it is assumed that ultradeformable and highly hydrophilic vesicles, such as transferosomes, tend to avoid dehydration, which may involve a transport process related to forward osmosis. Advantageously, a transferosome applied on an open biological surface, in particular skin, tends to penetrate its barrier and migrate into the water-rich deeper strata to secure adequate hydration. Barrier penetration may involve reversible bilayer deformation, but must not compromise either vesicle integrity or barrier properties for the underlying hydration affinity and gradient to remain unimpaired. Further details may be derived, for example, from Benson, 2017, Methods Mol. Biol., 1522: 107-117, or Sala et al., 2018, Int J. Pharm. 535 (1-2), 1-17.

In certain embodiments of the present invention, a part of the soft particle, e.g. an interacting moiety or compound, is bound directly via a covalent bond or via a moiety selected from the group consisting of —O—, —S—, —N($R^d$)—, —C($R^d$)($R^e$)—, —$R^d$C=C$R^e$—, —C(O)—, —C(O)O—, —OC(O)—, —C(O)S—, —C(O)N($R^d$)—, —N($R^d$)C(O)—, —N($R^d$)C(O)N($R^e$)—, —N($R^d$)C(S)N($R^e$)—, —N($R^d$)C(O)O—, —OC(O)N($R^d$)—, -cyclohexene-, -triazoles-, —NHS(O)$_2$—, —S(O)$_2$—, —OP(O)(H)O—, or —OP(O)(OH)O—;

wherein $R^d$ and $R^e$ are independently selected from the group consisting of hydrogen, substituted or non-substituted $C_{1-32}$ alkyl, $C_{2-32}$ alkenyl, $C_{3-8}$ cycloalkyl, aryl, $C_1$-$C_8$ alkyl aryl, heteroaryl, $C_1$-$C_8$ alkyl heteroaryl, e.g. via $Z^1$, as defined herein above, to the linker group A-D-B-L of the conjugate as defined herein above.

Figure 26:
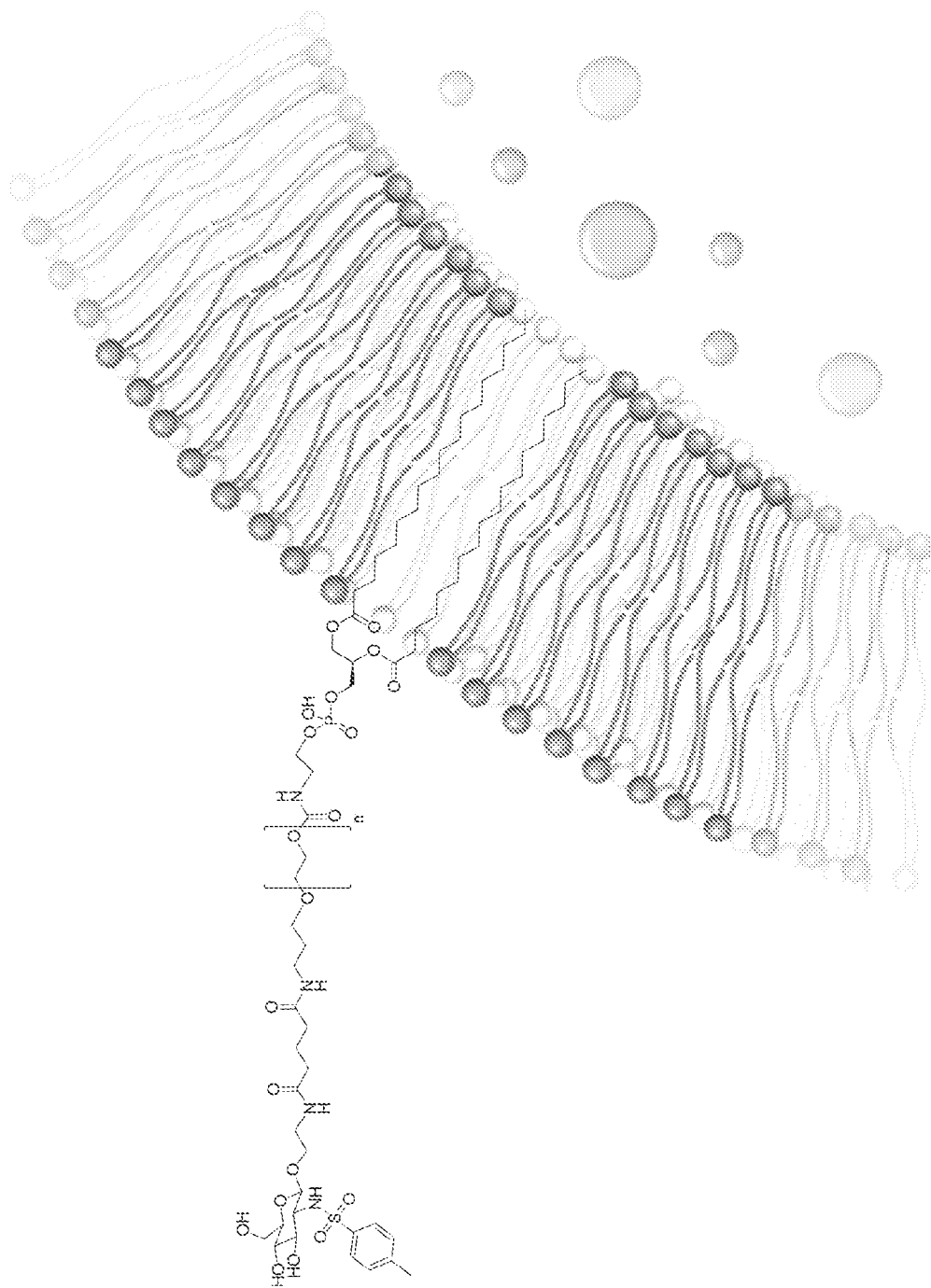
FIG. 26 schematically depicts a molecule wherein the tail region (hydrophobic section) of the conjugate is embedded in a lipid bilayer structure, whereas the head region is placed outside of the carrier and is thus capable of interacting with receptors.

The term "one part of the soft particle" refers to a typical constituent of a soft particle, e.g. of a liposome, such as a lipid, a modified lipid, a phospholipid, 1,2-distearoyl-sn-glycero-3-phosphoethanolamine (DSPE), a membrane lipid, or a modified phosphatidylcholine, or cholesterol, which is covalently connected to the Langerin ligand as defined herein via the A-D-B-L linker group. In certain embodiments, the conjugate comprising the Langerin ligand and the A-D-B-L linker group may comprise a hydrophobic region, which is named herein also a "tail region", as well as a hydrophilic region, which also comprises the Langerin ligand, also termed "head region". In specific embodiments, the tail region of the conjugate may be embedded in a lipid bilayer structure, whereas the head region is placed outside of the carrier and thus capable of interacting with receptors. An example of this embedding is schematically depicted in FIG. 26, which shows the tail region of the conjugate being inserted into a lipid bilayer structure, which belongs to a soft particle carrier, e.g. a liposome. The head region of the conjugate comprises, in preferred embodiments, a flexible linker between the ligand and the lipid, thus allowing an interaction with the cognate receptor. In specific embodiments, the length of this linker can be adapted to maintain a minimum distance between the ligand and the surface of the soft particle, e.g. the liposome. The present invention also envisages the presence of more than one conjugate in such a lipid bilayer or liposome as mentioned above. The amount conjugates and their distance in the bilayer can be adjusted, e.g. in correlation with the amount and frequency of cognate receptors on the surface of a Langerin+ cell. In one embodiment, the conjugate may be bound to a part of the soft particle, e.g. a lipid species or cholesterol, which forms a part of a liposome, micelle or similar structure. In another embodiment the lipids bound to a conjugate and the lipid which are not bound to a conjugate have a specific ratio of about 1:15, 1:20, 1:25, 1:50, 1:100, 1:150, 1:200, preferably 1:20. In further specific embodiments, the number of conjugates bound to a lipid may also be determined as number of conjugates present per $nm^2$ of the lipid bilayer area. In preferred embodiments, this number is to be adapted to the size of perimeter of the liposome. For example, for a liposome of a perimeter of 160 nm a number of about 0.05 to 0.075 conjugates per $nm^2$ may be present. In a very specific embodiment, a number of about 0.67 conjugates per $nm^2$ may be present.

In a preferred embodiment, the conjugate is bound to one part of a soft particle carrier resulting in the following formula (II-a):

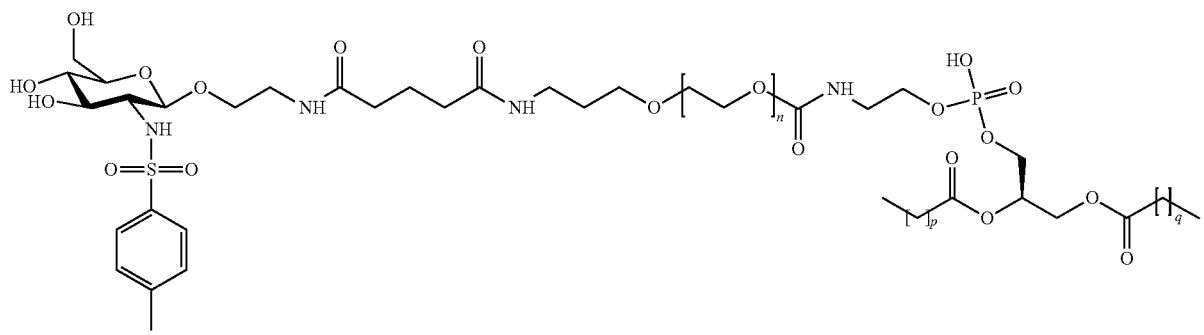

(II-a)

wherein p and q are each independently integers between 6 and 30; more preferably p and q are each independently integers between 8 and 28, still more preferably p and q are each independently 9, 10, 11, 12, 13, 14, 15, 16, 17, 18, 19, 20, 21, 22, 23, 24, 25, 26, 27 and 28; n is an integer from 0 to 150, preferably an integer from 10 to 100 and more preferably an integer from 20 to 75. In a more preferred embodiment, n is 20, 25, 30, 35, 40, 45, 50, 55, 60, 65, 75. In the most preferred embodiment, n is 45.

In a more preferred embodiment, the conjugate is bound to one part of a soft particle carrier resulting in the following formula (II):

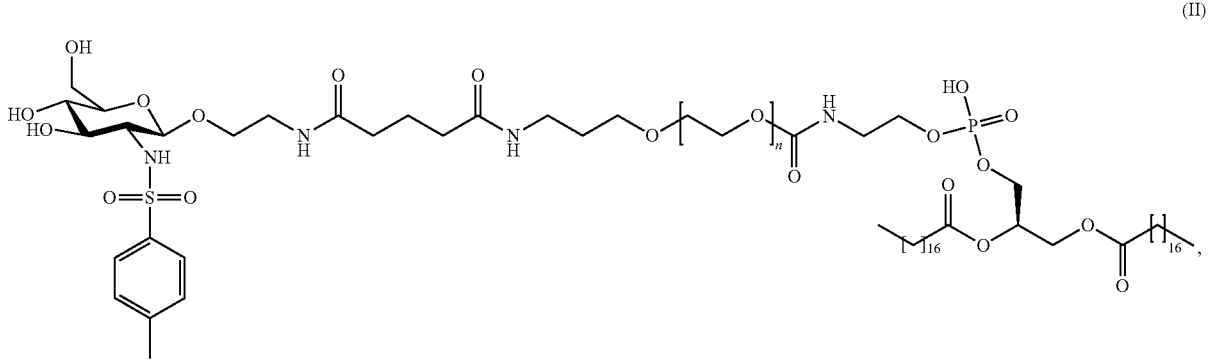

(II)

wherein the average number of ethylene glycol units n is an integer from 0 to 150, preferably an integer from about 20 to 110 and more preferably an integer from about 40 to 70.

In a more preferred embodiment, n is about 40, 50, 55, 60, or 70. In the most preferred embodiment, n is about 59. In specific embodiments a PEG linker is used. Particularly preferred is 3-(N-succinimidyloxyglutaryl)aminopropyl, polyethyleneglycol-carbamyl distearoylphosphatidyl-ethanolamine. The PEG linker may have any suitable weight. For example, the weight may be between about 1500 to 10 000 Da, e.g. 1500, 2000, 2500, 3000, 3200, 3500, 4000, 4500, 5000, 6000, 7000, 8000, 9000 or 10 000 Da or any value in between the mentioned values. Also envisaged is range of about 2000 to 5000 Da. It is particularly preferred to use a PEG linker having a molecular weight of 2000 Da.

In further preferred embodiments, the carrier may have a solid structure, be a nanoparticle, peptide, protein, toxin, dendrimer, fullerene or a carbon nanotube. The conjugate may be directly bound via a covalent bond to the carrier, or via a moiety selected from the group consisting of —O—, —S—, —N($R^d$)—, —C($R^d$)($R^e$)—, —$R^d$C=C$R^e$—, —C(O)—, —C(O)O—, —OC(O)—, —C(O)S—, —C(O)N($R^d$)—, —N($R^d$)C(O)—, —N($R^d$)C(O)N ($R^e$)—, —N($R^d$)C(S)N($R^e$)—, —N($R^d$)C(O)O—, —OC(O)N($R^d$)—, -cyclohexene-, -triazoles-, —NHS (O)$_2$—, —S(O)$_2$—, —OP(O)(H)O—, or —OP(O) (OH)O—;

wherein $R^d$ and $R^e$ are independently selected from the group consisting of hydrogen, substituted or non-substituted $C_{1-32}$ alkyl, $C_{2-32}$ alkenyl, $C_{3-8}$ cycloalkyl, aryl, $C_1$-$C_8$ alkyl aryl, heteroaryl, $C_1$-$C_8$ alkyl heteroaryl;

e.g. via $Z^1$, as defined herein above to the carrier. In a further embodiment, the conjugate may additionally be bound via an additional spacing element to the carrier.

The term "spacing element" as used herein, refers to any suitable group or a natural or synthetic polymer. It is particularly preferred that said natural or synthetic polymer is a natural or synthetic polymer as defined above.

The term "nanoparticle" as used herein relates to particles between 1 and 1000 nm, preferably between 5 nm and 1000 nm, in size, typically with a surrounding interfacial layer. A nanoparticle essentially behaves as a whole unit in terms of its transport and properties. Particles and hence their surfaces may accordingly be of a symmetrical, globular, essentially globular or spherical shape, or be of an irregular, asymmetric shape or form. The particle size (and hence the dimension of the surface) may vary. Preferred are particles and particle surfaces in the nanometer range up to several hundred nanometer. Particularly preferred are nanoparticles of about 1 to 700 nm. Particularly preferred are nanoparticles which may have a diameter of about 10 to 600 nm, e.g. 10 nm, 15 nm, 20 nm, 25 nm, 30 nm, 35 nm, 40 nm, 45 nm, 50 nm, 60 nm, 70 nm, 80 nm, 90 nm, 100 nm, 120 nm, 150 nm, 170 nm, 200 nm, 220 nm, 250 nm, 270 nm, 300 nm, 320 nm, 350 nm, 370 nm, 400 nm, 420 nm, 450 nm, 470 nm, 500 nm, 520 nm, 550 nm, 570 nm, 600 nm, 620 nm or any value in between. Even more preferred are nanoparticles having a diameter of about 500 nm. Nanoparticles may be constituted of any suitable material known to the person skilled in the art, e.g. they may comprise or consist of or essentially consist of inorganic or organic material. Typically, they may comprise or consist of or essentially consist of metal or an alloy of metals, or an organic material, or comprise or consist of or essentially consist of carbohydrate elements, or a mixture of the before mentioned materials. Examples of envisaged material further include agarose, polystyrene, latex, polyvinyl alcohol, silica and ferromagnetic metals, alloys or composition materials. Further envisaged examples of nanoparticle materials include gold, silver, silicon, cerium oxide, iron, titanium dioxide, zinc oxide, clay, aluminium oxide, copper oxide, metal carbides, metal nitrides, e.g. aluminium nitride or silicon nitride, aluminium or copper.

Typically, the ionic charge of the surface or the surface coating of nanoparticles determines many of their physical and chemical properties, including stability, solubility, and targeting. For biological applications as currently foreseen, the coating is envisaged to give high aqueous solubility and to prevent nanoparticle aggregation. On the cell surface, highly charged coatings typically promote non-specific binding, whereas polyethylene glycol linked to terminal hydroxyl or methoxy groups may repel non-specific interactions.

In certain embodiments, the nanoparticle may comprise one or more surface layers. It is, for example, envisaged that a first layer or shell structure is present. Also envisaged are multi-layer or mesh structures. Such structures may, for example, comprise PEG, biotin and streptavidin as structural components. The shell structure may comprise a conjugate according to the present invention, or, in addition, further affinity molecules, e.g. antibodies, ligands for a variety of receptors, protein interactors, lectins etc. In further specific embodiments, the multivalency of streptavidin typically leads to a mesh of non-affine spacer molecules on the surface of the nanoparticle. Such mesh structure around an interacting or targeting molecule, e.g. the conjugate according to the present invention, or an additional affinity molecule as mentioned above, the unspecific binding of molecules or entities to the interacting or targeting molecule or the affinity molecule or to molecules in its vicinity may be reduced, or completely abrogated or avoided.

In further embodiments, the nanoparticle may be composed of or have a biodegradable structure. The term "biodegradable" as used herein means that the nanoparticle can be disassembled or disintegrated by natural processes occurring in a cell or in the surrounding of a cell, i.e. outside of a cell. The biodegradable nanoparticles may accordingly have an enhanced biocompatibility, good encapsulation capability for cargos such as nucleic acids, proteins or small-molecule drugs. Biodegradable nanoparticles can be prepared from a variety of materials such as proteins, polysaccharides and synthetic biodegradable polymers. The selection of the base polymer is based on various designs and end application criteria. It depends on many factors such as size of the desired nanoparticles, properties of the cargo (aqueous solubility, stability, etc.) to be encapsulated in the polymer, surface characteristics and functionality, degree of biodegradability and biocompatibility, and cargo release profile of the final product. Depending upon selection of desired criteria for the preparation of the nanoparticles, the methods to be used for the production of biogradable nanoparticles may include dispersion of preformed polymers, polymerization of monomers and ionic gelation method for hydrophilic polymers. Particularly preferred is the employment of poly-lactic acid (PLA), poly-D-L-glycolide (PLG), poly-ε-caprolactone (PCL), poly-D-L-lactide-co-glycolide (PLGA) and poly-cyanoacrylate (PCA), chitosan, gelatin, Poly-alkyl-cyano-acrylates (PAC). The most preferred variant of the biodegradable nanoparticles are PLGA nanoparticles. For example, the nanoparticle or polymeric structures present on the surface of the nanoparticle may be degradable by enzymes such as lipases, esterases, alcalases, hydroxylases, dioxygenases etc.

In further specific embodiments of the present invention, the nanoparticle carrier may be associated with or provide a cell-penetrating agent. Such an agent may, for example, be the polyArg peptide TAT, the penetratin peptide, a polyarginine or polynliysine peptide, a peptide comprising cationic nuclear localization signal sequences, cationic moieties linked to scaffolds, e.g. peptides, oliogocarbamates, oligomers or PNA oligomers. Further details may be derived from suitable literature sources such as Fillon et al., 2005 J. Am. Chem. Soc, 127, 11798-11803.

In specific embodiments, nanoparticles may further be linked to biological molecules that direct the nanoparticles to specific sites within the body, specific organelles within the cell, or to follow specifically the movement of individual protein or RNA molecules in living cells. Such affinity molecules may include, besides the conjugates as defined herein, aptamers or peptides. These affinity molecules are typically covalently linked to the nanoparticle or to the layers on their surface. It is preferred that said conjugates or affinity molecules are present in a controlled number per nanoparticle. Multivalent nanoparticles, comprising more than one conjugate according to the present invention, bearing multiple targeting groups, can cluster receptors, which may activate certain cellular signalling pathways, and give stronger anchoring. Monovalent nanoparticles, bearing a single binding site or a single conjugate, tend to avoid clustering. In preferred embodiments, multivalent nanoparticles are provided. The amount of conjugates per nanoparticle may be adjusted to the size of the nanoparticle. For example, a ratio of 2:100 or 5:100 conjugates per nanoparticles may be used within the context of the present invention.

The linkage between the conjugate according to the present invention and the nanoparticle may be provided in any suitable form. For example, the linkage may be achieved through intermolecular attractions between the nanoparticle and biomolecule such as covalent bonding, adsorption, such as chemisorption, and noncovalent interactions. The linkage may, in certain embodiments, be an integration of liposomes into a bilayer structure, e.g. of a cell. In further embodiments the linkage may be implemented via a ligand which is covalently linked to a receptor structure on a cell. Further envisaged are nanoparticles which penetrate a cell or which are adsorbed to a cell. It is particularly preferred to make use of an uptake of liposomes via an endosomal pathway. Without wishing to be bound by theory, it is assumed that delivered liposomes will be released in the endosomal compartment. The release of the cargo itself from the bilayer of the liposome may subsequently be provided by lipases that are assumed to destroy the liposome in the late endosome or lysosomal compartment. It is preferred that the release of the cargo be performed in early endosomes. Additional factors, which may have an influence on the cargo release are the pH, which may, in certain embodiments, be influenced or changed to control said cargo release. The present invention further envisages an adaptation of the endosome form via the concentration and/or composition of the lipid bilayer of the liposomes.

The nanoparticle as envisaged by the present invention is to be used as carrier for cargo transport. Accordingly, the nanoparticle is linked to one or more cargo molecules as described herein, which are typically provided on the surface of the particle. These cargo molecules may also be linked to the nanoparticle in any suitable form, e.g. via intermolecular attraction, covalent bonding, adsorption, such as chemisorption, and noncovalent interactions. The amount of cargo per nanoparticle may be adjusted in view of the size of the nanoparticle, its material, its form and the size and/or form of the cargo. Typically, a ratio of 1 nanoparticle: 1-1000 cargo entities may be given.

In further embodiments, the nanoparticle may be provided as a magnetic nanoparticle, e.g. as superparamagnetic particle. Accordingly, preferred materials are magnetic or ferromagnetic metals, alloys or compositions. Such particles may particularly be used in the context of magnetic resonance imaging techniques. It is particularly preferred that the nanoparticle is a gold, silver or iron nanoparticle.

The nanoparticles may be provided as colloid or comprised within a colloid. The term "colloid" as used herein relates to a colloidal system, wherein polymolecular particles are dispersed in a medium, having at least one dimension of between 1 nm and 1 μm. Alternatively, in the systems discontinuities may be found at distances between 1 nm and 1 μm. Typically, a colloid is a mixture which has solid particles, e.g. nanoparticles as defined herein, dispersed in a liquid medium. The term typically applies if the particles are larger than atomic dimensions but small enough to exhibit Brownian motion, with the particle diameter typically ranging from nanometers to micrometers.

The term "peptide carrier" or "protein carrier" as used herein relates to peptide or protein structures as defined herein above, which fulfil a role as carrier. As such, the peptide or protein may itself be connected to one or more different molecules. Such a connection is, for example, a covalent binding to a further molecule via a side chain of an amino acid. Alternatively, the peptide or protein may be connected to further elements via non-covalent binding, e.g. intermolecular attractions, chemisorption, electrostatic attractions etc. In further, specific embodiments, the peptide or protein carrier may itself have one or more additional functions. Typically, the peptide or protein carrier may have the function of an antigen or have a vaccine function, e.g. representing an exposed or surface protein of a pathogen such as a bacterium, a virus, a eukaryotic parasite, or a cancer antigen or allergen.

The term "toxin carrier" or "toxin" as used herein in the context of carriers relates to a toxic compound which provides at least two functionalities (a) to poison, disturb, kill or damage a biological element, e.g. a cell or tissue and (b) to transport a cargo, e.g. as defined herein. To work as a cargo, the toxin may be linked, e.g. by covalent or non-covalent binding, to said cargo, e.g. an antigen, small molecule etc. The binding is optimized so that the domain leading to the killing, damaging or poisoning functionality is not impeded or negatively influenced. Examples of toxins to be used in the context of the present invention are small molecules, peptides, or proteins. These compounds may interact with biological macromolecules such as enzymes or cellular receptors. Toxins may vary greatly in their toxicity, ranging from usually minor toxicity such as a bee toxin to severe toxicity in the case of botulinum toxin. Preferred toxin carriers according to the present invention are cholera toxin, *E. coli* enterotoxin, pertussis toxin, botulinum toxin, *Clostridium botulinum* C2 toxin, *Clostridium perfringens* iota toxin, or streptolysin O.

The carrier may further be a dendrimer. The term "dendrimer" as used herein relates to repetitively branched molecules, which have tree-like structure. The dendrimers are typically characterized by structural perfection, and are comprised of monodisperse and symmetric spherical compounds. Dendrimers are typically considered to have three major portions: a core, an inner shell, and an outer shell. A dendrimer may, for example, be designed to have different functionality in each of these portions to control properties such as solubility, thermal stability, and attachment of compounds for particular applications. Dendrimers may be composed of a polymethylmethacrylate (PMMA), polystyrene, polyacetylene, polyphenylene, polythiophene, polyfluorene, poly(phenylene vinylene), poly(phenylene acetylene), polysiloxane, polyoxanorbornene, oligospiroketal, polyglycerol or poly(ethylene imine) (PEI) backbone, whose methyl group is replaced by a dendron structure. Particularly preferred are PMMA dendrimers. The resulting polymers may differ in thickness and charge, as well as the weight, ranging from low molecular weight to high molecular weight structure. The dendrimers may be linked to or comprise a cargo element to be transported. For example, the cargo may be linked by covalent or non-covalent binding to said cargo, e.g. an antigen, small molecule etc. The binding may be based on the formation of an ester, amide, triazole, amine or ether.

In further embodiments, the carrier may be a fullerene. The term "fullerene" as used herein relates to a molecule of carbon in the form of a hollow sphere, ellipsoid or tube or any other suitable hollow shape. A subtype of fullerenes is the Buckminsterfullerene or buckyball, which resembles a football and comprises pentagonal and hexagonal rings. Fullerenes may, in specific embodiments, comprise C69, C79, C76, C82, C84, C86, C88, C90, C92, C94, C96, C98 or C100 structures. A further alternative, which is also envisaged by the present invention is a boron based fulleren, e.g. with a B80 structure. Also envisaged are heterofullerenes comprising, for example, hetero atoms at some positions such as boron, nitrogen, oxygen or phosphor atoms. In further embodiments, the fullerenes may be provided as metal fullerenes, e.g. as graphite rods doped with metals or metal oxides typically of the Sc, Y, La, lanthanide series or actinide elements. Also envisaged are trimetallic nitride templated metallofullerenes, clusterfullerenes or trimetaspheres which contain a central nitrogen atom (nitride) bonded to three metal ions. In typical embodiments, the fullerenes may be functionalized or derivatized to increase the solubility of the fullerenes in organic media or aqueous media, e.g. by cyclopropanation, polyhydroxylation, or cycloaddition of azmethine ylides. In a specific embodiment, the fullerene may be detivatized with free radicals, which allows to scavenge for reactive oxygen species and renders the fullerene a highly active antioxidant. In another embodiment, the fullerene may transport cargos in a non-covalent association. One possibility is that the cargo, e.g. a protein, antibody, nucleic acid etc. is associated to the fullerene's surface via supramolecular interactions, or hydrophobic interactions, electrostatic interactions etc. In case of nucleic acid cargo transport, the carrier may preferably be a n-tetra (piperazino) fullerene epoxide derivative, or a cyclopropanated C60 fullerene, e.g. with neutral, cationic or anionic functional groups. In further embodiments, fullerene-immunoconjugates may be provided, where, for example, a disulfide bond is present between the fullerene and, e.g. an antibody. In this context, it is preferred to use a C60 malonodiserinolamide fullerene derivate, which may allow for non-covalent, spontaneous binding between the antibody or protein and the fullerene. In further preferred embodiments, fullerenes may be used in a configuration and derivatization, which allows for an aggregation into fullerene-based micelle, vesicle or liposome-like structures. These structures may encompass any suitable drug molecule in their hydrophobic core. In yet another group of embodiments, there may be a covalent attachment of cargos to the fullerene carrier. This may typically be provided with an additional linker element between the fullerene and the cargo molecule which is present on the surface of the fullerene. This allows, inter alia, for delayed cargo release. Further envisaged are glycofullerenes which may be connected to further entities via the formation of triazole linkages. Further details would be known to the skilled person or can be derived from suitable literature sources such as Bolskar, 2016, Encyclopedia of Nanotechnology, Springer, or Muñoz et al., 2016, Nature Chemistry, 8, 50-57.

In further embodiments, the carrier may have the form of a carbon nanotube. The term "carbon nanotube" as used herein relates to allotropes of carbon with a cylindrical nanostructure. These cylindrical carbon molecules typically have unusual properties, which may be used for cargo transportation and delivery activities. Carbon nanotubes typically show a vey high strength and stiffness. They are typically constructed with length-to-diameter ratio of up to 132,000,000:1. Carbon nanotubes further typically have a high thermal conductivity. They typically have a long, hollow structure with walls formed, e.g. by one-atom-thick sheets of carbon, which are typically called graphene. These sheets are typically rolled at specific and discrete angles, and the combination of the rolling angle and radius may decide the nanotube properties with respect to strength, stiffness etc. Nanotubes are typically categorized as single-walled nanotubes (SWNTs) and multi-walled nanotubes (MWNTs), which are both envisaged by the present invention. Nanotubes may further align into rope-like structures, which are assumed to be held together by van der Waals forces.

Carbon nanotubes are generally considered to belong to the fullerene structural family. In certain embodiments of the present invention the carbon nanotubes may be modified as described herein above in the context of fullerenes. Particularly preferred are linkages between carbon nanotubes and nucleic acids, proteins and peptides. Further envisaged are modifications via free carboxylic acids, which may be connected to further entities via the formation of ester or amine linkages.

In certain embodiments, the carrier as defined herein above may be used with or without cargo. In case the carrier is used without cargo, it may itself provide a functionality as described herein. In further embodiments, the carrier comprises or is associated to a cargo. The form in which the cargo is connected to the carrier may depend on the carrier form/nature as well as on the cargo form/nature. In some cases a covalent linkage may be envisaged, whereas in other cases a electrostatic linkage may be used. In some other embodiments, the association may be based on an embedding of cargo elements in a liposome or similar structure. For example, the cargo may be located within the carrier and/or be linked to the outside of the carrier and/or be integrated into a mono- or bilayer structure of the carrier, e.g. a liposome as mentioned herein above.

The term "cargo" as used herein refers to any suitable substance, compound or element, which is located within the carrier as defined above and/or is linked or associated to the outside, e.g. surface, of the carrier and/or is integrated into a mono- or bilayer structure of the carrier, e.g. in case the carrier is an entity comprising a membrane or bilayer such as a liposome and should be transported to the interior of a cell, a specific cell compartment, e.g. an endosome, or to the surface or surrounding of a cell. It is preferred that the cargo is unloaded into the interior of a cell. It is preferred that the cargo provides or mediates a beneficial effect to cell, the tissue comprising the cell, or the organism comprising the cell in a medical context. Examples of such beneficial effects are therapeutic activity/capabilities, diagnostic activity/capabilities, following delivery to or into a cell. This may be performed in vivo, but also, in certain embodiments ex vivo, e.g. in an in vitro environment, typically with an option of reintroduction into the organism afterwards, for instance via re-implantation of cells. A "therapeutic activity" may include treatment, amelioration and/or prophylaxis/avoidance of a disease or medical condition. The term "diagnostic activity" may include visualizing, detecting, distinguishing and/or identifying a pathological/medical condition and attributing the deviation to a clinical picture.

Preferably, a "cargo" relates, but is not limited, to a small molecule, a peptide, a protein, a cytotoxic substance, a nucleic acid, a colorant, a pigment, a dye, a metal, a radionuclide, a virus, a modified virus, a viral vector, an inoculant, a plasmid and/or a multicomponent system.

A "peptide" or "protein" as used herein in the context of the cargo is a peptide as defined herein above or a protein as defined herein above. It is preferred that such a peptide or protein fulfils a function for the cell to which the cargo is transported, or the organism which comprises said cell. Such function could be a therapeutic or diagnostic function. The peptide or protein may be derived from any suitable category. For example, it may be an antigenic element, an antibody, an enzyme, an allergen, a toxin, a catalysing entity, a receptor etc. In specific embodiments, the protein as part of the cargo according to the present invention may be selected from the group comprising: therapeutic proteins, suicide proteins, tumor suppressor proteins, transcription factors, kinase inhibitors, kinases, regulatory proteins, apoptotic proteins, anti-apoptotic proteins, microbial antigens, viral antigens, bacterial antigens, parasitic antigens, cellular antigens, cancer antigens, differentiation factors, immortalisation factors, protein/peptide toxin, enzymes, peptide/protein hormones, peptide/protein adhesion-molecules, receptor-molecules, peptide inhibitors or peptide/protein antiaging agents.

The term "therapeutic protein" as used herein in the context of the cargo relates to any protein, which has a therapeutic effect on the animal body, in particular on the human body as known to a person skilled in the art. Typically, the term relates to a therapeutic enzyme. Examples of such enzymes are alglucerase, which may be used in treating lysosomal glucocerebrosidase deficiency (Gaucher's disease), alpha-L-iduronidase, which may be used in treating mucopolysaccharidosis I or adenosine deaminase, which may be used in treating severe combined immunodeficiency syndrome.

The term "suicide protein" as used herein in the context of the cargo relates to any protein, which leads to the destruction of a cell due to the action of the protein, typically due to an enzymatic reaction in the presence of a corresponding substrate. Examples of such proteins are nucleoside kinases, such as the HSV-1 TK or multisubstrate deoxyribonucleoside kinase of Dm-dNK.

The term "tumor suppressor protein" as used herein in the context of the cargo relates to any protein, which protects a cell from one step on the path to cancer. Preferably, the term relates to any such protein known to the person skilled in the art. More preferably, the term relates to Rb protein, the p53 tumor suppressor, APC and CD95.

The term "transcription factor" as used herein in the context of the cargo relates to any protein, which binds to specific parts of DNA using DNA binding domains and is part of the system that controls the transcription of genetic information from DNA to RNA as known to the person skilled in the art. Preferably, the term relates to TFIIA, TFIIB, TFIID, TFIIE, TFIIF, TFIIH and TATA binding protein (TBP).

The term "kinase inhibitors" as used herein in the context of the cargo relates to any protein, which is a type of enzyme inhibitor that specifically blocks the action of protein kinase. Preferably, the term relates to Erbitux (cetuximab), and herceptin. The present invention of course also envisages the use of non-protein kinase inhibitors, which may, for example, be small organic molecules as defined herein.

The term "kinase" as used herein in the context of the cargo relates to any protein, which transfers phosphate groups from high-energy donor molecules, such as ATP, to specific target molecules. Preferably, the term relates to tyrosine kinase or MAP kinase, MEK1, or MEK2.

The term "apoptotic protein" as used herein in the context of the cargo relates to any protein, which leads to programmed cell death in multicellular organisms. More preferably, the term relates to the pro-apoptotic protein BAX, BID, BAK, or BAD.

The term "anti-apoptotic protein" as used herein in the context of the cargo relates to any protein, which impedes programmed cell death in multicellular organisms. Preferably, the term relates to the anti-apoptotic protein like Bcl-XI, Bcl-2, and further members of the Bcl-2 family.

The terms "microbial antigens", "viral antigens", "bacterial antigens", "parasitic antigens", and "cellular antigens" in the context of the cargo molecules relate to immunogens, which are able to stimulate an immune response derived from microbes, viruses, bacteria, parasites, or cells, respectively, in particular as defined herein below.

A "differentiation factor" as used as used herein in the context of the cargo relates to any factor, which functions predominantly in development and leads to the differentiation of tissues, cell groups of specific cells. Preferably, the term relates to growth differentiation factors (GDFs) like GDF1, GDF2, GDF3, GDF5, GDF6, GDF8, GDF9, GDF10, GDF11, and GDF15.

The term "immortalisation factors" as used herein in the context of the cargo relates to any factor, which provokes an absence of a sustained increase in the rate of mortality of a cell as a function of chronological age. Preferably, the term relates to any such factor known to the person skilled in the art. More preferably, the term relates to telomerase or large T-antigen.

The term "peptide/protein hormone" as used herein in the context of the cargo relates to any compound, which carriers as a messenger a signal from one cell (or group of cells) to another via the blood. More preferably, the term relates to prostaglandine, serotonine, histamine, bradykinin, kallidin, and gastrointestinal hormones, releasing hormones, pituitary hormones, insulin, vasopressin (ADH), glucagon, enkephalin, calcitonin, corticosteroids, corticotropin-releasing Hormone (CGRI), substance P, GRP, MSH, and neuromediators.

The term "peptide/protein adhesion-molecule" as used herein in the context of the cargo relates to peptides or proteins on the cell surface involved with the binding with other cells or with the extracellular matrix (ECM) in a cell adhesion process. Preferably, the term relates to any such molecule known to the person skilled in the art. More preferably, the term relates to IgSF CAMs like NCAM, ICAM-1, VCAM-1, PECAM-1, L1, CHL1, MAG, integrins, or selectins.

The term "receptor-molecules" as used herein in the context of the cargo relates to protein on the cell membrane or within the cytoplasm or cell nucleus that binds to a ligand and typically transduces a signal. Preferably, the term relates to metabotropic receptors, G protein-coupled receptors, muscarinic acetylcholine receptors, adenosine receptors, adrenoceptors, GABA receptors, angiotensin receptors, cannabinoid receptors, cholecystokinin receptors, dopamine receptors, glucagon receptors, metabotropic glutamate receptors, histamine receptors, olfactory receptors, opioid receptors, chemokine receptors, calcium-sensing receptor, somatostatin receptors, serotonin receptors or secretin receptors.

The term "peptide inhibitors" as used herein in the context of the cargo relates to peptides which have an inhibitory effect on physiological functions, preferably on protein function like enzymatic functions.

The term "protein/peptide anti-aging agent" as used herein in the context of the cargo relates to any compound that prevents, slows, or reverses the effects of aging. Preferably, the term relates to Human Growth Hormone (HGH).

The term "cytotoxic substance" as used herein relates in general to any compound which is toxic to a living cell, in particular to a cell of higher eukaryonts, more specifically, to a mammalian or human cell. As a result of the action of a cytotoxic substance, the cell my undergo necrosis, the cell can stop to grow activity or the divide, or the cell may undergo a program of apoptosis. Typically, cells undergoing necrosis exhibit rapid swelling, lose membrane integrity, decrease their metabolism and release contents into the environment. In contrast, apoptosis is characterized by certain cytological and molecular events including a change in the refractive index of the cell, cytoplasmic shrinkage, nuclear condensation and cleavage of DNA into regularly sized fragments. Cytotoxicity may be measured in accordance with suitable assays, e.g. by measuring the cell membrane integrity. The cytotoxic substance may, in case of cancer treatment be a chemotherapeutic compound. Alternatively, the cytotoxic substance may also be an antibody which conveys antibody-dependent cell-mediated cytotoxicity (ADCC), wherein cells are killed by lymphocytes which have been bound by an antibody. Examples of cytotoxic lymphocytes include cytotoxic T cells and natural killer cells.

The term "chemotherapeutic compound" as used herein in the context of the cargo relates to compounds of several different functional classes, which are used for the therapeutic treatment of cancerous cells. The compounds may, for example, be alkylating agents, anthracyclines, cytoskeletal disruptors (taxanes), epothilones, histone deacetylase inhibitors, inhibitors of topoisomerase I and II, kinase inhibitors, nucleotide analogs or precursor analogs, peptide antibiotics, platinum-based agents, retinoids, vinca alkaloids and derivatives thereof. A herein envisaged example of an alkylating agent is cyclophosphamide, which is a phosphoramide mustard metabolite formed in cells containing low level of ALDH (aldehyde dehydrogenase), e.g. in liver, intestine, bone marrow stem cells. The metabolite typically crosslinks DNA at guanine N-7 position, which is assumed to lead to cell apoptosis. A further example is mechlorethamine, which typically crosslinks DNA at guanine N-7 position and thus prevents cell duplication, leading to cell apoptosis. Another example is chlorambucil, which promotes nucleic acid alkylation and cross-links DNA, leading to cell-cycle arrest. This compound can be detoxified by human glutathione transferase Pi (GST P1-1), often over-expressed in cancer tissue. Further examples are nitrosoureas which are lipophilic DNA alkylating agents and can thus cross the blood brain barrier. Also envisaged is temozolomid which promotes alkylation/methylation of DNA of guanine at O-6/n-7 position. It may further be used as prodrug in the form of an imidazotetrazine derivative. An O-6-alkylguanine DNA alkyltransferase encoded as O-6-methylguanin-DNA methyltransferase may prevent cell damage. Herein envisaged examples of anthracyclines include daunorubicin, doxorubicin, epirubicin, idarubicin, mitoxantrone, pixantrone, losoxantrone, sabarubicin (which is a disaccharide analog of doxorubicin) and valrubicin (which is a semisynthetic analog of doxorubicin). These compounds typically work as DNA intercalators and thus inhibit, for example, topoisomerase II. Herein envisaged examples of cytoskeletal disruptors (taxanes) include paclitaxel, docetaxel, abraxane, and taxotere. These compounds typically targets tubulin, in particular by $\alpha\beta$-tubulin heterodimer subunit binding, which leads to defects in mitotic spindle assembly, chromosome segregation and cell division. Herein envisaged examples of epothilones include epothilone A to F. Further examples are ixabepilone, patupilone and utidelone. These compounds lead to tubulin interference. They have a better water-solubility than paclitaxel-like compounds which may lead to an increased efficacy. Herein envisaged examples of histone deacetylase inhibitors include vorinostat and romidepsin. These compounds typically bind to zink-dependent active sites and function as chelators for zinc ions, leading to the accumulation of acetylated proteins, in particular histones. Herein envisaged examples of inhibitors of topoisomerase I include irinotecan. Irinotecan binds to topoisomerase I and forms a ternary DNA complex, which prevents DNA re-ligation and causes DNA damage. Further examples include topotecan. Silatecan, cositecan, exatecan, lurtotecan, gimatecan, belotecan and rubitecan, which are semi-synthetic derivatives of campothecin. Herein envisaged examples of inhibitors of topoisomerase II include etoposide, which forms a ternary complex with DNA and the topoisomerase II enzyme, preventing DNA re-ligation. Also envisaged is teniposide, which stabilizes topoisomerase II-DNA intermediates and induces double-stranded DNA breaks. A further example is tafluposide. Herein envisaged examples of kinase inhibitors include bortezomib, which is a proteasome inhibitor, wherein its boron atom binds catalytic site of 26S proteasome. Further examples include erlotinib and gefitinib which inhibit EGFR tyrosine kinase by binding reversibly to an ATP binding site, and thereby prevent a signal cascade. Further envisaged is vemurafenib, which leads to the interruption of the B-Raf/MEK/ERK pathway if B-Raf has a V600E mutation. Also contemplated is imatinib, which is an inhibitor of a number of tyrosine kinase enzymes. It typically occupies TK active sites to decrease bcr-abl activity, e.g. in chronic myelogenous leukemia where fusion of abl with bcr occurs. Further envisaged is vismodegib, which is a cyclopamine-competitive antagonist of smoothened receptor (SMO, a part of the hedgehog signalling pathway). It may specifically be used for basal-cell carcinoma. Herein envisaged examples of nucleotide analogs or precursor analogs include azacitidine (which is an analogue of nucleoside cytidine, and causes hypomethylation at low concentrations and may lead to cytotoxicity at high concentrations), azathioprine (which inhibits purine synthesis), capecitabine, cytarabine (which combines cytosine base with arabinose sugar and is an antimetabolic agent; it works via incorporation into DNA by human cytosine deoxyribose and typically induces cell death), doxifluridine (which is a metabolite of capecitabine), fluorouracil (which is a-thymidylate synthase inhibitor, blocking pyrimidine thymidine synthesis), gemcitabine (which is typically integrated as cytidine in DNA strand leading to irreparable errors and cell death), hydroxyurea (which is an inhibitor of ribonucleotide reductase by scavenging tyrosyl free radicals and typically decreases production of deoxyribonucleotides), mercaptopurine (which inhibits xanthine oxidase), methotrexate (which inhibits synthesis of DNA, RNA, thymidylates and proteins) and thioguanine (which is an analogue of guanine and leads to inhibition of guanine nucleotide synthesis). Herein envisaged examples of peptide antibiotics include bleomycin (which leads to the induction of DNA strand breaks) and actinomycin (which binds DNA at the transcription initiation complex, and thus prevents elongation of RNA). Herein envisaged examples of platinum-based agents include carboplatin, cisplatin (which interferes with DNA replication by binding and crosslinking DNA) and oxaliplatin (which interferes with DNA replication by binding and crosslinking DNA). Herein envisaged examples of retinoids include tretinoin (which has been shown to force acute promyelocytic leukemia cell differentiation and stops proliferation), alitretinoin (which is assumed to be an endogenous ligand of retinoid X receptor) and bexarotene (which activates retinoid X receptors and induces cell differentiation and apoptosis). Herein envisaged examples of vinca alkaloids and derivatives include vinblastine, vincristine, vindesine and vinorelbine, which are assumed to work as microtubule inhibitors.

The present invention, in a further embodiment, particularly envisages the employment of alpha amantin and analogs or derivatives thereof as toxic substance. These compounds typically inhibit RNA polymerase II and III. In specific embodiments, the alpha amanitin or its analogs or derivatives may be linked to a protein or peptide and be transported in this form as cargo to a desired destination, i.e. cell or tissue.

According to their mode of action, the above characterized toxic substances may be employed for intracellular or extracellular administration. Accordingly, they may be provided in carrier systems which deliver the cargo intracellularly, as defined herein, or which deliver the cargo extracellularly, as defined herein.

The term "small molecule" as used herein in the context of the cargo relates to molecules, e.g. organic molecules, which are therapeutically useful and preferably include drugs or other biologically, therapeutically or diagnostically active agents, which act to ensure proper functioning of a cell, or molecules which may induce, for instance, apoptosis or cell lysis, where death of a cell, such as a cancerous cell or aberrant cell, is desired, or which induce immunologic reactions, or which marker functionalities. The small molecule typically has a low molecule weight of less than 900 Da. Typically small molecules having a molecule weight of about 900 Da or less are assumed to be capable of rapidly diffusing across cell membranes. Accordingly, small molecules may be provided as cargos to be delivered intracellularly and/or extracellularly. A small molecule may, in certain embodiments, have poor solubilities in aqueous liquids, such as serum and aqueous saline. Thus, compounds whose therapeutic efficacies are limited by their low solubilities, can be administered in greater dosages according to the present invention, and can be more efficacious on a molar basis due to higher uptake levels by cells. Likewise, the compounds may be effective already in low or very low concentrations. Thus, by specifically targeting these compounds as cargos in accordance with the present invention to specific cells, avoids a systemic and rather unspecific administration and thereby allows to reduce the overall amount of compound to be administered. Examples of envisaged small molecules to be transported as cargos according to the present invention are, for example, antibacterial agents, antifungal agents, antiviral agents, antiproliferative agents, cytostatics, immunosuppressive agents, histamine receptor antagonists, vitamins, analgesic agents, anti-neoplastic agents, antiinflammatory agents, therapeutic organic molecules, inhibitors, e.g. enzyme inhibitor such as kinase inhibitors and the like. Herein envisaged examples of antibacterial agents include aminoglycosides such as neomycin or gentamicin, polymyxin, chloramphenicol, bacitracin, framycetin, enrofloxacin, marbofloxacin, miconazole, silver sulfadiazine, povidone-iodine, chlorhexidine and acetic acid. Herein envisaged examples of antifungal agents include polyene antifungals s such as amphotericin B, candicidin, or hamycin etc.; imidazoles such as bifonazole, butoconazole, or clotrimazole etc.: triazoles such as albaconazole, efinaconazole, or epoxiconazole etc.); thiazoles such as abafungin; allylamines, and echinocandins. Herein envisaged examples of antiviral agents include amantadine, rimantadine, pleconaril, aciclovier, zidovudine, lamivudine (which is a reverse transcription inhibitor) and rifampicin (which is an assembly inhibitor). Herein envisaged examples of cytostatics include alkylating agent, e.g. as defined herein above; antimetabolites such as methotrexate, azothioprine, mercaptopurine, or fluorouracil, as defined herein above. Herein envisaged examples of immunosuppressive agents include glucocorticoids such as prednisone, dexamethasone, hydrocortisone; cytostatics; antibodies; drugs acting on immunophilins such as ciclosporin, tacrolimus, sirolimus, or everolimus; as well as interferons, opioids, TNF alpha binding proteins, mycophenolate, fingolimod and myriocin. Herein envisaged examples of histamine receptor antagonists include cimetidine, ranitidine, famotidine and zizatidine. Herein envisaged examples of analgesic agents include paracetamol, phenacetin, aspirin, ibuprofen, naproxen and opioids such as morphine. Herein envisaged examples of anti-neoplastic agents include nucleoside analogues, antifolates, topoisomerase I inhibitors, anthracyclines, podophyllotoxins, taxanes, vinca alkaloids, alkylating agents, platinum compounds, tyrosine kinase inhibitors, mTOR inhibitors, retinoids, immunomodulatory agents and histone deacetylase inhibitors, e.g. as defined herein above. Herein envisaged examples of antiinflammatory agents include anti-interleukin antibodies, resolvins, glucocorticoids, protease inhibitors, statins, histone deacetylase inhibitors, prostaglandin agonists, phosphodiesterase-4 inhibitors, agonists of peroxisome proliferator-activator receptor, inhibitors of the complement system, anticoagulants and thrombolytics.

The term "nucleic acid" as used herein in the context of the cargo refers to any nucleic acid known to the person skilled in the art, e.g. a polynucleotide like DNA, RNA, single stranded DNA, cDNA, or derivatives thereof. Preferably, the term refers to oligonucleotides and polynucleotides formed of DNA and RNA, and analogs thereof, which have selected sequences designed for hybridisation to complementary targets, such as antisense sequences for single- or double-stranded targets, or for expressing nucleic acid transcripts or proteins encoded by the sequences. The DNA may be provided in the form of, e.g. A-DNA, B-DNA or Z-DNA. Analogs include charged and preferably uncharged backbone analogs, such as phosphonates, methyl phosphonates, phosphoramidates, preferably N-3' or N-5', thiophosphates, uncharged morpholino-based polymers, PNAs, or CNAs, HNAs, LNAs or ANAs. Such molecules can be used in a variety of therapeutic regimens, including, for example, enzyme replacement therapy, gene therapy, or antisense therapy. The RNA may be in the form of, e.g. p-RNA, i.e. pyranosysl-RNA or structurally modified forms like hairpin RNA or a stem-loop RNA. Furthermore, the term refers to antisense RNA. The protein, RNA or ribosome encoded by the nucleic acid may, for example, be underrepresented, defunct or nonexistent in the cell and the antisense RNA encoded by the nucleic acid may allow for the elimination of an undesired function of a molecule. The term "PNA" relates to a peptide nucleic acid, i.e. an artificially synthesized polymer similar to DNA or RNA, which is used in biological research and medical treatments, but which is not known to occur naturally. The PNA backbone is typically composed of repeating N-(2-aminoethyl)-glycine units linked by peptide bonds. The various purine and pyrimidine bases are linked to the backbone by methylene carbonyl bonds. PNAs are generally depicted like peptides, with the N-terminus at the first (left) position and the C-terminus at the right. The term "CNA" relates to an aminocyclohexylethane acid nucleic acid. Furthermore, the term relates to a cyclopentane nucleic acid, i.e. a nucleic acid molecule comprising for example 2'-deoxycarbaguanosine. The term "HNA" relates to hexitol nucleic acids, i.e. DNA analogues which are built up from standard nucleobases and a phosphorylated 1,5-anhydrohexitol backbone. The term "LNA" relates to locked nucleic acids. Typically, a locked nucleic acid is a modified and thus inaccessible RNA nucleotide. The ribose moiety of an LNA nucleotide may be modified with an extra bridge connecting the 2' and 4' carbons. Such a bridge locks the ribose in a 3'-endo structural conformation. The locked ribose conformation enhances base stacking and backbone pre-organization. This may significantly increase the thermal stability, i.e. melting temperature of the oligonucleotide. The term "ANA" relates to arabinoic nucleic acids or derivatives thereof. A preferred ANA derivative in the context of the present invention is a 2'-deoxy-2'-fluoro-beta-D-arabinonucleoside (2'F-ANA). In a further preferred embodiment nucleic acid molecules may comprise a combination of any one of single stranded DNA, RNA, PNA, CNA, HNA, LNA and ANA. In specific embodiments of the present invention the nucleic acid as defined above codes for a protein or peptide of interest, e.g. a therapeutic protein or an immunological active protein, or a diagnostically detectable protein, e.g. a bioluminescent protein, i.e. a protein or peptide which is intended to be delivered to the target cell, i.e. the Langerin$^+$ cell. Such proteins may, in preferred embodiments, be cancer antigens or toxic proteins etc. as defined herein below. Accordingly, the nucleic acid provides elements allowing for the expression of the encoded proteins in a cellular context such as a promoter, a terminator, both operably linked to the gene, or elements allowing an integration into the genome of a cells, or elements allowing for the permanent or transient presence in the nucleus, e.g. as extrachromosomal entity. For example, the nucleic acid may be provided in the form of a plasmid as defined herein below.

The term "colorant" as used herein in the context of the cargo relates to any suitable molecular coloring agent which provides at least the functionality to color or stain a biological element, e.g. a cell or tissue. The colorant may be connected to a carrier structure as defined herein, e.g. a nanoparticle. The colorant may, for example, be linked, e.g. by covalent or non-covalent binding, to said carrier or be transported as cargo, e.g. in liposome carriers, or be connected to a further cargo such as an antigen, small molecule etc. The binding may be optimized so that the chromophore leading to the coloring or staining functionality is not impeded or negatively influenced. Typically, a colorant can act as either a pigment or a dye depending on the vehicle involved. It is preferred that the colorant is a dye.

The term "pigment" as used herein in the context of the cargo relates to any material that changes the color of reflected or transmitted light as the result of wavelength-selective absorption. This physical process differs from fluorescence, phosphorescence, and other forms of luminescence, in which a material emits light. Pigments are typically not soluble in water. In one example, the pigment may be an inorganic substance. Alternatively, the pigment may also be of organic nature. Typically, the pigment may be insoluble in aqueous liquids. In specific embodiments, the pigment may have a size of more than 1 μm. Examples of suitable pigments are heme or porphyrin-based such as chlorophyll, bilirubin, hemocyanin, hemoglobin, myoglobin, carotenoids, hematochromes, Carotenes such as alpha and beta carotene, lycopene, or rhodopsin, xanthophylls such as canthaxanthin, zeaxanthin, or lutein, phytochrome, phycobiliproteins, polyene enolates, melanin, urochrome, flavonoids.

The term "dye" as used herein in the context of the cargo relates to a colored substance which absorbs some specific wavelengths of the visible light, which is typically applied in an aqueous solution. In a typical example, the dye is a water insoluble small molecule. Examples of suitable dyes are acridine dyes, anthraquinone dyes, arylmethane dyes such as diarylmethane dyes, triarylmethane dyes, azo dyers, diazonium dyes, nitro dyes based on the nitro functional group, nitroso dyes base on the nitroso functional group, phtalocyanine dyes, quinone-imine dyes such as eurhodin dyes or safranin dyes, indamins, indophenol dyes, oxazone dyes, thiazine dyes, thiazole dyes, xanthene dyes, fluorene dyes, pyronin dyes, fluorone dyes, or rhodamine dyes. Particularly preferred are fluorescein, rhodamine, phycoerythrin, fluorescamine and rhodopsin.

In certain embodiments, the present invention also envisages the employment of further color providing compounds (e.g. as cargo to be transported to a cell/into a cell) such as chemiluminescent compounds, e.g. luminal, imidazole, bioluminescent proteins, e.g. luciferin, luciferase, green fluorescence protein (GFP), mCherry, mOrange, TagBFP, Cerulean, Citrine, mTurquoise, red fluorescene protein (RFP), yellow fluorescence protein (YFP) and derivatives thereof such as EGFP, ECFP, BFP, EBFP, EBFP2, or BFP. Further color providing compounds which may be used within the context of the present invention include 6-FAM, HEX, TET, ROX, Cy2, Cy3, Cy5, Cy7, Texas Red or Rhodamine, PerCP, Pacific Blue, APC, Alexa 405, 430, 488, 546, 559, 594, 633, 660, 674, 680, 700, Cascade Blue, TAMRA, Dabcyl, Black Hole Quencher, BHQ-1 or BHQ-2.

In certain embodiments, the term also extends to imaging agents. Examples of such imaging agents are diagnostic imaging or contrast agents. Envisaged are, for example, near infra red and photoaccustic agents, e.g. for in vivo applications.

The term "metal" as used herein in the context of the cargo refers to any metal known to the person skilled in the art. Preferably, the term relates to gold, platinum, osmium, silver, iron, lanthanide metals or actinides metals. In a further embodiment the term also relates to a radioactive metal.

The term "radionuclide" as used herein in the context of the cargo refers to a radioactive nuclide or radioactive isotope, which as excess nuclear energy which renders it unstable. The radionuclides may either be alpha emitting radionuclides, beta emitting radionuclides or Auger electron emitting radionuclides. Examples of suitable radionuclides are 3H, 14C, 32P, 33P, 35S, 125I, 11C, 13N, 15O, 18F, 64Cu, 67Cu, 89Sr, 99Tc, 99mTc, 153Sm, 123I, 125I, 129I, 131I, 77Br, 82Rb, 68Ga or 18F, 90Y, 177Lu, 166Ho, 186R$^e$, 188R$^e$, 149Pm, 199Au, and 105Rh. The radionuclides may further be formulated in suitable compositions or be linked to additional molecules or carriers.

The term "virus" as used herein in the context of the cargo relates to any type of virus known to the person skilled in the art. Preferably, a virus is selected from the group consisting of adenoviruses, adeno-associated viruses, herpes viruses, simplex virus, lentiviruses and retroviruses. The term, in particularly preferred embodiments, relates to a virus which is capable of eliciting an immunologic response, e.g. in the form of a vaccine.

The term "modified virus" as used herein in the context of the cargo relates to a virus molecule, which has been altered in comparison to a wildtype virus. Such a modification may preferably lead to a decreased vitality or have influence on binding or interaction capabilities of the virus, as the person skilled in the art would know. A typical example of a modified virus is an attenuated virus as provided in a vaccine.

The term "viral vector" as used herein in the context of the cargo refers to genetic elements derived from viruses, which are modified in such a way as to minimize the risk of handling them. Preferably, the term relates to any such element known to the person skilled in the art. Typically, in viral vectors a part of the viral genome critical for viral replication has been deleted. Preferably, such a virus can efficiently infect cells but, once the infection has taken place, requires a helper virus to provide the missing proteins for production of new virions. Furthermore, viral vectors typically show a low toxicity and are genetically stable and do not rearrange their genomes. More preferably, the term relates to viral genetic elements in accordance with the above definition derived from adenoviruses, adeno-associated viruses, or retroviruses. In particularly preferred embodiments, the viral vector is viral vector for vaccines. Such vectors are generally considered to be safe and typically show attenuation and removal of relevant functionalities. Suitable examples of such viral vectors are vaccinia, fowlpox, measles virus, adenovirus, ALVAC, MVA, poxvirus. Particularly preferred is MVA (Modified vaccinia Ankara).

The term "inoculant" as used herein in the context of the cargo refers to a compound or composition which provides acquired immunity to a specific disease. The inoculant may be, for example, an agent which resembles disease-causing element but is attenuated or provided in a killed or non-infectious form. Also comprised are toxins of microorganisms or parts thereof, surface elements such as proteins or glycoproteins or sugar molecules presented on the surface of a disease-causing element. Furthermore, the inoculant may comprise or be an antigen or an epitope of an antigen of a causes-causing element such as a cancer antigen as defined herein, a bacterial antigen as defined herein, a viral antigen as defined herein, an autoimmune disease antigen as defined herein, or an allergen as defined herein. The inoculant may further be provided in the form of a protein or peptide, or as expression competent nucleic acid, or as any other suitable compound known to the skilled person. Also envisaged is the use of suitable combinations of more than one inoculant, the combination of more than one type of inoculant, e.g. a protein and a nucleic acid. The inoculant may further be combined with suitable additional factors, e.g. in the form of adjuvants or formulated with suitable carriers.

The term "plasmid" as used herein in the context of the cargo refers to any extrachromosomal DNA molecule separate from the chromosomal DNA and capable of autonomous replication. Preferably, the term relates to any such molecule known to the person skilled in the art. More preferably, the term relates to a DNA molecule which is capable of autonomous replication in eukaryotic cells and which encodes a polypeptide of interest, e.g. a therapeutic protein or an immunological active protein, or a diagnostically detectable protein, e.g. a bioluminescent proteins such as GFP or a similar fluorescent protein, e.g. as mentioned herein.

The "multicomponent system" as used herein may refer to any system or kit of components which comprises more than one component. Such 2, 3, 4, 5 or more components may be different cargo types, such as different proteins, different nucleic acids etc., or mixtures of such different cargo types, e.g. a protein and a nucleic acid etc. In further, particularly preferred embodiments, the system comprises components which typically operate together or a required for a certain method to be functional or to achieve a certain goal. Examples of such components are components necessary for genomic editing including specific proteins such as nucleases, RNA elements, DNA inserts or other types of nucleic acids. Such genomic editing approaches may, for example, be the CRISPR/Cas system, a TALEN-based system, a zinc finger nuclease (ZFN)-based system, a meganuclease-based system, a system based on Cre or FLP recombinase and lox r FRT sites. The multicomponent system may, for example, be provided in the form of already expressed or ready to use components. Alternatively, the system may be provided in the form of encoded components, e.g. provided on a plasmid or transcript, requiring a cellular machinery to express and thus provide the elements necessary for its operation. The present invention specifically envisages the use of a DRACO based system, i.e. a system based on double-stranded RNA activated caspase oligomerizers. Particularly preferred is the use of the CRISPR (Clustered Regularly Interspaced Short Palindromic Repeats)/Cas system. CRISPR/Cas can be utilized to reduce expression of specific genes (or groups or similar genes) or to edit genomic sequences. This is typically achieved through the expression of single stranded RNA in addition to a CRISPR gene or nuclease. The technique typically relies on the expression of a CRISPR gene such as Cas9, or other similar genes in addition to an RNA guide sequences (see, for example, Cong et al. 2013, Science, 339, 6121, 819-823). Double stranded cleavage may accordingly be targeted to specific sequences using the expression of appropriate flanking RNA guide sequences, which may be provide as one component of the multicomponent system, e.g. together with Cas9 or a similar functionality. Alternatively, the CRISPR/Cas system may be used to cleave mRNA, thereby reducing expression. In a preferred embodiment RNA guide sequences and CRISPR gene expression (e.g. Cas9) may be included as part of an expression construct. The CRIPR/Cas system may accordingly comprise the necessary nucleic acids and enzymatic components to be provided as cargo.

The term "TALEN-based system" relates to the use of TALEN, i.e. the Transcription Activator-Like Effector Nuclease, which is an artificial restriction enzyme, generated by fusing the TAL effector DNA binding domain to a DNA cleavage domain. TAL effectors are proteins which are typically secreted by *Xanthomonas* bacteria or related species, or which are derived therefrom and have been modified. The DNA binding domain of the TAL effector may comprise a highly conserved sequence, e.g. of about 33-34 amino acid sequence with the exception of the 12th and 13th amino acids which are highly variable (Repeat Variable Diresidue or RVD) and typically show a strong correlation with specific nucleotide recognition. The TALEN DNA cleavage domain may be derived from suitable nucleases. For example, the DNA cleavage domain from the FokI endonuclease or from FokI endonuclease variants may be used to construct hybrid nucleases. TALENs may preferably be provided as separate entities due to the peculiarities of the FokI domain, which functions as a dimer. TALENs or TALEN components may preferably be engineered or modified in order to target any desired DNA sequence. Such engineering may be carried out according to suitable methodologies, e.g. Zhang et al., Nature Biotechnology, 1-6 (2011), or Reyon et al., Nature Biotechnology, 30, 460-465 (2012). The TALEN-based system may accordingly comprise the necessary nucleic acids, e.g. as genomic inserts or guiding sequences and enzymatic components to be provided as cargo.

The term "zinc finger nuclease (ZFN)-based system" as used herein refers to a system of artificial restriction enzymes, which are typically generated by fusing a zinc finger DNA-binding domain to a DNA-cleavage domain. Zinc finger domains may preferably be engineered or modified in order to target any desired DNA sequence. Such engineering methods would be known to the skilled person or can be derived from suitable literature sources such as Bae et al., 2003, Nat Biotechnol, 21, 275-80; Wright et al., 2006, Nature Protocols, 1, 1637-1652.) Typically, the non-specific cleavage domain from type IIs restriction endonucleases, e.g. from FokI, may be used as the cleavage domain in ZFNs. Since this cleavage domain dimerizes in order to cleave DNA a pair of ZFNs is typically required to target non-palindromic DNA sites. ZFNs envisaged by the present invention may further comprise a fusion of the non-specific cleavage to the C-terminus of each zinc finger domain. For instance, in order to allow two cleavage domains to dimerize and cleave DNA, two individual ZFNs are typically required to bind opposite strands of DNA with C-termini provided in a specific distance. It is to be understood that linker sequences between the zinc finger domain and the cleavage domain may requires the 5' terminus of each binding site to be separated by about 5 to 7 bp. The present invention envisages any suitable ZNF form or variant, e.g. classical FokI fusions, or optimized version of the FokI, as well as enzymes with modified dimerization interfaces, improved binding functionality or variants which are able to provide heterodimeric species. The zinc finger nuclease (ZFN)-based system may accordingly comprise the necessary nucleic acids, e.g. as genomic inserts or guiding sequences, and enzymatic components to be provided as cargo.

The term "meganuclease-based system" relates to a system using endodeoxyribonucleases, which typically have a recognition site in the form of a double-stranded DNA sequences of about 12 to 40 nucleotides. Meganucleases typically work as molecular DNA scissors, which provide the possibility of eliminating or modifying sequences in a sequence specific manner. Examples of suitable meganucleases include intron endonucleases and intein endonucleases. The recognition sequence of a meganuclease may be modified by genetic or protein engineering in order to target any desired DNA sequence. In order to provide a sequence specificity, the specificity of existing meganucleases may be modified by introducing a variation to the amino acid sequence, followed by the selection of functional proteins. Alternatively, protein domains from different enzymes may be fused to the nucleases, resulting in chimeric meganucleases. Such chimeric meganucleases may have, for example, a new recognition site composed of a half-site of a meganuclease and a half-site of a protein. In further embodiments, both approaches may be combined, i.e. the modification of the binding sequence of the meganuclease and the fusion to a protein domain from a different enzyme. Further details, in particular with regard to the possibilities of engineering meganucleases can be derived from suitable literature sources such as Gao et al., 2010, The Plant Journal for Cell and Molecular Biology, 61, 176-87. The meganuclease-based system may accordingly comprise the necessary nucleic acids, e.g. as genomic inserts or guiding sequences, and enzymatic components to be provided as cargo.

The term "Cre-lox system" as used herein relates to the combination of Cre recombinase and its respective recognition sites (lox sites). Alternatively, the system may be composed of FLP recombinase and its respective recognition sites (FRT sites). By providing the recognition sites in a direct repeated manner a deletion of sequences between the repeats can be achieved. Similarly, by providing other orientations or more than two recognition sites further rearrangement pattern may become possible, e.g. an inversion of the sequences. Further details may be derived from Ryder et al., 2004, Genetics, 167, 797-813 or Ito et al., 1997, Development, 771, 761-771.

In further preferred embodiments, the cargo may be a pharmaceutically or immunologically active compound. The term "pharmaceutically active compound" as used herein relates to any suitable substance, medicament, drug, cellular component, tissue, or active pharmaceutical ingredient (API) known to the skilled person. These compounds may comprise therapeutic proteins as defined above, radionuclides as defined above, cytotoxic substances as defined above, small molecules as defined above, peptide or protein inhibitors as defined above. In a particularly preferred embodiment, the pharmaceutically active compound is an inhibitor of cellular function. The term "inhibitor of cellular function" as used herein relates to any organic molecule, peptide or polypeptide which has an inhibitory effect on physiological functions, preferably on protein function like enzymatic functions. The inhibition may, for example be a decrease in the activity of an enzyme, as compared to the activity of the enzyme in the absence of the inhibitor. In some embodiments, the term "inhibit" thus means a decrease in enzyme activity of at least about 5%, at least about 10%, at least about 20%, at least about 25%, at least about 50%, at least about 60%, at least about 70%, at least about 80%, at least about 90%, or at least about 95%. In other embodiments, "inhibit" means a decrease in enzyme activity of about 5% to about 25%, about 25% to about 50%, about 50% to about 75%, or about 75% to 100%. Also envisaged is a decrease in enzyme activity of about 95% to 100%, e.g., a decrease in activity of 95%, 96%, 97%, 98%, 99%, or 100%. Such decreases can be measured using any suitable method or assay known to the skilled person would be recognizable by one of skill in the art.

Examples of such inhibitors are protease inhibitors, e.g. ritonavir, HIV protease inhibitor tipranavir, or sildenafil. Further particularly preferred are inhibitors of apoptosis. Examples of apoptosis inhibitors include proteins of the Bcl-2 family such as Bcl-2, Bcl-XL, or Bcl-w. Further examples include crmA (cytotoxin response modifier A), which may be used to inhibit caspase 1, 6, and 8. Also contemplated is the use of IAPB (inhibitors of apoptosis proteins), including Cp-IAP, Op-IAP, XIAP, cIAP1, C-IAP2, NAIP, Livin and Survivin.

The term "immunologically active compound" as used herein relates to any compound, which is capable eliciting an immunological reaction in the body. In further embodiments, it may alternatively be capable of immunomodulation. Also envisaged is that the immunologically active compound is an immunological tolerance inducer.

The term "compound capable of eliciting an immunological reaction in the body" as used herein relates to any substance or part of a substance which is recognized by elements of an animal's, preferably a mammal's, most preferably the human immune system and which leads to an activation of the innate immune system or the adaptive immune system.

Typical components of the innate immune system are the complement system or natural killer cells. The complement system comprises a cascade of more than 20 proteins, which are able to destroy pathogens by antibodies. The response is typically activated by complement binding to antibodies that have attached to pathogens or the binding of complement proteins to carbohydrates on the surfaces of foreign elements, e.g. bacteria or viruses. The complement system additionally comprises proteases which are capable of destroying foreign elements such as cells, parasites or part thereof (e.g. eggs), bacteria or viruses. A further consequence of complement activation is the production of signal peptides which attract additional immune cells. Natural killer (NK) cells are lymphocytes which typically destroy compromised host cells, e.g. cancerous cells or virus-infected cells. It is assumed that these cells show no self recognition by the immune system and are hence targetable by the NK cells. Such cells, e.g. cells being infected by viruses, may show a decreased number of MHC I cells at their surface which is apparently detected by the NK cells. The NK cells can be found in all primary and secondary immune compartments, as well as in mucosal tissues. They may additionally produce pro-inflammatory cytokines such as interferon-gamma. NK cells may, in particularly preferred embodiments, be activated in order to destroy cancerous cells. They may advantageously be used to communicate with other immune cells such as DCs, NKT cells or T cells, which may lead to an adaptive immune response in cancer. Without wishing to be bound by theory, it is believed that NK cells and DCs are in close communication. DC-mediated activation of NK cells typically contributes to the development of potent innate immunity, whereas, in turn, activated NK cells provide signals for DC activation, maturation, and cytokine production, promoting adaptive immunity. The provision of DC-derived exosomes (Dex), or the activation of DCs may particularly result in an activation of NK cells, thus allowing to destroy diseased cells, in particular cancer cells. Further details would be known to the skilled person or can be derived from suitable literature sources such as Lion et al., 2012, The Oncologist, 17, 1256-1270. Typically, Langerin$^+$ cells suppress NK cell fusion. According to specific embodiments of the present invention the activation of Langerin$^+$ cells, e.g. by delivering suitable cargoes to said cells which allow for such activation, may be used to activate NK cells and/or to contribute to said activation.

The adaptive immune system, on the other hand, is primarily based on the activity of specialized leukocytes, i.e. lymphocytes, namely B cells and T cells. The B cells are typically involved in humoral immune responses, whereas T cells are involved in cell-mediated immune responses. Both, B- and T cells comprise T-cell receptor (TCR) molecules which recognized specific targets being processed and subsequently presented on MHC molecules, which can be provided or expressed by all host cells. The T cells may be differentiated into cytotoxic T cells (CTLs) also known as CD8$^+$ T cells or killer T cells and helper T cells, as well as regulatory T cells. Antigens inside a cell are typically bound to class I MHC molecules, and brought to the surface of the cell by the class I MHC molecule, where they can be recognized by the T cell. If the TCR is specific for that antigen, it binds to the complex of the class I MHC molecule and the antigen, and the T cell destroys the presenting cell. MHC I molecules can be found on the surface of all nucleated cells. Class I MHC molecules typically bind peptides generated mainly from degradation of cytosolic proteins by the proteasome. The MHC I:peptide complex is subsequently inserted via endoplasmic reticulum into the external plasma membrane of the cell. The epitope peptide is bound on extracellular parts of the class I MHC molecule. Thus, the function of the class I MHC is believed to be mainly to display intracellular proteins to cytotoxic T cells (CTLs). In addition, class I MHC can also present peptides generated from exogenous proteins via cross-presentation, which is the ability of certain antigen-presenting cells, e.g. DCs, to take up, process and present extracellular antigens with MHC class I molecules to cytotoxic CD8$^+$ T cells. Cross-priming, the result of this process, describes the stimulation of naive cytotoxic CD8$^+$ T cells into activated cytotoxic CD8$^+$ T cells. This process may lead to immunity against tumors and viruses. Cross presentation may also advantageously be for the induction of cytotoxic immunity, e.g. by vaccination with protein antigens, for example, tumour vaccination as described herein. MHC I molecules typically bind peptides that are 8-10 amino acid in length.

Helper T cells (also known as CD4$^+$ T cells) and regulatory T cells (also known as Treg cells or suppressor T cells), on the other hand, recognize antigens which are coupled to class II MHC molecules. MHC II molecules are typically only found on antigen presenting cells (APCs), such as dendritic cells, mononuclear phagocytes, thymic epithelial cells or B cells. The loading of MHC class II molecules typically occurs in lysosomal compartments. For example, extracellular proteins may be endocytosed, digested in lysosomes and epitopic peptide fragments can be bound to MHC II molecules. Typically, MHC II molecules present antigens of a length of between about 15 to 24 amino acids.

In accordance with the present invention, any of the above described activities may be elicited by a suitable compound, e.g. an antigen, or an epitope. The length of the antigen, its cell compartment presence etc. may modulate the presentation on MHC I or MHC II molecules and thus also modulate the activation of certain branches of the immune system. For cancer and viral therapy, it is particularly preferred that a close interaction of the innate and adaptive immune system be elicited, e.g. via activation of the DCs. Further details may be derived from suitable literature sources such as Ortner et al., Oncoimmunology, 2017, 6, 2, e1260215; Watt et al., 2008, J Immunol., 181, 8, 5323-30 or Walzer et al., 2005, Blood, 106, 7, 2252-8.

The term "compound capable of immunomodulation" as used herein relates to any substance or part of a substance which conveys a regulatory adjustment of the immune system. Accordingly, immune responses can be induced, amplified, attenuated or prevented according to therapeutic goals. The immunomodulation may, thus, for example be an activation (for instance in the form of an activation immunotherapy), immune response is elicited or amplified, or it may be a suppression (for instance in the form of a suppression immunotherapy).

Examples of compounds capable of activating immunomodulation include stimulating factors such as granulocyte colony-stimulating factor (G-CSF), cytokines, interleukins, chemokines, Immunomodulatory imide drugs (IMiDs) synthetic cytosine phosphate-guanosine (CpG) oligodeoxynucleotides or glucans or an immune enhancement cream such as imiquimod. Preferred examples of suitable interleukins are IL-2, IL-7 and IL-12. Preferred examples of cytokines ae interferons and G-CSF. Preferred examples of suitable chemokines are CCL3, CCL26 and CXCL7. Preferred examples of suitable IMiDs are thalidomide and analogues thereof such as lenalidomide, pomalidomide and apremilast.

Examples of compounds capable of suppressive immunomodulation include immunosuppressive drugs such as glucocorticoids, cytostatics, antibodies, compounds acting in immunophilins. Preferred examples of suitable glucocorticoids are prednisone, dexamethasone and hydrocortisone. Glucocorticoids typically suppress cell-mediated immunity, e.g. by inhibiting genes that code for the cytokines IL-1, IL-2, IL-3, IL-4, IL-5, IL-6, IL-8, and TNF-alpha, wherein a reduction of cytokine production leads to decrease in the T cell proliferation. Glucocorticoids may also suppress humoral immunity, e.g. by causing B cells to express smaller amounts of IL-2 and IL-2 receptors, which decreases B cell clone expansion and antibody synthesis. Preferred examples of suitable cytostatics are alkylating agents such as nitrogen mustards, e.g. cyclophosphamide, nitrosoureas, platinum compounds. Other examples include antimetabolites such as folic acid analogues, e.g. methotrexate, purine analogues, e.g. azathriopine or mercaptopurine, pyrimidine analogues such as fluorouracil. In a further group of suitable examples are cytotoxic antibiotics such as dactinomycin, anthracycline, mitomycin C, bleomycin or mithramycin. Preferred examples of suitable antibodies include heterologous polyclonal antibodies, e.g. obtained from serum of animals such as horses immunized with human thymocytes or lymphocytes. Examples of polyclonal antibody preparations envisaged by the present invention include atgam and thymoglobuline. Also envisaged are monoclonal antibodies against CD25 and CD3. Preferred examples of suitable compounds acting on immunophilins are ciclosporin, tacrolimus, sirolimus and everolimus. Further compounds which are capable of suppressive immunomodulation are fingolimod, myriocin, mycophenolate, TNF-alpha binding molecules such as cell penetrating variants of infliximab, etanercept or adalimumab. Particularly envisaged specific examples include ciclosporin (which binds to cytosolic protein cyclophilin of lymphocytes and thereby inhibits calcireurin), tacrolimus (which is an intracellular calcineurin inhibitor), sirolimus and everolismus (which inhibit IL-2 production via mTOR by binding to cytosolic FK-binding protein 12 thereby blocking activation of T and B cells), fingolimod (which causes internalization of sphingosine-1-phosphate receptors and sequesters lymphocytes in lymph nodes), myriocin and mycophenolate (which provides a-selective inhibition of inosinmonophosphat-dehydrogenase and leads to the inhibition of biosynthesis of guanosin, thereby inhibiting proliferation of B- and T-lymphocytes).

The term "immunological tolerance inducer" as used herein relates to a compound which is capable of inducing a state of unresponsiveness of the immune system to substances or tissues which typically have the capacity of eliciting an immune response in an organism. Immunological tolerance may either be central tolerance or peripheral tolerance. A central tolerance is typically induced in the thymus or bone marrow, whereas a peripheral tolerance is induced in the lymph nodes. In the context of the present invention, the induction of central tolerance is preferred. Peripheral tolerance is believed to be responsible for the prevention of over-reactivity of the immune system to various environmental entities such as allergens or intestine microbes. Malfunction of the tolerance system typically leads to autoimmune diseases such as systemic lupus erythematosus, rheumatoid arthritis, type 1 diabetes, autoimmune polyendocrine syndrome type 1 (APS-1), immunodysregulation, polyendocrinopathy, or enteropathy and is assumed to contribute to asthma, allergy, and inflammatory bowel disease. The tolerance system is also pivotal to transplantations and allografts. Furthermore, allergy and hypersensitivity reactions are typically considered as misguided or excessive reactions by the immune system, possibly due to broken or underdeveloped mechanisms of peripheral tolerance. Typically, Treg cells, TR1, and Th3 cells at mucosal surfaces suppress type 2 CD4 helper cells, mast cells, and eosinophils, which mediate allergic response. Deficits in Treg cells or their localization to mucosa may play a role in allergic reactions. Dendritic cells (DCs) are assumed to be an important player in peripheral tolerance. DCs are widely present in the peripheral non-lymphatic tissues, e.g. the skin and lymphatic tissues in a variety of subsets of different differentiation lineages and levels of maturity, in particular as Langerin$^+$ cells. In the steady state, i.e. in a non-inflammatory state, the majority of dendritic cells remain immature, and upon weak antigenic stimulation and antigen presentation that may provide costimulation, immature dendritic cells typically induce clonal deletion and inactivation of naive T cells, while inducing and amplifying various regulatory T cells having immunosuppressive capacity. Accordingly immature dendritic cells are assumed to play a role in the maintenance of immunological homeostasis via induction of immune tolerance associated with regulatory mechanisms controlling T cell function. The employment of cytokines including at least IL-10 and TGF-beta may lead to tolerogenic DCs. Furthermore, the triggering of the surface expression of CD80high, CD86high, CD40high and CD83low may be used to induce tolerance. Also envisaged is the use of an IL-10 production promoting agent such as dexamethasone. In a further embodiment, the induction immunotolerance may be achieved by the use of 5-aminolevulinic acid (ALA) or derivatives thereof, as well as the use of sodium ferrous citrate (SFC). Further details may be derived from suitable literature sources such as U.S. Pat. No. 9,399,029. It is particularly preferred that the immunotolerance inducing compound is used in or for Langerin$^+$ cells as described herein, as well as in the context of medical conditions involving Langerin$^+$ cells.

In a further preferred embodiment of the present invention cargo as mentioned above comprises, essentially consists of or consists of (i) a cancer antigen or epitope or comprises a cancer antigen or epitope (ii) an autoimmune disease antigen or epitope or comprises an autoimmune disease antigen or epitope, (iii) a bacterial antigen or comprises a bacterial antigen or epitope, (iv) a viral antigen or comprises a viral antigen or epitope, (v) a parasitic antigen or comprises a parasitic antigen or epitope, or (vi) an allergen, or an epitope of an allergen, or comprises an allergen or an epitope of an allergen.

The term "cancer antigen" as used herein relates to antigenic substances produced in tumor cells. The term may thus typically also include cellular antigens as mentioned above. These antigenic substances may alternatively also be named "tumor antigens". These antigens typically trigger immune responses in the host. Without wishing to be bound by theory, it is currently believed that normal proteins in a body (i.e. proteins produced by the host itself) are not antigenic due to self-tolerance of the immune system, a concept in which autoreactive lymphocytes are deleted before they develop into fully immunocompetent cells. Other proteins which are not exposed to the immune system may trigger an immune response. This may include proteins which are sequestered from the immune system, proteins which are normally produced in very small quantities (but are produced, for example, in a much higher amount in cancerous cells), or proteins which are produced typically only during certain stages of the cellular/organism's development, or proteins whose structure or function is changed due to the presence of a mutation. Accordingly, the cancer antigens may be classified into different groups, e.g. as products of mutated oncogenes and tumor suppressor genes, products of other mutated genes such as (i) overexpressed or aberrantly expressed cellular proteins, (ii) cancer antigens produced by oncogenic viruses, (iii) oncofetal antigens, (iv) altered cell surface glycolipids and glycoproteins, and (v) cell type-specific differentiation antigens. In further specific embodiments, the antigen may be a tumor-specific antigen, which is an antigen that is produced by a mutation to a gene coding for a protein whose abnormal production is the cause of a cancer or tumor. An envisaged example of such tumor-specific antigens is an abnormal form of p53 or ras. Alternatively, if a mutation is unrelated to the tumor development, but lead to the production of an abnormal protein which is associated with the cancerous cells, it is considered as tumor-associated antigen (TAA). Also, this group of antigens is envisaged to be a part of the cargo according to the present invention. The group of TAAs is typically subdivided into the group of shared TAAs and unique TAAs. Among the shared TAAs are antigens which are shared by several classes of cancers, whereas unique TAAs are believed to result from random somatic point mutations included by carcinogens, thus constituting neo-antigens unique expressed by individual tumors. The presence of such unique TAAs may be advantageously be used for the preparation of specific antigen cargos, e.g. in the format of a vaccine, which are based on a personal genomic sequence obtained via next-generation sequencing approaches, providing information on the patient's mutanome and potentially offering information on unique mutated peptides associated with cancer, which can be used for the elicitation of anti-tumor T cells when presented as antigens.

The present invention preferably envisages the use of one or more of the following cancer antigens: MAGE-A1, NY-ESO-1, SSX-2, Gp-100, MeIan-A/Mart-1, Tyrosinase, PSA, Mammaglobin-A, URLC10, GAA, OFA, cyclin B1/WT-1/CEF, VEGFR1, VEGFR2, TTK, MUC1-KLH, HER2, HPV16 E7, HPV16/18, CEA, KOC1, SL-701, WT1, p53, survivin, telomerase, GSK2302025A, MAGE-3.1, OVA BiP, CO16, DEPDC1, MPHOSPH1, ONT-10, GD2L and GD3L, TF, rsPSMA, MUC-2, PAP; KLH, STF-II, G17DT, ICT-107, LMP2A, NA17-A, NA17.A2, IMA901, hTERT, tyrosinase-related peptide 2 (TRP2), PANVAC, EBNA1/LMP2, TRICOM 5T4, MPHOSPH1 and DEPDC1. Furthermore, the present invention also relates to any combinations of the above-mentioned antigens, as well as derivatives or modified versions thereof or homologous protein/peptide sequences derived therefrom. Also envisaged is the employment of additional cancer antigens which may be discovered and described in the future. Also envisaged is the use of any other suitable antigen as known to the skilled person. Further details may be derived from Tagliamonte et al., 2014, Hum Vaccin Immunother, 10(11), 3332-3346. The term "cancer epitope" as used herein relates to a specific epitope of the MHC I or MHC II class present in a cancer antigen, e.g. as defined herein above. The employment of cancer epitopes may, in specific embodiments, be combined with the additional characterization of a recipient's HLA allele background.

Particularly preferred is the employment of the cancer antigens NY-ESO-1, URLC10, G17DT, MART-1; NA17-A; gp100; hTERT, PAP, MPHOSPH1, DEPDC1, HPV16/18 or STF-II, or of epitopes present on these antigens.

The term "autoimmune disease antigen" as used herein relates to an antigenic substance which leads to inappropriate immune responses that attack either self-tissues or innocuous environmental components. The autoimmune disease is thus typically, in most cases, a condition arising from abnormal immune responses to a normal body part, wherein almost all body parts may be involved. The disease involves the appearance or presence of a reservoir of self-reactive cells that become functional within the immune system, i.e. in these cases the mechanisms of preventing self-reactive T cells from being created by negative selection process within the thymus as the T cell is developing into a mature immune cell fails. The disease involves the presence of autoantibodies as well as autoreactive lymphocytes, e.g. self-reactive T cells. The disease may be restricted to certain organs or involve a particular tissue in different places. The use of autoimmune disease antigens in the context of the present invention involves the induction of immune tolerance against said antigens, e.g. as described herein above. In specific embodiments of the present invention migratory immature Langerin$^+$ cells may be used for the induction of immune tolerance. In particular, a presentation as mentioned above may subsequently generate an immunological tolerance effect for said antigen if the DC is not activated. Accordingly, it is envisaged by the present invention, that a treatment of an autoimmune disease antigen comprises the cytosolic delivery of an antigen leading to the subsequent presentation of it to effector immune cells and the explicit absence of a component, which may lead to an activation of DCs such as activation through an adjuvant. Without wishing to be bound by theory, it is believed that the presentation of antigens to DCs, e.g. via cytosolic delivery, will lead to an MHC I based presentation of said antigen. Such a presentation may subsequently generate an immunological tolerance effect for said antigen if the DC is not activated. Accordingly, is is envisaged by the present invention that a treatment of an autoimmune disease antigen comprises the cytosolic prevision of an antigen and the explicit absence of a component which may lead to an activation of DCs such as an adjuvant.

Autoimmune diseases for which antigens may be provided in the form of cargos include, for example, Antiphospholipid-Syndrome (aPL syndrome), Pemphigus, Multiple Sclerosis (MS), Myasthenia gravis, Grave's disease, Goodpasture's syndrome, Microscopic angiitis, Granulomatosis with polyangiits, Systemic Autoimmune Rheumatic Diseases (SARD), Mixed Connective Tissue Disease, Systemic Lupus Erythematosus, Sjøgrens Syndrome, Systemic Sclerosis/CREST Syndrome, Polymyositis/Dermatomyositis, Autoimmune Thyroid Diseases, Celiac Disease, Autoimmune Hepatitis, Primary Biliary Cirrhosis, ANCA Associated Diseases, Antiphospholipid Syndrome/Thromboembolic Syndrome, Anti-GBM Disease, Diabetes Mellitus, Pernicious Anemia, or Crohn's Disease. Suitable antigens would be known to the skilled person or can be derived form literature sources such as Wang et al., Nucleic Acids Research, 2017, 45, D1, D769-D776. In particular embodiments, the present invention envisages the use of corresponding antigens such as beta2-GP1 for aPL syndrome, Dsg3 for Pemphigus, MBP, PLP and/or MOG-1 for Multiple Sclerosis, ACh receptor for Myasthenia gravis, TSH receptor for Grave's disease, Type IV collagen for Goodpasture's syndrome, p-ANCA for Microscopic angiitis, c-ANCA for Granulomatosis with polyangiits, DFS70 or lens epithelium-derived growth factor/transcription coactivator p75

(LEDGF/p75) for Systemic Autoimmune Rheumatic Diseases (SARD), U1-snRNP 68/70, U1-snRNP A, U1-snRNP C or U-snRNP B/BT for Mixed Connective Tissue Disease, Sm, RNP/Sm, SmD, SmD1, SmD2, SmD or ribosomal phosophoprotein PO for Systemic Lupus Erythematosus, Ro/SS-A, or La/SS-B for Sjøgrens Syndrome, Centromere Protein B (CENP-B), Centromere Protein A (CENP-A), DNA Topoisomerase I (Scl-70) for Systemic Sclerosis/CREST Syndrome, Histidyl-tRNA synthetase (Jo-1), Threonyl-tRNA synthetase (PL-7), Alanyl-tRNA synthetase (PL-12), Glycyl-tRNA synthetase (EJ) or SRP54 for Polymyositis/Dermatomyositis, thyroid peroxidase (TPO; syn. MSA), thyroglobulin Autoimmune Thyroid Diseases, Tissue transglutaminase (tTG; syn. TGase-2 or Gliadin for Celiac Disease, Cytochrome p450 2D6, formiminotransferase cyclodeamidase (FTCD) for Autoimmune Hepatitis, M2, Branched chain 2-oxo acid dehydrogenase complex (BCOADC), OGDC-E2, or PDC-E2 Primary Biliary Cirrhosis, Myeloperoxidase (MPO) or Proteinase 3 (PR3) for ANCA Associated Diseases, beta2-glycoprotein 1 (beta2-GP1), formerly known as Apolipoprotein H (Apo H) for Antiphospholipid Syndrome/Thromboembolic Syndrome, glomerular basement membrane (GBM) for Anti-GBM Disease, glutamate decarboxylase (GAD65) for Diabetes Mellitus, intrinsic factor for Pernicious Anemia, or Glycoprotein 2 (GP2) for Crohn's Disease. Further envisaged are autoimmune disease epitopes present on an antigen, preferably as defined above. The term "autoimmune disease epitope" as used herein relates to a specific epitope of the MHC I or MHC II class present in an autoimmune disease antigen as defined herein above. The employment of autoimmune disease epitopes may, in specific embodiments, be combined with the additional characterization of a recipient's HLA allele background.

The term "bacterial antigen" as used herein relates to an antigenic substance produced or presented by a bacterium. Bacterial antigens may, for example, be carried by proteins and polysaccharides, or lipids. They may include coats, capsules, cell walls, flagella, fimbriae or toxins of bacteria. Typically, such substances are displayed at the surface of bacteria. In many cases carbohydrates in the form of capsular polysaccharides and/or lipopolysaccharides are major components on the surface of bacterial and may accordingly be seen as antigenic structures. It is also envisaged that such polysaccharides and/or lipopolysaccharides be mimicked by peptides or proteins, which accordingly provide the relevant antigen or epitope. The present invention envisages any suitable bacterial antigen known to the skilled person. It is preferred that the bacterial antigen or the bacterial epitope is, comprises or is derived from tetanus toxoid, diphtheria toxoid, a *Neisseria meningitidis* polysaccharide or *Bordetella pertussis* in acellular form. For example, the bacterial antigen or epitope is a T cell epitop derived from an antigen present in CRM, tetanus toxoid, diphtheria toxoid, *Neisseria meningitidis* outer membrane complex, or *Hemophilus influenzae* protein D. Further examples and details may be derived from suitable literature sources such as Detmer and Glenting, 2006, Microbial Cell Factories, 5, 23.

The term "viral antigen" as used herein relates to antigenic substances produced by viruses. The viral antigen is typically a protein or peptide element, which is usually encoded by the virus genome. It may be presented on the surface of the virus, e.g. as a coat or envelop or part of it, or be an integral part of the virus core or of other viral structures, which may, for example be presented by cells after viral disintegration in the interior of a cell. Examples of viral antigens include viral structural elements such as a capsid protein, a matrix protein, an envelop protein etc., as well as non-structural proteins such as holins, movement proteins, NS proteins, e.g. NS2, NSP1 etc., or enzymatic activities encoded by viruses such as integrase, reverse transcriptase, neuraminidase, esterase etc. Preferred antigens are derived from hepatitis A virus (heat whole virus inactivated), hepatitis B, and human papilloma virus (HPV). Particularly preferred is the HepB-surface antigen. Also envisaged is the use of viral epitops. The term "viral epitope" as used herein relates to a specific epitope of the MHC I or MHC II class present in a viral antigen as defined herein above. The employment of viral epitopes may, in specific embodiments, be combined with the additional characterization of a recipient's HLA allele background. Further information may be derived from suitable internet resources.

The term "parasitic antigen" as used herein, relates to antigenic substances produced by or presented on parasites. The term "parasite" relates to parasites of mammals, preferably parasites of humans. Parasites typically belong to protozoa or metazoan. The major parasitic groups are parasitic protozoa and parasitic helminths. Protozoa are unicellular eukaryotes. Parasitic protozoa are typically divided into four groups based on their means of locomotion and mode of reproduction: flagellates, amebae, sporozoa, and ciliates. Within the group of flagellates there are intestinal and genitourinary flagellates such as *Giardia* and *Trichomonas*, as well as blood and tissue flagellates such as *Trypanosoma* and *Leishmania*. Examples of amebae include *Entamoeba, Naegleria*, and *Acanthamoeba*. The group of Sporozoa typically undergo a complex life cycle with alternating sexual and asexual reproductive phases and includes *Cryptosporidium, Cyclospora*, and *Toxoplasma* and the malarial parasites, i.e. *Plasmodium* species. This Sporozoa are typically intracellular parasites. Ciliates are complex protozoa bearing cilia. An example of this group is *Balantidium coli*, an intestinal ciliate of humans and pigs. Parasitic helminths usually belong to the groups of nematode and plathelminthes. Examples of plathelminthes include trematodes, such as *Fasciola hepatica*, or cestoda such as *Taenia*. Also envisaged are *Schistosoma* or Filarial parasites such as *Wuchereria bancrofti* or *Onchocerca volvulus*. The present invention envisages antigens of any of the above-mentioned parasites or any other suitable parasite known to the skilled person. In specific embodiments, the antigen may be present in certain life cycle forms, e.g. on eggs. Particularly preferred is the employment of malaria antigens, e.g. protein structures displayed by *Plasmodium* during one of its life cycle forms such as cysteine-Rich Protective Antigen (CyRPA) which is a crucial component of a ternary complex, including Reticulocyte binding-like Homologous protein 5 (RH5) and the RH5-interacting protein (Ripr). The term "parasitic epitope" as used herein relates to a specific epitope of the MHC I or MHC II class present in a parasitic antigen as defined herein above. The employment of parasitic epitopes may, in specific embodiments, be combined with the additional characterization of a recipient's HLA allele background. Further information may be derived from suitable literature sources such as Tarleton, 2005, Cellular Microbiology, 7, 10, 1379-1386 or Higashi, 1988, Ann Rev Public Health, 9, 483-501.

The term "allergen" as used herein relates to antigenic substances capable of stimulating a type-I hypersensitivity reaction in atopic individuals through Immunoglobulin E (IgE) responses. Accordingly, the allergen is a type of antigen that produces an abnormally vigorous immune response in which the immune system defends the organism against a perceived threat that would otherwise be harmless to the body. Within the context of the present invention, the allergen is mainly understood to comprise a protein or peptide. Allergens can be found in a variety of sources, including dust mite excretion, pollen, or pet dander. They can also be found in food such as peanuts, nuts, seafood or shellfish. A list of allergenic proteins, which is incorporated herein by reference, can be found at the SDAP (structural database of allergenic proteins), which can be found at http://fermi.utmb.edu. All allergens mentioned in said database are envisaged by the present invention. Also envisages are any other allergen known to the skilled person. The term "epitope of an allergen" as used herein relates to a specific epitope of the MHC I or MHC II class present in an allergen as defined herein above. The employment of epitopes of an allergen may, in specific embodiments, be combined with the additional characterization of a recipient's HLA allele background. Further information would be known the skilled person or can be derived from suitable literature sources such as the "Opinion of the Scientific Panel on Dietetic Products, Nutrition and Allergies on a request from the Commission relating to the evaluation of allergenic foods for labelling purposes" as published in The EFSA Journal, 2004, 32, 1-197.

In a further embodiment of the present invention, the vehicle may have an average size from about 1 to 2000 nm, preferably from about 1 to 1000 nm. The "size of the vehicle" as used herein relates to either the combination of the conjugate as defined herein and an unloaded or empty carrier as defined herein, or to the combination of the conjugate as defined herein and a carrier comprising or associated with a cargo as defined herein. The size of the vehicle largely depends on the nature and form of the carrier, e.g. a liposome or nanoparticle or a protein etc. It may hence be in the range of 1 nm to 100 nm, or in the range of about 100 nm to 250 nm, or in the range of 250 nm to 1000 nm, or in the range of 1000 to 2000 nm. The size of the vehicle is advantageously adapted to the use intended for the vehicle, and/or the form and nature of the carrier included in the vehicle. For example, the vehicle may be used in nanosize range, which allows for efficient uptake by a variety of cell types and selective drug accumulation at target sites. Further information in this respect may be known to the skilled person or can be derived from suitable literature sources such as Desai et al., 1997, Pharm Res. 14, 1568-73 or Panyam and Labhasetwar, 2003, Adv Drug Del Rev. 55:329-347. In further embodiments it is envisaged that the size of the vehicles is adapted to the dimension of bloodstream. Accordingly, the vehicle may have a size of less than 5 µm, which allows for the avoidance of aggregation formation and the reduction of risk for developing embolism. The size of the vehicle may, in a preferred embodiment, may preferably be measured in an aqueous solution.

An average vehicle length may accordingly be measured via Dynamic Light Scattering (DLS). The DLS technique is physical method used to determine the size distribution profile of small particles in suspension or polymers in solution. In the scope of DLS, temporal fluctuations are usually analyzed by means of the intensity or photon auto-correlation function. In the time domain analysis, the auto-correlation function (ACF) usually decays starting from zero delay time, and faster dynamics due to smaller particles lead to faster decorrelation of scattered intensity trace. It has been shown that the intensity ACF is the Fourier transformation of the power spectrum, and therefore the DLS measurements can be equally well performed in the spectral domain. Further details would be known to the skilled person or can be derived from suitable literature sources such as Stetefeld et al., 2016, Biophysical Reviews, 8, 4, 409-427.

In another aspect, the invention relates to a composition comprising at least one vehicle of the invention for specific molecular targeting of Langerin$^+$ cells as defined above comprising or associated with a cargo as defined above for a targeted cargo delivery into a Langerin$^+$ cell. In a preferred embodiment, said composition additionally comprises an additive. The term "additive" as used herein relates to any substance or compound which facilitates the (i) interaction between the ligand and the target cell as defined herein, (ii) cargo delivery into or to the target cell as defined herein, (iii) stabilizes the vehicle during shelfing, storage and/or use or (iv) helps to promote subsequent steps associated with the induction of activities in the target cell, e.g. endosomal escape or nuclear translocation of vehicle or cargo and more specifically antigen processing and presentation in Langerin$^+$ cells.

Examples of suitable envisaged additives include divalent ions. Preferred divalent ions are $Ca^{2+}$ or $Zn^{2+}$. Langerin is known to be a divalent ion dependent lectin, in particular a $Ca^{2+}$ dependent lectin, wherein the presence of the divalent ion has an influence on the interaction between the ligand and its cognate receptor Langerin. It is furtehr assumed that the presence of chelators such as EDTA or EGTA has further will lead to a loss or function of Langerinr, as can, for example, be derived from Valladeau, 2000, Immunity, 12(1), 71-81. Accordingly, the present invention particularly envisages that no chelator such as EDTA be present in the composition of the invention. In specific embodiments the concentration of calcium ions, i.e. $Ca^+$, may be in the range of 4 µM to 1 mM, e.g. 4-40 µM, 40 to 500 µM, 500 µM to 1 mM or any value in between the mentioned values. In further specific embodiments the concentration of zinc ions, i.e. $Zn^{2+}$ may be in the range of 4 µM to 1 mM, e.g. 4-40 µM, 40 to 500 µM, 500 µM to 1 mM or any value in between the mentioned values. In specific embodiments, the use of additives may be adjusted to the site of application of the composition of the present invention. Accordingly, the use of $Ca^{2+}$ ions may be envisaged only in situations in which a natural $Ca^{2+}$ provision is not given. Without wishing to the bound by theory, it is believed that the concentration of $Ca^{2+}$ in the human epidermis is at about 1-2 mM which is further assumed to saturate all Langerins and rending them functional. It is particularly preferred to use an additive as described above in patients or situations in which the $Ca^{2+}$ concentration deviates from the above described typical status.

A further example of a suitable additive is an adjuvant. The term "adjuvant" as used in the context of the composition as defined above relates generally to an immunological agent that modifies the effect of other agents, in particular, the effect of the vehicle comprising the cargo or associated to the cargo as mentioned above, more specifically of the cargo entities as mentioned above. The adjuvant may have, for example, a boosting effect with respect to immunologically eliciting cargos. Adjuvants may further have selective effects tailor-made for DCs or Langerin$^+$ cells. It is particularly preferred that an adjuvant is used which induces the maturation of DCs and/or the emigration of DCs from the skin to the lymph nodes, typically leading to a T cell activation. Examples of preferred adjuvants include immunologically active compounds such as aluminium hydroxide, paraffin oil, MF59, AS03, MPL, QS21, AS04, AS01, AS02, IC31, CpG-Oligonucleotides, ISCO-MATRIX or virosomes, incomplete Freund-Adjuvans, KLH or BCG.

Another example of a suitable additive is a factor which promotes the binding of the ligand on the vehicle to Langerin. Such a promoting factor may, for example, be an allosteric activator of protein function, e.g. a small molecule such as molecules described in Aretz et al., 2018, Am. Chem. Soc., 140, 44, 14915-14925, or an antibody or an aptamer. The promoting factor can also be a metal allowing tighter binding of the carbohydrate binding.

In preferred embodiments, a composition in accordance with the present invention is provided in the form of a liquid. This may, for example, include a liquid solution, an emulsion or a suspension. In further embodiments, the composition may comprise a solvent such as $H_2O$, an aqueous sucrose solution, a buffer, e.g. a phosphate buffered saline, a tricine buffer, or HEPES buffer. Further envisaged is the combination of aforementioned aqueous systems and additives, e.g. any of the before mentioned and Dimethylsulfoxide (DMSO). DMSO may be used in any suitable amount or concentration up to about 15 vol %, e.g. in a concentration of about 5 vol %, 7 vol %, 8 vol %, 9 vol %, 10 vol %, 12 vol %, or 15 vol %. Also ten sides such as Tween or TritonX can act as additives and may be used within the context of the present invention.

In yet another preferred embodiment, the composition according to the present invention comprise the vehicle as defined above, i.e. including the cargo, in any suitable amount. The amount may be adjusted in accordance with the carrier form or type, e.g. liposome, nanoparticle, protein etc. Furthermore, the amount of vehicle may be adjusted in accordance with the number of receptors to be bound, as well as the location of a target cell; e.g. skin or other tissues may require different amounts of vehicle. It is preferred that the vehicle is provided in an amount of about 0.5 to 30 mol %, more preferably in an amount of about 1 to 10 mol %, even more preferably in an amount of about 4 to 6 mol %, most preferably in an amount of about 4.75 to 5 mol %. In a typical embodiment, the about mentioned values apply to liposomes, e.g. as defined herein above. Further alternative carriers the amount may vary and be adapted according to suitable calculations as known to the skilled person.

In further specific embodiments, the composition according to the present invention comprise the vehicle as defined above, i.e. including the cargo, in any suitable density. The density may be adjusted in accordance with the carrier form or type, e.g. liposome, nanoparticle, protein etc. Furthermore, the density of vehicle may be adjusted in accordance with the number of receptors to be bound, as well as the location of a target cell; e.g. skin or other tissues may require different density of vehicle. It is preferred that the vehicle is provided in a density of about 0.05 to about 0.08 vehicles per $nm^2$, more preferably in a density of about 0.065 vehicles per $nm^2$, e.g. about 0.067 vehicles per $nm^2$ for a carrier of a diameter of about 160 nm. Also envisaged are further suitable density values, which may be determined in view of the size or diameter of the carrier, e.g. liposome. It is further envisaged that the density be adjusted such that the distance between two vehicles is approx. 4.4 nm. According to a specific embodiment, the calculation of suitable vehicle densities may be based on a lipid concentration value of about 26 µM and an average liposome concentration of about 75 µM. These values may vary and/or be adapted depending on the liposome type, carrier size, diameter or type, vehicle form and size etc. Further details concerning the calculation and adaptation of density of vehicles in a carrier according to the present invention may be derived from suitable literature sources such as Güven et al., 2009, Journal of Liposome Research, 19, 2, 148-154 or Methods of Enzymology, Vol. 391, 2005, Liposomes, Part E, Chapter 13, Use of Liposomes to deliver Bactericides to bacterial biofilms, p. 21.

In a further aspect, the present invention relates to a method for targeted cargo delivery into a Langerin$^+$ cell, comprising contacting the vehicle for specific molecular targeting of Langerin$^+$ cells as defined above, or the composition as above with a dendritic cell. In specific embodiments, the carrier is provided in an unloaded or empty state, or the carrier comprises or is associated with a cargo as defined herein above. The method may, for example, comprise the steps of providing the vehicle in a suitable form or constitution, locating the vehicle in the vicinity of a target cell or facilitating the entirety of the vehicle to the target cell and allowing for a contacting of the ligand with the cognate receptor (Langerin) at the target cell. Factors which may suitably be used to improve or facilitate the targeted cargo delivery are the concentration and presence of $Ca^{2+}$ as described herein. Furthermore, the temperature may be set to a suitable range, e.g. any temperature or temperature range which allows for endocytosis of the the cargo such as 4° C. to 37° C. In a preferred embodiment, the method may be performed in accordance with the steps mentioned in Example 7.

In another aspect, the present invention relates to a pharmaceutical composition comprising the vehicle as defined above or the composition as defined above, wherein the carrier comprises or is associated to a pharmaceutically active cargo, e.g. as defined above. It is particularly preferred that said pharmaceutical composition comprises a vehicle as defined above, wherein the carrier comprises or is associated to a cargo selected from any of the following: a small molecule, a peptide, a protein, a cytotoxic substance, a nucleic acid, a metal, a radionuclide, a virus, a modified virus, a viral vector, an inoculant, a plasmid, a multicomponent system, a pharmaceutically active compound such as inhibitor of cellular function, e.g. an inhibitor of apoptosis, an immunologically active compound including a compound capable of eliciting an immunological reaction in the body, an immunomodulator, and an immunological tolerance inducer, or a cancer antigen or epitope or a compound comprising a cancer antigen or epitope, an autoimmune disease antigen or epitope or a compound comprising an autoimmune disease antigen or epitope, a bacterial antigen or a compound comprising a bacterial antigen or epitope, a viral antigen or a compound comprising a viral antigen or epitope, a parasitic antigen or a compound comprising a parasitic antigen or epitope, or an allergen, or an epitope of an allergen, or a compound comprising an allergen or an epitope of an allergen. Also envisaged are one or more ingredients or components necessary for a gene therapeutic or molecular editing approaches such as, for example, CRISPR/Cas or TALEN components as described herein. It is further preferred that all of the mentioned elements correspond to those defined herein above in the context of the cargo, including additional examples of the mentioned elements. Also envisaged are combinations of the above-mentioned cargos, e.g. a protein and a nucleic acid, or a virus or viral vector and a protein, or a small molecule and a nucleic acid or protein etc. Particularly preferred are combinations of adjuvants and antigens, e.g. as defined herein above, or RNA-protein complexes etc., e.g. for gene therapeutic or molecular editing approaches as defined herein.

Optionally, i.e. in certain embodiments, the pharmaceutical composition as defined above comprises a pharmaceutically acceptable carrier or a pharmaceutical adjuvant. The term "pharmaceutically acceptable" means approved by a regulatory agency or other generally recognized pharmacopeia for use in animals, and more particularly in humans. The term "carrier" refers to a diluent, excipient, or pharmaceutical vehicle with which the cargo or therapeutic is administered. Such a carrier is pharmaceutically acceptable, i.e. is non-toxic to a recipient at the dosage and concentration employed. It is preferably isotonic, hypotonic or weakly hypertonic and has a relatively low ionic strength, such as provided by a sucrose solution. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers. Suitable pharmaceutical excipients include starch, glucose, sucrose, gelatin, malt, rice, flour, chalk, silica gel, sodium stearate, glycerol monostearate, talc, sodium ion, dried skim milk, glycerol, propylene, glycol, water, ethanol and the like. The composition, if desired, can also contain minor amounts of wetting or emulsifying agents, or pH buffering agents. These compositions can take the form of, e.g., solutions, suspensions, emulsion, powders, sustained-release formulations and the like. Examples of suitable pharmaceutical carriers are described, for example, in "Remington's Pharmaceutical Sciences" by E. W. Martin. Some other examples of substances which can serve as pharmaceutical carriers are sugars, such as glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; calcium carbonate; vegetable oils, such as peanut oils, cotton seed oil, sesame oil, olive oil, corn oil and oil of *theobroma*; polyols such as propylene glycol, glycerine, sorbitol, mannitol, and polyethylene glycol; agar; alginic acids; pyrogen-free water; isotonic saline; cranberry extracts and phosphate buffer solution; skim milk powder; as well as other non-toxic compatible substances used in pharmaceutical formulations such as Vitamin C, estrogen and *echinacea*, for example. Wetting agents and lubricants such as sodium lauryl sulfate, as well as coloring agents, flavoring agents, lubricants, excipients, tabletting agents, stabilizers, anti-oxidants and preservatives, can also be present. In certain embodiments, the ingredients of the pharmaceutical composition may be administered in encapsulated form, e.g. as cellulose encapsulation, in gelatine, with polyamides, wax matrices, or with cyclodextrins encapsulated.

Generally, the ingredients may be supplied either separately or mixed together in unit dosage form, for example, as a dry lyophilised powder or water free concentrate in a hermetically sealed container such as an ampoule or sachette indicating the quantity of active agent.

In a specific embodiment, the pharmaceutical composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The term "pharmaceutical adjuvant" as used herein relates to additional ingredients such as chloroquine, protic polar compounds, such as propylene glycol, polyethylene glycol, glycerol, EtOH, 1-methyl L-2-pyrrolidone or their derivatives, or aprotic polar compounds such as dimethylsulfoxide (DMSO), diethylsulfoxide, di-n-propylsulfoxide, dimethylsulfone, sulfolane, dimethylformamide, dimethylacetamide, tetramethylurea, acetonitrile or their derivatives. The pharmaceutical adjuvant may further be one or more of a surfactant, wetting agent, dispersing agent, suspending agent, buffer, stabilizer or isotonic agent. Furthermore, an adjuvant may promote the binding of the vehicle/ligand to Langerin. The present invention also envisages any suitable pharmaceutical adjuvant as known to the skilled person. The above-mentioned compounds are added in conditions respecting pH limitations.

The pharmaceutical composition of the present invention can also comprise a preservative. Preservatives according to certain compositions of the invention include, without limitation: butylparaben; ethylparaben; imidazolidinyl urea; methylparaben; O-phenylphenol; propylparaben; quaternium-14; quaternium-15; sodium dehydroacetate; zinc pyrithione; and the like. The preservatives are used in amounts effective to prevent or retard microbial growth. Generally, the preservatives are used in amounts of about 0.1% to about 1% by weight of the total composition with about 0.1% to about 0.8% being preferred and about 0.1% to about 0.5% being most preferred.

The composition of the present invention can be administered to a subject or patient. The term "subject" or "patient" refers to a mammal. "Mammal" as used herein is intended to have the same meaning as commonly understood by one of ordinary skill in the art. Preferred mammals are primates, cows, sheep, goats, horses, dogs, cats, rabbits, rats, mice and the like. In particularly preferred embodiments, the subject is a human.

The term "administered" means administration of a therapeutically effective dose of the aforementioned pharmaceutical composition by any suitable route. By "therapeutically effective amount" is meant a dose that produces the effects for which it is administered in a patient. The exact dose will depend on the purpose of the treatment, and will be ascertainable by one skilled in the art using known techniques. As is known in the art and described herein, adjustments for systemic versus localized delivery, age, body weight, general health, sex, diet, time of administration, drug interaction and the severity of the condition may be necessary, and will be ascertainable with routine experimentation by those skilled in the art. It is preferred that the administration is localized, more preferably, that the administration is topical, in particular over or through the skin.

The pharmaceutical composition may be used in both human therapy and veterinary therapy, preferably in human therapy. The vehicles described herein being associated with cargos having the desired therapeutic activity may be administered in a physiologically acceptable carrier to a patient, as described herein. Depending upon the manner of administration, these elements may be formulated in a variety of ways as discussed below. The concentration of the vehicles described herein being associated with cargos having the desired therapeutic activity in the formulation may vary from about 0.00001-100 wt %. For instance, the formulation may provide the vehicle in an amount of about 0.5 to 30 mol %, more preferably in an amount of about 1 to 10 mol %, even more preferably in an amount of about 4 to 6 mol %, most preferably in an amount of about 4.75 to 5 mol %. In a typical embodiment, the about mentioned values apply to liposomes, e.g. as defined herein above. Further alternative carriers the amount may vary and be adapted according to suitable calculations as known to the skilled person.

Also envisaged are formulations, which comprise the vehicle in a suitable density. Accordingly, in further specific embodiments, the pharmaceutical composition according to the present invention may comprise the vehicle as defined above, i.e. including the cargo, in any suitable density, which may be adjusted in accordance with the carrier form or type, e.g. liposome, nanoparticle, protein etc. Furthermore, the density of vehicle may be adjusted in accordance with the number of receptors to be bound, as well as the location of a target cell; e.g., skin or other tissues may require different density of vehicle. It is preferred that the vehicle is provided in a density of about 0.05 to about 0.08 vehicles per $nm^2$, more preferably in a density of about 0.065 vehicles per $nm^2$, e.g. about 0.067 vehicles per $nm^2$ for a carrier of a diameter of about 160 nm. Also envisaged are further suitable density values, which may be determined in view of the size or diameter of the carrier, e.g. liposome. It is further envisaged that the density be adjusted such that the distance between two vehicles is approx. 4.4 nm. According to a specific embodiment, the calculation of suitable vehicle densities may be based on a lipid concentration value of about 26 µM and an average liposome concentration of about 75 µM. These values may vary and/or be adapted de-pending on the liposome type, carrier size, diameter or type, vehicle form and size etc. Further details concerning the calculation and adaptation of density of vehicles in a carrier according to the present invention may be derived from suitable literature sources such as Methods of Enzymology, Vol. 391, 2005, Liposomes, Part E, Chapter 13, Use of Liposomes to deliver Bactericides to bacterial biofilms, p. 21.

The concentration of the compounds of a pharmaceutical composition according to the present invention may be further adjusted to the intended dosage regimen, the intended usage duration, the exact amount and ratio of all ingredients of the composition and further factors and parameter known to the person skilled in the art.

The vehicles described herein being associated with cargos having the desired therapeutic activity according to the present invention may be administered alone or in combination with other treatments. Combination treatments are envisioned for cancer immunotherapy, for example via co-administration of checkpoint inhibitors such as anti-CTLA-4 and anti-PD1 antibodies, for chemotherapy, for example by co-administration of alkylating agents or DNA and RNA polymerase inhibitors, for antiviral therapy, for example by co-administration of entry, protease or DNA and RNA polymerase inhibitors and for autoimmune disease therapy, for example by co-administration of glucocorticoids or immunophilin inhibitors.

The administration of the pharmaceutical composition can be done in a variety of ways. The administration may be, for example, oral, intravenous, topical, corneal, nasal, subcutaneous, intradermal, or transdermal administration. In further embodiments, the administration is for vaccination, or for administration via hair follicles.

Further, alternative routes of administration include, without limitation, ocular or intra-tumor administration or by intrasternal injection.

In further embodiments, the administration may be performed with a specific medical device, e.g a needle, a vaccination gun, a plaster/adhesive, or an inhaler, as will be explained in detail below.

The present invention centrally focuses on vaccination approaches. The term "vaccination" in general relates to the administration of antigenic material (e.g. as a vaccine) to stimulate an individual's immune system. Accordingly, the pharmaceutical composition as defined herein may be administered as a vaccine. A vaccine may be (i) an inactivated vaccine, (ii) an attenuated vaccine, (iii) a subunit vaccine or (iv) a DNA vaccine. The term "inactivated vaccine" means a vaccine or composition comprising infectant particles which were grown in culture and subsequently killed or destroyed, preferably by using heat or formaldehyde. Such infectant particles, e.g. viruses, typically cannot replicate, but certain proteins, e.g. capsid proteins, are intact enough to be recognized by the immune system and evoke a response. The term "attenuated vaccine" means a vaccine or composition comprising live infectant particles with a low virulence. Typically, live attenuated infectant particles may reproduce, but very slowly. These vaccines may be produced by any suitable method known to the skilled person, normally by growing infectants tissue cultures that will select for less virulent strains, or by mutagenesis or targeted deletions in genes required for virulence. The term "subunit vaccine" means a vaccine or composition comprising an antigen, which is provided to the immune system without the introduction of infectant particles, whole or otherwise. A subunit vaccine may be produced by any suitable method known to the person skilled in the art. Typically the production may involve the isolation of a specific protein or protein portion or of sugar structures and their administration as vaccine or vaccine composition. The subunit strategy may further be used for the presentation of suitable cancer antigens. The term "DNA vaccine" relates to DNA compositions created from an infectious agent's DNA or encoding corresponding structural components, which is typically inserted into cells, e.g. human or animal cells, and expressed therein. The DNA vaccine may accordingly encode any antigen or epitope as defined herein above.

Vaccines of the present invention may be administered to a subject or individual by any suitable method, preferably via injection using either a conventional syringe or a gene gun or vaccination gen, such as the Accell® gene delivery system. Delivery of DNA into cells of the epidermis is particularly preferred as this mode of administration provides access to skin-associated lymphoid cells and provides for a transient presence of DNA in the recipient. Both, nucleic acids and/or proteins/peptides can be injected either subcutaneously, epidermally, intradermally, intramucosally such as nasally, rectally and vaginally, intraperitoneally, intravenously, orally or intramuscularly. Other modes of administration include oral and pulmonary administration, suppositories, needle-less injection, transcutaneous and transdermal applications. If solids are employed as auxiliary agents for the vaccine formulation, e.g. an adsorbate or a suspended mixture of vaccine ingredient with the auxiliary agent is administered. In special embodiments, the vaccine is administered as a solution, or liquid vaccine, respectively, in an aqueous solvent. It is preferred that the administration is epidermally, intradermally or intramucosally.

In a particularly preferred embodiment the administration is via hair follicles. The method is based on the finding that the pilosebaceous unit (consisting of the hair follicle and sebaceous gland) can play a role in the passive transport of drugs into the skin. To reach the epidermis and egress from the skin into circulation, the pharmaceutical composition must additionally penetrate the keratinocyte layers surrounding the hair shaft. By using particles such poly(lactic-co-glycolic acid) (PLGA) nanoparticles, the pharmaceutical composition may be kept at the hair follicles, which allow for drug perfusion in the skin. Also, a depot effect may be used. Optionally, the adjuvant bis-(3',5')-cyclic dimeric adenosine monophosphate may be employed.

Further envisaged administration routes include iontophoresis, microneedles, lasers and jet injectors.

Microneedles are typically considered as part of a transdermal patch, which is placed on the skin to deliver the pharmaceutical composition or a part of it to and across the skin. The microneedles are typically smaller than a human hair, composed of metals, Si or biodegradable polymers. Typically, the microneedles are provided in the form of an array. The use of the microneedles is advantageously virtually painless. A preferred embodiment of the microneedle approach is the nanopatch.

The term "nanopatch" used herein relates to an array of thousands of vaccine-coated microprojections that perforate into the outer layers of the skin when applied with an applicator device. The tips of Nanopatch's microprojections are typically coated with a vaccine material including the composition according to the present invention and release this material directly to the large numbers of immune cells immediately below the skin surface. The central element of this technology is the Nanopatch array itself which typically consists of a 1 cm2 square of silicon with ~20,000 microprojections on its surface. The Nanopatch array penetrates through the protective outer skin layer (stratum corneum) and targets immune-activating material to the immune-cell rich layers just beneath the outermost skin layer utilising the microprojections with optimised spacing and length.

A further preferred route of administering is the topical route. Topical administration of the pharmaceutical composition of the present invention is useful when the desired treatment involves areas or organs readily accessible by topical administration. For a topically application, e.g. to the skin, mucous membrane, the pharmaceutical composition is preferably formulated as hydrogel patch, liquid, cream, ointment, paste, gel, lotion, tape, film, sublingual, buccal, tablet, spray, or suppository.

The term "hydrogel patch" as used herein relates to patches which are composed of a breathable non-woven cloth layered with an advanced adhering hydrogel which is typically protected by a transparent film cover. Hydrogel is a network of polymer chains that are water-insoluble, sometimes found as a colloidal gel in which water is the dispersion medium. Hydrogels are superabsorbent, natural or synthetic polymers an possess a degree of flexibility similar to natural tissue, due to their significant water content. According to certain embodiments, the hydropatch comprises the composition according to the present invention in a suitable amount.

A suitable paste comprises the vehicles described herein being associated with cargos having the desired therapeutic activity according to the present invention suspended in a carrier. Such carriers include, but are not limited to, petroleum, soft white paraffin, yellow petroleum jelly and glycerol.

The pharmaceutical composition may also be formulated with a suitable ointment comprising the active components suspended or dissolved in a carrier. Such carriers include, but are not limited to, one or more of glycerol, mineral oil, liquid oil, liquid petroleum, white petroleum, yellow petroleum jelly, propylene glycol, alcohols, triglycerides, fatty acid esters such as cetyl ester, polyoxyethylene polyoxypropylene compound, waxes such as white wax and yellow beeswax, fatty acid alcohols such as cetyl alcohol, stearyl alcohol and cetylstearylalcohol, fatty acids such as stearic acid, cetyl stearate, lanolin, magnesium hydroxide, kaolin and water.

Alternatively, the pharmaceutical composition may also be formulated with a suitable lotion or cream comprising the active components suspended or dissolved in a carrier. Such carriers include, but are not limited to, one or more of mineral oil such as paraffin, vegetable oils such as castor oil, castor seed oil and hydrogenated castor oil, sorbitan monostearat, polysorbat, fatty acid esters such as cetyl ester, wax, fatty acid alcohols such as cetyl alcohol, stearyl alcohol, 2-octyldodecanol, benzyl alcohol, alcohols, triglycerides and water.

The pharmaceutical composition may also be formulated as a tape or adhesive for transdermal application. The tape typically sticks to the skin as a patch and comprises the active components typically in a delayed release format. It is envisaged that the adhesive is a pressure sensitive adhesive wherein permeation enhancers, namely surfactants, fatty acids, terpenes and solvents, may have been introduced into the transdermal formulation. The pressure-sensitive adhesive typically begins as a highly viscous and sticky liquid and remains in the same form throughout their application life cycle. Alternatively, rubber-based pressure-sensitive adhesives may be employed which comprises of either natural or synthetic rubber, in addition to oils, resins and antioxidants as tackifier and stabiliser. Also envisaged are acrylic-based pressure-sensitive adhesive is prepared from acrylate esters, methacrylic acid, acrylamide, methacrylamide, N-alkoxyalkyl or N-alkyl-acrylamides without or with the addition of tackifier, or silicone-based pressure-sensitive adhesive is prepared mainly from gum and resin. The resin is a resultant product of the reaction of silicic or polysilicic hydrosol with trimethylchlorosilane.

A "sublingual administration" relates to pharmacological route of administration by which substances diffuse into the blood through tissues under the tongue. When the substance comes into contact with the mucous membrane beneath the tongue, it is absorbed. Because the connective tissue beneath the epithelium contains a profusion of capillaries, the substance then diffuses into them and enters the venous circulation. Typical administration forms for sublingual administration include sublingual tablets, sublingual strips, sublingual drops, sublingual spray, lozenges etc.

Similar to the sublingual administration, the buccal administration refers to a topical route of administration by which drugs held or applied in the buccal area (in the cheek) diffuse through the oral mucosa and enter either directly into the bloodstream or being taken up by Langerin-positive antigen presenting cells residing in the tissue. Buccal administration is believed to provide better bioavailability and a more rapid onset of action compared to oral administration because the medication does not pass through the digestive system and thereby avoids first pass metabolism. Modern approaches for buccal administration envisaged for the present invention include composite materials such as nanofiber-based mucoadhesive films. These materials typically consist of a mucoahesive layer, a reservoir layer to enable controlled release of the carrier. It is preferred that the materials comprise lipid-based nanoparticles and a protective backing layer. The further envisaged use of permeation enhancers such as surfactants, fatty acids as well as cationic and anionic amino acids may advantageously increase buccal bioavailability. Further details may be derived from suitable literature sources such as Morales et al., 2017, Curr Opin Pharmacol, 36, 22-28.

Alternatively, the pharmaceutical composition may also be formulated with a suitable gel comprising the active components suspended or dissolved in a carrier. Such carriers include, but are not limited to, one or more of water, glycerol, propyleneglycole, liquid paraffin, polyethylene, fatty oils, cellulose derivatives, bentonite and colloidal silicon dioxide.

The preparations according to the invention may generally comprise further auxiliaries as are customarily used in such preparations, e.g. preservatives, perfumes, antifoams, dyes, pigments, thickeners, surface-active substances, emulsifiers, emollients, finishing agents, fats, oils, waxes or other customary constituents, of a cosmetic or dermatological formulation, such as alcohols, polyols, polymers, foam stabilizers, solubility promoters, electrolytes, organic acids, organic solvents, or silicone derivatives.

The pharmaceutical composition according to the invention may comprise emollients. Emollients may be used in amounts, which are effective to prevent or relieve dryness. Useful emollients include, without limitation: hydrocarbon oils and waxes; silicone oils; triglyceride esters; acetoglyceride esters; ethoxylated glyceride; alkyl esters; alkenyl esters; fatty acids; fatty alcohols; fatty alcohol ethers; etheresters; lanolin and derivatives; polyhydric alcohols (polyols) and polyether derivatives; polyhydric alcohol (polyol) esters; wax esters; beeswax derivatives; vegetable waxes; phospholipids; sterols; and amides.

Thus, for example, typical emollients include mineral oil, especially mineral oils having a viscosity in the range of 50 to 500 SUS, lanolin oil, mink oil, coconut oil, cocoa butter, olive oil, almond oil, macadamia nut oil, aloa extract, jojoba oil, safflower oil, corn oil, liquid lanolin, cottonseed oil, peanut oil, purcellin oil, perhydrosqualene (squalene), caster oil, polybutene, odorless mineral spirits, sweet almond oil, avocado oil, calophyllum oil, ricin oil, vitamin E acetate, olive oil, mineral spirits, cetearyl alcohol (mixture of fatty alcohols consisting predominantly of cetyl and stearyl alcohols), linolenic alcohol, oleyl alcohol, octyl dodecanol, the oil of cereal germs such as the oil of wheat germ cetearyl octanoate (ester of cetearyl alcohol and 2-ethylhexanoic acid), cetyl palmitate, diisopropyl adipate, isopropyl palmitate, octyl palmitate, isopropyl myristate, butyl myristate, glyceryl stearate, hexadecyl stearate, isocetyl stearate, octyl stearate, octylhydroxy stearate, propylene glycol stearate, butyl stearate, decyl oleate, glyceryl oleate, acetyl glycerides, the octanoates and benzoates of (C12-C15) alcohols, the octanoates and decanoates of alcohols and polyalcohols such as those of glycol and glycerol, and ricin-oleates of alcohols and poly alcohols such as those of isopropyl adipate, hexyl laurate, octyl dodecanoate, dimethicone copolyol, dimethiconol, lanolin, lanolin alcohol, lanolin wax, hydrogenated lanolin, hydroxylated lanolin, acetylated lanolin, petrolatum, isopropyl lanolate, cetyl myristate, glyceryl myristate, myristyl myristate, myristyl lactate, cetyl alcohol, isostearyl alcohol stearyl alcohol, and isocetyl lanolate, and the like.

Moreover, the pharmaceutical composition according to the invention may also comprise emulsifiers. Emulsifiers (i.e., emulsifying agents) are preferably used in amounts effective to provide uniform blending of ingredients of the composition. Useful emulsifiers include (i) anionics such as fatty acid soaps, e.g., potassium stearate, sodium stearate, ammonium stearate, and triethanolamine stearate; polyol fatty acid monoesters containing fatty acid soaps, e.g., glycerol monostearate containing either potassium or sodium salt; sulfuric esters (sodium salts), e.g., sodium lauryl 5 sulfate, and sodium cetyl sulfate; and polyol fatty acid monoesters containing sulfuric esters, e.g., glyceryl monostearate containing sodium lauryl surfate; (ii) cationics chloride such as N(stearoyl colamino formylmethyl) pyridium; N-soya-N-ethyl morpholinium ethosulfate; alkyl dimethyl benzyl ammonium chloride; diisobutylphenoxytheoxyethyl dimethyl benzyl ammonium chloride; and cetyl pyridium chloride; and (iii) nonionics such as polyoxyethylene fatty alcohol ethers, e.g., monostearate; polyoxyethylene lauryl alcohol; polyoxypropylene fatty alcohol ethers, e.g., propoxylated oleyl alcohol; polyoxyethylene fatty acid esters, e.g., polyoxyethylene stearate; polyoxyethylene sorbitan fatty acid esters, e.g., polyoxyethylene sorbitan monostearate; sorbitan fatty acid esters, e.g., sorbitan; polyoxyethylene glycol fatty acid esters, e.g., polyoxyethylene glycol monostearate; and polyol fatty acid esters, e.g., glyceryl monostearate and propylene glycol monostearate; and ethoxylated lanolin derivatives, e.g., ethoxylated lanolins, ethoxylated lanolin alcohols and ethoxylated cholesterol.

The pharmaceutical composition according to the invention may also include a surfactant. Suitable surfactants may include, for example, those surfactants generally grouped as cleansing agents, emulsifying agents, foam boosters, hydrotropes, solubilizing agents, suspending agents and nonsurfactants (facilitates the dispersion of solids in liquids).

The surfactants are usually classified as amphoteric, anionic, cationic and nonionic surfactants. Amphoteric surfactants include acylamino acids and derivatives and N-alkylamino acids. Anionic surfactants include: acylamino acids and salts, such as, acylglutamates, acylpeptides, acylsarcosinates, and acyltaurates; carboxylic acids and salts, such as, alkanoic acids, ester carboxylic acids, and ether carboxylic acids; sulfonic acids and salts, such as, acyl isethionates, alkylaryl sulfonates, alkyl sulfonates, and sulfosuccinates; sulfuric acid esters, such as, alkyl ether sulfates and alkyl sulfates. Cationic surfactants include: alkylamines, alkyl imidazolines, ethoxylated amines, and quaternaries (such as, alkylbenzyldimethylammonium salts, alkyl betaines, heterocyclic ammonium salts, and tetra alkylammonium salts). And nonionic surfactants include: alcohols, such as primary alcohols containing 8 to 18 carbon atoms; alkanolamides such as alkanolamine derived amides and ethoxylated amides; amine oxides; esters such as ethoxylated carboxylic acids, ethoxylated glycerides, glycol esters and derivatives, monoglycerides, polyglyceryl esters, polyhydric alcohol esters and ethers, sorbitan/sorbitol esters, and triesters of phosphoric acid; and ethers such as ethoxylated alcohols, ethoxylated lanolin, ethoxylated polysiloxanes, and propoxylated polyoxyethylene ethers.

In case of the provision of the pharmaceutical composition as a film it may comprise a film former. Suitable film formers which are used in accord with the invention keep the composition smooth and even and include, without limitation: acrylamide/sodium acrylate copolymer; ammonium acrylates copolymer; Balsam Peru; cellulose gum; ethylene/ maleic anhydride copolymer; hydroxyethylcellulose; hydroxypropylcellulose; polyacrylamide; polyethylene; polyvinyl alcohol; pvm/MA copolymer (polyvinyl methylether/maleic anhydride); PVP (polyvinylpyrrolidone); maleic anhydride copolymer such as PA-18 available from Gulf Science and Technology; PVP/hexadecene copolymer such as Ganex V-216 available from GAF Corporation; acryliclacrylate copolymer; and the like.

Generally, film formers can be used in amounts of about 0.1% to about 10% by weight of the total composition with about 1% to about 8% being preferred and about 0.1 DEG/O to about 5% being most preferred. Humectants can also be used in effective amounts, including: fructose; glucose; glulamic acid; glycerin; honey; maltitol; methyl gluceth-10; methyl gluceth-20; propylene glycol; sodium lactate; sucrose; and the like.

In a further embodiment of the present invention, the pharmaceutical composition may be administered via inhalation. The pharmaceutical preparations can accordingly be in the form of a spray, e.g. a pump spray or an aerosol. Typically, aerosols according to the present invention comprise the medicament or pharmaceutical composition, one or more chlorofluorocarbon propellants and either a surfactant or a solvent, such as ethanol. For instance, aerosol propellants like propellant 11 and/or propellant 114 and/or propellant 12 may be used. Further suitable propellants for aerosols according to the invention are propane, butane, pentane and others. Additional propellants which may be used and which are believed to have minimal ozone-depleting effects in comparison to conventional chlorofluorocarbons comprise fluorocarbons and hydrogen-containing chlorofluorocarbons. Additional aerosols for medicinal aerosol formulations are disclosed in, for example, EP 0372777. Typically, one or more adjuvants such as alcohols, alkanes, dimethyl ether, surfactants (including fluorinated and non-fluorinated surfactants, carboxylic acids, polyethoxylates etc) and conventional chlorofluorocarbon propellants in small amounts may be added to the formulations.

Further preferred is the use of 1,1,1,2-tetrafluoroethane in combination with both a cosolvent having greater polarity than 1,1,1,2-tetrafluoroethane (e.g. an alcohol or a lower alkane) and a surfactant in order to achieve a stable formulation of a pharmaceutical composition powder. Additionally, surfactants may be used as important components of aerosol formulations, in order to reduce the aggregation of the pharmaceutical composition and to lubricate, e.g. valves of a dispersing apparatus, if employed according to a further preferred embodiment of the present invention, thereby ensuring consistent reproducibility of valve actuation and accuracy of dose dispensed. Typically, the pharmaceutical composition according to the present invention may be pre-coated with surfactant prior to dispersal in 1,1,1,2-tetrafluoroethane.

In a further preferred embodiment of the present invention a pharmaceutical aerosol formulation may be dispersed with any suitable apparatus known to the person skilled in the art, preferably through a metered dose inhaler (MDI), a nebulizer, Rotahaler or an autohaler apparatus.

Oral delivery can be performed by complexing the composition as defined herein carrier capable of withstanding degradation by digestive enzymes in the gut of an animal. Examples of such carriers include plastic capsules or tablets, such as those known in the art.

A suitable suppository may comprise the composition as defined herein together with colloidal silicon dioxide, and an oleaginous base that includes triglycerides.

Assays, e.g. as derivable from known and qualified literature sources, may optionally be employed to help identify optimal ratios and/or dosage ranges for ingredients of pharmaceutical compositions of the present invention. The precise dose and the ratio between the ingredients of the pharmaceutical composition as defined herein above to be employed in the formulation will also depend on the route of administration, and the exact type of disease or disorder, and should be decided according to the judgment of the practitioner and each patient's circumstances. Effective doses or ingredient ratios may be extrapolated from dose-response curves derived from in vitro or (animal) model test systems.

Typically, the attending physician and clinical factors may determine the dosage regimen. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 mg; however, doses below or above this exemplary range are also envisioned, especially considering the aforementioned factors.

In a preferred embodiment, the pharmaceutical composition as defined herein above is for use in the treatment or prevention of a disease or pathological condition.

A "disease" or "pathological condition" as used herein is any condition that would benefit from treatment with a pharmaceutical composition as defined above, in particular with a vehicle wherein the carrier comprises or is associated to a cargo, preferably a cargo as defined herein above.

The terms "treat" or "treatment", unless otherwise indicated by context, refer to therapeutic treatment and/or prophylactic measures to prevent the outbreak or relapse of a disease or pathological condition, wherein the objective is to inhibit or slow down (lessen) an undesired physiological condition. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already having the condition or disorder as well as those prone to have the condition or disorder. The treatment may further, in specific embodiments, involve a single administration of a pharmaceutical composition as defined above, or multiple administrations. A corresponding administration scheme may be adjusted to the sex or weight of the patient, the disease, the pharmaceutical composition to be used, the general health status of the patient etc. For example, the administration scheme may contemplate an administration every 12 h, 24 h, 28 h, 72 h, 96 h, once a week, once very two weeks, once every 3 weeks, once a month etc. Also envisaged are pauses or breaks between administration phases. These regimens can of course be adjusted or changed by the medical practitioner in accordance with the patient's reaction to the treatment and/or the course of disease or of the pathological condition.

In a particularly preferred embodiment of the present invention, the pharmaceutical composition as defined herein above is for use in the treatment or prevention of cancer. The term "cancer" as used herein relates to a pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms typically show partial or complete lack of structural organization and functional coordination with the normal tissue and most invade surrounding tissues, metastasize to several sites, and are likely to recur after attempted removal and to cause the death of the patient unless adequately treated. The tem thus also includes the existence and development of metastases. As used herein, the term "neoplasia" is used to describe all cancerous disease states and embraces or encompasses the pathological process associated with malignant hematogenous, ascitic and solid tumors.

Representative cancers include, for example, stomach, colon, rectal, liver, pancreatic, lung, breast, cervix uteri, corpus uteri, ovary, prostate, including metastatic prostate cancer, testis, bladder, renal, brain/CNS, head and neck, throat, Hodgkin's disease, non-Hodgkin's lymphoma, multiple myeloma, leukemia, melanoma skin cancer, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma Also envisaged are further cancer forms known to the skilled person or derivable from suitable literature sources such as Pavlopoulou et al., 2015, Oncol Rep., 33, 1, 3-18.

The cancer may, in certain embodiments, be a refractory cancer. A cancer may be assumed to be residually present if a subject has undergone surgery as treatment for the cancer. Also envisaged are metastasizing cancer forms, e.g. of thee above mentioned cancer forms.

The cancer forms mentioned above may preferably be treated by using tumor associated antigens or cancer antigens or cancer epitopes as described above, which are provided to Langerin$^+$ DCs in the form of cargos as described herein above. These antigens or epitopes thereof are subsequently processed and presented by the Langerin$^+$ cells to further immune cells and activate these immune cells leading to an immune response, e.g. via CTLs or antibodies against entities, e.g. cells, showing said antigen or epitope. The activation of these immune cells, in turn, depends on the maturation and activation of Langerin$^+$ DCs which may be achieved by co-administration of suitable adjuvants. Non-limiting examples of such adjuvants are TLR or Rig-I-like receptors (RLR) agonists.

It is also envisaged that different antigens and/or different epitopes, e.g. either derived from different cancer forms, or derived from different proteins or glycoproteins, which may be present on the same cancerous cell or in the same tumor, are provided. These antigens or epitopes may, for example, be provided in a multiantigen fusion protein or a multi-epitope protein (e.g. comprising 2, 3, 4, 5, 6, 7, 8 or more epitopes), or as single antigen/epitope units which are packed together in a cargo load. For example, different antigens may be mixed and subsequently be formulated in a carrier, e.g. a liposome as defined herein. Also preferred is the use of different molecular forms of the tumor antigen/epitopes within the cargo load. For example, it may be provided as protein/peptide, or as nucleic acid.

In a further, particularly preferred embodiment the term "cancer" also relates to Langerhans cell histiocytosis (LCH), i.e. a cancerous change in Langerhans cells. Langerhans cell histiocytosis is a rare disease involving clonal proliferation of Langerhans cells. Clinically, its manifestations range from isolated bone lesions to multisystem disease. Langerhans cell histiocytosis is part of a group of clinical syndromes called histiocytoses, which are characterized by an abnormal proliferation of histiocytes (i.e. activated dendritic cells and macrophages). This cancer form is related to leukemia and lymphomas. The disease typically manifests at Langerin$^+$ cell, i.e. cells expressing Langerin on the surface. Without wishing to be bound by theory, it is believed that hyperactive ERK can drive LCH pathogenesis. It is further believed that BRAF-V600E is involved in high-risk LCH due to its presence in hematopoietic cells in bone marrow. This can, for example, be explained by a misguided myeloid DC model of LCH pathogenesis where the state of cell differentiation in which pathologic ERK activation arises determines the clinical extent of LCH. Further factors which may contribute to aspects of pathogenesis are inflammatory infiltrates. LCH is hence assumed to be a myeloproliferative neoplasm or an inflammatory myeloid neoplasia. LCH may preferably be treated by using cytotoxic substances, small molecules, radionuclides or proteins, e.g. suitable antibodies such as antibodies against surface markers or proteins present on the cell surface, more specifically anti-Langerin antibodies and/or multicomponent systems as described above, which are provided to Langerin$^+$ cells in the form of cargos as described herein above. Suitable antibodies to be used in the context of treatment of LCH include, for example, antibodies against BRAF V600E based on the finding that BRAF V600E. Also envisaged are antibodies against further mutations in the context of LCH as known to the skilled person.

In a further particularly preferred embodiment of the present invention, the pharmaceutical composition as defined herein above is for use in the treatment or prevention of an autoimmune disease. The term "autoimmune disease" as used herein relates to inappropriate immune responses that attack either self-tissues or innocuous environmental components as defined herein above. Examples of autoimmune diseases, which are envisaged by the present invention and can be treated with the described pharmaceutical composition, include Antiphospholipid-Syndrome (aPL syndrome), Pemphigus, Multiple Sclerosis (MS), Myasthenia gravis, Grave's disease, Goodpasture's syndrome, Microscopic angiitis, Granulomatosis with polyangiits, Systemic Autoimmune Rheumatic Diseases (SARD), Mixed Connective Tissue Disease, Systemic Lupus Erythematosus, Sjøgrens Syndrome, Systemic Sclerosis/CREST Syndrome, Polymyositis/Dermatomyositis, Autoimmune Thyroid Diseases, Celiac Disease, Autoimmune Hepatitis, Primary Biliary Cirrhosis, ANCA Associated Diseases, Antiphospholipid Syndrome/Thromboembolic Syndrome, Anti-GBM Disease, Diabetes Mellitus, Pernicious Anemia, Vitiligo and Crohn's Disease. The treatment of autoimmune diseases as described above is based on the use of autoimmune disease antigens or autoimmune disease epitopes as described above, which are provided to Langerin$^+$ DCs in the form of cargos as described herein above. In particular, Langerin$^+$ DCs are known to induce the expansion of regulatory T cells and the antigen-specific deletion of CTLs, i.e. an antigen-specific tolerance, in absence of co-stimulatory signals, i.e. without the co-delivery of adjuvants. In the context of this treatment scheme the autoimmune disease antigens or autoimmune disease epitopes as described above is hence preferably provided without co-delivery of any adjuvant. It is further preferred that any co-stimulatory signal which leads to an activation of Langerin$^+$ DCs be inhibited by any suitable means known to the skilled person.

In yet another particularly preferred embodiment of the present invention, the pharmaceutical composition as defined herein above is for use in the treatment or prevention of a bacterial infection. The term "bacterial infection" relates to the infection a patient, in particular of a human, with a pathogenic bacterium or a bacterium whose presence in the organism is unwanted, e.g. a part of a bacterial consortium or bioflora. Preferred examples include intracellular bacterial infections, e.g. conveyed by bacteria such as *Chlamydophila*, *Ehrlichia*, *Rickettsia*, *Salmonella*, *Neisseria*, *Brucella*, *Mycobacterium*, *Nocardia*, *Listeria*, *Francisella*, *Legionella*, or *Yersinia*. Further examples of pathogenic bacteria, whose infection is envisaged to be treated with the pharmaceutical composition according to the present invention include bacteria of the genus *Bacillus, Bartonella, Bordetella, Borrelia, Campylobacter, Chlamydia, Clostridium, Corynebacterium, Enterococcus, Escherichia, Haemophilus, Helicobacter, Leptospira, Mycoplasma, Pseudomonas, Shigella, Staphylococcus, Streptococcus, Treponema, Ureaplasma* and *Vibrio*. In specific embodiments, the bacterial infection to be treated may be an infection by one or more of the following species: *Bacillus anthracis, Bacillus cereus, Bartonella henselae, Bartonella quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Ureaplasma urealyticum, Vibrio cholerae, Yersinia pestis, Yersinia enterocolitica* and *Yersinia pseudotuberculosis*. Particularly preferred is the treatment of infections with *Neisseria meningitides, Corynebacterium diphtheria, Bordetella pertussis* or *Clostridium tetani*.

In the context of a bacterial infection, the term "treating" includes any or all of: inhibiting the growth of bacteria, multiplication or replication of the pathogen that causes the infectious disease and ameliorating one or more symptoms of an infectious disease. The infections with bacteria as mentioned above may preferably be treated by using bacterial antigens or bacterial epitopes as described herein, or which are known to the skilled person, e.g. from suitable literature source such as Detmer and Glenting, 2006, Microbial Cell Factories, 5, 23, which are provided to Langerin$^+$ DCs in the form of cargos as described herein above. These antigens or epitopes thereof are subsequently processed and presented by the Langerin$^+$ cells to further immune cells and activate these immune cells leading to an immune response, e.g. via CTLs or antibodies against entities, e.g. bacteria or parts thereof, showing said antigen or epitope. It is also envisaged that different antigens and/or different epitopes, e.g. either derived from different bacteria, or derived from different proteins or glycoproteins, which may be present on the same bacterium are provided. These antigens or epitopes may, for example, be provided in a multiantigen fusion protein or a multiepitope protein (e.g. comprising 2, 3, 4, 5, 6, 7, 8 or more epitopes), or as single antigen/epitope units which are packed together in a cargo load. Also preferred is the use of different molecular forms of the bacterial antigen/epitopes within the cargo load. For example, it may be provided as protein/peptide, as an oligosaccharide or as nucleic acid. It is further preferred that bacterial antigens/epitopes, if several are provided, are provided in combination or as mixtures of antigens/epitipoes, e.g. when a liposome is formulated or generated.

In another particularly preferred embodiment of the present invention, the pharmaceutical composition as defined herein above is for use in the treatment or prevention of a viral infection. The term "viral infection" as used herein refers to an infection and/or disease caused by a pathogenic virus or an infectious virus particle (virion). Examples of pathogenic viruses or virions, whose infection is envisaged to be treated with the pharmaceutical composition according to the present invention include viruses of the groups: Adenoviridae, Picornaviridae, Herpesviridae, Hepadnaviridae, Flaviviridae, Retroviridae, Orthomyxoviridae, Paramyxoviridae, Papillomaviridae, Rhabdoviridae, Togaviridae. In specific embodiments, the viral infection to be treated may be an infection by one or more of the following virus types: Adenovirus, Coxsackievirus, Epstein-Barr virus, Hepatitis A virus, Hepatitis B virus, Hepatitis C virus, Herpes simplex virus, type 1, Herpes simplex virus, type 2, Cytomegalovirus, Human herpesvirus, type 8, HIV, Influenza virus, Measles virus, Mumps virus, Human papillomavirus, Parainfluenza virus, Poliovirus, Rabies virus, Respiratory syncytial virus, Rubella virus, Varicella-zoster virus. Particularly preferred is the treatment of infections with Human papillomavirus, Hepatitis A virus and Hepatitis B virus.

In the context of a viral infection, the term "treating" includes any or all of: inhibiting the growth of viruses, multiplication or replication of the pathogen that causes the infectious disease and ameliorating one or more symptoms of an infectious disease. The infections with viruses or virions as mentioned above may preferably be treated by using viral antigens or viral epitopes as described herein, or which are known to the skilled person, e.g. from suitable literature source such as Ansari et al., 2010, Nucleic Acids Res, 38, D847-D853 or from internet resources, which are provided to Langerin$^+$ DCs in the form of cargos as described herein above. These antigens or epitopes thereof are subsequently processed and presented by the Langerin$^+$ cells to further immune cells and activate these immune cells leading to an immune response, e.g. via CTLs or antibodies against entities, e.g. viruses or parts thereof, showing said antigen or epitope. It is also envisaged that different antigens and/or different epitopes, e.g. either derived from different viruses, or derived from different proteins or glycoproteins, which may be present on or in the same virus are provided. These antigens or epitopes may, for example, be provided in a multiantigen fusion protein or a multiepitope protein (e.g. comprising 2, 3, 4, 5, 6, 7, 8 or more epitopes), or as single antigen/epitope units which are packed together in a cargo load. For example, different antigens may be mixed and subsequently be formulated in carrier, e.g. a liposome as defined herein. Also preferred is the use of different molecular forms of the virus antigen/epitopes within the cargo load. For example, it may be provided as protein/peptide, as an oligosaccharide or as nucleic acid.

In yet another particularly preferred embodiment of the present invention, the pharmaceutical composition as defined herein above is for use in the treatment or prevention of a parasitic infection. The term "parasitic infection" relates to the infection a patient, in particular of a human, with a parasite. Such an infection may, but must not necessarily lead to a parasitic disease or parasitosis, i.e. an infectious disease caused or transmitted by a parasite. The present invention thus not only envisages the treatment of parasitic diseases per se, but also the treatment of infections by parasites which may not lead to a disease. Such infection may still be considered problematic for a patient's health, e.g. due to use of energy or food resources by the parasite, fatigue, or psychic problems due to, e.g. the knowledge of being infected. Also, from an epidemiologic perspective the treatment of such infections is advantageous since thereby a further dissimilation can be prevented. The parasite whose infection is to be treated is, as described above, a parasite of mammals, in particular of humans. The parasite typically belongs to the group of protozoa or metazoan. Examples of parasites, whose infection is envisaged to be treated with the pharmaceutical composition according to the present invention include flagellates, amebae, sporozoa, and ciliates, as well as plathelminthes. In specific embodiments, the parasitic infection to be treated may be an infection by one or more of the following genuses or species: *Giardia, Trichomonas, Trypanosoma, Leishmania, Entamoeba, Naegleria, Acanthamoeba, Cryptosporidium, Cyclospora, Toxoplasma, Plasmodium, Balantidium coli, Fasciola hepatica, Taenia, Schistosoma, Wuchereria bancrofti* and *Onchocerca volvulus*. Particularly preferred is the treatment of infections with *Plasmodium*.

In the context of a viral infection, the term "treating" includes any or all of: inhibiting the growth of parasites, multiplication or replication of the pathogen that causes the infectious disease and ameliorating one or more symptoms of the parasitic infection. The infections with parasites as mentioned above may preferably be treated by using parasitic antigens or parasitic epitopes as described herein, or which are known to the skilled person, e.g. from suitable literature source such as Ansari et al., 2010, Nucleic Acids Res, 38, D847-D853, Tarleton, 2005, Cellular Microbiology, 7, 10, 1379-1386 or Higashi, 1988, Ann Rev Public Health, 9, 483-501, which are provided to Langerin$^+$ DCs in the form of cargos as described herein above. These antigens or epitopes thereof are subsequently processed and presented by the Langerin$^+$ cells to further immune cells and activate these immune cells leading to an immune response, e.g. via CTLs or antibodies against entities, e.g. viruses or parts thereof, showing said antigen or epitope. It is also envisaged that different antigens and/or different epitopes, e.g. either derived from different parasites, or derived from different proteins or glycoproteins, which may be present on or in the same parasite are provided. These antigens or epitopes may, for example, be provided in a multiantigen fusion protein or a multiepitope protein (e.g. comprising 2, 3, 4, 5, 6, 7, 8 or more epitopes), or as single antigen/epitope units which are packed together in a cargo load. For example, different antigens may be mixed and subsequently be formulated in carrier, e.g. a liposome as defined herein. Also preferred is the use of different molecular forms of the parasite antigen/epitopes within the cargo load. For example, it may be provided as protein/peptide, as an oligosaccharide or as nucleic acid.

In yet another particularly preferred embodiment of the present invention, the pharmaceutical composition as defined herein above is for use in the treatment or prevention or of a graft-vs. host disease. The term "graft-vs. host disease" as used herein relates to a medical complication following the receipt of transplanted tissue from a genetically different person. Graft-vs. host disease is typically associated with stem cell transplants such as those that occur with bone marrow transplants. Graft-vs. host disease may also apply to other forms of transplanted tissues such as solid organ transplants. Without wishing to be bound by theory, it is assumed that the disease is caused by the fact that white blood cells of the donor's immune system which remain within the donated tissue (the graft) recognize the recipient (the host) as foreign (non-self). The white blood cells present within the transplanted tissue then typically attack the recipient's body's cells, which leads to graft-vs. host disease. The graft-vs. host disease is different from a transplant rejection, which occurs when the immune system of the transplant recipient rejects the transplanted tissue; graft-vs. host disease, on the other hand, occurs when the donor's immune system's white blood cells reject the recipient. Graft-vs. host disease can also occur after a blood transfusion if the blood products used have not been irradiated or treated with an approved pathogen reduction system. The present invention envisages that the host of the donated tissue (the graft) is provided with an MHC antigen comprised in the donated tissue, e.g. an antigen of the graft or the donor of the tissue. This antigen may advantageously be provided to Langerin$^+$ DCs cells via as cargo in a suitable carrier as defined herein. This step may be followed is typically followed by an expansion and activation of MHC specific regulatory T cells, which leads to an antigen-specific deletion of CTLs, i.e. an antigen-specific tolerance in the absence of co-stimulatory signals, e.g. without the co-delivery of adjuvants. In the context of this treatment scheme the antigens or autoimmune disease epitopes as described above are preferably provided without co-delivery of any adjuvant. It is further preferred that any co-stimulatory signal which leads to an activation of Langerin$^+$ DCs-cells be inhibited by any suitable means known to the skilled person. Further details may be derived from suitable literature sources such as Sela et al., 2011, J. Exp. Med., 208, 12, 2489-2496.

In a further embodiment, the present invention further envisages that the immunological reaction of the donor of the donated tissue (the graft) be inhibited, e.g. ex vivo. Accordingly, the present invention relates, for example, to the use of skin transplants in which LCs in the donor graft are specifically killed ex vivo. Further details can be derived, for example, from Zell et al., 2008, Journal of Investigative Dermatology, 128, 8, 1874, Obhrai et al., 2008, Journal of Investigative Dermatology, 128, 8, 1950-1955; Molinero et al., 2007, American Journal of Transplantation, 8, 1; Adhikary et al., 2018, Transplantation, 102, S235 or Yamano et al., 2011, Blood, 117, 2640-2648.

In additional, particularly preferred embodiment of the present invention, the pharmaceutical composition as defined herein above is for use in the treatment or prevention of local or systemic inflammation. The term "inflammation" as used herein relates to complex biological response of body tissues to damaging or harmful stimuli, such as pathogens, damaged cells, or irritants. The inflammation is a protective response involving immune cells, blood vessels, and molecular mediators. The function of inflammation is to eliminate the initial cause of cell injury, clear out necrotic cells and tissues damaged from the original insult and the inflammatory process, and initiate tissue repair. Inflammation is a generic response, and therefore it is considered as a mechanism of innate immunity. The process of inflammation is initiated by resident immune cells already present in the involved tissue, in particular resident macrophages, dendritic cells, histiocytes (Langerhans cells), Kupffer cells and mast cells. These cells possess surface receptors known as pattern recognition receptors (PRRs), which recognize two subclasses of molecules: pathogen-associated molecular patterns (PAMPs) and damage-associated molecular patterns (DAMPs). PAMPs are compounds that are associated with various pathogens, but which are distinguishable from host molecules. DAMPs are compounds that are associated with host-related injury and cell damage. At the onset of an infection, burn, or other injuries, these cells undergo activation (one of the PRRs recognize a PAMP or DAMP) and release inflammatory mediators responsible for the clinical signs of inflammation. Vasodilation and its resulting increased blood flow cause the redness and increased heat. Increased permeability of the blood vessels results in an exudation of plasma proteins and fluid into the tissue, which manifests itself as swelling. Some of the released mediators such as bradykinin increase the sensitivity to pain. The mediator molecules also alter the blood vessels to permit the migration of leukocytes, mainly neutrophils and macrophages, outside of the blood vessels into the tissue. The neutrophils migrate along a chemotactic gradient created by the local cells to reach the site of injury. The loss of function is probably the result of a neurological reflex in response to pain.

When inflammation overwhelms the host, i.e. becomes a "systemic inflammation", a systemic inflammatory response syndrome is given. When it is due to infection, the syndrome is considered as sepsis. Vasodilation and organ dysfunction may occur with widespread infection that may lead to septic shock and death. In contrast thereto, a "local inflammation" is confined to the location or tissue region of the first harmful stimulus, injury or damage. Without wishing to be bound by theory, it is currently believed that Langerhans cells modulate regulatory, T cells which in turn can shut down inflammatory responses, e.g. as described in Sharabi et al., 2018, Nature Reviews Drug Discovery, 17, 823-844. It is further assumed that fact that Langerhans cells can induce an anti-inflammatory response via Tregs, as is derivable from suitable literature resources such as Stary et al., 2011, J Immunol, 186, 1, 103-112. The envisaged treatment approach involves the provision of suitable compounds such as glucocorticosteroids which may be comprised in a carrier as defined herein to Langerin$^+$ cells via the vehicle of the present invention. There an anti-inflammatory response may accordingly be initiated. Further information can be derived from Bartneck et al., 2014, Nanomedicine, 10, 6, 1209-20.

In a further particularly preferred embodiment of the present invention, the pharmaceutical composition as defined herein above is for use in the treatment or prevention of allergy. The term "allergy" as used herein relates to a pathological condition caused by hypersensitivity of the immune system to a stimulus from the environment that normally, i.e. in a healthy subject cause little or no problem. The allergy is hence a condition in which the patient produces an abnormally vigorous immune response in which the immune system defends the organism against a perceived threat that would otherwise be harmless to the body. The underlying mechanism is assumed to involve immunoglobulin E antibodies (IgE), binding to an allergen, e.g. as defined herein above and to a receptor on mast cells or basophils where it triggers the release of inflammatory chemicals such as histamine.

In a further particularly preferred embodiment of the present invention, the pharmaceutical composition as defined herein above is for use in hyposensitization. The term "hyposensitization" which is also known as desensitization or hypo-sensitization, is an allergen immunotherapy in the form of a medical treatment for some types of allergies which relies on the administration of increasing doses of allergens to drive immune responses from IgE production towards the induction of regulatory T cell responses, thereby promoting allergen-specific tolerance. The present invention can be used to directly induce regulatory T cell responses with higher efficiency via the selective delivery of allergens to Langerin$^+$ DCs, specifically Langerhans cells, in the absence of adjuvants.

The present invention further envisages the treatment of any other disease or medical condition which is directly or indirectly linked to cells expression Langerin on their surface, in particular DCs. In particular, the cargo, which may be comprised in or associated with the carrier as defined herein above, may be an active pharmaceutical or immunological compound, which is, for example, capable of eliciting an immunological reaction in the body, which operates as an immunomodulator, as an immunological tolerance inducer or as an inhibitor of cellular function, such as an inhibitor of apoptosis. Moreover, the active pharmaceutical or immunological compound which is delivered into a Langerin$^+$ cell may, upon said delivery, allow for a specific activation or suppression of the immune system, preferably via pathways typical for DCs. This activation or modulation of the immune system may be useful for in vivo treatment or prevention of a disease. The disease to be treated may accordingly not be developed or already exists in the subject to be treated.

In another aspect, the invention relates to a diagnostic composition comprising the vehicle as defined above or the composition as defined above, wherein the carrier comprises or is associated to a diagnostically suitable cargo. The term "diagnostically suitable cargo" as used herein relates to cargo entities selected from any of the following: a small molecule, a peptide, a protein, a nucleic acid, a metal, a radionuclide, a toxin, a dye, and a pigment. It is preferred that all of the mentioned elements correspond to those defined herein above in the context of the cargo, including additional examples of the mentioned elements. Particularly preferred are dyes, which can be used to target and visualize Langerin$^+$ cells in different contexts, e.g. the skin or lymphatic tissue. Also envisaged are combinations of the above-mentioned cargos, e.g. a protein and a nucleic acid, or a protein and a dye, or a small molecule and a dye etc. In further, preferred embodiments, the carrier as mentioned may comprise or be associated to a diagnostically suitable cargo, e.g. a dye, and at the same time to a therapeutically suitable cargo, e.g. a small molecule etc. as defined herein. The presence of the diagnostically suitable cargo may accordingly be used to detect and/or count the delivery of the therapeutically suitable cargo. The diagnostic composition may further comprise a pharmaceutically acceptable carrier as defined herein above in the context of the pharmaceutical compositions, or a pharmaceutical adjuvant as defined herein above in the context of the pharmaceutical compositions.

In specific embodiments, the diagnostic composition as defined herein may be used to directly diagnose Langerhans cell-related diseases, e.g. LC-histocytosis, wherein the diagnostic composition may comprise a disease specific marker/biomarker or comprise a suitable component which allows to detect LC histocytosis.

In further embodiments the diagnostic composition as described herein may be used for prognostic and/or predictive uses. For example, the diagnostic composition may be used to assess changes in the Langerhans cell activation level and/or the cross-presentation levels of disease-specific antigens or allergens, e.g. before, during or after a treatment, preferably directly following a treatment. Such uses particularly envisage diagnostisc compositions comprising labelled markers for activation signalesignals such as RNA, peptide or protein level markers. These markers may be delivered or co-delivered, together with further components such as pharmaceutically active compounds as defined herein, to the target cell, i.e. a Langerin$^+$ cell via the vehicle and carrier as defined herein.

Therefore a labeled marker for activation signals (on RNA, peptide/protein level) could be co-delivered using the system In a preferred embodiment, the diagnostic composition as defined above is for use in detecting or monitoring a treatment approach and/or the efficacy of said treatment approach based on a pharmaceutical composition as defined herein against cancer, an autoimmune disease, a bacterial infection, a viral infection, or a graft-vs. host disease local or systemic inflammation or allergy.

In a further aspect, the invention relates to a method of identifying a suitable dose for a dendritic cell-targeting therapy of a disease comprising: (a) contacting a population of Langerin$^+$ cells with a compound capable of being introduced into the cells; (b) determining the number of cells which incorporated said compound; (c) determining a suitable dose of the compound by comparing the number of cells with incorporated the compound and the starting population. The term "dendritic cell-targeting therapy" as used herein relates to the use of a pharmaceutical composition as described herein. Preferably, the term relates to therapy forms or uses of pharmaceutical compositions which involve an interaction of a vehicle as defined herein, more preferably comprising a cargo as defined herein, via a ligand as part of the conjugate as defined herein and the cognate receptor Langerin. Accordingly, the disease may be any disease mentioned herein above, e.g. cancer, or a bacterial, viral, parasitic infection, allergy etc. The step "contacting a population of Langerin$^+$ cells with a compound" means that said compound is brought into contact with or is brought into the vicinity of said cell or is delivered to said cell, preferably via the vehicle as defined above. The cells are either derived from a cell culture in vitro, or are ex vivo cells obtained form a patient's skin. It is particularly preferred that the number of cells which are used is determined or known. These cells may accordingly be provided in a confined environment, e.g. a reaction chamber etc. The compound is a "compound capable of being introduced into the cells", which means that the compound can be internalized by the Langerin$^+$ cells, for example by endocytosis. Such approach may, for example, comprise an in vitro step, wherein LCs are stained, or wherein a flow cytometric analysis is performed. The introduction of the compound may preferably be performed via endocytosis of the Langerin$^+$ cells.

For example, in a specific embodiment, the approach may be is implemented as in vitro approach, wherein Langerin$^+$ cells may be labeled with a composition according to the present invention, e.g. comprising a dye. Further envisaged is the employment of flow cytometry to separate labeled from not labeled cells. Also envisaged is the implementation as in vivo approach or as a combined in vitro/ex vivo approach. The compound may, in specific embodiments, be a cargo as defined herein above, preferably a dye or pigment, more preferably it is Alexa Fluor 647.

The step of "determining the number of cells which incorporated said compound" as used in step b) of the method relates to any suitable analysis process, which allows differentiating the cells which have incorporated the compound from those which have not. Preferably, this process is a fluorescence detection process, which identifies those cells which have incorporated a dye or pigment form those which have not. More preferably it is a process based on the use of Alexa Fluor 647. Accordingly, the number of cells which have incorporated the compound vs. the cells which have not incorporated said compound can be determined by counting those cells which show, for example, a fluorescence signal or stain and deduct the number from the number of originally provided cells, i.e. the overall number of cells used in the assay, thus resulting in the number of non-fluorescent or non-stained cells. Finally, the dose of a compound, or of any similar or comparable compound by analogy, may be determined by correlating the amount of compound used with the number or percentage of cells with incorporated compounds. Accordingly, by increasing the amount of compound delivered to the cells, the percentage of cells with incorporation of compounds may be increased. In additional embodiments, also alternative parameters may be changed, e.g. the presence of additives, the formulation of the compound, the presence of divalent ions etc. A "suitable dose" may thus, according to certain embodiments be a percentage of 50%, 60%, 70%, 75%, 80%, 85%, 90% or more than 90% of cells which show an incorporation of the compound, e.g. by fluorescence accordingly to the above described steps. Furthermore, the method may be performed as described in the Examples, e.g. in Example 10. Further information may be derived from suitable literature sources such as Boyd and Jackson, 2015, Cell Host & Microbe, 17, 301-307.

In a preferred embodiment, the comparison of cells with incorporated compounds vs. non-incorporated compound may be performed after a period of 1-3 days, e.g. after 24 h, 30 h, 36 h, 40 h, 48 h, 55 h, 60 h, 65 h, or 72 h.

In a further embodiment, the number of cells with incorporated compound may be compared with observed literature results or results derivable from a database or internet repository. For example, the incorporation percentage, the calculated suitable dose etc. of compound may, for example, be compared with data for other compounds in the same assay or a similar assay from a database. In certain embodiments, the database may be a database developed with information from different approaches/different compounds according to the present invention. Also, information from further projects outside of the present invention may be used for such a database.

In a further aspect the present invention relates to a medical kit comprising at least one element selected from the vehicle as defined herein above and/or the composition as defined herein above, wherein the carrier comprises or is associated to a pharmaceutically active cargo. The kit may optionally comprise a leaflet with instructions. The term "medical kit" includes any pharmaceutical composition as defined above, a medical device, a therapeutic as mentioned above etc. In further specific embodiments the medical kit may also be a vaccine, diagnostic, prognsotic or predictive kit comprising suitable ingredients for the performance of vaccination, for the performance of a diagnosis of a disease associated with Langerin, e.g. as defined herein, or the prognostic or predictive determination of a e health status with respect to such a disease. In further embodiments, a medical kit may comprise any medical device in a package. The term "medical device" comprises a syringe, a needle, e.g. a needle of syringe, a vaccination gun, a plaster, or an inhaler, preferably as defined herein above. The vehicle of the invention or a composition thereof may, for example, be administered via a medical device. Moreover, the vehicle or a composition thereof may be stored in the medical device. The term "package insert" or "leaflet with instructions" is used to refer to instructions customarily included in commercial packages of therapeutic products that contain information about the indication(s), usage, dosage, administration, contraindications and/or warnings concerning the use of such therapeutic products. The leaflet with instructions may be part of a medical kit.

In yet another aspect the present invention relates to a vaccine comprising the vehicle as defined above, or the composition as defined above, wherein the carrier comprises or is associated to an inoculant cargo, e.g. as defined herein above.

The term "vaccine" is to be seen as composition including, in preferred embodiments, the vehicle or the composition as defined above, which is suitable for a vaccination of a subject. A vaccine composition has been described herein above in the context of pharmaceutical compositions. It is particularly preferred that the vaccine comprises an adjuvant, in particular an immunologic adjuvant as described above. The vaccine may, for example comprise a therapeutically effective amount of the vehicle comprising a cargo as defined above. For example, the vaccine may, in preferred embodiment comprise proteins and/or nucleic acids as immunogenic elements.

The term "vaccination" refers to the elicitation of an immune response against a tumro via a cancer antigen, a bacterial infection via a bacterial antigen, a viral infection via a viral antigen, a parasitic infection via parasitic antigen as defined above, in a subject comprising administering to said subject a therapeutically effective amount of the vehicle comprising a cargo as defined above. Preferably, the carrier of the vehicle of the invention comprises a cargo which is or comprises a cancer antigen or epitope as defined above, a bacterial antigen or epitope as defined above, a viral antigen or epitope as defined above, a parasitic antigen or epitope, as defined above. Also envisaged is the vaccination with entities described in the context of graft-vs. host disease as defined above. The present invention, in particular, envisages the use of liposome or nanoparticle carriers as defined herein for vaccination purposes. It is further preferred that the liposome or nanoparticle carrier comprises a peptide or protein antigen as described herein. The peptide or protein antigen may accordingly be comprised in or encapsulated in said liposome or nanoparticle carrier as described herein. The administration of said carrier is preferably an intradermal injection as described herein or a transcutaneous administration as described herein, preferably an administration via microneedle patches.

The vaccine may, in preferred embodiments, be for use in treating or preventing cancer, an autoimmune disease, bacterial infection, viral infection, a parasitic infection or graft-vs. host disease.

The immunisation may be performed according to any scheme or schedule known to the skilled person or similar sources of information. The schedule may, for example, comprise several doses of the vaccine composition comprising the vehicle or the composition as defined above. In one embodiment of the invention, at least 1 dose of the vaccine composition is administered to the subject. In another embodiment, the vaccination consists of 1 dose of the vaccine composition. In another embodiment a subject receives an initial 2 dose vaccination, but does not receive further administrations of the vaccine composition, or receives a further administration after a predefined period of time of at least 1 month, or 2, 3, 4, 5, 6, 7, 8, 9, 10, 11 or 12 months or 1, 2, 3, 4, 5, 6, 7, 8, 9, 10, etc. years. The interval in between administration of several, e.g. two or more, doses of the vaccine may further be varied between 1 week and about one year or more, or between 1 month and one year, or between 1 and 3 months.

The administration of the vaccine may be performed according to any suitable administration scheme and on any suitable route, e.g. subcutaneously, transdermally, intradermally, intramuscularly, orally, via corneal or nasal route, intravenously, topically, or via hair follicles etc. It is particularly preferred to use transdermal, intradermal or subcutaneous routes, e.g. as intradermal injection. The application is preferably performed with needles, microneedles, nanopatches, hydrogel patches, vaccination guns etc. as described above.

Similarly, in a further aspect the present invention relates to a method of inducing an immune response against cancer, a bacterial infection, a viral infection or a parasitic infection in a subject comprising administering to said subject a therapeutically effective amount of the vehicle as defined above, wherein the carrier comprises or is associated to a pharmaceutically active cargo as defined above, or the composition as defined above, wherein the carrier comprises or is associated to a pharmaceutically active cargo as defined above, or the pharmaceutical composition as defined above, or the vaccine as defined above. The method essentially comprises the steps of providing an immunoactive compound as mentioned herein to a Langerin$^+$ cell and thereby cause said Langerin$^+$ cell to incorporate said compound, process it and displays it or one or more parts of it on its surface to induce a reaction of other immune cells, or of the immune system, or to elicit in any other suitable manner an immune response via Langerin$^+$ cells. The method may, in particularly preferred embodiments, comprise vaccination steps as defined herein above. In particular, vaccination schemes and schedules as mentioned may be employed.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the inhibitor compound are outweighed by the therapeutically beneficial effects.

The term "therapeutically effective amount" refers to that amount of the compound being administered sufficient to prevent development of, or alleviate to some extent one or more of the symptoms of the condition or disorder being treated.

A therapeutically effective amount of compound (i.e., an effective dosage) may may be determined in view of the body weight of the patient and other factors known to the skilled person. The therapeutically effective amount may further be defined as concentration, e.g. in the pM or μM range. The skilled person will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound one or several times per day for between about 1 to 50 weeks, or any other suitable period of time. In another example, a subject may be treated daily for two or more years in the setting of a chronic condition or illness. It will also be appreciated that the effective dosage of a compound used for treatment may increase or decrease over the course of a particular treatment.

In yet another aspect the present invention relates to a method of treatment or prevention of cancer, of an autoimmune disease, of a bacterial infection, of a viral infection, of a parasitic infection, or of a graft-vs. host disease, of a local or systemic inflammation, or of allergy, comprising administering to a subject a therapeutically effective amount of the vehicle as defined above, wherein the carrier comprises or is associated to a pharmaceutically active cargo, the composition as defined herein above, wherein the carrier comprises or is associated to a pharmaceutically active cargo, the pharmaceutical composition as defined above, or the vaccine as defined above. The method may any suitable administration scheme as described herein above. The compound to be used for the method is in a particularly preferred embodiment a pharmaceutical composition as described above, or a vaccine as described herein above. The method of treatment, in particularly preferred embodiments, contemplates an administration via an oral, corneal, nasal, intravenous, topical, subcutaneous, epicutaneous, intradermal, transdermal route or a vaccination or an administration via hair follicles.

The administration of the vehicle, composition, pharmaceutical composition or vaccine may be in combination with a chemotherapeutic agent in particular if the treatment of against cancer. Suitable examples include checkpoint inhibitors or CAR T-cells. The chemotherapeutic agent may preferably be any cytotoxic substance as mentioned above. The treatment with a chemotherapeutic agent preferably is performed on another way than the presently described interaction with DCs, i.e. not via Langerin$^+$ cell. For example, the chemotherapeutic agent may be administered in a systemic manner, or intravenously etc. The chemotherapeutic agent may accordingly support a vaccination approach against cancer by destroying cancerous cells chemotherapeutically. For example, an approach based on a combination with a chemotherapeutic agent may be based on systemic chemotherapy which is capable of modulating immune phenotypes of residual tumor cells, e.g. after the tumor mass has been optimally reduced with surgery. Another approach may be based on the enhancement of tumor antigen presentation by upregulating the expression of tumor antigens themselves, or of the MHC Class I molecules to which the antigens bind. Furthermore, chemotherapy may be used to upregulate co-stimulatory molecules (e.g. B7-1) or down-regulate co-inhibitory molecules (e.g. PD-L1/B7-H1 or B7-H4) expressed on the tumor cell surface, which leads to an enhancement of the strength of effector T cell activity. In a further embodiment, chemotherapy may be used to render tumor cells more sensitive to T cell-mediated lysis through fas-, perforin-, or granzyme B-dependent mechanisms.

In a further aspect the present invention relates to a method of hyposensitization. The present invention accordingly envisages that the allergic patient is provided with an antigenic allergen. This allergen may advantageously be provided to Langerin$^+$ cell via as cargo in a suitable carrier as defined herein. It is particularly preferred that the antigenic allergen be provided in more than one dose. The number of doses and/or the concentration of allergen may be increased over the treatment period. This provision step, which may be repeated one or several times, is typically followed by an expansion and activation of antigenic allergen specific regulatory T cells, which leads to an allergen-specific deletion of CTLs, i.e. an allergen-specific tolerance in the absence of co-stimulatory signals, e.g. without the co-delivery of adjuvants. In the context of this treatment scheme the allergens as described above are preferably provided without co-delivery of any adjuvant. It is further preferred that any co-stimulatory signal which leads to an activation of Langerin$^+$ cells be inhibited by any suitable means known to the skilled person. Further details may be derived from suitable literature sources such as Sela et al., 2011, J. Exp. Med., 208, 12, 2489-2496.

The invention is further described in the following examples, which are not intended to limit the scope of the invention.

EXAMPLES

Example 1

Langerin-Expressing Hek293 Cells

The human embryonic kidney cell line Hek293 was maintained in DMEM medium with GlutaMax supplemented with 10% FCS (Biochrom) and 100 U/ml Penicillin-Streptomycin. Cells were cultured to 70% confluence and subcultured with trypsin every 2-3 days. Unless stated otherwise, all media and supplements were purchased from Thermo Fisher Scientific. Cells were grown under controlled conditions at 37° C. and 5% CO2. Cells were monitored with a light microscope (IT40 SPH, VWR) and cultured in Petri dishes (Corning). Cells were subcultured with the proteolytic enzyme trypsin in combination with 0.25% EDTA. In routine subculture, all cells were centrifuged at 500 g for 3 min (Heraeus Megafuge 8R, Thermo Fisher Scientific). The supernatant was aspirated and cells were resuspended in fresh growth medium. As a quality control, cells were frequently tested free from *mycoplasma* contamination using a MycoAlert® *Mycoplasma* Detection Kit (Lonza). No contamination was detected. Cells were counted with an automatic cell counter (Eve, Montreal Biotech). To cryopreserve cells, vital cells were counted, centrifuged, aspirated and resuspended in freezing medium consisting of 90% growth medium and 10% DMSO (cell culture grade, Euro Clone). Cryo vials were then transferred into a cryo vial container filled with isopropanol (Mr. Frosty, Nalgene). The container was stored at −80° C. for at least 24 h and for long-time storage vials were preserved in liquid nitrogen.

The cDNA ORF clone of human Langerin was purchased from sinobiological, The gene was cloned from a pcDNA5/FRT/V5-His-TOPO TA vector (life technologies) into an RP172 expression vector (K. J. Koymans et al., Staphylococcal Superantigen-Like Protein 1 and 5 (SSL1 & 55L5) Limit Neutrophil Chemotaxis and Migration through MMP-Inhibition. International journal of molecular sciences 17, 2016) by Gibson Assembly, according to the manufacturer's instruction. Briefly, gene fragments were amplified with an overhang from the destination vector by PCR using a Phusion high-fidelity DNA polymerase (NEB). For the PCR reaction a master mix was prepared consisting of 10 µl Phusion HF buffer (NEB), 5 µl of 2 mM dNTPs (Carl Roth), 0.5 µl Phusion polymerase (NEB) and 29 µl H$_2$O per reaction. To each reaction 0.5 µl of 50 µM primer and 2.5 µl of approximately 10 ng/ml template vectors were added. The destination vector was linearized by PCR (Mastercycler nexus gradient, Eppendorf). Here, 0.6 µl DMSO (NEB) was added. The PCR products were quality checked by agarose gel electrophoresis and DNA concentration was measured with a nanodrop (Implen Nanophotometer).

In particular, for the generation of Langerin clones, Langerin variant clones and mLangerin clones, as well as for the generation of DC-SIGN and mDectin clones the following primer sequences and PCR conditions were used:

| Name | Sequence (5' to 3') | Direction | SEQ ID NO | PCR conditions |
|---|---|---|---|---|
| hLangerin pcDNA3.1(+) | CTGGCTAGCGTTTAAACTTAAGCATGACTGTGGAGAAGGAGGCC | forward primer | 17 | 62° C./30 sec/35 |
| hLangerin pcDNA3.1(+) | CTAGACTCGAGCGGCCTCACGGTTCTGATGGGAC | reverse primer | 18 | 62° C./30 sec/35 |
| hLangerin Backbone plasmid pcDNA3.1(+) | GCTTAAGTTTAAACGCTAGCC | forward primer | 19 | 59° C./2.5 min/20 |
| hLangerin Backbone plasmid pcDNA3.1(+) | GGCCGCTCGAGTCTAGAG | reverse primer | 20 | 59° C./2.5 min/20 |
| hLangerin pcDNA5 | CTGGCTAGCGTTTAAACTTAAGCATGACTGTGGAGAAGGAGGCC | forward primer | 21 | 59° C./1 min/35 |
| hLangerin pcDNA5 | GTGATGGTGATGATGACTCACGGTTCTGATGGGAC | reverse primer | 22 | 59° C./1 min/35 |
| hLangerin Backbone plasmid pcDNA5 | GCTTAAGTTTAAACGCTAGCC | forward primer | 23 | 62° C./3.5 min/20 |
| hLangerin Backbone plasmid pcDNA5 | GTCATCATCACCATCACC | reverse primer | 24 | 62° C./3.5 min/20 |
| hLangerin RP172 | CTGGCTAGCGTTTAAACTTAAG | forward primer | 25 | 60° C./1 min/35 |
| hLangerin RP172 | CAATGGTGATGGTGATGATG | reverse primer | 26 | 60° C./1 min/35 |
| hLangerin Backbone plasmid RP172 | GAGCTAGCAGtaTTAATTAACCACCCTGGCTAGCGTTTAAACTTAAG | forward primer | 27 | 60° C./3.5 min/20 |
| hLangerin Backbone plasmid RP172 | GTACCGGTTAGGATGCATGCCAATGGTGATGGTGATGATG | reverse primer | 28 | 60° C./3.5 min/20 |
| hLangerin SNP Backbone | GAGCTAGCAGtaTTAATTAACCACCATGACTGTGGAGAAGGAG | forward primer | 34 | |
| hLangerin-FLAG Backbone SNP | ACGTTTCTTTTCATTTGTAAGCGACCCTATGTCCCATCAGAACCGGACTACAAAGACGATGACGACAAGTGAGCATGCATCCTAACCGGTAC | reverse primer | 35 | |
| N288D | CCAGGTGAGCCCAACgATGCTGGGAACAATGAACACTG | forward primer | 36 | |
| N288D | CATTGTTCCCAGCATcGTTGGGCTCACCTGGAATCCAG | reverse primer | 37 | |
| K313I | GTACCGGTTAGGATGCATGCTCACGGTTCTGATGGGACATAGGGTCGCTTACAAATGAAAAGAAACGTTaTGTCACATGGGGCATCATTCCAG | forward primer | 38 | |
| K313I | GAGCTAGCAGtaTTAATTAACCACCATGACTGTGGAGAAGGAG | reverse primer | 39 | |
| DC-SIGN pcDNA3.1(+) | CTGGCTAGCGTTTAAACTTAAGCATGAGTGACTCCAAGGAACCAAG | forward primer | 40 | 62° C./30 sec/35 |

-continued

| Name | Sequence (5' to 3') | Direction | SEQ ID NO: | PCR conditions |
|---|---|---|---|---|
| DC-SIGN pcDNA3.1(+) | CTAGACTCGAGCGGCC CTACGCAGGAGGGGG | reverse primer | 41 | 62° C./30 sec/35 |
| DC-SIGN Backbone plasmid pcDNA3.1(+) | GCTTAAGTTTAAACGC TAGCC | forward primer | 42 | 59° C./2.5 min/20 |
| DC-SIGN Backbone plasmid pcDNA3.1(+) | GGCCGCTCGAGTCTAG AG | reverse primer | 43 | 59° C./2.5 min/20 |
| DC-SIGN pcDNA5 | CTGGCTAGCGTTTAAA CTTAAGCATGAGTGAC TCCAAGGAACCAAG | forward primer | 44 | 59° C./1 min/35 |
| DC-SIGN pcDNA5 | GTGATGGTGATGATG ACCTACGCAGGAGGG GGGTT | reverse primer | 45 | 59° C./1 min/35 |
| DC-SIGN Backbone plasmid pcDNA5 | GCTTAAGTTTAAACGC TAGCC | forward primer | 46 | 62° C./3.5 min/20 |
| DC-SIGN Backbone plasmid pcDNA5 | GTCATCATCACCATCA CC | reverse primer | 47 | 62° C./3.5 min/20 |
| DC-SIGN RP172 | CTGGCTAGCGTTTAAA CTTAAG | forward primer | 48 | 60° C./1 min/35 |
| DC-SIGN RP172 | CAATGGTGATGGTGAT GATG | reverse primer | 49 | 60° C./1 min/35 |
| DC-SIGN Backbone plasmid RP172 | GAGCTAGCAGTATTAA TTAACCACCCTGGCTA GCGTTTAAACTTAAG | forward primer | 50 | 60° C./3.5 min/20 |
| DC-SIGN Backbone plasmid RP172 | GTACCGGTTAGGATGC ATGCCAATGGTGATGG TGATGATG | reverse primer | 51 | 60° C./3.5 min/20 |
| mLangerin pcDNA3.1(+) | CTGGCTAGCGTTTAAA CTTAAGCATGCCAGAG GCAGAGATGAAG | forward primer | 57 | 62° C./30 sec/35 |
| mLangerin pcDNA3.1(+) | CTAGACTCGAGCGGCC TCATTCAGTTGTTTGG ACG | reverse primer | 58 | 62° C./30 sec/35 |
| mLangerin Backbone plasmid pcDNA3.1(+) | GCTTAAGTTTAAACGC TAGCC | forward primer | 59 | 59° C./2.5 min/20 |
| mLangerin Backbone plasmid pcDNA3.1(+) | GGCCGCTCGAGTCTAG AG | reverse primer | 60 | 59° C./2.5 min/20 |
| mLangerin pcDNA5 | CTGGCTAGCGTTTAAA CTTAAGCATGCCAGAG GCAGAGATGAAG | forward primer | 61 | 59° C./1 min/35 |
| mLangerin pcDNA5 | GTGATGGTGATGATG ACTCATTCAGTTGTTTG GACG | reverse primer | 62 | 59° C./1 min/35 |
| mLangerin Backbone plasmid pcDNA5 | GCTTAAGTTTAAACGC TAGCC | forward primer | 63 | 62° C./3.5 min/20 |
| mLangerin Backbone plasmid pcDNA5 | GTCATCATCACCATCA CC | reverse primer | 64 | 62° C./3.5 min/20 |
| mLangerin RP172 | CTGGCTAGCGTTTAAA CTTAAG | forward primer | 65 | 60° C./1 min/35 |
| mLangerin RP172 | CAATGGTGATGGTGAT GATG | reverse primer | 66 | 60° C./1 min/35 |
| mLangerin Backbone plasmid RP172 | GAGCTAGCAGTATTAA TTAACCACCCTGGCTA GCGTTTAAACTTAAG | forward primer | 67 | 60° C./3.5 min/20 |

| Name | Sequence (5' to 3') | Direction | SEQ ID NO: | PCR conditions |
|---|---|---|---|---|
| mLangerin Backbone plasmid RP172 | GTACCGGTTAGGATGC ATGCCAATGGTGATGG TGATGATG | reverse primer | 68 | 60° C./3.5 min/20 |
| mDectin-1 pcDNA3.1 (+) | TAGCGTTTAAACTTAA GCATGAAATATCACTC TCATATAGAGAATC | forward primer | 69 | 62° C./30 sec/ 35 |
| mDectin-1 pcDNA3.1 (+) | TAGACTCGAGCGGCCT TACAGTTCCTTCTCACA GATAC | reverse primer | 70 | 62° C./30 sec/ 35 |
| mDectin-1 Backbone plasmid pcDNA3.1(+) | GCTTAAGTTTAAACGC TAGCC | forward primer | 71 | 59° C./2.5 min/20 |
| mDectin-1 Backbone plasmid pcDNA3.1(+) | GGCCGCTCGAGTCTAG AG | reverse primer | 72 | 59° C./2.5 min/20 |
| mDectin-1 pcDNA5 | TAGCGTTTAAACTTAA GCATGAAATATCACTC TCATATAGAGAATC | forward primer | 73 | 59° C./1 min/ 35 |
| mDectin-1 pcDNA5 | GTGATGGTGATGATG ACTTACAGTTCCTTCTC ACAGATAC | reverse primer | 74 | 59° C./1 min/ 35 |
| mDectin-1 Backbone plasmid pcDNA5 | GCTTAAGTTTAAACGC TAGCC | forward primer | 75 | 62° C./3.5 min/20 |
| mDectin-1 Backbone plasmid pcDNA5 | GTCATCATCACCATCA CC | reverse primer | 76 | 62° C./3.5 min/20 |
| mDectin-1 RP172 | CTGGCTAGCGTTTAAA CTTAAG | forward primer | 77 | 60° C./1 min/ 35 |
| mDectin-1 RP172 | CAATGGTGATGGTGAT GATG | reverse primer | 78 | 60° C./1 min/ 35 |
| mDectin-1 Backbone plasmid RP172 | GAGCTAGCAGTATTAA TTAACCACCCTGGCTA GCGTTTAAACTTAAG | forward primer | 79 | 60° C./3.5 min/20 |
| mDectin-1 Backbone plasmid RP172 | GTACCGGTTAGGATGC ATGCCAATGGTGATGG TGATGATG | reverse primer | 80 | 60° C./3.5 min/20 |

Finally, PCR products were assembled by Gibson Assembly. Equal volumes (2-10 µl) of DNA containing 0.02-0.5 pmols of DNA fragments with a 2-3 excess of insert and Gibson Assembly Master Mix were incubated at 50° C. for 20 min. The master mix contained T5 exonucleases, Phusion DNA polyermases and Taq DNA ligases to create single-stranded DNA overhangs, incorporate nucleotides into DNA gaps and to anneal complementary DNA fragments. After Gibson Assembly, 1 µl DpnI (NEB) was added to digest the given cloning vector. The digested PCR reaction (1 µl) was then transformed into 10 µl 5-alpha competent E. colis (NEB) by heat shock transformation at 42° C. for 30 sec. After 2-3 min on ice, 200 µl SOC medium (SOB medium containing 20 mM glucose, Carl Roth) were added to the reaction vials and incubated for 1 h at 37° C. E. coli cells were plated on LB agar plates (Luria/Miller, Carl Roth) containing 100 µg/ml ampicillin (Panreac AppliChem) and incubated at 37° C. overnight. To isolate DNA, a MiniPrep kit was used following the manufacturer's instructions (GeneJET Plasmid Miniprep Kit, Thermo Fisher Scientific). The DNA concentration was measured with a nanodrop, and plasmid DNA was sequenced.

The Lentivirus used for transduction of the cell lines was produced in 293T cells using a lipopolyplex transfection (LT) reagent Mirus LT1 (Sopachem). Using this system the RP172 vector (BIC-PGK-Zeo-T2a-mAmetrine; EF1A) containing the Langerin sequence and a packaging mix containing all three necessary plasmids (pVSV-G, pMDL, and pRSV) were introduced into the 293T cells. After transfection with the LT system, 293T cells produced virus for 3-4 days which was harvested and frozen down at −80²C to kill remaining 293T cells. This supernatant was then used to transduce Langerin/RP172 into the different cell lines.

Lentivirus-containing supernatants were mixed with Raji cells and gently spun centrifuged in full media containing polybrene (Santa Cruz Biotechnology) at 33²C. The RP172 vector (BIC-PGK-Zeo-T2a-mAmetrine; EF1A) includes a Zeocin resistance cassette and a fluorescent GFP derived protein mAmetrine. Transduction of 50000 Raji cells was facilitated by spin infection at 1000*g for approximately 90 min at 33° C. After 2-3 days, the (partially) infected cells were exposed to Zeocin (Life technologies) pressure to select for RP172 containing cells. Transduced cells were selected with selection medium containing 300 µg/ml Zeocin (life technologies) for two weeks. Presence of RP172 is assessed by mAmetrine expression measured by FACS (BD FACS canto II). The initial mAmetrine check (performed before selection) is crucial as the percentage of infected cells gauges the lentiviral titer. In all transductions, we aimed for an initial mAmetrine percentage of 5-10%.

Recombinantly expressed receptors were detected with CLR-specific antibodies. For antibody staining, 50000 cells were incubated with 25 µl medium containing a 1:100 dilution of PE anti-mouse/human CD207 (4C7, Biolegend) to stain murine Langerin, PE anti-human CD209 (9E9A8, Biolegend) to stain DC-SIGN, PE anti-mouse Dectin-1 (bg1fpj, eBioscience) to stain mDectin-1 cells or PE anti-mouse/IgG2a (RMG2a-62, Biolegend) or PE anti-normal mouse/IgG1 (sc-2866, Santa CruzBiotechnology) for iso-type staining. To stain cell surface expression of human Langerin expressing cells, 50000 cells were incubated with a 1:5 dilution of CD207-PE conjugated antibody (DCGM4, Beckman Coulter). After incubation at 4° C. for 30 min, cells were washed and PE staining was analyzed by flow cytometry with a 488 laser with a 574/26 filter (Attune Nxt, life technologies). FIG. 1 shows the results.

Example 2

CLR-Expressing Raji Cells

Figure 2:
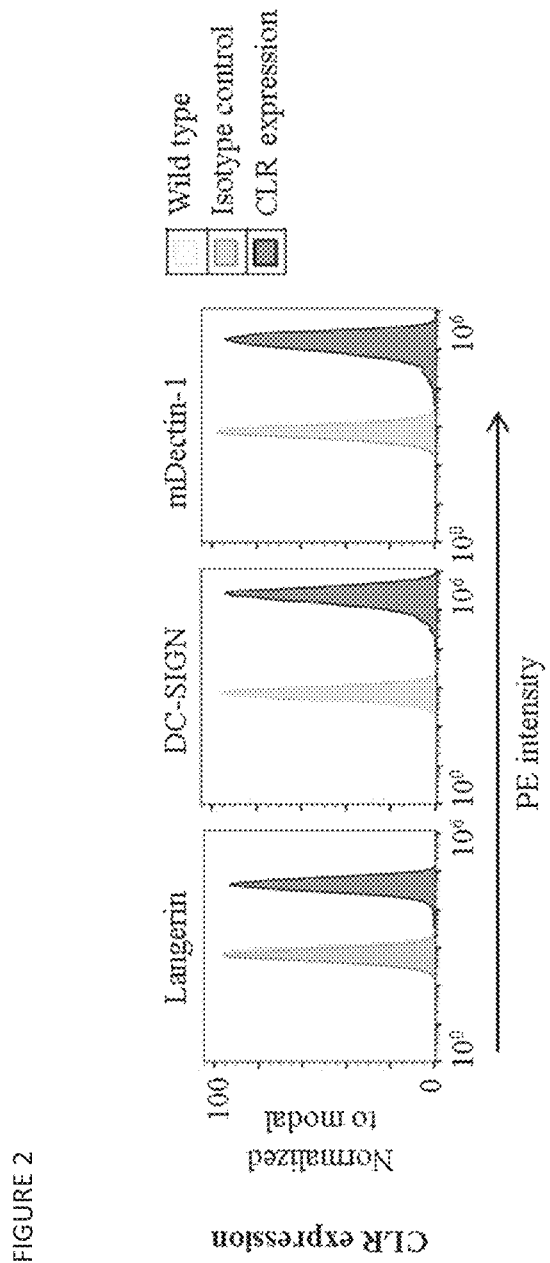
FIG. 2 shows stable receptor expression at the plasma membrane of Raji cells which was detected via CLR specific antibodies. Isotype staining was applied as a negative control. Fluorescence intensities were compared to background fluorescence from wild type cells and plotted in a histogram plot.

The human Raji cell line from hematopoietic origin was grown in RPMI base medium containing 10% FCS, 100 U/ml Penicillin-Streptomycin and GlutaMax. Cells were maintained between 0.5-3 Mio cells/ml by addition or replacement of the complete growth medium and grown, maintained, monitored and stored under the same conditions as mentioned for Hek293 (see above). The cDNA ORF clones of DC-SIGN and mouse Dectin-1 were also transferred from a pcDNA5/FRT/V5-His-TOPO TA vector (life technologies) into a RP172 vector (Koymans et al., 2016, Int. J. Mol. Sci., 17, 7, 1072) for stable expression in Raji cells by transduction. Cloning was done using Gibson Assembly, according to the manufacturer's instruction (see above). DNA concentration was measured with a nanodrop, and plasmid DNA was sequenced. Transduction of human Langerin, DC-SIGN and mouse Dectin-1 into Raji cell lines was conducted as described for Hek293 cells (see Example 1). Recombinantly expressed receptors were detected with CLR-specific antibodies and measured using flow cytometry (see Example 1 and FIG. 2). Taken together, these experimental results describe the recombinant cell lines used here.

Example 3

Synthesis of the Targeting Ligand

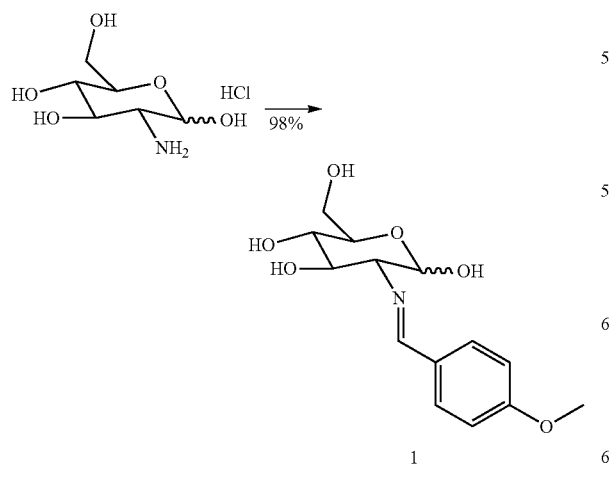

Glucoseamine hydrochloride (46.4 mmol, 10 g) was dissolved in a aqueous NaOH solution (1M, 47 mL) at 0° C. p-anisaldehyde (47 mmol, 5.7 mL) was added dropwise over 5 min and the reaction was left to stir at 0° C. for 2 h during which the solution solidified. The crystalline slurry was suction-filtered, washed with $H_2O$ and small amounts of Et2O and dried under high vacuum at 45° C. to obtain 1 as a colourless solid in 97% yield (45.34 mmol, 13.48 g).

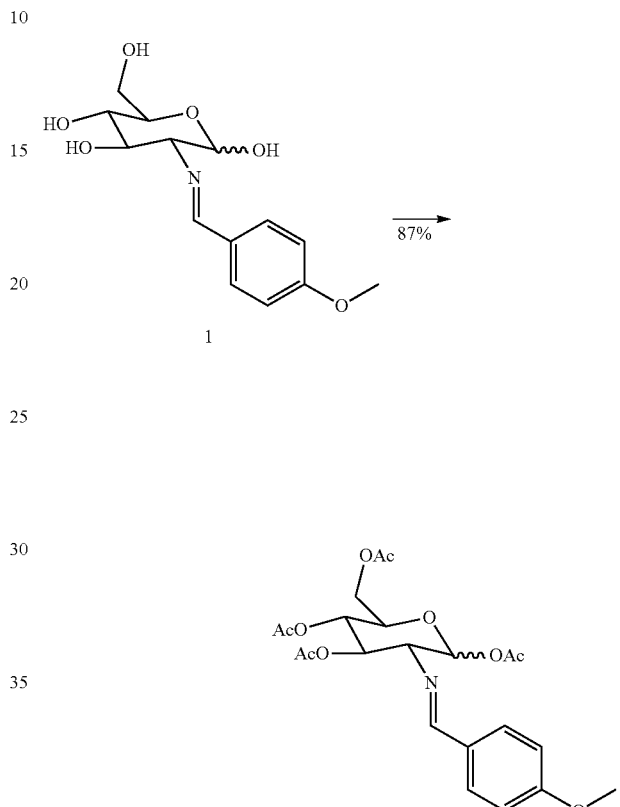

1 (40.3 mmol, 11.98 g) was dissolved in pyridine (71 mL) under Ar and cooled to 0° C. Acetic anhydrite (36 mL) was added under stirring, the cooling bath was removed and the mixture was allowed to warm to room temperature under stirring overnight. The mixture was poured into ice water (240 mL). The resulting precipitate was suction filtered, washed with water (350 mL) and dried in high vacuo to obtain 2 as colourless solid in 87% yield (35.15 mmol, 16.36 g).

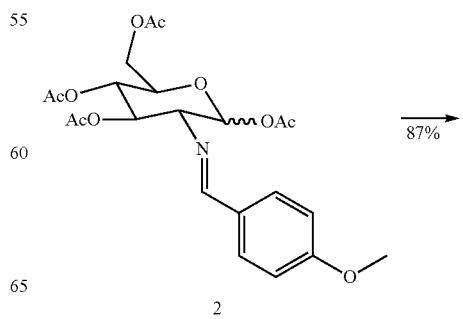

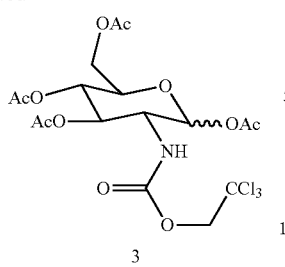

3

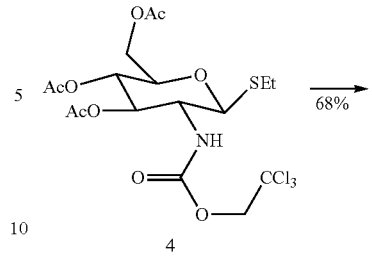

4

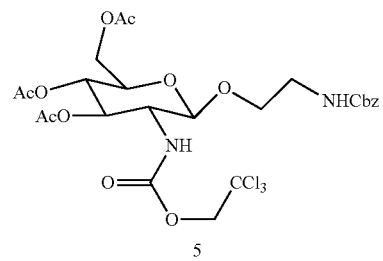

5

2 (35.15 mmol, 16.36 g) was heavy stirring in boiling acetone in a beaker (boiling 70 mL). 7.03 mL (35 mmol) of aqueous HCl (5 M) were quickly added. The immediately solidifying mass was allowed to cool to room temperature, subsequently suction filtered, washed with cold Et2O and dried in vacuo. The resulting solid (35.15 mmol, 11.67 g) was suspended in 180 mL pyridine and cooled to 0° C. under heavy stirring. 2,2,2-Trichloroethyl chloroformate (76 mmol, 10.4 mL) was added the mixture at once and left stirring for 3 hours. 30 mL of methanol were added to quench excess of Troc-Cl and the mixture subsequently concentrated in vacuo. 250 mL of DCM were added, the resulting precipitate was filtered off and the filtrate concentrated in vacuo. The residue was redissolved in little DCM and purified using liquid chromatography to obtain 3 as a colourless solid in 87% yield (30.61 mmol, 16 g).

A suspension of 4 (2.48 mmol, 1.30 g) and benzyl-2-hydroxyethylcarbamate (3.96 mmol, 790 mg) in 60 mL anhydrous DCM was stirred for 45 min under an Ar atmosphere. Dimethyl(methylthio)sulfonium tetrafluoroborate (4.95 mmol, 1 g) was added and the reaction left stirring overnight at room temperature. The solvent was removed in vacuo and the residue purified by liquid chromatography to obtain 5 as a white solid in 68% yield (1.67 mmol, 1.1 g).

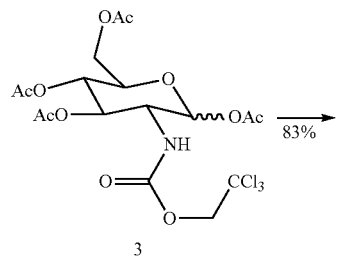

3

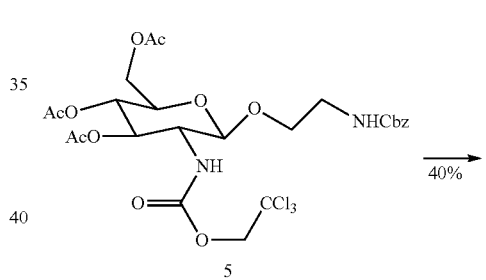

5

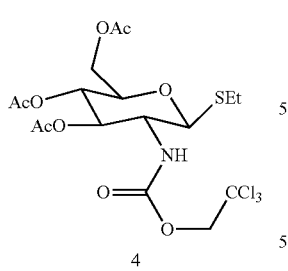

4

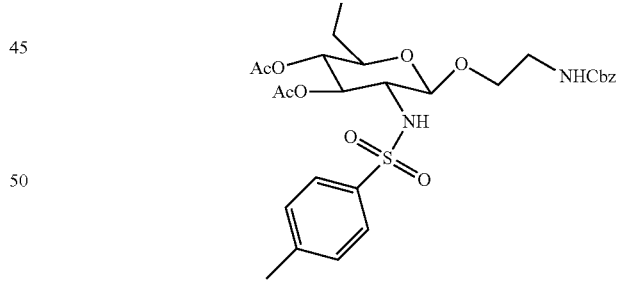

6

3 (13.32 mmol, 6.96 g) and ethanethiol (18.64 mmol, 1.38 mL) were dissolved in 35 mL anhydrous DCM under an Ar atmosphere and cooled to 0° C. BF3.Et2O (18.64 mmol, 2.36 mL) was added over 5 min and the reaction stirred for 40 min at 0° C., then at room temperature for 4 hours. The reaction was quenched by addition of 1.1 mL NEt3 and the mixture concentrated in vacuo. Purification using liquid chromatography obtained 4 as a white solid in 83% yield (11.05 mmol, 5.8 g).

A suspension of 5 (0.76 mmol, 500 mg) and freshly activated zinc (6.46 g, 99 mmol) in 27 mL acetic acid was stirred for 4 h. The reaction mixture was filtered over celite and dried in high vacuo overnight. The resulting solid was then dissolved in pyridine (12 mL) and p-toluenesulfonyl chloride (1.52 mmol, 290 mg; dissolved in 12 mL pyridine) were added dropwise. The reaction mixture was left to stir overnight. The solvent was then removed in vacuo and the residue purified by liquid chromatography to obtain 6 as a white powder in 43% yield (209 mg, 0.33 mmol).

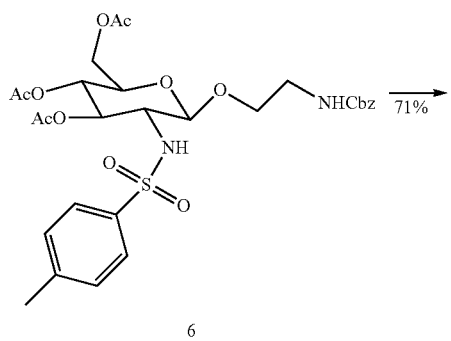

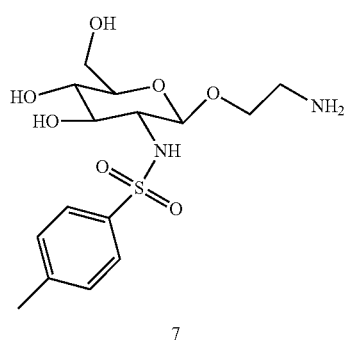

To a solution of 6 (0.30 mmol, 190 mg) in anhydrous methanol (8 mL) sodium methanolate solution (c=0.5 mM. 149 mmol 2.98 mL) was added under an Ar atmosphere and left to stir for 2 hours. The solvent was removed in vacuo. The resulting white powder was re-dissolved in anhydrous methanol (30 mL), 30 mg of palladium on charcoal (10%) were added and the reaction mixture was left to stir under an hydrogen atmosphere overnight. The catalyst was filtered off through Celite and washed with methanol. The solvents were removed and the residue purified by reverse phase high performance liquid chromatography to obtain 7 as a white solid in 71% yield (0.21 mmol, 80 mg).

Example 4

Lipid Conjugation

Ligands and dyes were coupled to PEG-DSPE by NHS conjugation. Alexa Fluor 647 NHS Ester (A647, life technologies) was conjugated to the primary amine of NH2-PEG-DSPE (PEG MW 2000, Sunbright) via amide coupling. The lipid (1.024 mg) dissolved in 500 µl DMSO was stirred in a pear shaped flask, and 1 mg dye (1.5 equiv.) dissolved in 500 µl DMSO was added dropwise to the lipid. The reaction was stirred overnight in the dark at room temperature. DMSO was freeze dried (Alpha 2-4 LDplus, CHRIST) and the reaction product was dissolved in 2-3 ml buffer containing 0.1 M sodium bicarbonate (Sigma-Aldrich) at pH8.4. Unconjugated dye was removed by dialysis with a Slide-A-Lyzer cassette (7MWCO, 0.5-3 ml, Thermo Fisher Scientific) first against 500 ml buffer for several hours with two times of buffer exchange as well as an overnight incubation and then three more times dialyzed against water with at least 1 h of dialysis under permanent stirring. Water was removed by freeze drying and the final product was dissolved in DMSO at a concentration of 8 mg/ml. The glycomimetic Langerin ligand, mannose as well as mannose polymers contained a terminal primary amine and were coupled to NHS-PEG-DSPE (PEG MW 2000, NOF Europe) via amide coupling equally as described for A647 conjugation except that 2 mg ligands were dissolved in 900 µl buffer and 0.125 equivalent lipids were dissolved in 100 µl DMF. Lipids were added dropwise in a pear shape flask and DMF was removed in vacuo (Heidolph). The final product was dissolved in DMSO-d6 (Euriso-Top) and the conjugation efficiency was determined by 1H-proton NMR spectroscopy with 265 scans (400 MHz, Variant).

Example 5

Formulation Liposomes

Targeted and naked PEGylated liposomes were prepared by hydration film extrusion method (Chen et al., 2010, Blood, 115, 23, 4778-4786). Unless stated otherwise, liposomes contained DSPE:cholesterol:ligand-PEG-DSPE/PEG-DSPE:dye-PEG-DSPE at a mole ratio of 57:38:4.75:0.25. If liposomes contained less than 4.75 mol % ligand-conjugated lipids then liposomes were filled up with PEG-DSPE to always obtain a total mole ratio of 5% PEGylated lipids. PEGylated lipids were dissolved in DMSO at a concentration of 8 mg/ml and stored at −20° C. for long term storage. DSPE (NOF Europe) and cholesterol (Sigma-Aldrich) were always freshly prepared and dissolved in chloroform at a concentration of 20 mg/ml and 10 mg/ml, respectively. PEGylated lipids were added to a glass tube and DMSO was freeze dried. Next, DSPE and cholesterol were added and Chloroform was removed in vaccuo overnight. The dry lipid film was hydrated with DPBS (w/o calcium and magnesium; life technologies) at a concentration of 1.6 mM if not stated otherwise. Lipid containing solution was first vortexed and then sonicated (Ultrabath 1510, Branson) for 3 sec with three repetitions and a short time lag in between. This step was repeated until a homogenous suspension was obtained. Large unilamellar liposomes were produced by pore extrusion (extruder, Avanti Polar Lipids) with 30 strokes first with a polycarbonate membrane of 200 nm and then of 100 nm (Avanti Polar Lipids). Liposome concentration refers to total lipid concentration.

Example 6

Characterization of Liposomes

To characterize liposomes prepared following the procedure described in Example 4 regarding particle size and stability, dynamic light scattering measurements (Malvern Instruments Zetasizer) were carried out on dilute liposome solutions (32 µM in pure water). Liposomes exhibiting Zeta potentials between −35 mV and −15 mV as well as average particle sizes between 100 and 200 nm (% Intensity plot) and poly dispersity indices up to 0.3 were considered to be feasible for further usage.

Example 7

Liposomal Loading and Purification

Several proteins were devised as cargo for liposomal loading. In the following the recombinant expression of these proteins is presented and its loading into liposomes is described.

2 mg Bovine Serum Albumin (BSA) (PAA) was dissolved in 1 ml HBSS buffer (life technologies) and transferred into a 5 ml pear shaped flask with septum and stir bar. Fluorescein isothiocyanate (Thermo Fisher Scientific) was dissolved in DMSO (1 mg/ml) and 200 µl were added slowly in 5 µl steps to BSA. The flask was covered in aluminum foil and stirred overnight at room temperatures. The reaction was quenched by adding a final concentration of 50 mM ethanolamine (Sigma-Aldrich) and stirred for 1 hour at room temperature. Unconjugated fluorescein was removed by dialysis with a Slide-A-Lyzer cassette (7MWCO, 0.5-3 ml, Thermo Fisher Scientific) against HBS buffer (25 mM HEPES, Carl Roth; 150 mM NaCl, Panreac AppliChem; pH 7.5). Buffer was twice exchanged after 1 h of stirring and after another overnight incubation. Protein concentration of FITC conjugated proteins were measured with absorbance at 280 nm and the conjugation efficiency was determined at 495 nm with a nanodrop (Implen Nanophotometer). Protein samples were stored at 4° C.

Liposomes were loaded with FITC-BSA by hydration of the thin film lipid with DPBS containing the FITC-BSA. FITC-BSA concentrations ranged from 1 mg/ml to 20 mg/ml. Followed by sonication and pore extrusion, liposomes were purified by ultracentrifugation or size exclusion. To remove free proteins by ultracentrifugation, liposomal suspension was transferred into ultracentrifugation tube (Thinwall, Ultra-Clear™, 4 mL, Beckman coulter). The tube was filled up with DPBS to prevent implosion. Liposomes were ultracentrifuged at 55000 rpm for 1 h at 4° C. with a SW 60 Ti rotor (Beckman coulter) in an ultracentrifuge (Optima L-80 XP Ultracentrifuge, Beckman Coulter). The supernatant was removed and the pellet was resuspended in DPBS. Ultracentrifugation was repeated twice. Purification by size exclusion was performed with 20 ml sepharose CL gel filtration media (CL-4B, cross-linked, Sigma-Aldrich) that was packed into a chromatography column (Econocolumn, 1.5×30 cm, BioRad). The column was equilibrated with DPBS before liposome solution was loaded to the column. Fractions of 1.5 ml were collected until liposomes and free FITC-BSA eluted (10-15 fractions). After fractionation, the column was regenerated with regeneration buffer containing 0.5 M NaCl in 0.1 M NaOH, equilibrated with DPBS until the pH was neutral and the next liposomal solution was separated by size exclusion. Encapsulation efficiencies were analyzed with a plate reader (SpectraMax M5, Molecular Devices) and calculated on the basis of standard curves. Liposome concentration was measured via Alexa 647 decorated liposomes (ex. 640, em. 670) and FITC-BSA concentration via (ex. 485, em. 525). Encapsulation efficiencies were calculated per 1 mM total lipid concentration.

Example 8

Liposome Characterization

Liposomal dispersity and stability were determined as described before (see Examples 4 to 6).

Figure 3:
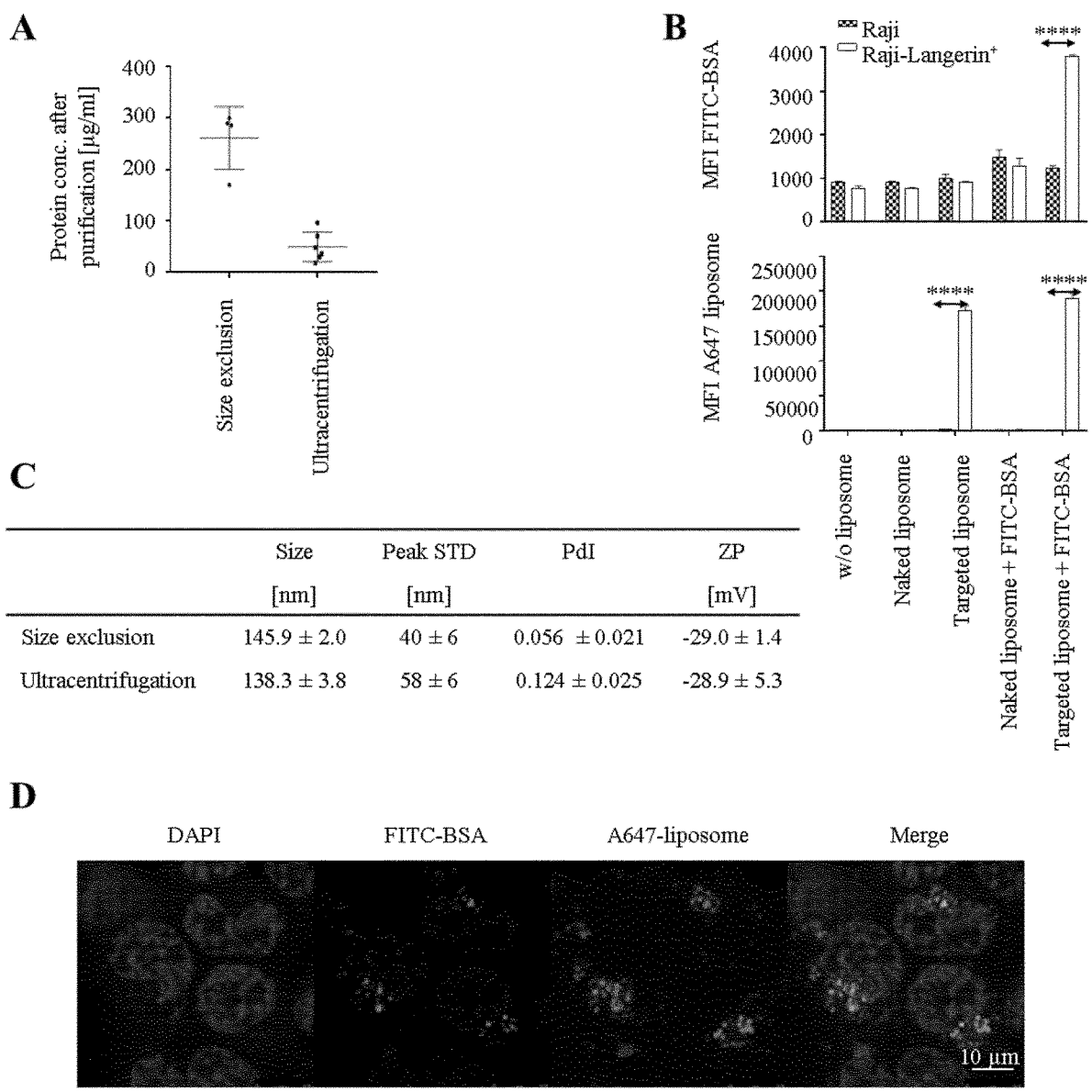
FIG. 3 shows FITC-BSA encapsulation and delivery to Langerin expressing cells.

FITC-BSA was utilized to show encapsulation and purification methods for a protein. The total FITC-BSA protein concentration was measured after ultracentrifugation. Next, purified liposomes were then tested in a cell-based assay. FITC-BSA encapsulated liposomes were incubated with Langerin+ Raji cells for 2 h at 37° C. to induce internalization. A647 and FITC fluorescence of single cells was measured simultaneously by flow cytometry (see FIG. 3). As previously shown for targeted liposomes with or without encapsulated FITC-BSA a fluorescence signal of Alexa647 was detected, but more importantly, only for FITC-BSA encapsulated liposomes a FITC signal was detected. FITC-BSA was significantly increased in cells targeted with encapsulated liposomes, whereas naked FITC-BSA encapsulated liposomes showed no FITC signal. Liposome integrity of ultracentrifuged liposomes was analyzed by DLS (see FIG. 3 (C)). Size and zeta potential were similar to untreated liposomes (see Example 6, and FIG. 5 (C)) or liposomes purified by size exclusion which indicates maintained structural integrity. Next, FITC-BSA encapsulated liposomes were incubated with Langerin+ Hek293 cells for 6 h at 37° C., and cells were subsequently analyzed by microscopy after staining the nucleus (see FIG. 3 (D)). FITC-BSA highly co-localized with the co-formulated liposomal dye A647 indicating similar endosomal compartments after 6 h.

Figure 4:
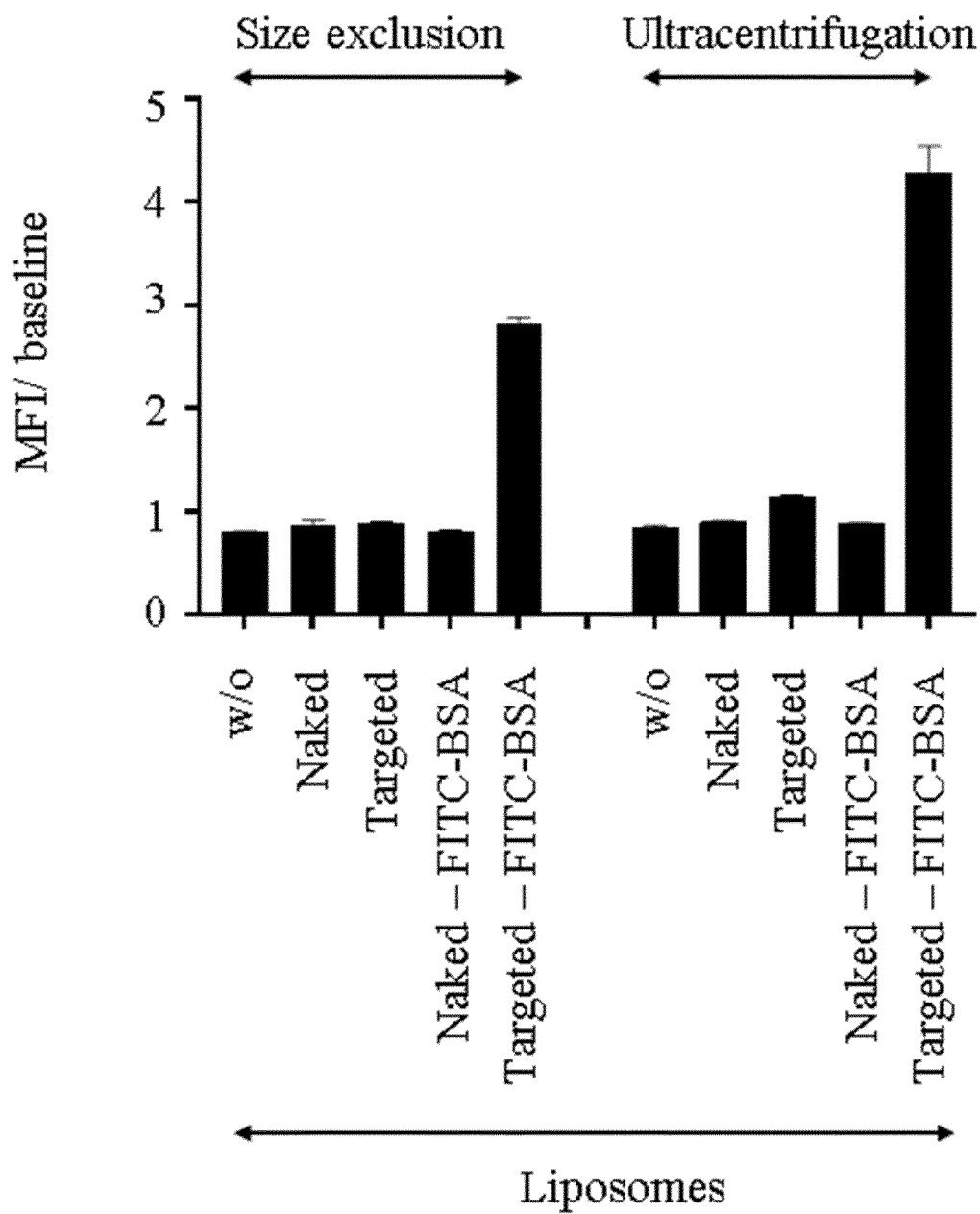
FIG. 4 shows FITC-BSA encapsulated liposomes which were either purified by size exclusion or by ultracentrifugation. Purified liposomes were subsequently tested in a cell-based assay. 16 μM liposomes were incubated with hLangerin+ Raji cells for 2 h at 37° C. Cells were analyzed for their FITC staining by flow cytometry. MFI values were baseline corrected.

To exclude that high centripetal forces during ultracentrifugation, liposomes released their cargo into the supernatant resulting in lower encapsulation efficiencies, liposomes purified by size exclusion and ultracentrifugation were compared in a cell-based assay (see FIG. 4). The FITC-BSA signal of the latter was even higher compared to liposomes purified by size exclusion concluding that centripetal forces had no impact on the integrity of liposomes and that it resembles the most efficient purification method. Consequently, all further liposomes were purified by ultracentrifugation if not stated otherwise.

Figure 5:
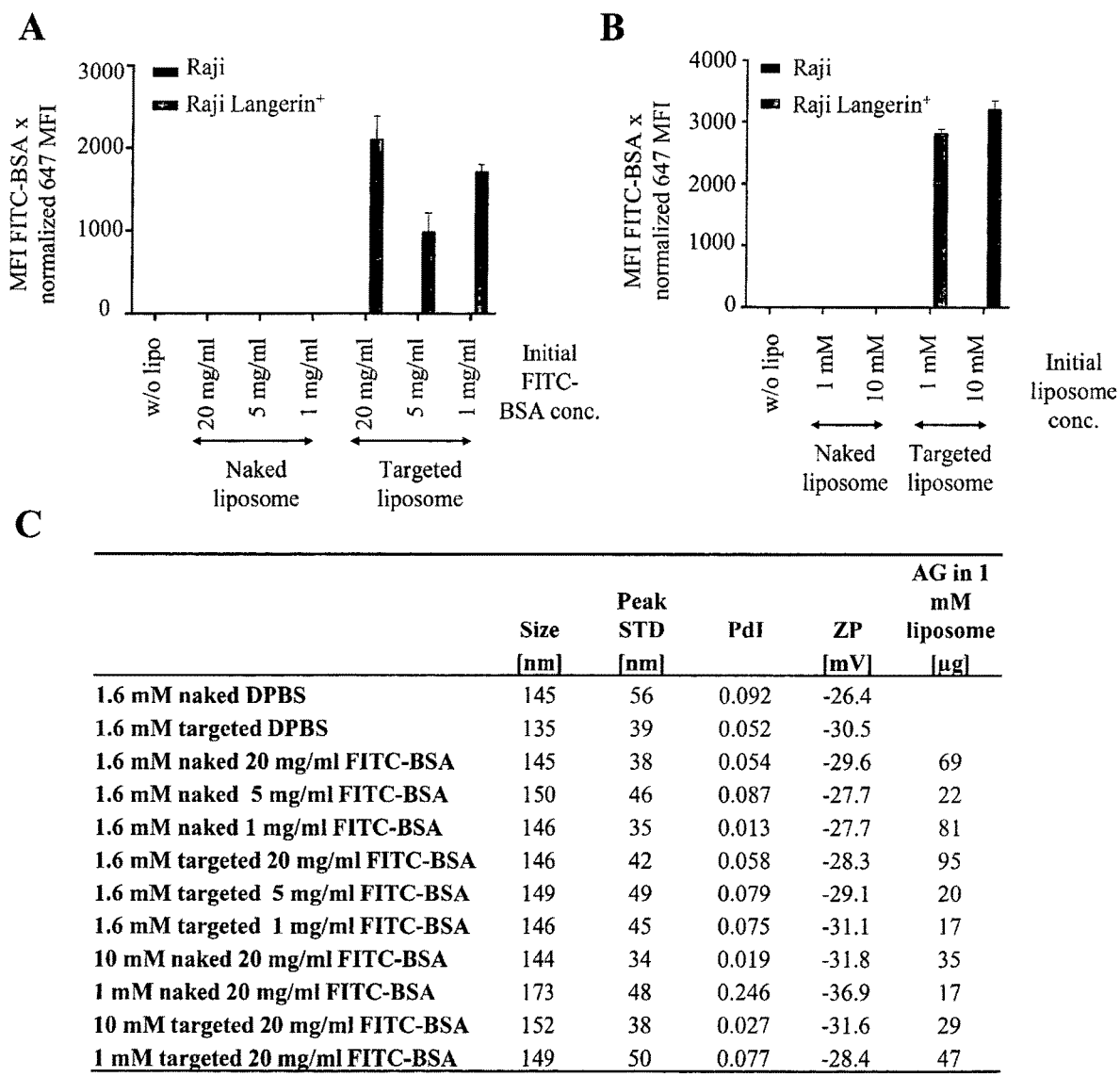
FIG. 5 reports on the optimization of protein encapsulation with a test protein FITC-BSA.

To analyse the impact of the initial concentration of FITC-BSA on the encapsulation efficiency the protein concentration was varied from 20 mg/ml to 1 mg/ml, and encapsulated liposomes were tested in a cell-based assay (see FIG. 5 (A)). The fluorescence signal was normalized to the co-formulated dye A647. The highest fluorescence signal was detected at 20 mg/ml FITC-BSA formulated liposomes. The fluorescence signal, however, did not correlate with the initial protein concentration utilized to formulate the liposomes. This result indicates that between 1 mg/ml and 20 mg/ml the encapsulation efficiency was in a similar range and independent of initial protein concentration.

Furthermore, the initial liposome concentration was varied. 10 mM were compared to 1 mM rehydrated liposomes in a cell-based assay (see FIG. 5). Liposomes were rehydrated with 20 mg/ml FITC-BSA. FITC fluorescence of cells incubated with FITC-BSA encapsulated liposomes was very similar of 10 mM and 1 mM formulated liposomes indicating that different liposomal concentrations had no impact on encapsulation efficiency. All liposomes were analyzed by DLS for size and zeta potential (see FIG. 5 (C)). In addition, the encapsulation efficiency of FITC-BSA was analyzed with a plate reader after ultracentrifugation and calculated for 1 mM liposomes (Fehler! Verweisquelle konnte nicht gefunden werden. FIG. 5 (B)). Here again, the encapsulation efficiencies of all formulated liposomes were in a similar range between 17 µg to 95 µg per 1 mM liposome and showed no trend of improved encapsulation efficiencies.

Figure 6:
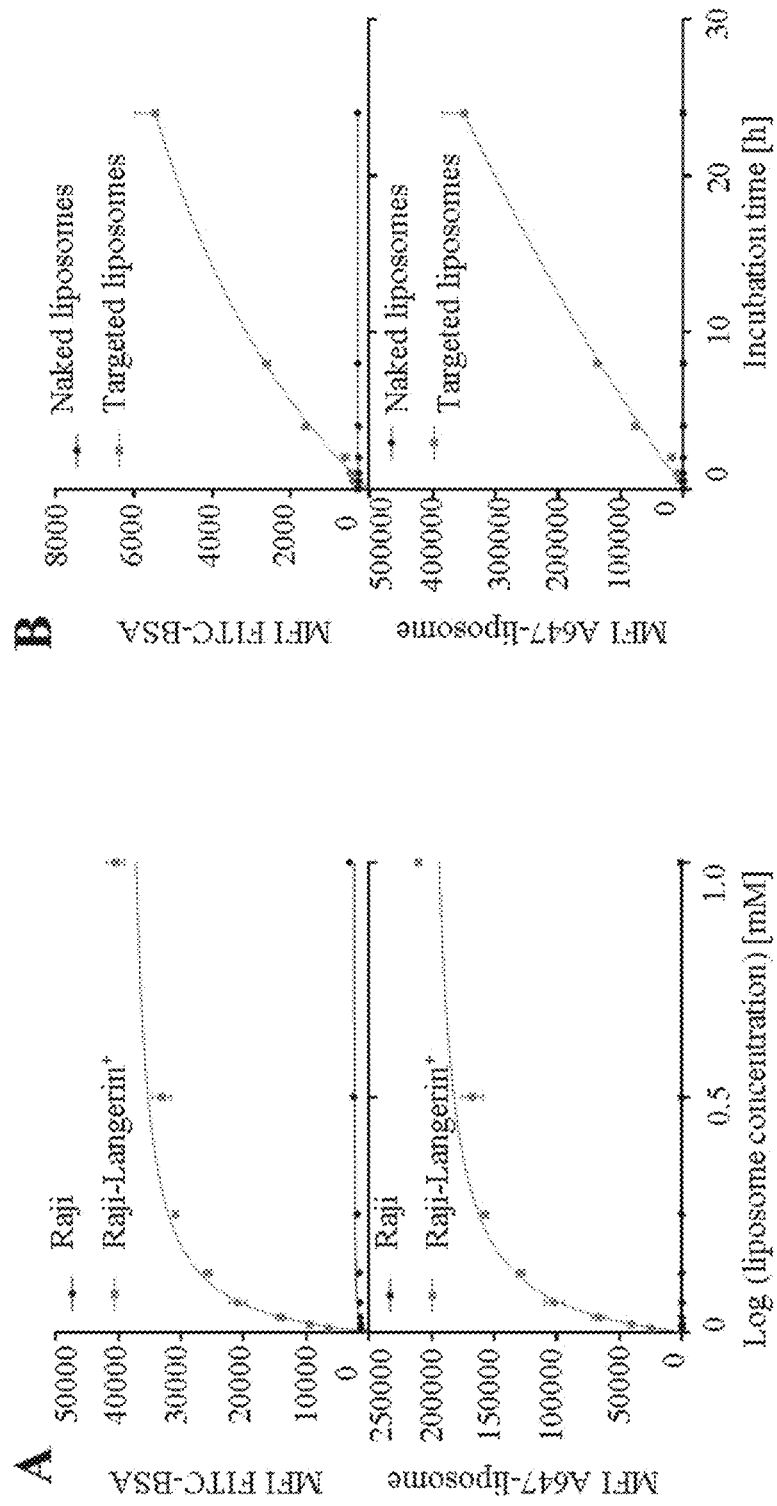
FIG. 6 shows dose-dependent internalization and kinetic rate of FITC-BSA encapsulated liposomes.

Next, encapsulated liposomes were dose-dependently incubated and a kinetic study was carried out to detect differences between the encapsulated FITC-BSA cargo and the A647 labeled delivery vehicle (see FIG. 6). Encapsulated FITC labeled proteins were measured with a 488 nm laser and a 574/26 nm filter (Attune Nxt, life technologies). These studies validated the results of FIGS. 14 (B) and 14 (C) showing again that with 16 µM liposomes internalization was not saturated after 24 h and liposomal internalization of higher concentrations saturated above 250 µM liposomes. More importantly, however, FITC-BSA encapsulated cargo and A647 labeled liposomes showed almost identical dose-dependent internalization rates and highly correlating internalization kinetics indicating that the cargo and the delivery vehicle enter similar processing pathways as already seen by microscopy in FIG. 3 (D).

These optimized encapsulation methods were then utilized to formulate liposomes containing immune-active EBNA1 protein. EBNA (Epstein-Barr nuclear antigen) was selected as a model peptide. It is a short immune-active peptide of the Epstein Barr virus (EBV) which has a prevalence of more than 90% in the adult population (see Cohen, 2000, N Engl J Med, 343, 7, 481-492). In addition, a housekeeping peptide PCNA (proliferating-cell-nuclear antigen) is associated with cancer progression and is thought to promote immune evasion (Rosental et al., 2011, J Immunol, 187, 11, 5693-5702). In addition, a housekeeping peptide PCNA (proliferating-cell-nuclear antigen) is associated with cancer progression and is thought to promote immune evasion. Hence, this peptide was used as a negative control.

Example 9

Bacterial Protein Expression and Purification of EBNA1 and PNCA

EBNA1 BL21 and PCNA BL21 *E. coli* cells were used LCs (see Barwell et al., 1995, J Biol Chem, 270, 35, 20556-20559). Proteins are fused to a His-tag and a thrombin recognition site. For protein expression, cells were cultured in 50 ml LB medium (Luria/Miller, Carl Roth) with 200 µg/ml Ampicillin in a 250 ml Erlenmeyer flask overnight at 37° C. and 300 rpm (MaxQ 4000, Thermo Fisher Scientific). Next day, pre-culture was centrifuged at 3000 g for 12 min (Multifuge X3R Heraus, Thermo Scientific Fisher). The pellet was resuspended in fresh LB medium. For inoculation of 500 ml medium supplemented with 200 µg/ml Ampicillin, 20 ml pre-culture was added to a 2000 ml Erlenmeyer flask and shacked at 300 rpm at 37° C. The culture was incubated until an optical density (OD at 600 nm) value of approximately 0.8 was reached to induce protein expression with 1 mM IPTG for overnight expression at 30° C. The next day, 500 ml bacterial cell suspensions were centrifuged at 4000 g for 15 min. Supernatant was discarded and the pellet was resuspended in PBS, transferred into a 50 ml tube, again centrifuged and the final *E. coli* pellet was either frozen at −80° C. or directly used for protein purification by affinity chromatography with a His-tag column (HisTrap HP, 1×1 ml; GE Healthcare).

To purify the recombinant expressed protein, *E. coli* cells were lysed with 5 ml lysis buffer (50 mM Na2PO4, Carl Roth; 300 mM NaCl, Panreac AppliChem; 10 mM imidazole, Carl Roth; pH 8) per 1 g *E. coli* pellet. 1 mg lysozyme (Fluka) was added per 1 ml lysate and cells were incubated at 4° C. for 30 min. Afterwards, cells were sonicated three times 20 sec at 30% amplitude and 10 sec off in between (Bransen, Digital Sonifier). The lysate was centrifuged at 10000 g for 15 min and the supernatant, containing the overexpressed protein, was filtered with a 0.45 µm membrane filter (Corning) to remove cell debris.

Recombinantly expressed proteins were purified by his-tag affinity chromatography using a fast protein liquid chromatography (FPLC, MWD2.1L Azura, Knauer) FPLC was equilibrated with binding buffer (in line A: 50 mM Na2PO4, 300 mM NaCl, 10 mM imidazole, pH 8), washing buffer (in line B: 50 mM Na2PO4, 300 mM NaCl, 20 mM imidazole, pH 8), distilled water (in line C), and elution buffer (in line D: 50 mM Na2PO4, 300 mM NaCl, 250 mM imidazole, pH 8). Filtered supernatant containing the overexpressed protein was injected into the FPLC. Supernatant was loaded on his-trap column with binding buffer at a flow rate of 1 ml/min and a maximum pressure of 1 bar for 20 min. Protein concentration was measured at 280 nm with a UV detector. Loaded column was washed for 20 min with washing buffer before the protein was eluted by applying a gradient from washing buffer to elution buffer for 10 min. Fractions of 1 ml were collected in small reaction tubes. For additional 5 min, 100% elution buffer was applied to elute all his-trapped protein. Column was equilibrated with binding buffer before the next run was started. Fractions with his-tagged proteins were collected and combined to dialyze proteins (CelluTrans dialysis, Cral Roth) against HBS buffer (25 mM HEPES, 150 mM NaCl, pH 7.5) containing 2 mM CaCl2). Protein quality was checked by SDS-PAGE gel and protein concentration was measured by nanodrop (Implen Nanophotometer).

Figure 7:
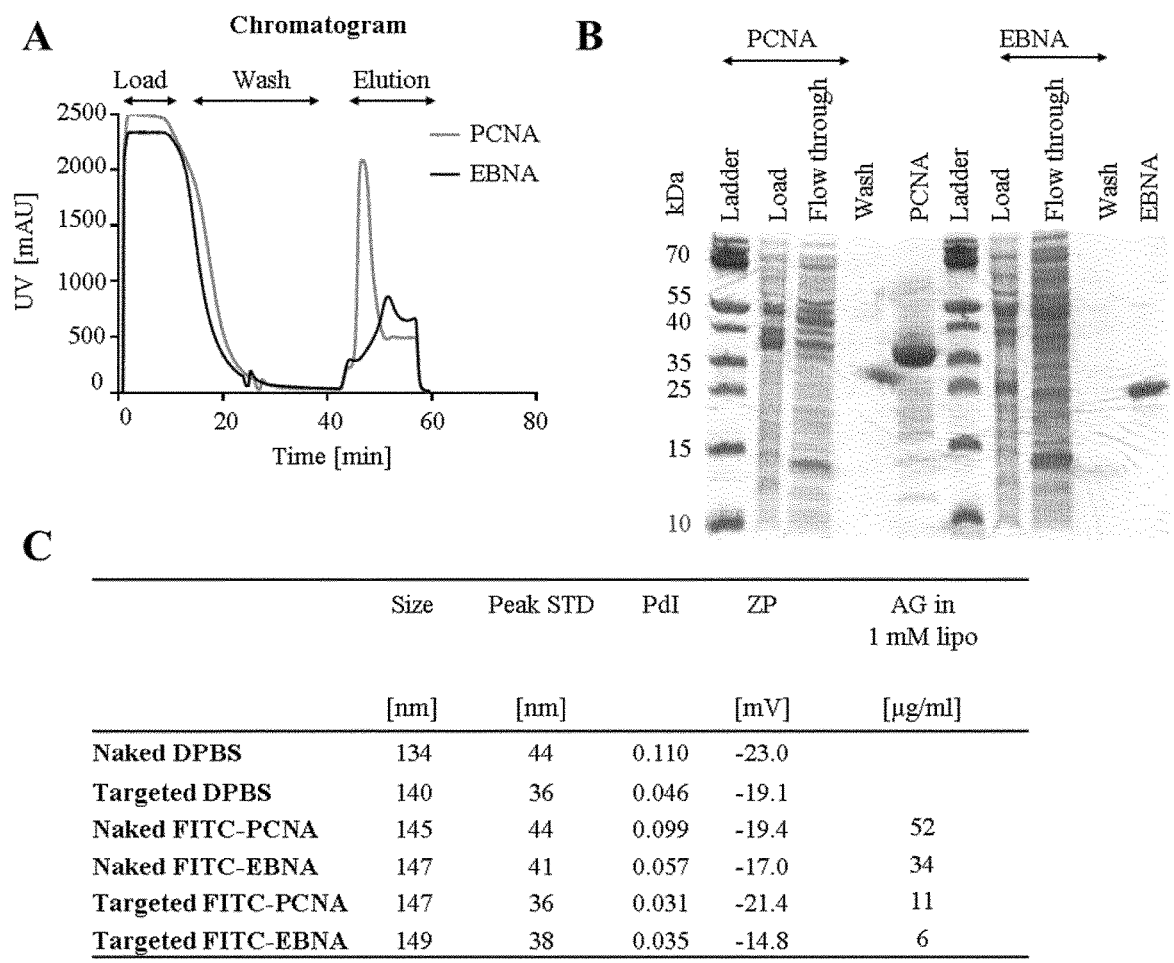
FIG. 7 depicts expression and encapsulation of an immune-active protein EBNA and an immune-inactive control protein PCNA.
Figure 8:
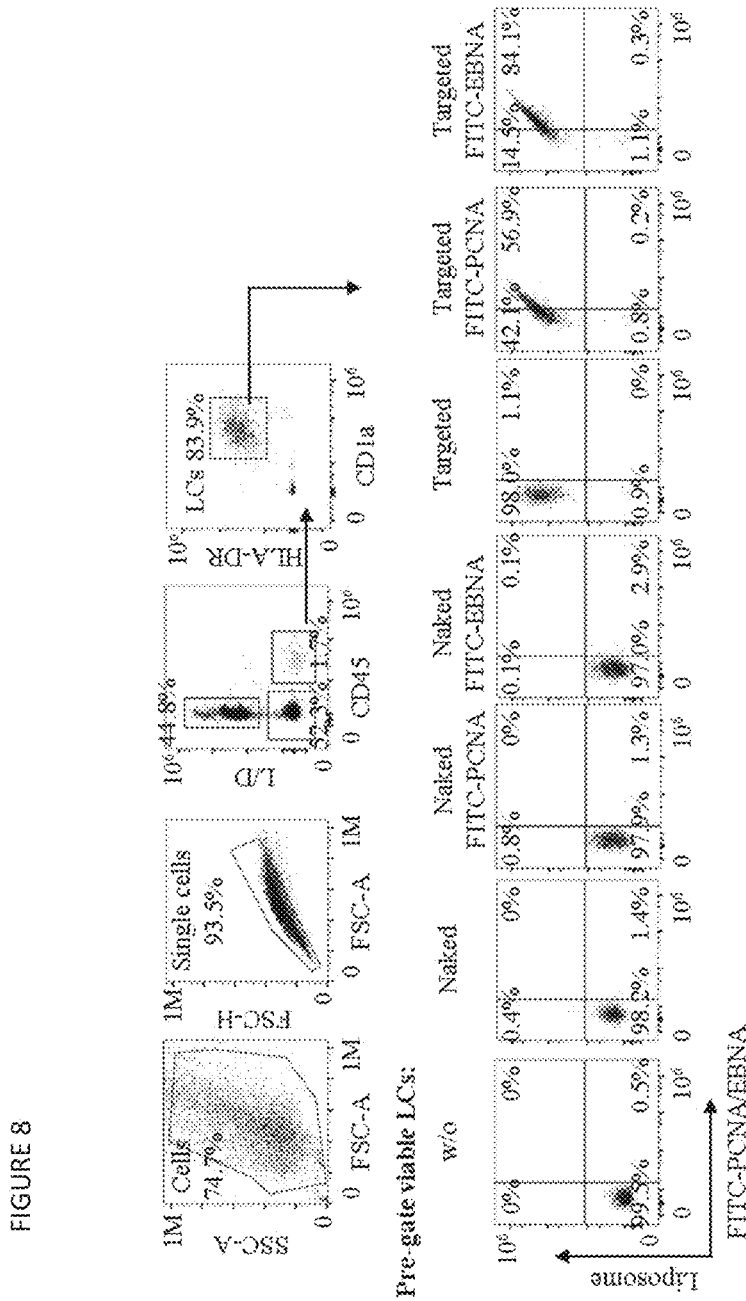
FIG. 8 depicts PCNA and EBNA delivery to LCs via Langerin targeted liposomes. FITC-PCNA and -EBNA encapsulated liposomes were incubated with epidermal cells suspensions at 37° C. After liposome incubation, cells were stained with Langerhans cell markers, including CD45, HLA-DR, CD1a and Langerin. In addition, cells were stained with a viability dye eFluor 780 for live/dead (LID) determination. Epidermal cell suspensions were analyzed by flow cytometry and Langerhans cells were evaluated for liposome and FITC staining.

The peptides were overexpressed in *E. coli* and results are shown in FIG. 7. After cell lysis, His-fused peptides were purified via a His-tag affinity column (see FIG. 7 (A)). SDS-PAGE was then applied to determine the peptide's quality (see FIG. 7 (B)). The load, flow through and wash fractions were used to track peptide purification. PCNA and EBNA peptides were then FITC labeled and encapsulated in liposomes.

Proteins were loaded as described in section of 'Liposome loading and purification' except that FITC conjugated EBNA proteins were digested with tenfold volume of trypsin, purified by size exclusion and concentrated with ultracentrifugation. All other steps were according to the protocol.

Liposomes were analyzed by DLS and the encapsulation efficiencies were detected by a fluorescence plate reader (see FIG. 7 (C)). Size, zeta potential and encapsulation efficiencies were in typical the range of previous liposomal formulations (see FIG. 5 (C)).

Next, FITC-PCNA and FITC-EBNA antigens were delivered to LCs. Antigen encapsulated liposomes targeted to LCs stained 56.9% and 84.1% LCs with FITC-PCNA and FITC-EBNA, respectively, whereas naked liposomes showed no FITC fluorescence increase. This demonstrates specific delivery of antigens via encapsulated liposomes.

Taken together, proteins encapsulated in liposomes can specifically be delivery to Langerin-positive cells.

Example 10

Cellular Liposome-Binding and Internalization Assay

Liposome specificity was investigated by expressing several CLRs with overlapping binding patterns in model cell lines and analyzing liposome binding. 50000 Raji cells were plated in 100 µl complete growth medium containing 16 µM liposomes. To measure liposomal binding, the plate was incubated at 4° C., whereas receptor internalization was induced with incubation at 37° C. After incubation, cells were centrifuged at 500 g for 3 min and the supernatant was discarded. Cells were resuspended in 100 µl ice cold culture medium and analyzed by detecting the co-formulated Alexa647 dye via flow cytometry with a 633 nm laser and a 570/20 nm filter (BD FACSCanto II, BD Biosciences) or a 654 nm laser with a 670/14 nm filter (Attune Nxt, life technologies).

Figure 9:
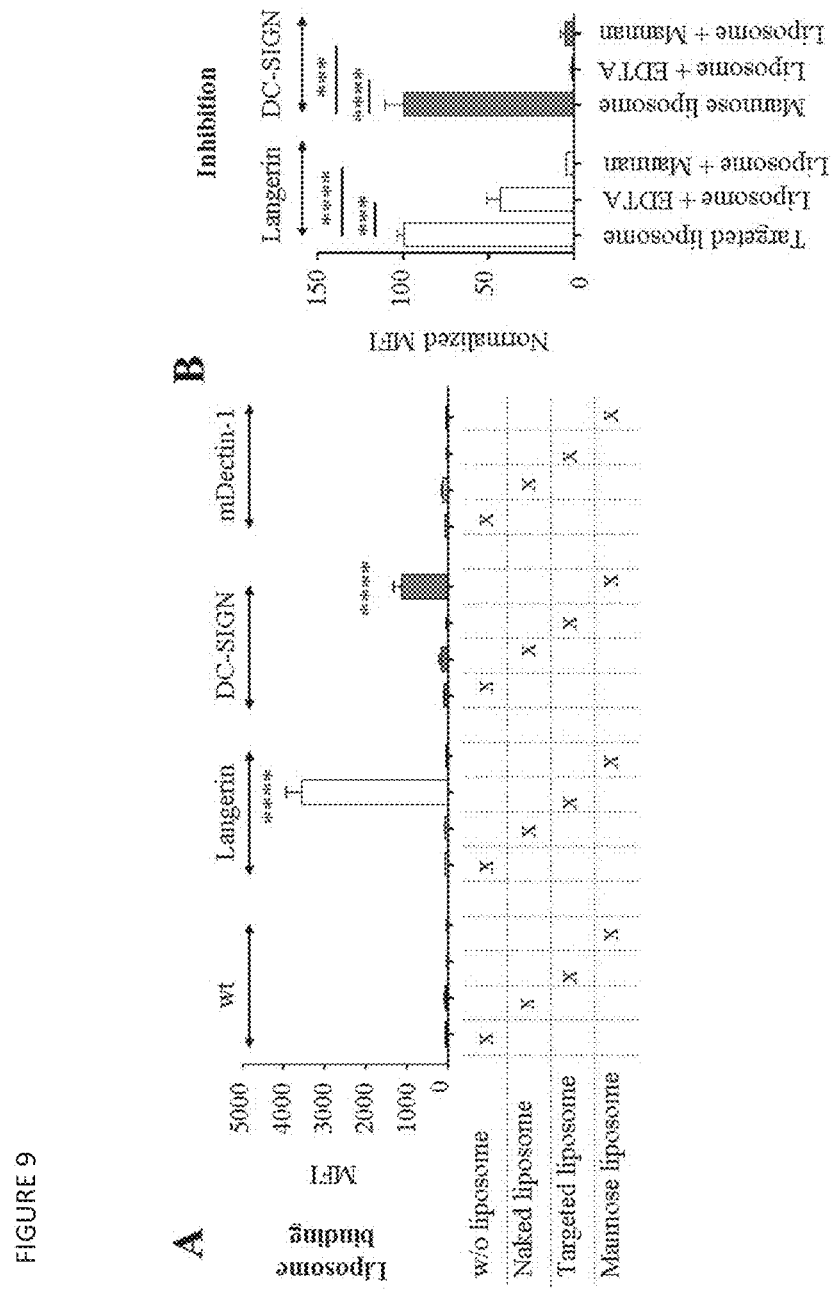
FIG. 9 shows liposome specificity of the human Langerin targeting ligand towards CLR expressing cells.

As presented in FIG. 9, naked, GlcNTosyl and mannose conjugated liposomes were tested for liposomal binding towards wt, Langerin$^+$, mouse Langerin$^+$ (mLangerin$^+$), DC-SIGN$^+$ and mouse Dectin-1$^+$ (mDectin-1$^+$) cells. Liposomal binding was detected after incubation with CLR expressing cells at 4° C. Fluorescence signals of co-formulated A647 lipids showed significant binding of GlcNTosyl functionalized liposomes to Langerin$^+$ Raji cells. The fluorescence signal increased 46-fold and was specific for Langerin$^+$ cells. Mannose functionalized liposomes were not able to bind Langerin$^+$ cells, but significantly bound DC-SIGN$^+$ cells with a 12-fold fluorescence increase. Liposomal binding of various liposome preparations with functionalized GlcNTosyl showed consistent binding to Langerin+ cells. Liposomal binding was further characterized using laminarin, mannan and EDTA as competitors. The natural ligand mannan that binds to the primary binding site of Langerin and DC-SIGN completely abolished the liposomal binding to both CLRs. EDTA partly inhibited binding of GlcNTosyl functionalized liposomes and completely prevented liposomal binding of mannose conjugated liposomes (see FIG. 9 (B)). Hence, heparin-inspired glycomimetic-based liposomes showed specific binding to the primary binding site of human Langerin in a calcium-dependent way.

Example 11

Figure 10:
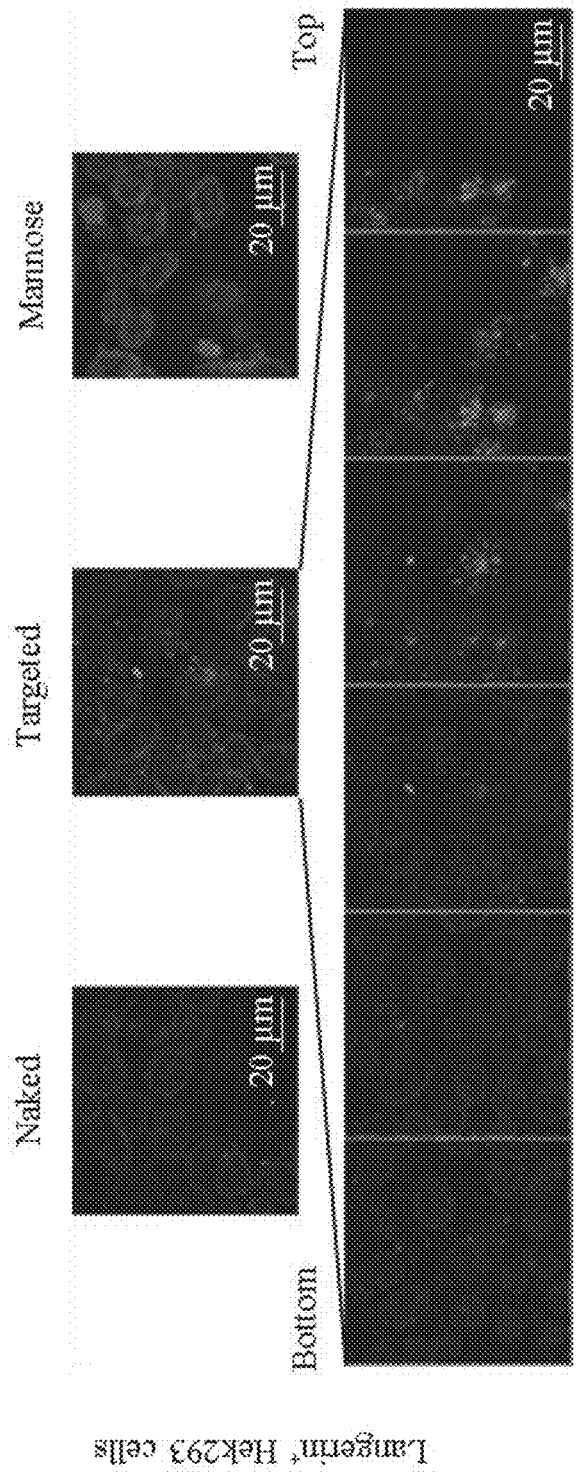
FIG. 10 shows a microscopy image of liposomal internalization into Langerin+ Hek293 cells. Naked, Langerin targeted and mannose conjugated liposomes were incubated with Langerin+ Hek293 cells at 37° C. for 2 h. The nucleus was stained with DAPI and the cell membrane with a lipophilic dye DiO. A Z-stack was taken of Langerin+ cells incubated with Langerin targeting liposomes showing cell layers of different focal height.

Liposome Internalization of Heparin-Inspired Langerin Ligand Functionalized Liposomes So far, specific binding of Langerin targeting liposomes was detected to Langerin expressing cells. However, for the delivery of immune-modulating agents, liposomes need to be internalized into cells; therefore, microscopy studies were performed with non-functionalized and functionalized liposomes. Laser scanning microscopy (LSM) in combination with fluorescence proteins or synthetic fluorophores enables the detection of co-localization of particles and cellular organelles. Cells were cultured on coverslips (Carl Roth) in 24 culture well plates (Corning). Before cell seeding, coverslips were coated with poly-L-Lysine (Sigma Aldrich) by overnight incubation. After washing the coverslips with DPBS, 200000 wt or Langerin+ Hek293 cells were seeded in 500 µl culture medium. The 24 well plate was incubated overnight at 37° C. and 5% CO2. Next day, 16 µM liposomes were added for 1 h at 37° C. unless stated otherwise. After liposome incubation, cells were fixed with 4% paraformaldehyde (Roti-Histofix, Carl Roth) for 10 min, and the cell membrane was stained with 10 µM DiO (Thermo Fisher Scientific) for 15 min. To stain the nucleus, cells were first permeabilized with 0.1% saponin (Sigma Aldrich) for 10 min and subsequently stained with 1 µg/ml DAPI (Sigma Aldrich) for 5 min. For long-term storage, coverslips were fixed on microscope slides (Carl Roth) using a mounting solution (Carl Roth). Slides were analyzed by microscopy (confocal light-sheet microscope DLS-DMi8, Leica). Internalization of Langerin targeted liposomes was detected by scanning different cell focus layers (see FIG. 10). Although, liposomes were mainly located at the top regions, central and lower cell layers showed also A647 fluorescence signals affirming liposomal internalization.

Next, receptor-ligand interactions were studied in more detail with binding- and internalization-kinetics of Langerin functionalized liposomes. Binding kinetics revealed that liposomal adhesion to Langerin+ cells was saturated after 4 h (see FIG. 11 (A)). In contrast, internalization-kinetics were conducted at 37° C. up to 24 h (see FIG. 11 (B)). Even after 24 h of incubation, the A647 fluorescence signal was not saturated implying high uptake of Langerin targeting liposomes. However, liposomal internalization was limited by applying higher concentrations (see FIG. 11 (C))Fehler! Verweisquelle konnte nicht gefunden werden.

Figure 11:
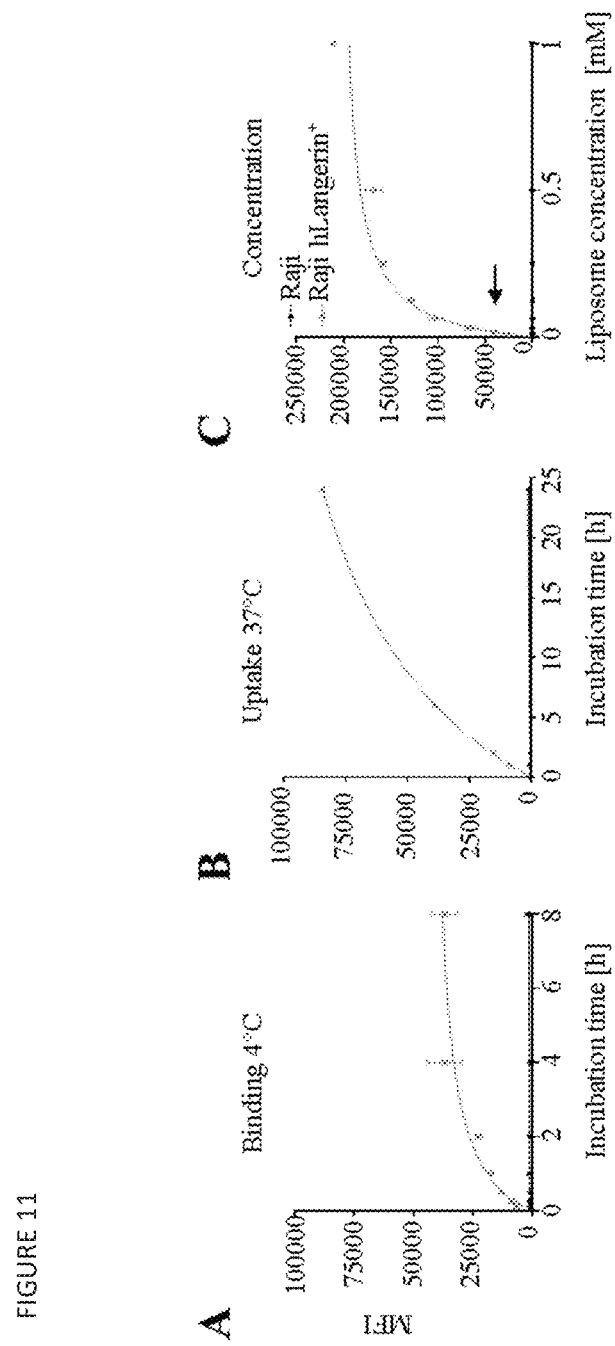
FIG. 11 depicts binding- and internalization kinetics of Langerin targeting liposomes.

Concentrations applied in previous studies (16 µM) are indicated with a black arrow in FIG. 11 (C). Saturation was reached with concentrations above 250 µM. Binding, uptake and concentration studies were not directly comparable because the laser power were adapted for each measurement. In all experiments, no binding was observed to Raji wt cells (solid black lines).

Figure 12:
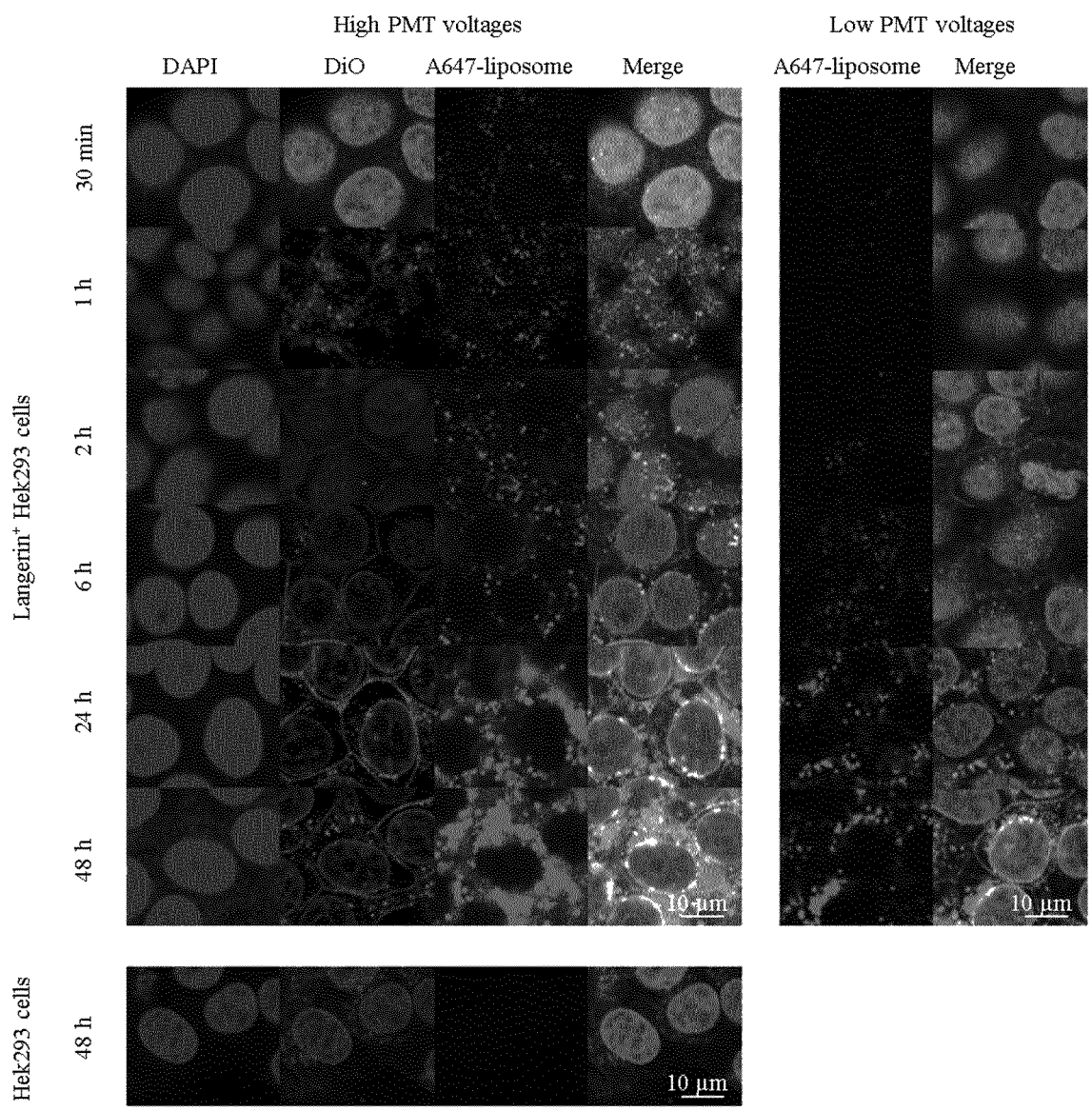
FIG. 12 shows liposomal internalization kinetics measured by microscopy. Langerin targeting liposomes were incubated for different time points with hLangerin+ and wild type Hek293 cells. High and low PMT voltages for Alexa647 were used to detect very sensitive events at early incubation points and strong fluorescence signals from late incubation points.

To visualize and verify high liposomal uptake rates, microcopy studies were performed. Targeted liposomes were incubated with Langerin+ Hek293 cells for various time points up to 48 h (see FIG. 12). After 30 min, liposomal internalization was already observed.

After 24 h, liposomes accumulated so strongly that the A647 signal was completely oversaturated. Therefore, PMT voltages were reduced visible in the right panel. Wt Hek293 cells showed even at high PMTs after 48 h no detectable fluorescence signal of A647 lipids.

Taken together, specific binding and uptake of targeted liposomes to Langerin expressing cell lines was shown to be dose- and time dependent.

Example 12

Targeted Delivery to Model Cell Lines: Mol % Ligand Density

Figure 13:
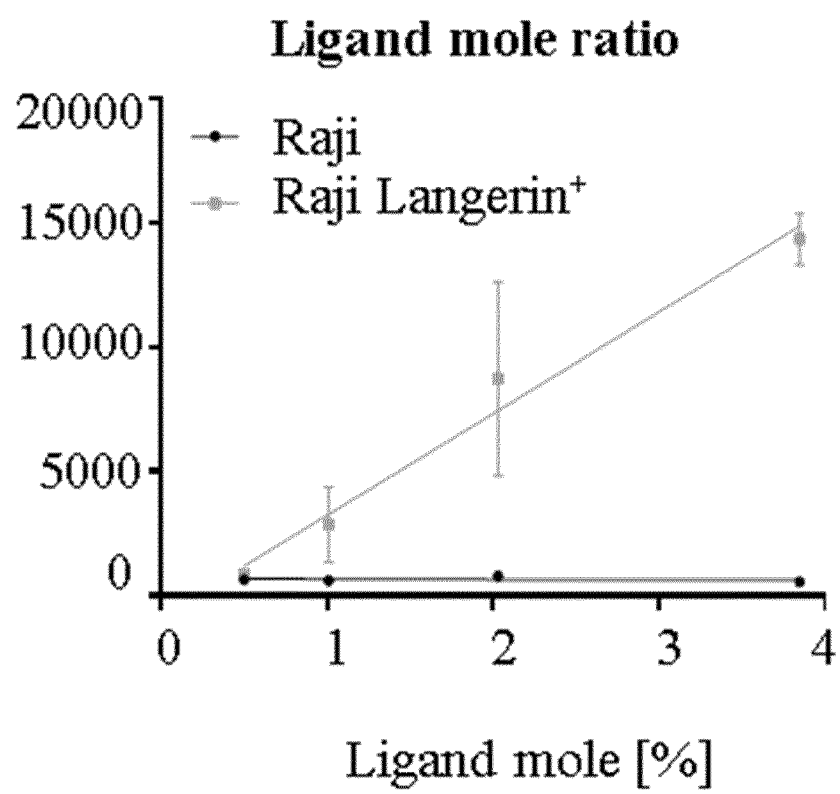
FIG. 13 depicts targeting human Langerin expressing Raji cells with GlcNTosyl functionalized liposomes. The ligand mole ratio of the targeting ligand was varied on liposomes and 16 μM liposomes were incubated for 1 h at 4° C. Cells were analyzed with the same gating strategy and the fluorescence signals of hLangerin+ and wild type Raji cells were plotted with a linear fit in GraphPad Prism.

A dependency of fluorescence signal to ligand mole ratio was detected demonstrating a relationship between the concentration of the targeting ligand and the binding efficiency to Langerin+ cells (see FIG. 13).

Figure 14:
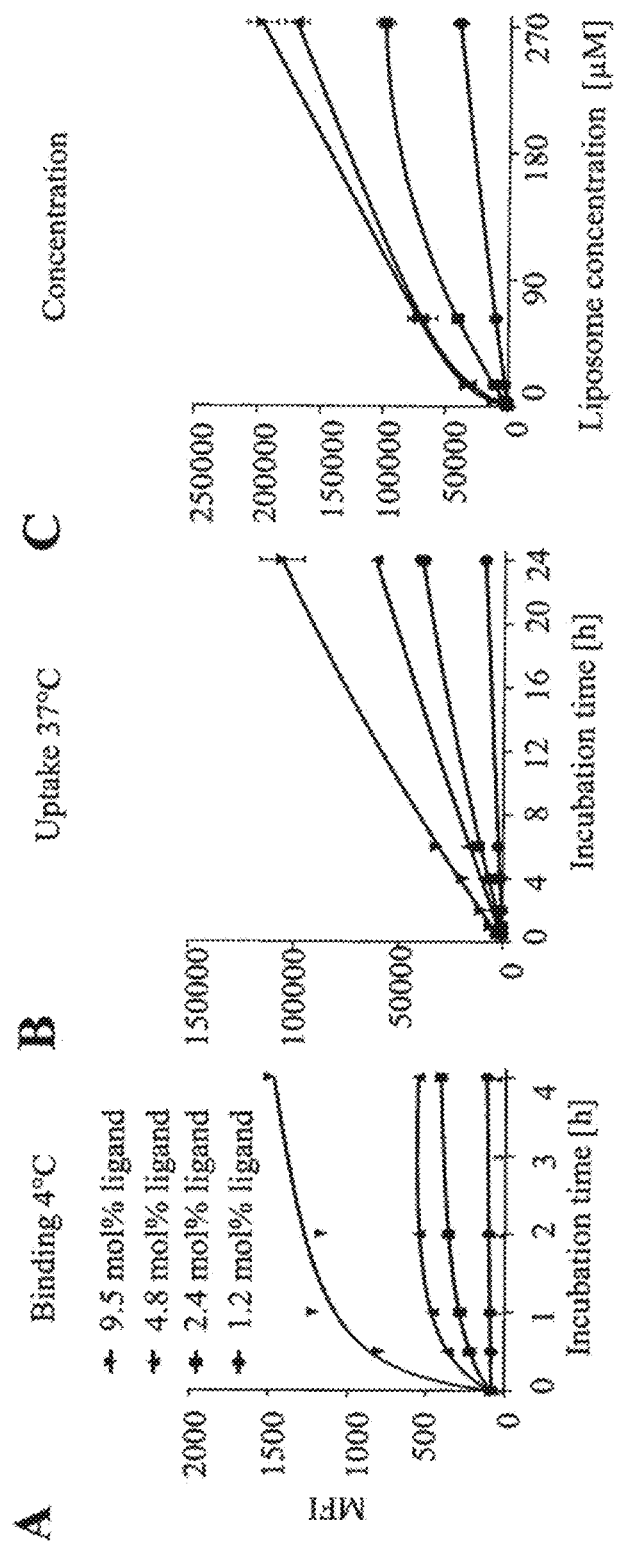
FIG. 14 shows binding- and internalization kinetics of Langerin targeting liposomes containing different ligand mole ratios.

Liposomal formulations with different mole ratios were also incubated dose- and time-dependently (see FIG. 14).

Example 13

Liposomal Routing and Antigen Delivery Via Langerin Targeted Liposomes

The fate of antigen presentation on MHCI or MHCII is highly dependent on intracellular processing pathways. Therefore, liposomal routing was analyzed with endosomal markers. Liposome localization was studied by microscopy after 2 h of liposome incubation with immunostaining against Rab5, Rab7, Rab11, EEA1 and Lamp-1 (see FIG. 15). In FIG. 15 (A) co-localization is visible by merging both channels with medium grey intensity into a single bright grey tone. Most overlapping fluorescence signals arising from close or identical proximities of liposomes were detected with late endosomal/lysosomal marker Lamp-1.

Figure 16:
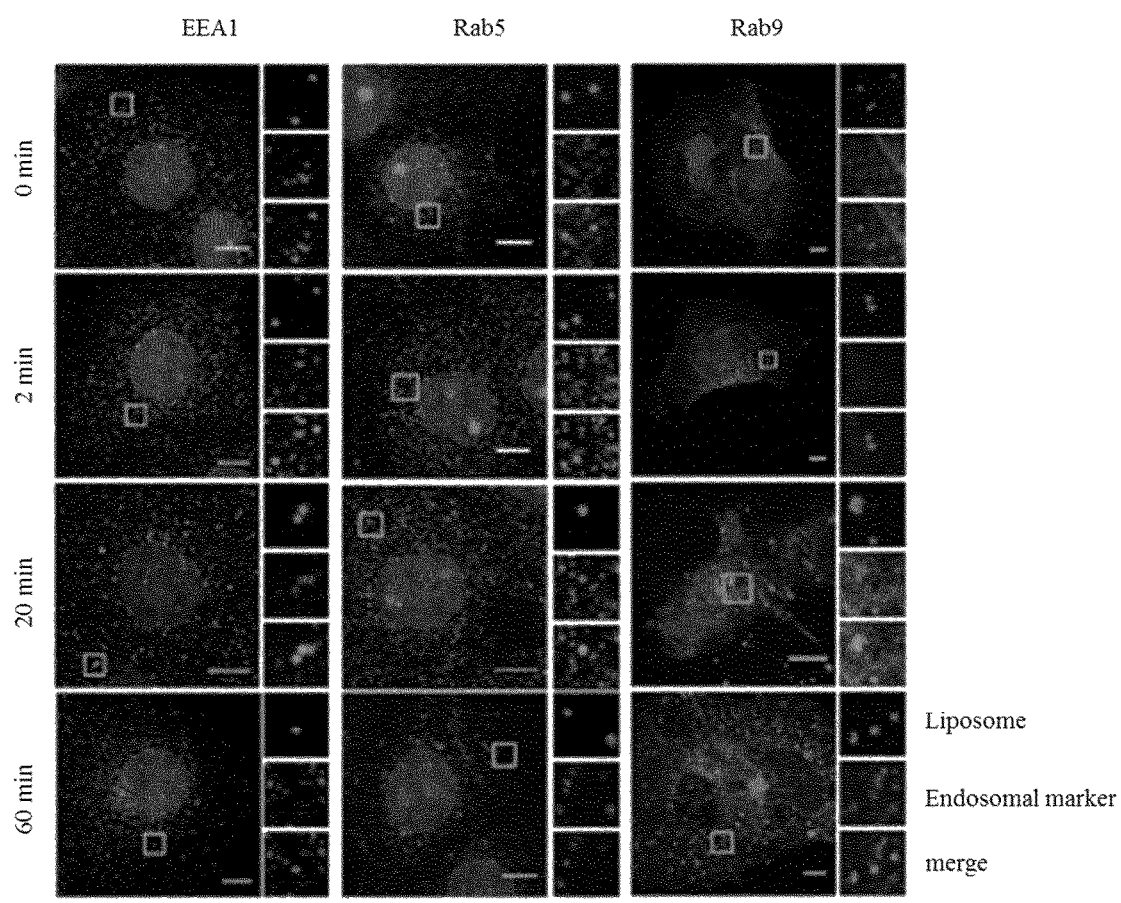
FIG. 16 shows liposome internalization into endosomal compartments at early time points. COS-7 cells were transiently transfected with YFP-Rab9. Targeted liposomes were added and incubated for different time periods at 37° C. After incubation, cells were fixed and immunofluorescence staining was performed for EEA1 with a primary anti-EEA1 antibody (rabbit, clone C45B10) and Rab5 (rabbit, clone C8B1) (Cell Signaling Technology) and for Rab9 with a primary anti-GFP antibody. An Alexa488 conjugated anti-rabbit antibody was used for secondary staining. Additionally, the cell nucleus was stained by DAPI.

Less co-localization compared to Lamp-1 was detected for the early endosomal markers EEA1 and Rab5 as well as with the recycling marker Rab11. In conclusion, after 2 h of liposome incubation most of the Langerin targeting vehicles were located in late endosomes and lysosomes. However, liposomes were co-localized with early endosomal markers EEA1 and Rab5 at earlier time points of 2 min and 20 min (see FIG. 16).

Taken together, these data demonstrate that targeted liposomes are taken up into Langerin positive cell lines and follow an intracellular routing in the endosomal compartment starting in the early endosome (2-20 min), then move into the late endosomal and lysosomal compartment (60-120 min).

Example 14

In Vitro Cytotoxicity of Heparin-Inspired Langerin Targeting Liposomes

Liposomes consist mainly of phospholipids and cholesterol. These naturally occurring and biocompatible compounds have revealed liposomes to be highly safe in clinical trials (Immordino et al., 2006, Int J Nanomedicine 1, 3, 297-315. Nevertheless, longer incubation periods and high concentrations of functionalized liposomes can lead to cytotoxic effects. To rule out toxicity induced by the fluorescence dye and the glycomimetic Langerin ligand toxicity assays were performed. To analyze cytotoxic effects induced by liposomes, cells were stained with Annexin-V and 7-AAD.

Figure 17:
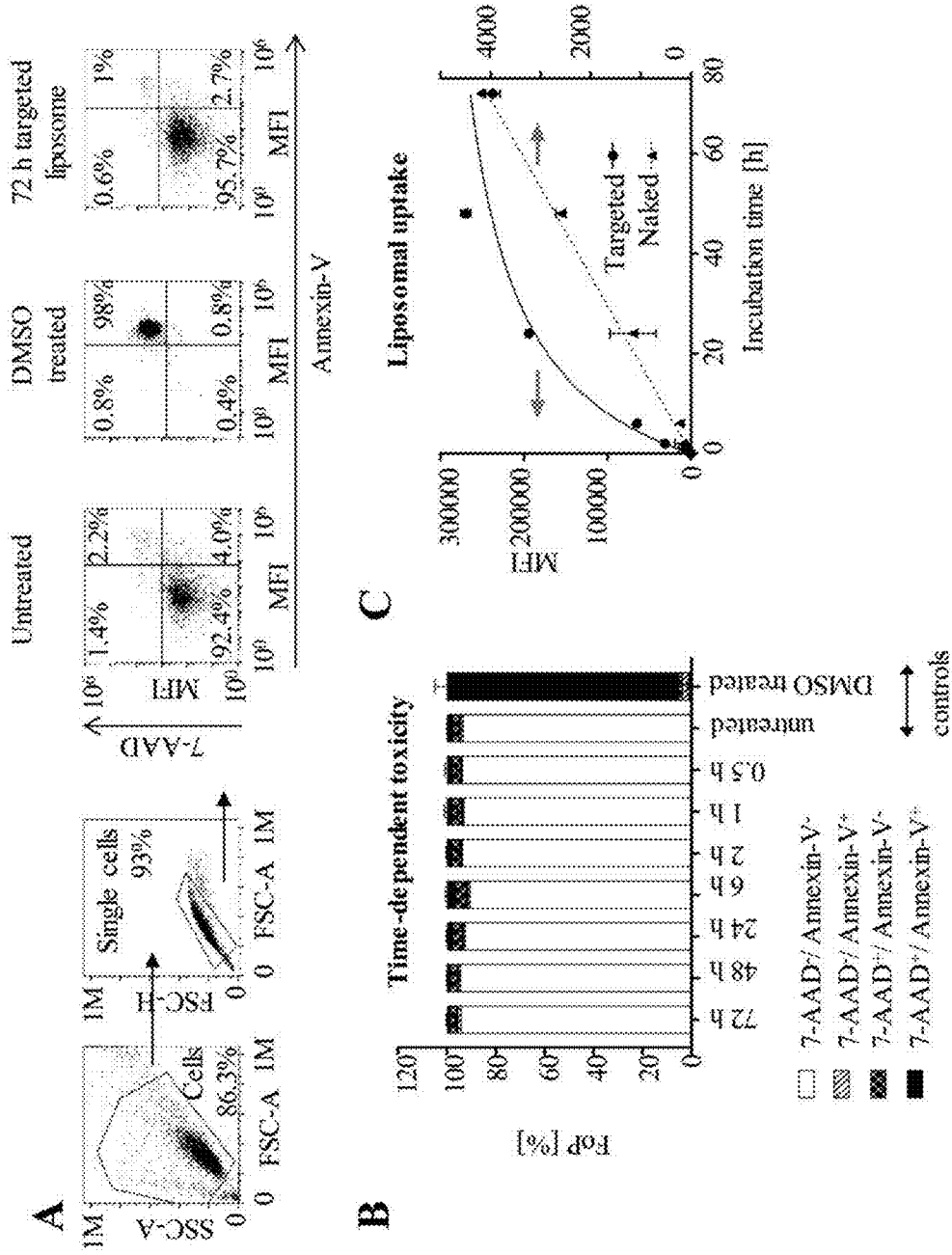
FIG. 17 depicts a time-dependent cytotoxicity study of functionalized liposomes.

To analyze early and late apoptosis, 10000 cells were incubated with various liposomal concentrations in 50 µl for 24 h or 16 µM liposomes were incubated for various time points at 37° C. and 5% CO2. As a positive control, cells were treated for 3 min with 50% DMSO. Untreated cells were applied as negative controls. Cells were washed and resuspended in 25 µl buffer (10 mM HEPES, 140 mM NaCl and 2.5 mM CaCl2), pH7.4) containing 1:100 diluted Annexin-V-FITC (Adipogen). Cells were incubated for 10 min in the dark at room temperature. After washing, cells were resuspended in 100 µl buffer containing 1 µl 7-AAD solution (Biolegend) and incubated for 5-10 min in the dark at room temperature. Cells were directly measured without any further washing steps by flow cytometry. Annexin-V and 7-AAD were excited with the 488 laser, Alexa 647 with the 654 laser. Annexin-V was detected with a 530/30 filter, 7-AAD with a 695/40 filter and Alexa647 with a 670/14 filter (Attune Nxt, life technologies). Spectral overlaps were compensated. Langerin targeted liposomes were incubated with cells for extended time periods up to 72 h, and cell toxicity was subsequently analyzed (see FIG. 17).

Early apoptotic effects were detected with Annexin-V staining that binds translocated phosphatidylserine, whereas late apoptotic cells were stained with 7-AAD a cell impermeable fluorescent intercalator that associates to DNA and undergoes a spectral shift. 7-AAD however is membrane permeable in dead cells. Cell debris was omitted when gating live and dead cells in the FSC-A/SSC-A plot. After doublet discrimination, single cells were analyzed for Annexin-V-FITC and 7-AAD staining in a bivariate histogram by dividing the plot in four quadrants. Untreated, DMSO treated and liposome treated cells were exemplarily presented in FIG. 17 (A). Following the same gating strategy, the frequent of parent (FoP) of all four quadrants was analyzed from samples that were incubated at various time periods. The FoPs of double negative cells (live cells), of Annexin-V$^+$ cells (early apoptotic cells), and of 7-AAD as well as double positive cells (late apoptotic cells) were visualized in a grouped column plot (see FIG. 17 (B)). Untreated cells, representing the negative control, showed more than 90% viable cells. On the other hand, DMSO treated cells (50% DMSO for 3 min) served as a positive control revealing 98% dead cells. Thus, control samples represent a functional assay. Even extended time periods, up to 72 h, showed no indication of any cytotoxic effects induced by liposomes. In addition, liposomal internalization was tracked by analyzing the fluorescence of the co-formulated A647 lipid (see FIG. 17 (C)). Similar to previous results, no saturation of liposomal internalization was detected later than 24 h (compare with FIG. 14). However, liposomal internalization saturated after 48 h to 72 h. It is noteworthy, that 10000 cells were platted in only 50 µl growth medium.

Figure 18:
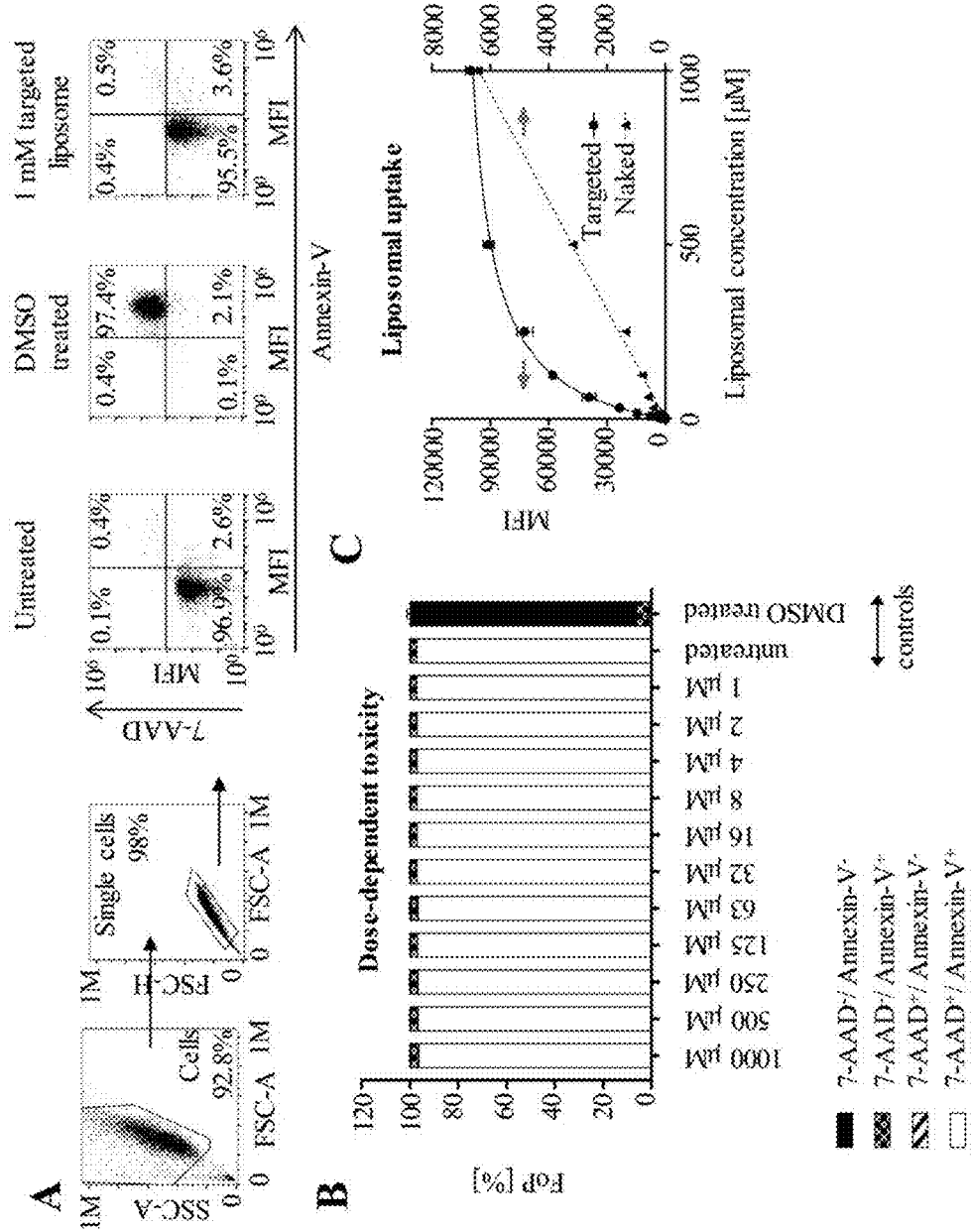
FIG. 18 shows a dose-dependent cytotoxicity study of Langerin targeting liposomes.

Similar to the kinetic study, a dose-dependent toxicity study was performed (see FIG. 18). Gating strategy and control samples were identical to those in the previous toxicity study (see FIG. 17). Here, liposome concentrations between 1 µM to 1 mM were incubated for 24 h. After incubation, toxicity was analyzed by Annexin-V and 7-AAD staining as mentioned before. Even at the highest concentration of 1 mM liposomes showed no toxic effects to Langerin$^+$ cells (see FIG. 18 (B)). As before, liposomal internalization was detected with the co-formulated A647 lipids. Uptake was saturated with concentrations above 250 µM as shown before (see FIG. 18 (C) and FIG. 14 (C)).

Taken together, targeted liposomes did not show any toxicity over an extended period of time as well as no induction of cell death when applied at very high concentrations for 24 h.

Example 15

Targeted Delivery to Model Cell Lines: SNPs Mutagenesis

N288D and K313I mutations were introduced into the wild type (wt) DNA of human Langerin by in vitro site-directed mutagenesis. For site-directed mutagenesis, a commercially available mutagenesis kit (QuikChange II XL Site-Directed Mutagenesis Kit, Agilent) was used. All steps were followed according to the manufacturer. Briefly, primers for site-directed mutational PCR were designed with the online tool QuickChange Primer Design (Agilent). A master mix was prepared and 48 µl were transferred to a PCR reaction tube for each mutational reaction. 1 µl 10 µM forward primer and 1 µl 10 µM reverse primer were added per mutational reaction (see also Example 1). The reaction mixture was transferred to a thermal cycler and a PCR program according to the manufacturer's guidelines was applied. After PCR reaction, 1 µl Dpn I was added for 1 h at 37° C. to digest the parental methylated and hemi-methylated DNA strands. Digested PCR reactions were then transformed, cultured and harvested in 5-alpha competent *E. coli* cells (NEB). Cells were seated on L-Ampicillin containing Agar plates, and next day two to three bacterial colonies were picked per clone and cultured for plasmid isolation (GeneJET Plasmid Miniprep Kit, Thermo Fisher Scientific). The DNA concentration was measured with a nanodrop (Implen Nanophotometer) and plasmid DNA was sequenced. To introduce the second mutation, mutagenesis was repeated with a mutated plasmid.

Assessing Liposomal Binding to Relevant Nucleotide Polymorphisms of Human Langerin The effect of polymorphic residues on the activity of liposomal binding and internalization into human Langerin expressing cells was determined. Relevant single nucleotide polymorphisms (SNPs) were introduced into wt cDNA of Langerin. Wt Langerin that is referred to in this text contains the V278A polymorphism and is present in the human population at 49.9% (rs741326, National Center for Biotechnology Information (NCBI) SNP database). As Langerin has several SNP variations, the focus was placed on the most important polymorphism for this study a double polymorphism N288D/K313I that showed enhanced binding affinities for glycans with terminal GlcNAc residues and reduced affinities for 6504-Gal glycans presented in previous studies (J Biol Chem, 288, 52, 36762-36771). The N288D/K313I mutant has a heterozygosity of 13.5% (rs13383830 and rs57302492, respectively, NCBI SNP database). The double polymorphism N288D and K313I occurs always together in the human population.

Figure 19D:
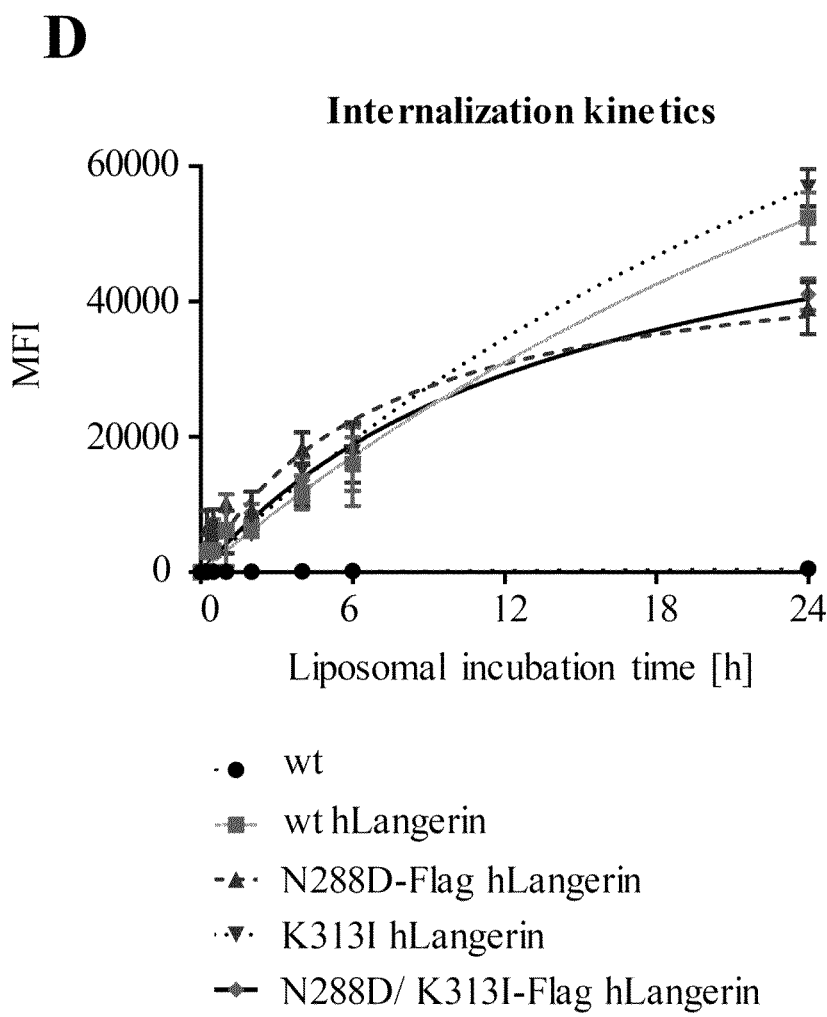
FIG. 19 shows liposomal activity towards relevant Langerin polymorphisms.
Figure 20:
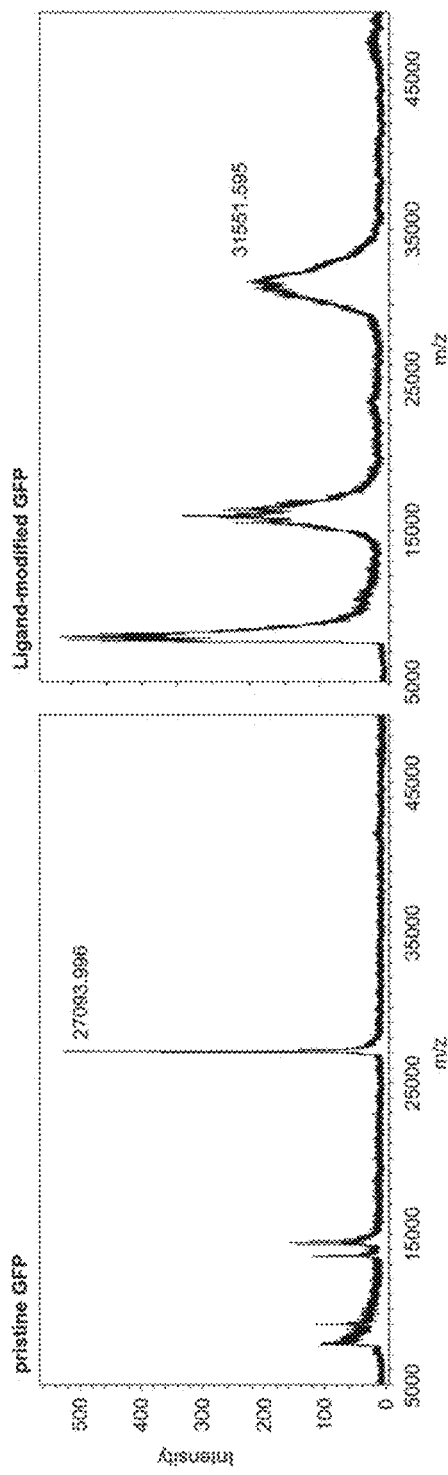
FIG. 20 shows the quantification of targeting ligand loaded GFP by MALDI-TOF.

The single mutant N288D and the double mutant were fused to a flag tag at the N-terminal end of Langerin. First, liposomal binding of targeted and naked liposomes was tested to wt Langerin$^+$ and compared to the Langerin mutants N288D, K313I and the double mutant N288D/K313I (see FIG. 19 (A)). The binding of targeted liposomes to the mutant K313I was in a similar range as to wt Langerin. The N288D and the double mutant N288D/K313I showed significantly enhanced liposomal binding. Noticeable is the correlation between the increased binding values for those mutants that also contain a flag tag. As liposomal binding is directly linked to the cell surface expression of Langerin, extracellular receptor expression was detected with an anti-human Langerin antibody. An analogous antibody staining was detected as observed for binding of targeted liposomes (see FIG. 19 (B)). The normalized MFI values of mutant K313I were comparable to those of wt Langerin whereas the MFI values of the N288D and of the N288D/K313I mutant were significantly enhanced. The only difference to the liposomal binding was that the antibody staining revealed a higher expression of the N288D mutant compared to the double mutant. Consequently, the distinct receptor expressions affected the fold change of liposome to antibody staining (see FIG. 19 (C)). The N288D mutant and the double mutant showed significantly increased binding strength to targeted liposomes relative to receptor expression. But only the double mutant had a fold change more than double as wt Langerin indicating an improved affinity to the targeting ligand. Secondly, the effect of mutants on the outcome of liposomal internalization was studied. For this, liposomes were incubated for different time periods in combination with the mutants at 37° C. to induce receptor internalization. In contrast to liposomal binding, the highest MFI values were detected for the K313I mutant and for wt Langerin after 24 h of receptor internalization. Before the 6 h time point, wt Langerin and the K313I mutant showed lower internalization rates similar to the results of liposomal binding. The effect of the mutants, however, was negligible with regard to wt Langerin. As a consequence, the natural occurring N288D/K313I polymorphism of Langerin had no impact on liposome engulfment.

Example 16

Targeted Delivery of Directly Modified Proteins to Model Cell Lines
Preparation of Reactive Ligand Liker Construct to React with Amino Groups of Proteins Compound 7 (0.87 mg, 2.3 μmop was dissolved in 300 μL DMSO and 43 μL pyridine in presence of 17.4 uL trimethylamine under an inert atmosphere. 8.63 mg (22 μmop bis(4-nitrophenyl) adipate (dissolved in 193 μL DMSO) were added and the solution left to stir for 3 hours. The solvent was subsequently removed by freeze-drying. The residue was washed with toluene and the solvent removed in vacuo to obtain compound 8.
Preparation of Ligand Modified Green Fluorescent Protein (GFP)

Green Fluorescence Protein (GFP) was used as a model for direct ligand modification of proteins. The amino acid sequence of GFP was:

```
                                        (SEQ ID NO: 82)
MVSKGEELFTGVVPILVELDGDVNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIEDGSVQLADHYQQNTPIGDGPVLLPDNH

YLSTQSALSKDPNEKRDHMVLLEFVTAAGITLGMDELYKA
```

A solution of 1 mg GFP in 175 μL PBS (pH 8) was added to 1.45 mg (2.31 μmop reactive compound 8 (see above, Example 16) and left to stir for 23 hours at room temperature. The mixture was diluted with PBS (pH 7.4) to 2.5 mL and centrifuged. The supernatant dialyzed twice for 12 hours against PBS (pH 7.4) at 4° C. and the solution subsequently concentrated to 1.06 mg/mL modified protein.
Characterization of Ligand Modified Green Fluorescent Protein (GFP)

To estimate the total number of ligands on the modified GFP, obtained following the procedure as described in

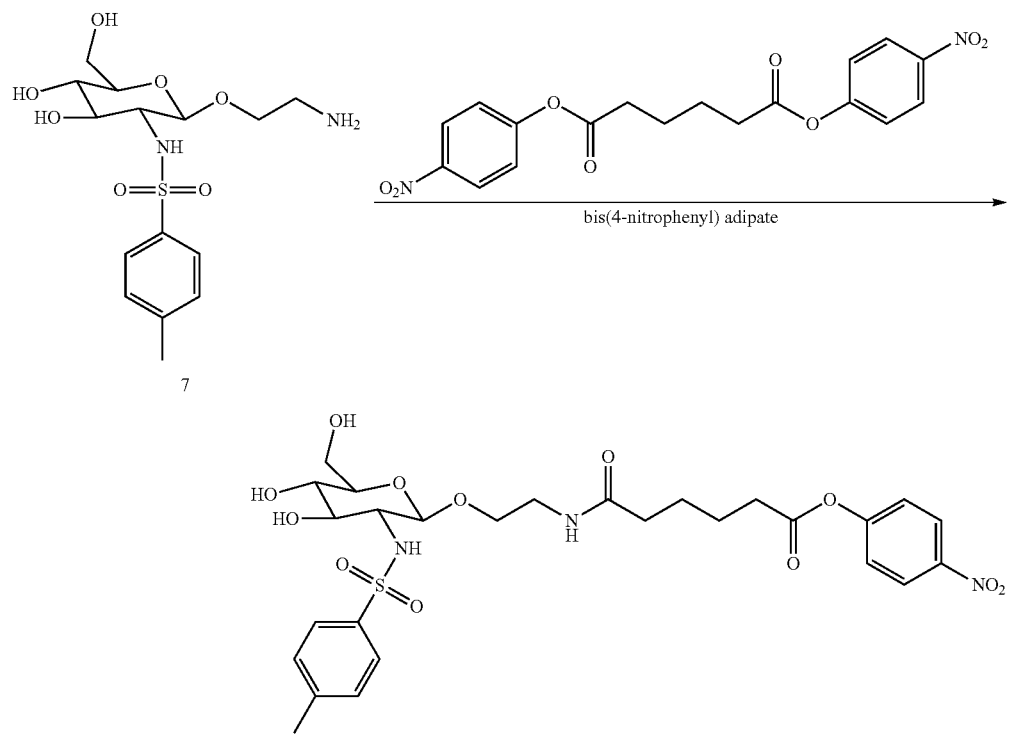

Example 17, Matrix Assisted Laser Desorption/Ionization (Bruker MALDI-TOF Autoflex speed) measurements were carried out using a 2,5-dihydroxyacetophenone matrix. Comparing the average molecular weight of pristine GFP and ligand modified GFP gave an average of around 7 ligand moieties per protein molecule.
Targeted delivery to model cell lines: Protein cargo uptake Functionalized GFP was then tested in a cell-based binding and internalization assay. Both GlcNTosyl functionalized GFP and unconjugated GFP were incubated with WT or hLangerin$^+$ Raji cells at 4° C. and at 37° C. for 1 h or 2 h, respectively (see FIG. 21). Targeted GFP specifically bound to Langerin expressing cells and saturated at concentrations above 1 µg/ml (see FIG. 21 (A)). Unconjugated GFP and targeted GFP incubated with WT Raji cells did not show increased fluorescence signals. Furthermore, targeted GFP incubated at 37° C. showed also fluorescence increase for Langerin$^+$ cells. GFP fluorescence was slightly elevated compared to the binding assay and also saturated above 1 µg/ml.

Figure 21:
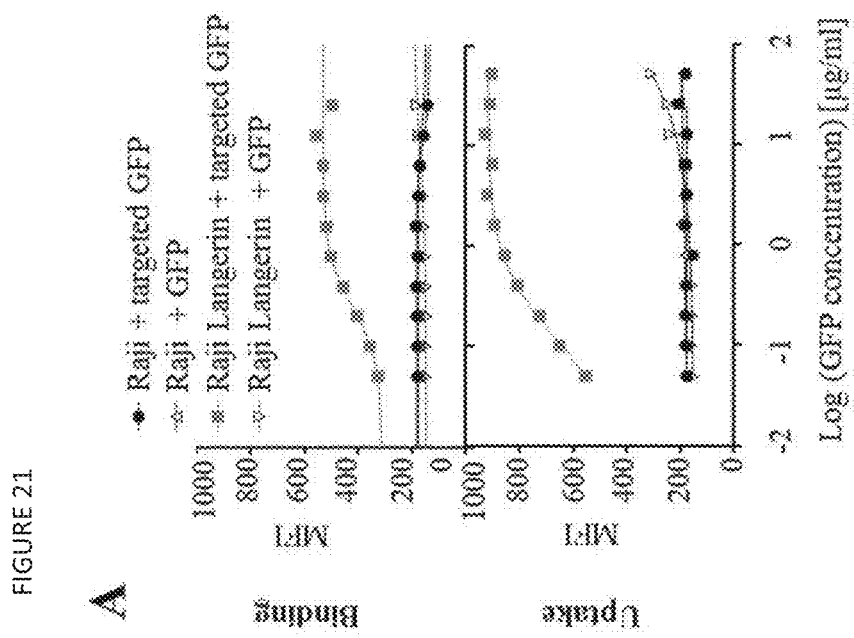
FIG. 21 shows the binding and internalization of conjugated proteins versus FITC-BSA encapsulated liposomes.

However, as opposed to liposomal internalization, the uptake of GFP was hardly visible, indicting an impaired internalization rate or fast degradation (see FIG. 21 (B)).

Figure 22:
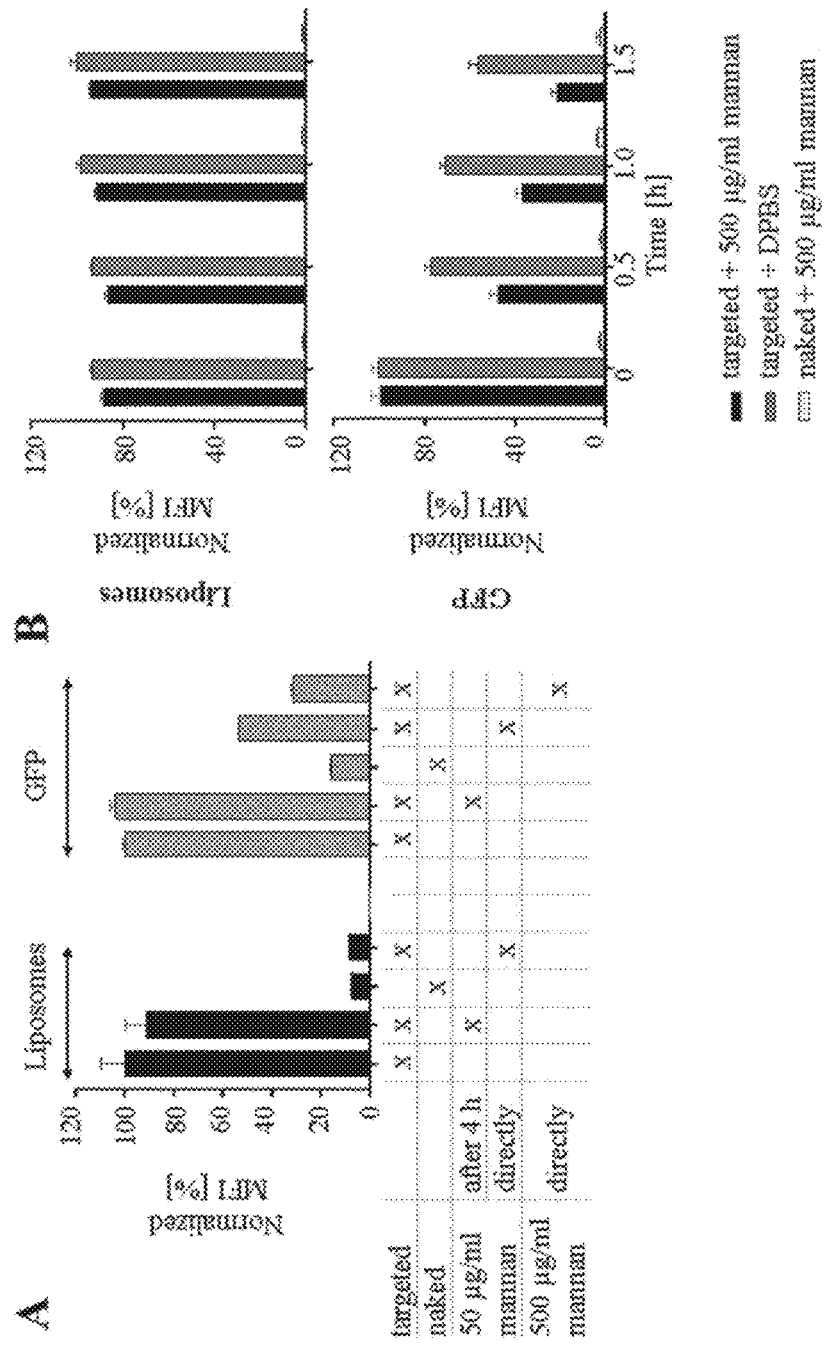
FIG. 22 depicts a binding competition with mannan.
Figure 23:
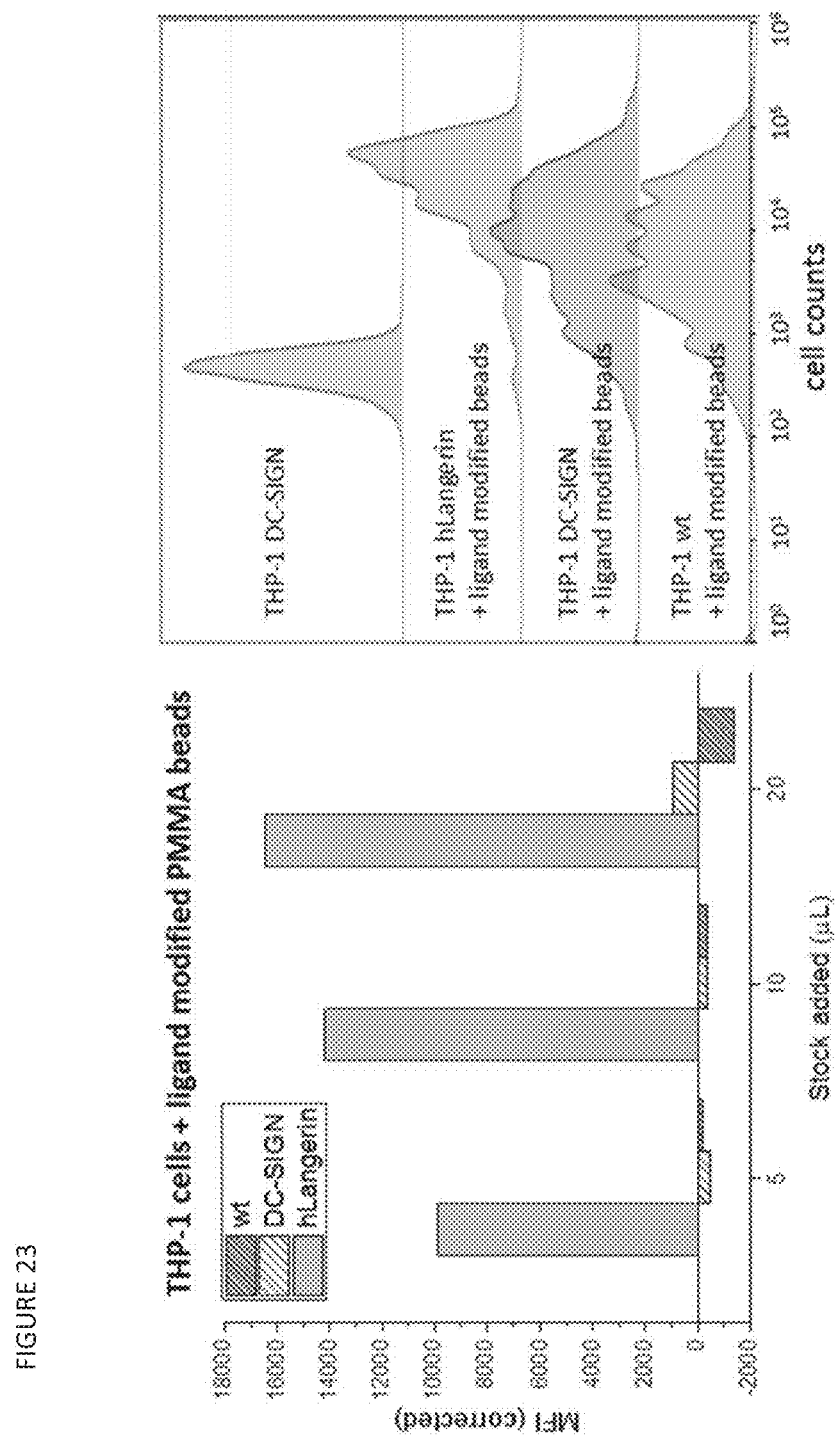
FIG. 23 depicts a flow cytometric analysis of targeting ligand loaded PMMA beads shows specific binding to human Langerin expressing THP-1 cells.

Employing fluorescence microscopy, functionalized GFP and unconjugated GFP were investigated after incubation with Langerin$^+$ COS-7 cells (see FIG. 16Fehler! Verweisquelle konnte nicht gefunden werden). Cells incubated with functionalized GFP showed increased fluorescence signals, whereas unconjugated GFP did not bind to Langerin$^+$ cells. After a mere 5 min of incubation at 37° C., functionalized GFP was redistributed and after 60 min, appeared to be located in endosomal compartments. The distinct cell membrane staining at time point 0 min was completely abolished at time point 60 min suggesting GFP internalization. Moreover, binding and competition studies with mannan demonstrated that functionalized GFP displayed increased binding affinities (see FIG. 22 (A)). Mannan concentrations of up to 500 µg/ml had to be applied to compete the binding of GlcNTosyl functionalized GFP whereas in contrast 50 µg/ml mannan was sufficient to compete functionalized liposomes. To differentiate binding and internalization, mannan was added after the 4 h incubation step at 4° C. (see FIG. 22 (A)). Neither liposomes nor GFP could be competed, again indicating that both carriers are internalized. However, when mannan was added over a longer incubation time at 37° C., GFP fluorescence decreased strongly compared to liposomes (see FIG. 22 (B)). The signal reduction was also visible when incubated with DPBS but mannan addition enhanced the effect.

In summary, functionalized GFP conjugated with approximately seven ligands displayed increased binding affinities in comparison to ligand conjugated liposomes. However, GFP internalization was drastically impaired compared to GlcNTosyl decorated liposomes.

Example 17

Targeted Delivery of Alternative Nanoparticles
Preparation of Ligand Modified PMMA Beads 0.01 mL of carboxylated poly(methyl methacrylate) beads (0.5% stock solution, diameter 130 nm, PolyAn) were dissolved in 200 µL activation buffer (MES 50 mM pH=5+ 0.001% tween). 12 µL of a 1.5 M aqueous 1-ethyl-3-(3-dimethylaminopropyl) carbodiimide solution and 12 µL of a 0.3 M N-hydroxysuccinimide solution were added and vigorously stirred for 1 hour. Subsequently the beads were washed three times with coupling buffer (HBS, pH=7, 5 mM Ca$^+$). 2 µL of a 10 mM aqueous targeting ligand solution were added and left to stir over night at room temperature. The modified beads were washed twice with ethanolamine (1 M in coupling buffer, pH=8+0.02% tween) followed by washing and storing in with HBS buffer (pH=7, 5 mM Ca$^+$, 0.02% Tween) at 4° C.
Interaction of Ligand Modified PMMA Beads with THP-1 Cells Different dosages (5, 10, 20 µL) of a ligand modified PMMA beads solution (c=2.5×10$^1$ beads/mL (preparation as described in Example 18) were added to THP-1 cell suspensions of 50 µL (cell count was 2×10$^6$ cells/ml). After 45 min incubation on ice and exclusion of light, the mixtures were spun down, fixated with 120 µL of an aqueous paraformaldehyde solution (4%) and finally re-suspended in 150 µL medium. Beads-cell-interaction was analyzed using fluorescence-activated cell sorting (FACS) flow cytometry gating for THP1 cells detecting the beads' red fluorescence.

Example 18

Targeted Delivery to Primary Langerhans Cells
Liposomal Delivery in Epidermal Cell Suspensions Primary cells are an excellent model prior translating the studies in vivo. From skin samples from healthy donors were removed from subcutaneous fat with a scalpel. Epidermal cell suspensions were incubated in RPMI1640 medium (Lonza) supplemented with 1.5 U/ml dispasell (Roche) and 0.1% trypsin (Sigma-Aldrich) overnight at 4° C. On the other hand, whole skin cell suspensions were obtained by incubation in RPMI1640 medium supplemented with 10% FCS (Pan-Biotech) and 1 mg/ml collagenaseIV (Worthington Biochemical Corporation) overnight at 37° C. Peeled off epidermis or whole skin was filtered through a 100 µm cell strainer (Thermo Fisher Scientific) to obtain single cell suspensions. Cell suspensions were incubated with 16 µM liposomes in HBSS buffer (Mg' and Ca$^+$; Biochrom GmbH) containing 1% BSA (Serva Electrophoresis GmbH) for 1 h at 37° C. For the kinetic study liposomes were incubated for various time periods at 37° C. or 4° C. As a control, 10 mM EDTA (Lonza) was added. Before analyzing cells by flow cytometry (FACS Canto II, BD Biosciences), cells were stained with an eFluor® 780 viability dye (eBioscience) and fluorochrome-conjugated antibodies (CD1a, clone: H1149; CD14, clone: HCD14; HLA-DR, clone: L243; CD45, clone: H130—Biolegend; Langerin, clone: MB22-9F5—Miltenyi Biotec; isotype-matched control antibodies) for 15 min at 4° C. For confocal microscopy, epidermal cell suspensions were stained with FITC-conjugated CD1a antibody (clone: H1149; Biolegend) for 15 min at 4° C. After 1 h liposomal incubation at 37° C., cells were analyzed by microscopy (Zeiss AxioObserver Z1).

Figure 24:
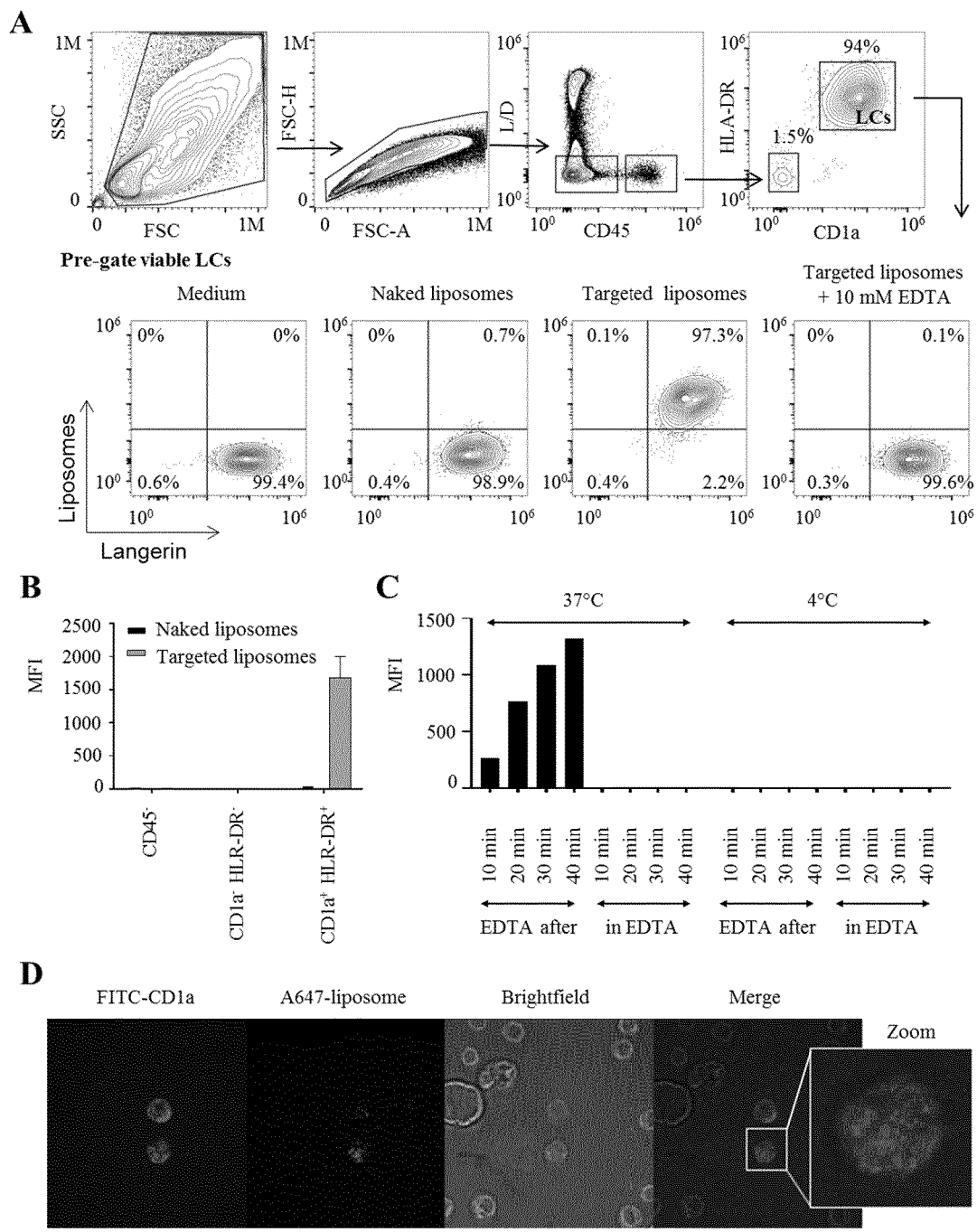
FIG. 24 shows targeting primary Langerhans cells in epidermal cell suspensions.

For the utilization of primary cells, epidermal cell suspensions were prepared from human skin samples and liposomal binding to Langerhans cells was analyzed by flow cytometry (see FIG. 24 (A)). Langerhans cells were identified via CD45$^+$, HLA-DR$^+$ and CD1a$^+$ expression. In addition, a viability dye (eFluor 780) discriminates dead cells (LID). Viable CD45$^+$ hematopoetic cells contained 94% HLA-DR$^+$, CD1a$^+$ Langerhans cells.

More than 97% epidermal Langerhans cells were Langerin positive and stained with the A647 co-formulated dye present on liposomes. Liposomal binding to Langerhans cells was specific for liposomes that were decorated with the targeting ligand and Ca$^{2+}$-dependent liposomal binding was competed with 10 mM EDTA. These results confirm a specific ligand-receptor interaction at the primary binding site of the CRD of Langerin. In addition, liposomal staining was specific for LCs since CD45− and CD45−, HLR-DR− cells were not able to bind Langerin targeted liposomes (see FIG. 24 (B)). Furthermore, the fact that EDTA prevents liposomal binding renders it an ideal tool for analyzing liposome internalization by adding EDTA after the incubation step to remove extracellularly bound liposomes (see FIG. 24 (C)). EDTA addition after the incubation step was not able to inhibit the fluorescence signal suggesting that liposomes were internalized, whereas addition directly to the medium completely inhibited liposomal binding as well as uptake. Additionally, liposomes were incubated at 4° C. to prevent internalization even when liposomes bind to the cell surface receptor. This step completely abolished the fluorescence signal confirming liposomes internalization into LCs. Liposome internalization was further verified by microscopy (see FIG. 24 (C)). Here, FITC-conjugated CD1a antibodies stained Langerhans cells in epidermal cell suspensions. Targeted liposomes were exclusively detected in FITC labeled Langerhans cells.

Liposomal Delivery in in Whole Skin Cell Suspensions

Figure 25:
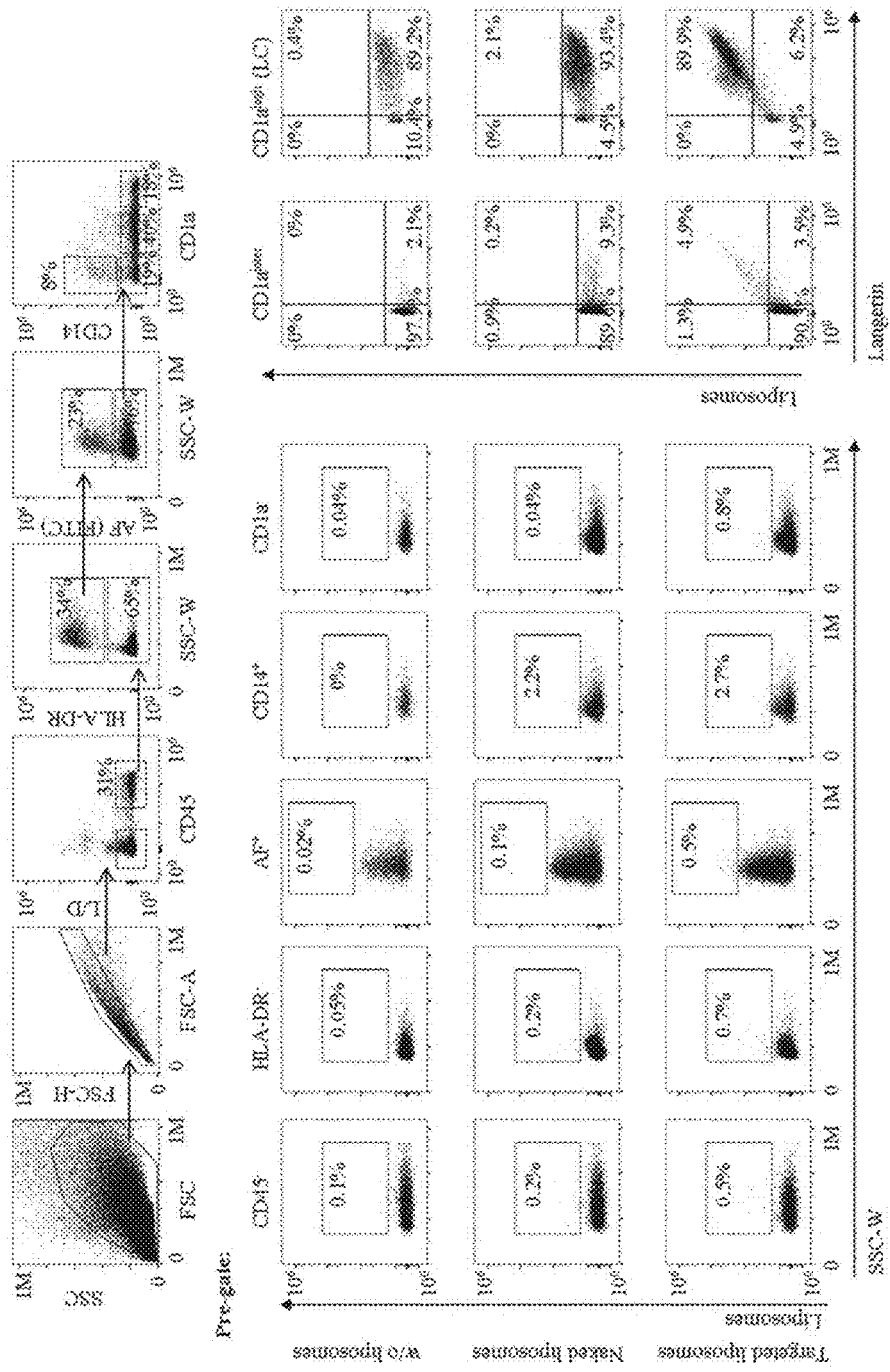
FIG. 25 shows liposomal specificity to Langerhans cells via a Langerin targeting ligand. Whole skin cell suspensions were prepared from human skin samples. Skin cells were subsequently incubated with liposomes at a concentration of 16 μM for 1 h at 37° C. After liposome incubation, cells were stained with Langerhans cell markers, including CD45, HLA-DR, CD1a and Langerin. In addition, cells were stained with a viability dye eFluor 780 for live/dead (LID) determination and with a CD14 antibody to stain monocytes and macrophages. Whole skin cell suspensions were analyzed by flow cytometry and various cell subsets were evaluated for liposome staining.

LCs are known to be the only professional antigen presenting cells in the epidermis. To show liposomal specificity towards LCs over other dendritic cell lines, whole skin cell suspensions were prepared from human skin samples and analyzed by flow cytometry to detect liposome staining (see FIG. 25). A647 fluorescence of Langerhans distinct cell subsets was plotted against SSC-W, whereas liposome staining of LCs was plotted against extracellular Langerin expression. First, 18% cells of CD45$^+$, HLR-DR$^+$, non-autofluorescent (AF) cells were identified as viable CD1ahigh LCs, 40% cells contained CD1a intermediate (CD1ainter) expression and 27% cells were CD1a-, wherein 8% were CD14$^+$, a marker for monocytes and macrophages. In the viable CD1ahigh LC population, more than 96% cells showed Langerin expression and 89.9% LCs incorporated targeted liposomes. CD1ainter cells contained 8.3% Langerin$^+$ cells and 4.9% cells were positively stained with the liposomal dye. The vast majority of liposomal staining correlated with Langerin expression, indicating that targeted liposomes specifically bound to Langerin. Langerhans distinct cell subsets (including CD45− cells; CD45$^+$, HLA-DR− cells; CD45$^+$, HLA-DR$^+$, AF$^+$ cells; CD45$^+$, HLA-DR$^+$, CD14$^+$ cells; and CD45$^+$, HLA-DR$^+$, CD1a$^-$ cells) were not able to bind liposomes. However, CD45$^+$, HLA-DR$^+$, CD14$^+$ named monocytes and macrophages showed an unspecific binding to naked and targeted liposomes with less than 3%. But in general, naked liposomes bound neither LCs nor LC distinct cell subsets. These results confirm our previous studies employing Langerin expressing model cell lines. Consequently, targeted liposomes are specifically internalized by Langerin expressing cells in a Ca$^{2+}$-dependent manner by binding to the primary binding site of the CRD of Langerin.

To sum up, targeted liposomes are delivered specifically to Langerin-positive cells in epidermal as well as whole skin cell suspensions.

Example 19

Biophysical Characterization of Human Langerin Ligands

Receptor Expression and Purification

General remarks. Codon-optimized genes for the expression of Langerin and DC-SIGN in *E. coli* were purchased from GenScript and Life Technologies, respectively. All growth media or chemicals used for receptor expression and purification were purchased from Carl Roth if not stated otherwise.

The codon-optimized gene sequence for Langerin containing a StreptagII and TEV site at the C-terminus for expression in *E. coli* is presented by SEQ ID NO: 29. For the *E. coli* expression of said sequence the following primer sequences were used:

| Name | Sequence (5' to 3') | Direction | SEQ ID NO: |
|---|---|---|---|
| truncated Langerin extracellular domain (ECD) - residues 148 to 328 | GGTGGTCATATGGCC TCGACGCTGAATGCC CAGATTCCGG | forward primer | 30 |
| truncated Langerin extracellular domain (ECD) - residues 148 to 328 | ACCACCAAGCTTTTA TTTTTCAAAC TGCGGATG | reverse primer | 31 |
| Langerin carbohydrate recognition domain (CRD) - residues 193 to 328 | GGTGGTCATATGGCC CAGGTGGTTAGCCAA GGCTGGAAATAC | forward primer | 32 |
| Langerin carbohydrate recognition domain (CRD) - residues 193 to 328 | ACCACCAAGCTTTTA TTTTTCAAACTGCGG ATG | reverse primer | 33 |

The codon-optimized gene sequence for DC-SIGN containing a StreptagII and TEV site at the C-terminus for expression in *E. coli* is presented by SEQ ID NO: 52. For the *E. coli* expression of said sequence the following primer sequences were used:

| Name | Sequence (5' to 3') | Direction | SEQ ID NO: |
|---|---|---|---|
| DC-SIGN extracellular domain (ECD) - residues 60 to 404 | GCCGCCTCTAGAGAG TAATACGACTCACTA TAGGGACTAGAGAA AGAGGAGAAAACTA GATGCCAAAGTTCC GAGCAGCATT | forward primer | 53 |
| DC-SIGN extracellular domain (ECD) | GGCGGCCTGCAGGT ACAAAAAAGCAGGC TACTAGT | reverse primer | 54 |
| DC-SIGN carbohydrate recognition domain (CRD) - residues 205 to 404 | CCGCCTCTAGAGGAG TAATACGACTCACTA TAGGGACTAGAGAA AGAGGAGAAAACTA GATGGCTGAACGTCT GTGTCATCCGTG | forward primer | 55 |
| DC-SIGN carbohydrate recognition domain (CRD) | GGCGGCCTGCAGGT ACAAAAAAGCAGGC TACTAGT | reverse primer | 56 |

Langerin extracellular domain. Expression and purification were conducted as previously published (Wamhoff, E. C. et al. (19)F Nmr-Guided Design of Glycomimetic Langerin Ligands. ACS Chem Biol, 11, 2407-13 (2016)). Briefly, the trimeric Langerin extracellular domain (ECD) was expressed insolubly in *E. coli* BL21* (DE3) (Invitrogen). Following enzymatic cell lysis, inclusion bodies were harvested and subsequently solubilized. The sample was centrifuged and the Langerin ECD was refolded overnight via rapid dilution. Next, the sample was dialyzed overnight, centrifuged and purified via mannan-agarose affinity chromatography (Sigma Aldrich). For $^{19}$F $R_2$-filtered NMR and lipid-enzyme-linked lectin assay (Lipid-ELLA) experiments, the buffer was exchanged to 25 mM Tris with 150 mM NaCl and 5 mM $CaCl_2$ at pH 7.8 using 7 kDa size-exclusion desalting columns (Thermo Scientific). For STD NMR experiments, Langerin ECD samples were dialyzed five times for at least 8 h against $H_2O$. Subsequently, the $H_2O$ was removed via lyophilization and the residue was stored at −80° C. Prior to STD NMR experiments, the Langerin ECD was dissolved in in 25 mM Tris-$d_{11}$ (Eurisotope) with 100% $D_2O$, 150 mM NaCl and 5 mM $CaCl_2$ at pH 7. The concentration of Langerin ECD was determined via UV spectroscopy ($A_{280, 0.1\%}$=2.45). Purity and monodispersity of Langerin ECD samples were analyzed via SDS PAGE and DLS.

Langerin and DC-SIGN carbohydrate recognition domain. Expression and purification were conducted as previously published. Briefly, the monomeric $^{15}$N-labeled Langerin and DC-SIGN carbohydrate recognition domains (CRDs) were expressed insolubly in E. coli BL21* (DE3) (Invitrogen). Following enzymatic cell lysis, inclusion bodies were harvested and subsequently solubilized. The sample was centrifuged and the Langerin and DC-SIGN CRDs were refolded overnight via rapid dilution. Next, the sample was dialyzed overnight, centrifuged and purified via StrepTactin affinity chromatography (Iba). After an additional dialysis step overnight, the sample was centrifuged and the buffer was exchanged to 25 mM HEPES with 150 mM NaCl at pH 7.0 using 7 kDa size-exclusion desalting columns (Thermo Scientific) for $^{19}$F $R_2$-filtered and $^{15}$N HSQC NMR experiments. The concentration of Langerin and DC-SIGN CRDs was determined via UV spectroscopy ($A_{280, 0.1\%}$=3.19 and $A_{280, 0.1\%}$=2.98). Purity and monodispersity of Langerin and DC-SIGN CRD samples were analyzed via SDS PAGE and DLS.

$^{19}$F $R_2$-Filtered NMR

General remarks. $^{19}$F $R_2$-filtered NMR experiments were conducted on a PremiumCompact 600 MHz spectrometer (Agilent). Spectra were processed in MestReNova and data analysis was performed with OriginPro (Mestrelab Research. Mestrenova. 11.0.2. (2016); OriginLab. Originpro. 9.1. (2015)). Experiments with the Langerin ECD were performed at a receptor concentration of 50 µM in 25 mM Tris with 10% $D_2O$, 150 mM NaCl and 5 mM $CaCl_2$ at pH 7.8 and 25° C. Experiments with the DC-SIGN CRD were performed at a receptor concentration of 50 µM in 25 mM HEPES with 10% $D_2O$, 150 mM NaCl and 5 mM $CaCl_2$ at pH 7.0 and 25° C. TFA served as an internal reference at a concentration of 50 µM. Apparent relaxation rates $R_{2,obs}$ for the reporter ligand were determined using the CPMG pulse sequence as previously published (Wamhoff, E. C. et al. (19)F Nmr-Guided Design of Glycomimetic Langerin Ligands. ACS Chem Biol, 11, 2407-13 (2016): Carr, H. Y. & Purcell, E. M. Effects of Diffusion on Free Precession in Nuclear Magnetic Resonance Experiments. Phys Rev, 94, 630-638 (1954); Meiboom, S. & Gill, D. Modified Spin-Echo Method for Measuring Nuclear Relaxation Times. Rev Sci Instrum 29, 688-691 (1958)).

Assay development for DC-SIGN. The $^{19}$F $R_2$-filtered NMR reporter displacement assay for DC-SIGN was developed following the procedure previously published for Langerin (Wamhoff, E. C. et al. (19)F Nmr-Guided Design of Glycomimetic Langerin Ligands. ACS Chem Biol 11, 2407-13 (2016)). Briefly, the $K_D$ value and the relaxation rate in bound state $R_{2,b}$ were determined at five concentrations $[L]_T$ of reporter ligand 24 in three independent titration experiments. Samples were prepared via serial dilution. The addition of 10 mM EDTA served to validate the $Ca^{2+}$-dependency of the interaction between DC-SIGN and the reporter ligand. To ensure the validity of the equations for $K_D$ and $K_I$ determination, the chemical exchange contribution $R_{2,ex}$ was estimated by $^{19}$F NMR relaxation dispersion experiments at a reporter ligand concentration of 0.1 mM in presence of receptor.

$K_i$ determination. $K_i$ values were determined as previously published for Langerin (Wamhoff, E. C. et al. (19)F NMR-Guided Design of Glycomimetic Langerin Ligands. ACS Chem Biol 11, 2407-13 (2016)). Briefly, titration experiments were conducted at a concentration of 0.1 mM of reporter ligand 24 at five competitor concentrations $[I]_T$. Samples were prepared via serial dilution. For the acids GlcNS, GlcNAc-6-OS and GlcNS-6-OS the pH values were monitored and adjusted to 7.8 if necessary.

$^{15}$N HSQC NMR

General remarks. $^{15}$N HSQC NMR experiments were conducted on an Ascend 700 MHz spectrometer (Bruker) (Bodenhausen, G. & Ruben, D. J. Natural Abundance Nitrogen-15 NMR by Enhanced Heteronuclear Spectroscopy. Chem Phys Lett 69, 185-189 (1980)). Spectra were processed in NMRPipe (Delaglio, F. et al. Nmrpipe: A Multidimensional Spectral Processing System Based on Unix Pipes. J Biomol NMR 6, 277-93 (1995)). Data analysis was performed using CCPN Analysis, MatLab and OriginPro (OriginLab. Originpro. 9.1. (2015); Vranken, W. F. et al. The Ccpn Data Model for NMR Spectroscopy: Development of a Software Pipeline. Proteins, 59, 687-96 (2005); MathWorks. Matlab. 9.0. Natick, U.S.A. (2016)). Experiments with the Langerin CRD were performed at a receptor concentration of 100 µM in 25 mM HEPES with 10% $D_2O$, 150 mM NaCl and 5 mM $CaCl_2$ at pH 7.8 and 25° C. DSS-d6 served as an internal reference at a concentration of 100 µM. Spectra were referenced via the internal spectrometer reference. Spectra were acquired with 128 increments and 32 scans per increments for 150 µL samples in 3 mm sample tubes. The relaxation delay $d_1$ was set to 1.4 s and the acquisition time $t_{acq}$ was set to 100 ms. The W5 Watergate pulse sequence was used for solvent suppression (Liu, M. et al. Improved Watergate Pulse Sequences for Solvent Suppression in NMR Spectroscopy. J Magn Reson 132, 125-129 (1998)). The used resonance assignment for the Langerin CRD has been published previously (Hanske, J. et al. Intradomain Allosteric Network Modulates Calcium Affinity of the C-Type Lectin Receptor Langerin. J Am Chem Soc, 138, 12176-86 (2016)).

$K_D$ determination. $K_D$ values were determined in titration experiments at six ligand concentrations $[L]_T$. Samples were prepared via serial dilution. Chemical shift perturbations CSPs for Langerin CRD resonances in the fast or fast-to-intermediate exchange regime observed upon titration with ligand were calculated via Equation 1 (Williamson, M. P. Using Chemical Shift Perturbation to Characterise Ligand Binding. Prog Nucl Magn Reson Spectrosc 73, 1-16 (2013)).

$$CSP = \sqrt{\frac{\delta(^1H) + (0.15\delta(^{15}N))^2}{2}} \quad \text{Equation 1}$$

A standard deviation σ of 0.02 ppm was previously determined for the measurement of chemical shifts in $^{15}$N HSQC NMR experiments with the Langerin CRD (Hanske, J. et al. Intradomain Allosteric Network Modulates Calcium Affinity of the C-Type Lectin Receptor Langerin. J Am Chem Soc, 138, 12176-86 (2016)). Accordingly, only assigned resonances that displayed CSP values higher than a threshold of 2σ at the highest ligand concentration were selected for the determination of $K_D$ values via Equation 2 in a global two parameter fit (Williamson, M. P. Using Chemical Shift Perturbation to Characterise Ligand Binding. Prog Nucl Magn Reson Spectrosc, 73, 1-16 (2013)). Standard errors were derived directly from the fitting procedures. Additionally, resonances that displayed line broadening $\Delta v_{0.5}$ larger than 10 Hz upon titration in either the $^1$H or the $^{15}$N dimension were not considered for the determination of $K_D$ values. $CSP_{max}$ represents the CSP value observed upon saturation of the binding site.

$$CSP = CSP_{max} p_b \qquad \text{Equation 2}$$

with $$p_b = \frac{[P]_T + [L]_T + K_D - \sqrt{([P]_T + [L]_T + K_D)^2 - 4[P]_T[L]_T}}{2[P]_T}$$

For resonances assumed to be in the slow exchange regime upon titration, $K_D$ values were derived from integrals $V_b$ and $V_f$ corresponding to the bound and free state of the Langerin CRD, respectively. V values served to calculate the bound fraction of the receptor $p_b$ via Equation 3. Integrals V were normalized via integral V of the N-terminal K347 and served to calculate the bound fraction of the receptor $p_b$ via Equation 3. For these calculations, only resonances for which the bound state could be assigned were considered. Selected data points displaying a low SNR or issues with the baseline correction were treated as outliers and not considered for the determination of pb values. Next, a one parameter fit of Equation 3 to mean $p_b$ values served to determine $K_D$ values.

$$\frac{V_b}{V_b + V_f} = p_b \qquad \text{Equation 3}$$

with $$p_b = \frac{[P]_T + [L]_T + K_D - \sqrt{([P]_T + [L]_T + K_D)^2 - 4[P]_T[L]_T}}{2[P]_T}$$

Binding mode analysis. Based on the resonance assignment, CSP values observed at maximal ligand concentrations $[L]_T$ were mapped on the X-ray structure of the Langerin CRD (PDB code: 4N32) using Matlab's Bioinformatics Toolbox via substitution of the B-factor values (Feinberg, H. et al. Common Polymorphisms in Human Langerin Change Specificity for Glycan Ligands. J Biol Chem, 288, 36762-71 (2013); MathWorks. Bioinformatics Toolbox. 4.7. Natick, U.S.A. (2016)). The CSP patterns obtained were visualized in MOE using Chain B of the Langerin CRD in complex with GlcNAc (ChemicalComputingGroup. Molecular Operating Enviroment. 2016.08. Montreal, Canada (2016)). Model quality was maintained using MOE's Structure Preparation followed by the simulation of protonation states and the hydrogen bond network of the complex with MOE's Protonate 3D. Receptor surfaces were visualized in Connolly representation (Connolly, M. L. The Molecular Surface Package. J Mol Graph, 11, 139-41 (1993)).

STD NMR

General remarks. STD NMR experiments were conducted on a PremiumCompact 600 MHz spectrometer (Agilent) (Mayer, M. & Meyer, B. Characterization of Ligand Binding by Saturation Transfer Difference NMR Spectroscopy. Angew Chem Int Ed, 38, 1784-1788 (1999)). Spectra were processed in MestReNova and data analysis was performed with OriginPro (Mestrelab Research. Mestrenova. 11.0.2. (2016): OriginLab. Originpro. 9.1. (2015)). Experiments with the Langerin ECD were conducted at a receptor concentration of 50 µM in 25 mM Tris-$d_{11}$ (Eurisotope) with 100% D20, 150 mM NaCl and 5 mM CaCl2) at pH 7.8 and 25° C. Experiments were repeated in absence of receptor to exclude STD effects due to direct saturation of ligands. Residual $H_2O$ or TSP-d6 at 0.1 mM served as an internal reference. Spectra were recorded in 5 mm sample tubes at sample volumes of 500 µL. Saturation was implemented via a train of 50 ms Gauss pulses at varying saturation times $t_{sat}$. The on-resonance irradiation frequency $v_{sat}$ was set to 0.0 ppm and the off-resonance irradiation frequency $v_{ref}$ was set to 80.0 ppm. The acquisition time $t_{acq}$ was set to 2.0 s and the DPFGSE pulse sequence was utilized for solvent suppression (Hwang, T. L. & Shaka, A. J. Water Suppression That Works-Excitation Sculpting Using Arbitrary Wave-Forms and Pulsed-Field Gradients. J Magn Reson, 112, 275-279 (1995)). Receptor resonances were suppressed using a T1,rho filter at a relaxation time τ of 35 ms.

Epitope mapping. The binding epitope for 16 was determined at a concentration of 500 µM. For each spectrum 512 scans were recorded. The relaxation delay $d_1$ was set to 6 s and spectra were recorded at 5 different saturation time $t_{sat}$ varying from 0.25 to 6.00 s. Equation 4 served to derive the STD effect STD for each analyzed resonance from the corresponding on- and off-resonance spectra (Mayer, M. & Meyer, B. Group Epitope Mapping by Saturation Transfer Difference NMR to Identify Segments of a Ligand in Direct Contact with a Protein Receptor. J Am Chem Soc, 123, 6108-17 (2001)). $I_0$ represents the integral of a resonance in the off-resonance spectrum and $I_{sat}$ represents the integral of a resonance in the on-resonance spectrum.

$$STD = \frac{I_0 - I_{sat}}{I_0} \qquad \text{Equation 4}$$

The apparent saturation rate ksat and the maximal STD effect $STD_{max}$ were derived from Equation 5 in a two parameter fit (Angulo, J. & Nieto, P. M. Std-Nmr: Application to Transient Interactions between Biomolecules-a Quantitative Approach. Eur Biophys J, 40, 1357-69 (2011)). Standard errors were derived directly from the fitting procedures. These parameters were used to calculate the initial slope of the STD build-up curves $STD'_0$ via Equation 6. $STD'_0$ values were normalized and mapped on the corresponding ligand structure. Only resonances for which at least part of a multiplet was isolated were considered for the epitope mapping.

$$STD = STD_{max}(1 - e^{k_{sat} t_{sat}}) \qquad \text{Equation 5}$$

$$STD'_0 = STD_{max} k_{sat} \qquad \text{Equation 6}$$

Molecular Modelling

General remarks. Molecular modelling procedures were performed in MOE (ChemicalComputingGroup. Molecular Operating Environment. 2016.08. Montreal, Canada (2016)). Deviations from default options and parameters are noted. The AMBER10:EHT force field was selected for the refinement of docking poses and the hydrogen bond network while the MMFF94x force field was utilized for the generation conformers (Case, D. A., Darden, T. A., Cheatham, T. E., Simmerling, C. L., Wang, J., Duke, R. E., Luo, R., Crowley, M., R. C. Walker, Zhang, W., Merz, K. M., B. Wang, Hayik, S., Roitberg, A., Seabra, G., Kolossváry, I., K. F. Wong, Paesani, F., Vanicek, J., X. Wu, Brozell, S. R., Steinbrecher, T., Gohlke, H., Yang, L., Tan, C., Mongan, J., Hornak, V., Cui, G., Mathews, D. H., Seetin, M. G., Sagui, C., Babin, V. and P. A. Kollman. Amber. 10. San Francisco, U.S.A. (2008); Gerber, P. R. & Muller, K. Mab, a Generally Applicable Molecular Force Field for Structure Modelling in Medicinal Chemistry. J Comput Aided Mol Des, 9, 251-68 (1995); Halgren, T. A. Merck Molecular Force Field. I. Basis, Form, Scope, Parameterization, and Performance of Mmff94. J Comput Chem, 17, 490-519 (1996)). Receptor surfaces were visualized in Connolly representation (Connolly, M. L. The Molecular Surface Package. J Mol Graph, 11, 139-41 (1993)).

Development of the pharmacophore model and preparation of the Langerin complex. A structural alignment of Langerin carbohydrate binding sites in complex with GlcNAc was performed (PDB codes: 4N32) (Feinberg, H. et al. Common Polymorphisms in Human Langerin Change Specificity for Glycan Ligands. J Biol Chem, 288, 36762-71 (2013)). Based on this visualization, a pharmacophore model was defined with features for O3, O4 and O5 of the Glc scaffold. The spatial constraint on the O3 and O4 was defined by a sphere with a radius r of 0.5 Å while the position of O5 was constrained by a sphere with a radius r of 1.0 Å. Chain B of the Langerin CRD in complex with GlcNAc served as the structural basis for the conducted molecular docking study. Additionally, an alternative conformation for K313 observed for the Langerin complex with Gal-6-OS was modeled and included in the study (Feinberg, H. et al. Structural Basis for Langerin Recognition of Diverse Pathogen and Mammalian Glycans through a Single Binding Site. J Mol Biol, 405, 1027-39 (2011)). Overall model quality and protein geometry were evaluated and maintained using MOE's Structure Preparation. Next, protonation states and the hydrogen bond network of the complex were simulated with MOE's Protonate 3D followed by the removal of all solvent molecules.

Molecular docking. Conformations for 16 were generated utilizing MOE's Conformation Import. A pharmacophore-based placement method was utilized to generate docking poses that we scored using the London AG function. Highly scored poses were refined utilizing molecular mechanics simulations, rescored via the GBIV/WSA ΔG function, filtered using the pharmacophore model and written into the output database (Corbeil, C. R., Williams, C. I. & Labute, P. Variability in Docking Success Rates Due to Dataset Preparation. J Comput Aided Mol Des, 26, 775-86 (2012)). Conformational flexibility of the carbohydrate binding site was accounted for by introducing B-factor-derived tethers to side chain atoms. Refined docking poses were ranked according to their the GBIV/WSA ΔG score and evaluated visually in the context of the conducted $^{15}$N HSQC and STD NMR experiments.

Example 20

Figure 30:
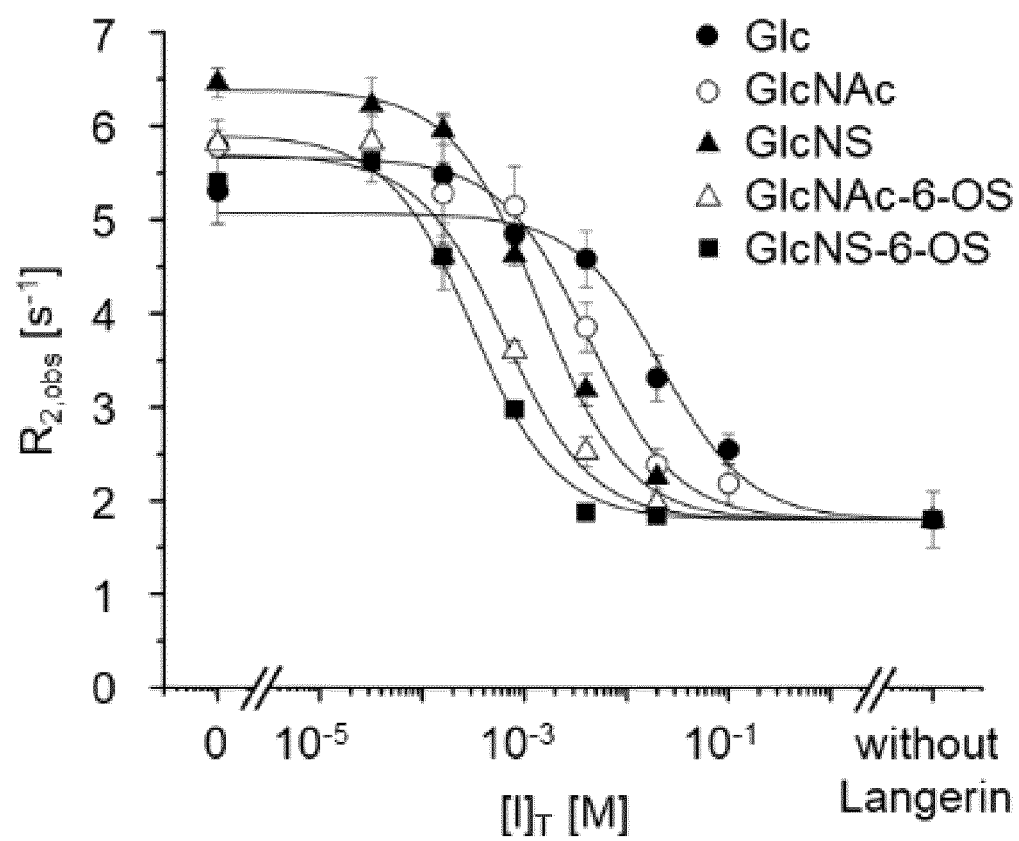
FIG. 30 shows the $K_i$ determination for sulfated GlcNAc derivatives. The $K_i$ determination for heparin-derived GlcNAc derivatives via $^{19}$F R$_2$-filtered NMR revealed the impact of sulfation patterns on monosaccharide affinity. Obtained KI values are given in FIG. 39.
Figure 39:
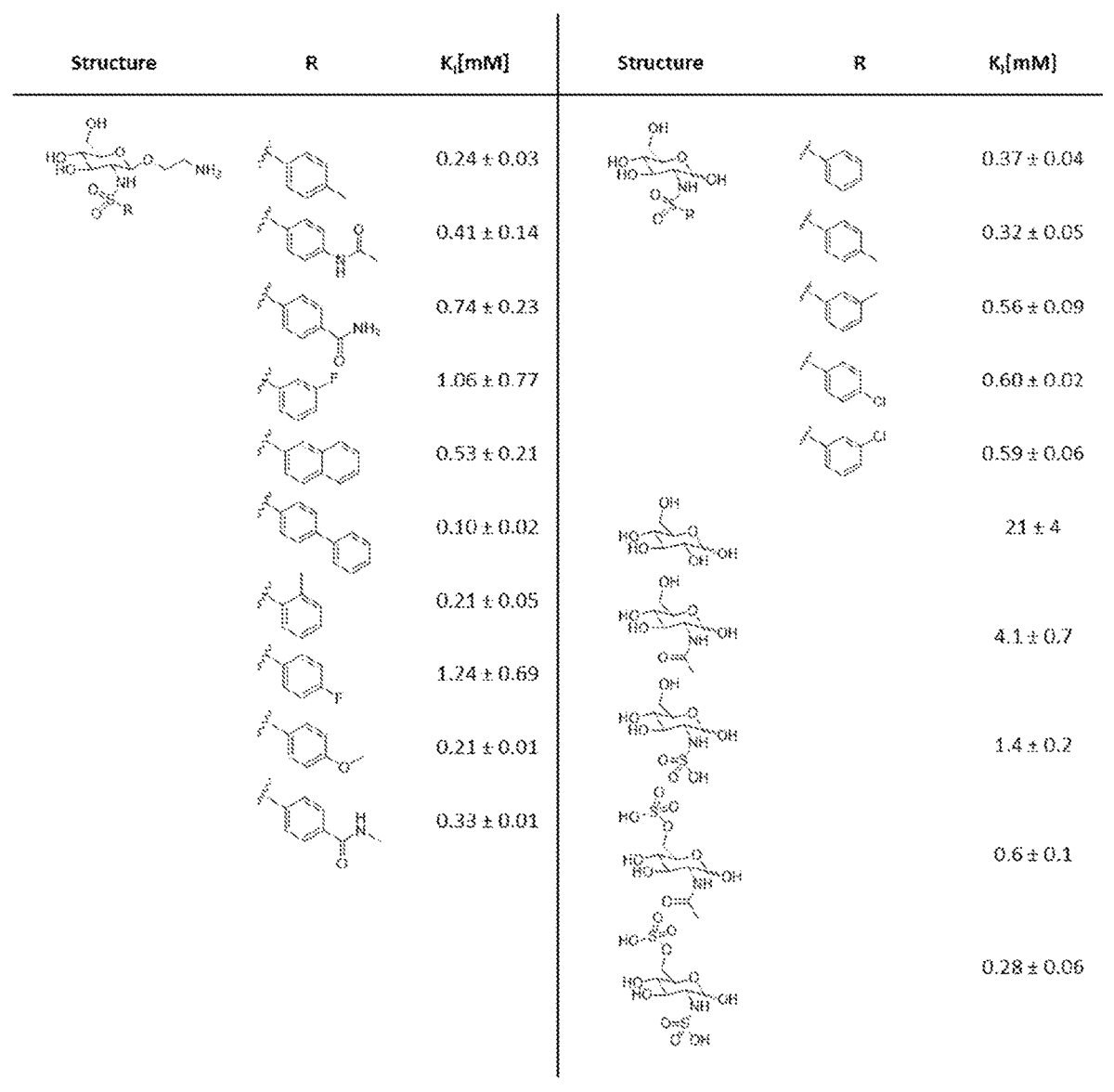

Heparin-Derived Monosaccharides Represent Favorable Scaffolds for Glycomimetic Ligand Design Aside from its function as a pathogen recognition receptor, Langerin interacts with self-antigens such as glycosaminoglycans including heparin (Munoz-Garcia, J. C. et al. Langerin-Heparin Interaction: Two Binding Sites for Small and Large Ligands as Revealed by a Combination of NMR Spectroscopy and Cross-Linking Mapping Experiments. J Am Chem Soc, 137, 4100-10 (2015); Hanske, J. et al. Calcium-Independent Activation of an Allosteric Network in Langerin by Heparin Oligosaccharides. ChemBioChem, accepted (2017); Zhao, J. et al. Kinetic and Structural Studies of Interactions between Glycosaminoglycans and Langerin. Biochemistry (2016)). These linear polysaccharides are composed of disaccharide repeating units consisting of galactose or uronic acids and differentially sulfated N-acetyl glucosamine (GlcNAc). Prompted by the 10-fold affinity increase ($K_D$=0.49±0.05 mM) over mannose (Man) disaccharides ($K_D$=ca. 4 mM) recently reported for a heparin-derived trisaccharide, ligand-observed $^{19}$F $R_2$-filtered NMR experiments were employed to determine $K_i$ values for a set of differentially sulfated GlcNAc derivatives (see FIG. 27 A) (Holla, A. & Skerra, A. Comparative Analysis Reveals Selective Recognition of Glycans by the Dendritic Cell Receptors Dc-Sign and Langerin. Protein Eng Des Sel, 24, 659-69 (2011); Munoz-Garcia, J. C. et al. Langerin-Heparin Interaction: Two Binding Sites for Small and Large Ligands as Revealed by a Combination of NMR Spectroscopy and Cross-Linking Mapping Experiments. J Am Chem Soc, 137, 4100-10 (2015); Wamhoff, E. C. et al. (19)F NMR-Guided Design of Glycomimetic Langerin Ligands. ACS Chem Biol, 11, 2407-13 (2016)). Interestingly, the affinities of glucosamine-2-sulfate (GlcNS) ($K_i$=1.4±0.2 mM), N-acetyl glucosamine-6-sulfate (GlcNAc-6-OS) ($K_i$=0.6±0.1 mM) and glucosamine-2-sulfate-6-sulfate (GlcNS-6-OS) ($K_i$=0.28±0.06 mM) were comparable or higher than those observed for heparin-derived oligosaccharides and other monosaccharides including Glc ($K_i$=21±4 mM), GlcNAc ($K_i$=4.1±0.7 mM) and Man ($K_i$=4.5±0.5 mM) (see FIG. 30 and FIG. 39) (Hanske, J. et al. Calcium-Independent Activation of an Allosteric Network in Langerin by Heparin Oligosaccharides. ChemBioChem, 2017).

GlcNS-6-OS, representing the most potent monosaccharide identified, displayed an additive structure-activity relationship (SAR) for the sulfation in C2 and C6. This affinity increase is based on the formation of salt bridges with K299 and K313 as previously shown by X-ray crystallography (Porkolab, V. et al. Rational-Differential Design of Highly Specific Glycomimetic Ligands: Targeting Dc-Sign and Excluding Langerin Recognition. ACS Chem Biol (2018)). GlcNS-6-OS displayed an altered orientation of the Glc scaffold compared to the Langerin-GlcNAc complex (FIG. 27 (B))(Feinberg, H. et al. Common Polymorphisms in Human Langerin Change Specificity for Glycan Ligands. J Biol Chem, 288, 36762-71 (2013)). The affinity increase observed over Glc observed for GlcNAc, on the other hand, is the result of an $H_2O$-mediated hydrogen bond with K299. Importantly, either of these interactions might be leveraged for glycomimetic ligand design via the bioisosteric substitution of the sulfate groups with a sulfonamide linker. In particular, the synthesis of GlcNS analogs represents a feasible fragment growing approach to explore the carbohydrate binding site for favorable interactions (see FIG. 27

(A)). These characteristics render sulfated GlcNAc derivatives favorable scaffolds for the design of glycomimetic Langerin ligands.

Example 21

Figure 27E:
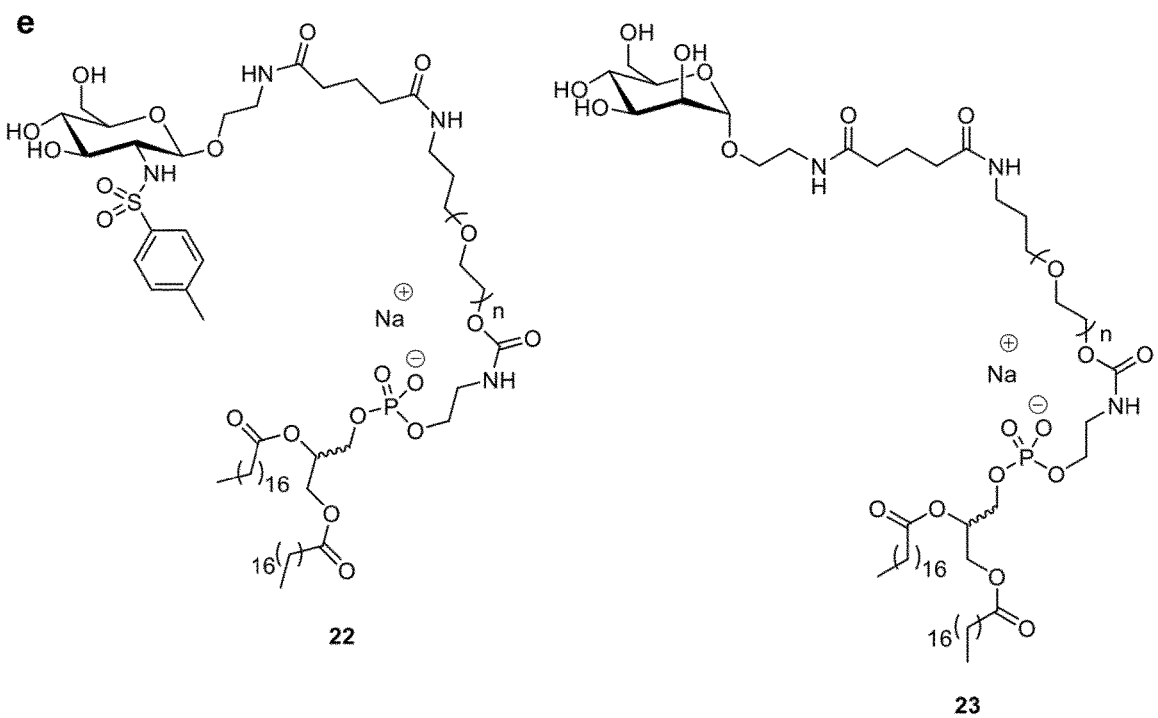
FIG. 27 shows Heparin-inspired design of a glycomimetic targeting ligand for human Langerin.
Figure 31:
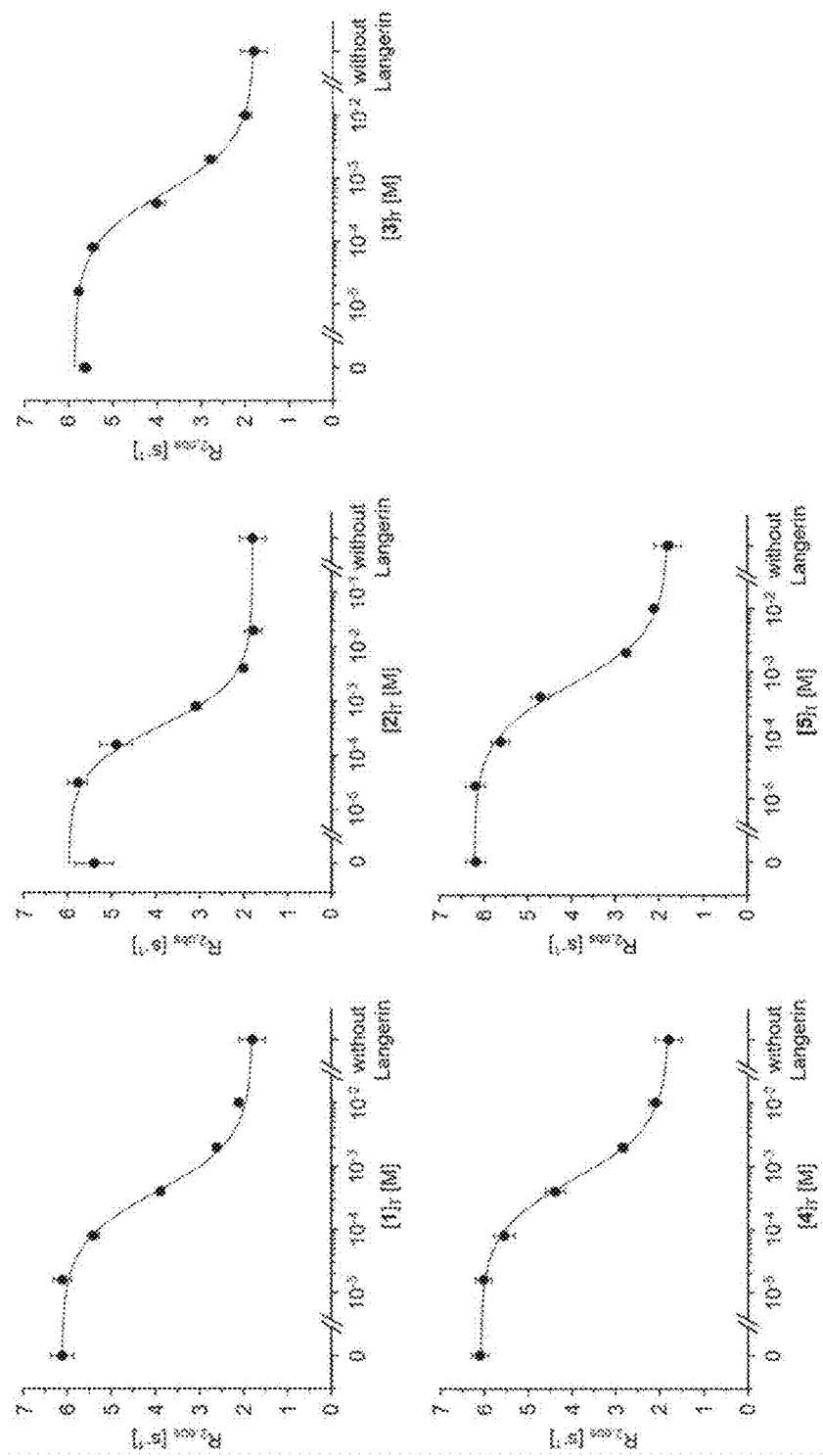
FIG. 31 shows the $K_i$ determination for GlcNS analogs 1 to 5. Competitive binding experiments served to determine the affinities for the GlcNS analog library. Obtained $K_i$ values are given in FIG. 39.

Small Aromatic Sulfonamide Substituents Render Glycomimetics Potent Targeting Ligands for Langerin and Provide Specificity Against DC-SIGN Assuming the conservation of the Glc scaffold orientation observed for GlcNAc, small aromatic substituents in C2 were hypothesized to increase the affinity by the formation of cation-π interactions with K299 and K313 or π-π and H-π interactions with F315 and P310, respectively (see FIG. 27 (B)). Accordingly, a panel of GlcNS analogs 1 to 5 bearing differentially substituted phenyl rings was prepared and followed by the determination of $K_i$ values (see FIG. 39). Increased affinities over GlcNAc were observed for all analogs, with a 13-fold affinity increase for 2 ($K_i$=0.32±0.05 mM), the most potent panel member (see FIG. 29, FIG. 31 and FIG. 39). The analog bears a methyl group in para position of the phenyl ring that does not contribute substantially to the affinity increase, as exemplified by the $K_i$ value obtained for 1 ($K_i$=0.37±0.04 mM).

Despite its low complexity, 2 displays an affinity superior to that of glycans previously applied as targeting ligands for DC subsets distinct from LCs (Fehres, C. M. et al. Cross-Presentation through Langerin and Dc-Sign Targeting Requires Different Formulations of Glycan-Modified Antigens. J Control Release, 203, 67-76 (2015)). Here, the blood group antigen Le$^X$ ($K_{D,DC-SIGN}$=ca. 1 mM) was demonstrated to promote the DC-SIGN-dependent internalization of liposomes by isolated dermal DCs to activate T cells in vitro (Pederson, K., Mitchell, D. A. & Prestegard, J. H. Structural Characterization of the Dc-Sign-Lex Complex. Biochemistry, 53, 5700-5709 (2014)). Encouraged by these reports, 2 was advanced towards targeted delivery applications via the introduction of an ethylamino linker in β-orientation of C1 of the Glc scaffold to yield targeting ligand 15 (see FIG. 27 (A)).

After acetylation of the amino group, model ligand 16 was obtained (FIG. 27 (A)). The $K_i$ value determination for 16 ($K_i$=0.24±0.03 mM) revealed a 42-fold affinity increase over the Man-based reference molecule 21 ($K_i$=10±1 mM) (FIGS. 27 (A) and 27 (C) and FIG. 29). To validate these affinities and to expand the insight into the recognition process, orthogonal protein-observed $^{15}$N HSQC NMR experiments were performed (FIGS. 27 (D) and 28 (A), FIG. 29, and FIG. 32). Notably, a considerable fraction of the resonances displaying chemical shift perturbations (CSPs) upon the addition of 16 also displayed line broadening $\Delta v_{0.5}$ of more than 10 Hz, indicative of intermediate exchange phenomena. Accordingly, these resonances were not considered for $K_D$ determination. Simultaneously, slow exchange phenomena were observed for a set of resonances corresponding to Y251, I253, N297 and K299 (FIG. 27 (A)). Analysis of both fast- and slow-exchanging peaks revealed affinities comparable to the $K_i$ values obtained for 16 ($K_{D,fast}$=0.23±0.07 mM, $K_{D,slow}$=0.3±0.1 mM) as well as 21 ($K_D$=12±1 mM) (FIG. 27 (D), FIG. 29, FIG. 32). Likewise, the affinity of 2 was validated using $^{15}$N HSQC NMR ($K_{D,fast}$=0.46±0.04 mM, $K_{D,slow}$=0.5±0.2 mM) (FIG. 29 and FIG. 33).

Next, the specificity of targeting ligand 16 (see FIG. 27A) was explored against DC-SIGN as such off-target affinity would imply a reduced efficiency of the approach and the potential induction of adverse effects. For this purpose, the $^{19}$F R$_2$-filtered NMR reporter displacement assay was transferred to DC-SIGN ( ). 16 ($K_{i,DC-SIGN}$=15±3 mM) displayed a considerably decreased $K_i$ for DC-SIGN compared to Langerin corresponding to 63-fold specificity (FIG. 27 (C) and FIG. 29). At the same time 21 displayed 3.7-fold specificity for DC-SIGN over Langerin ($K_{i,DC-SIGN}$=2.7±0.3 mM). A comparison with the affinities determined for 2 ($K_{i,DC-SIGN}$=17±1 mM) and Man ($K_{i,DC-SIGN}$=3.0±0.3 mM) revealed that the differential recognition of α- and β-glycosides by these CLRs contributes to specificity (FIG. 29).

Example 22

Binding Mode Analysis Derived from NMR and Molecular Modelling Insights: The Formation of π-π Interactions and Hydrogen Bonds by Aromatic Sulfonamide Substituents Mediate an Affinity Increase for Langerin To investigate the binding mode of model ligand 16 (see FIG. 27A), $^{15}$N HSQC and STD NMR experiments were combined with molecular docking studies (FIGS. 28 (A) to 28 (E)). Here, the orientation of the linker was of particular interest to evaluate the compatibility of the binding mode with the presentation of targeting ligand 15 on liposomes.

Figure 28C:
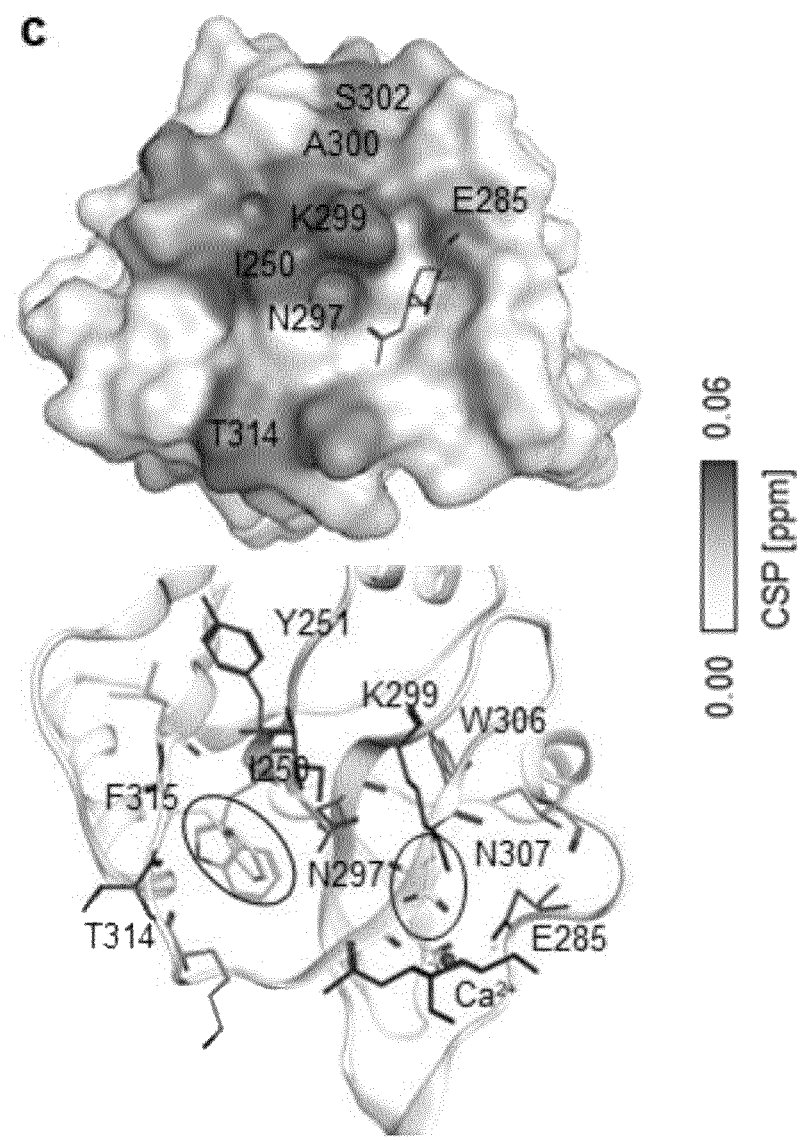
FIG. 28 shows the binding mode analysis for the glycomimetic targeting ligand.
Figure 32:
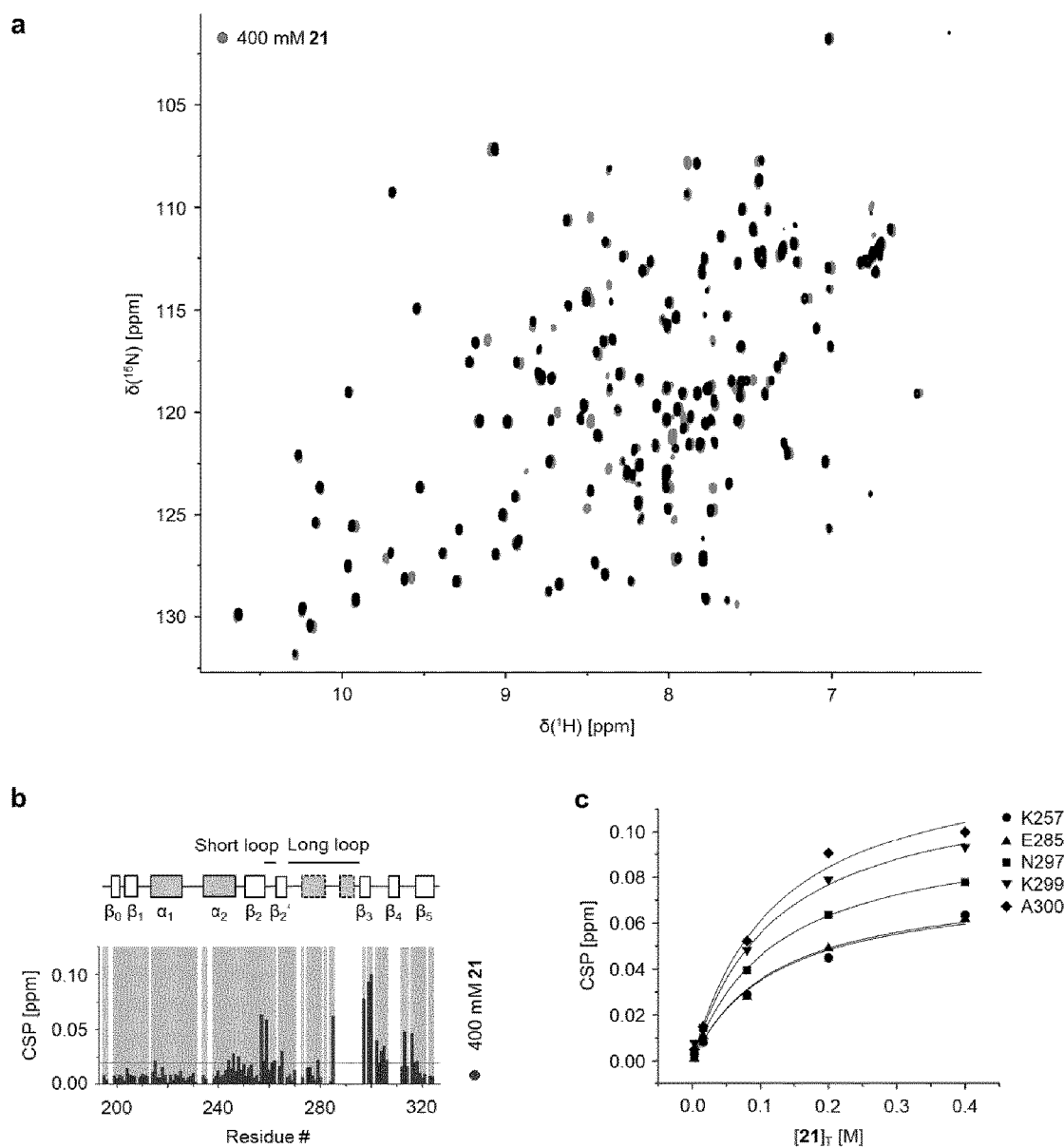
FIG. 32 shows the $K_D$ determination for Man analog 21.
Figure 34A:
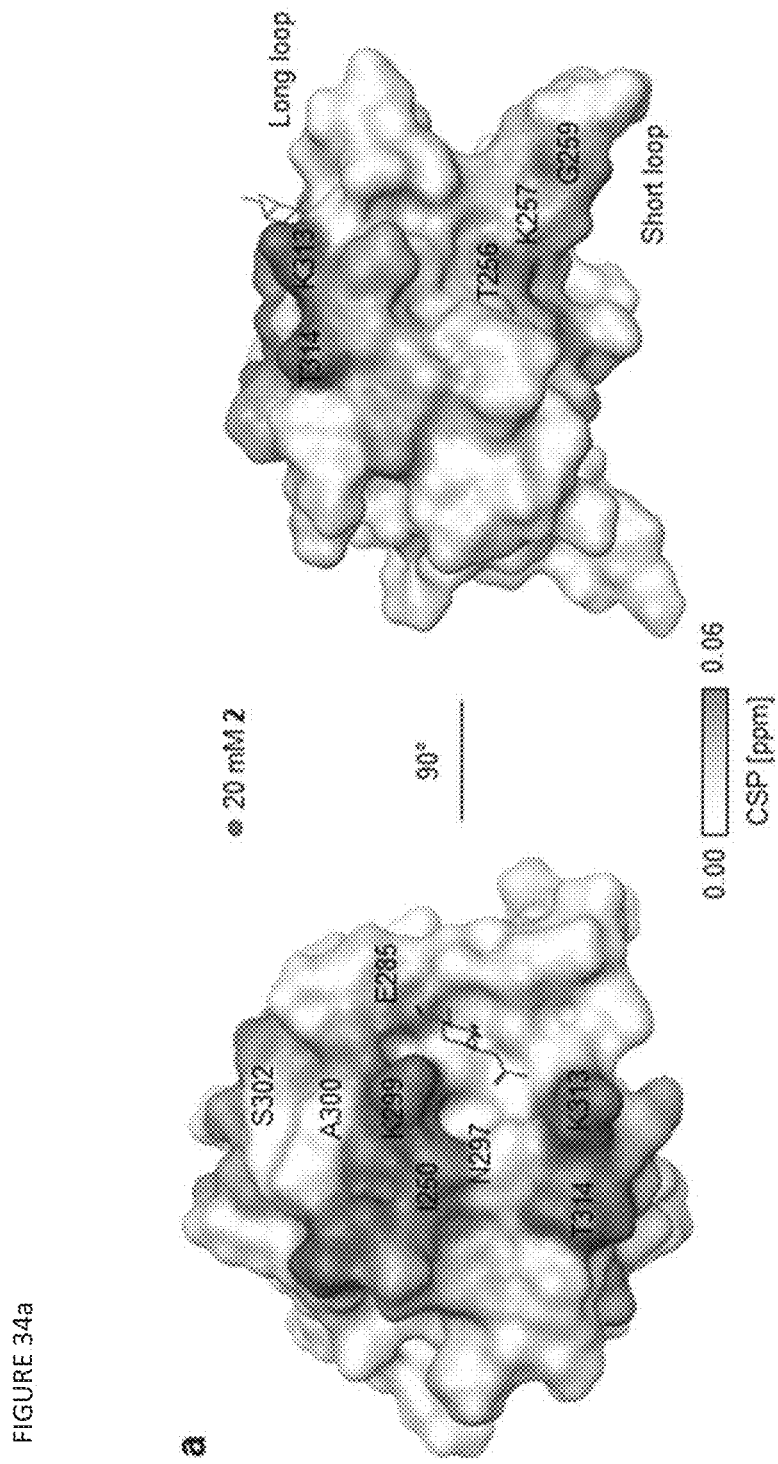
FIG. 34 shows the $^{15}$N HSQC NMR binding mode analysis for GlcNS analogs 2, 16 and Man analog 21.
Figure 34B:
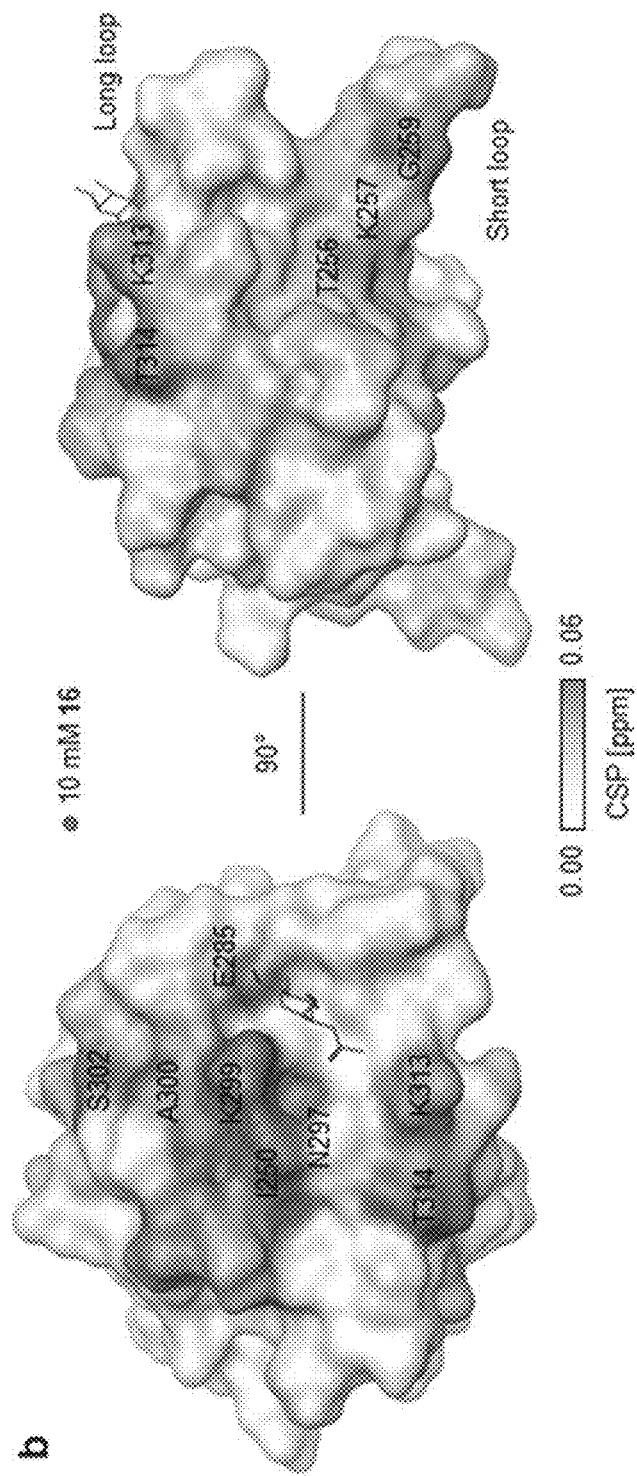
Figure 34C:
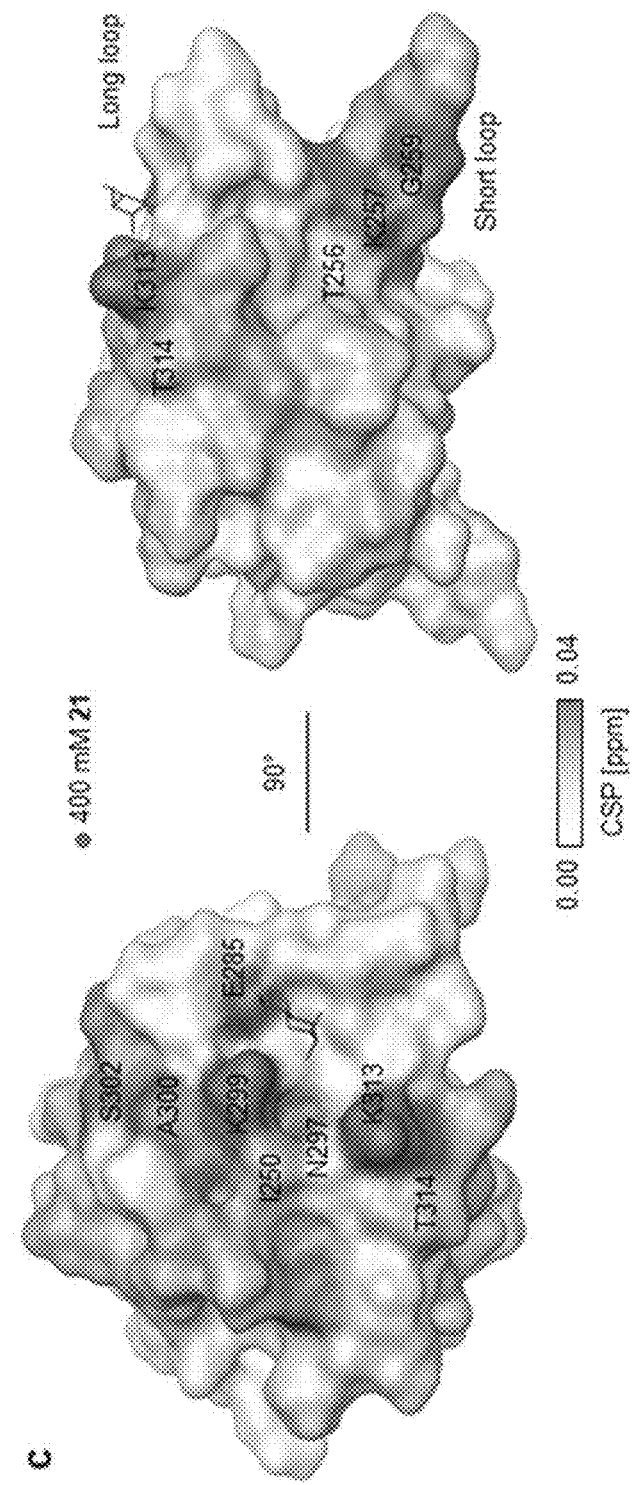
Figure 34D:
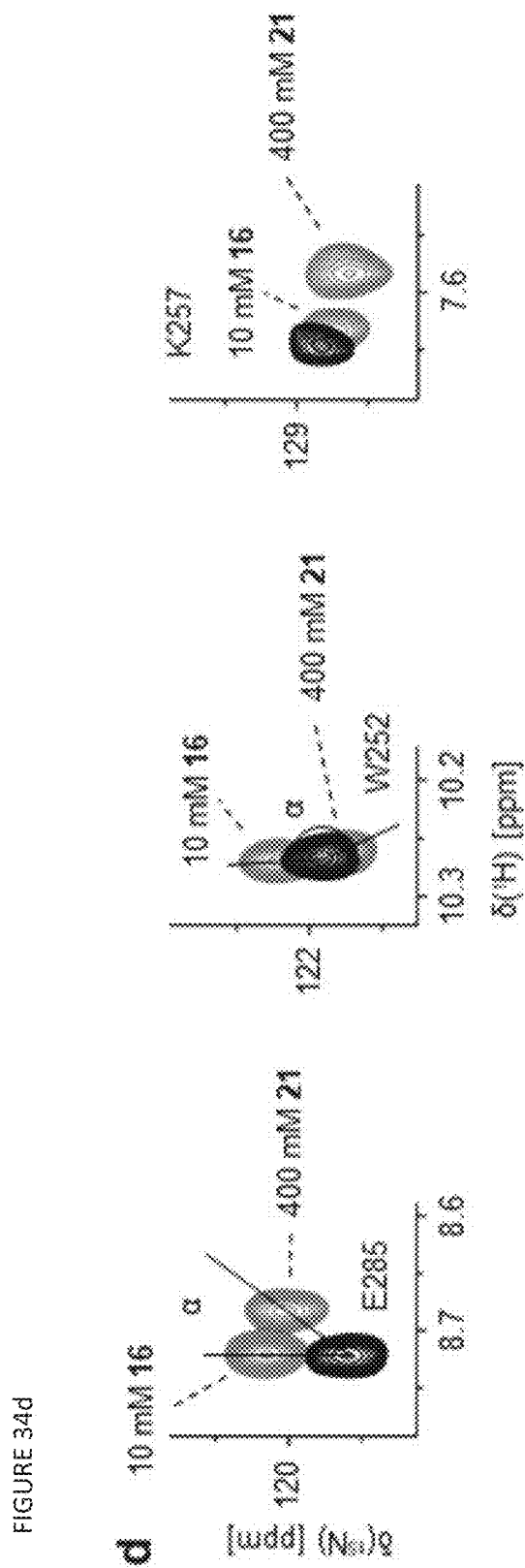

Titration of 16 (see FIG. 27 (A)) induced CSPs for E285 and K299 providing further evidence for a canonical Ca$^{2+}$-dependent binding mode of the Glc scaffold of the glycomimetic (FIGS. 28 (B) and 28 (C)). These protein-observed NMR experiments additionally revealed strong CSPs for residues in proximity of F315 and N307. Notably, both residues could not be assigned, likely due to their association with the flexible long loop (Hanske, J. et al. Intradomain Allosteric Network Modulates Calcium Affinity of the C-Type Lectin Receptor Langerin. J Am Chem Soc 138, 12176-86 (2016). This effect is accompanied by a decreased the CSP for K313 compared to titrations with Man analog 21 from FIG. 27 (A) (FIGS. 32 and 34). Both observations are conserved in titrations with 2 from FIG. 27 (A) and indicate an orientation of the phenyl ring towards F315 or K299 rather than K313 or P310 (FIGS. 33 and 34). Interestingly, additional CSPs were induced for residues remote from the carbohydrate binding, suggesting the modulation of an allosteric network involved in the regulation of Ca$^{2+}$ recognition by Langerin.

Figures 1, 35:
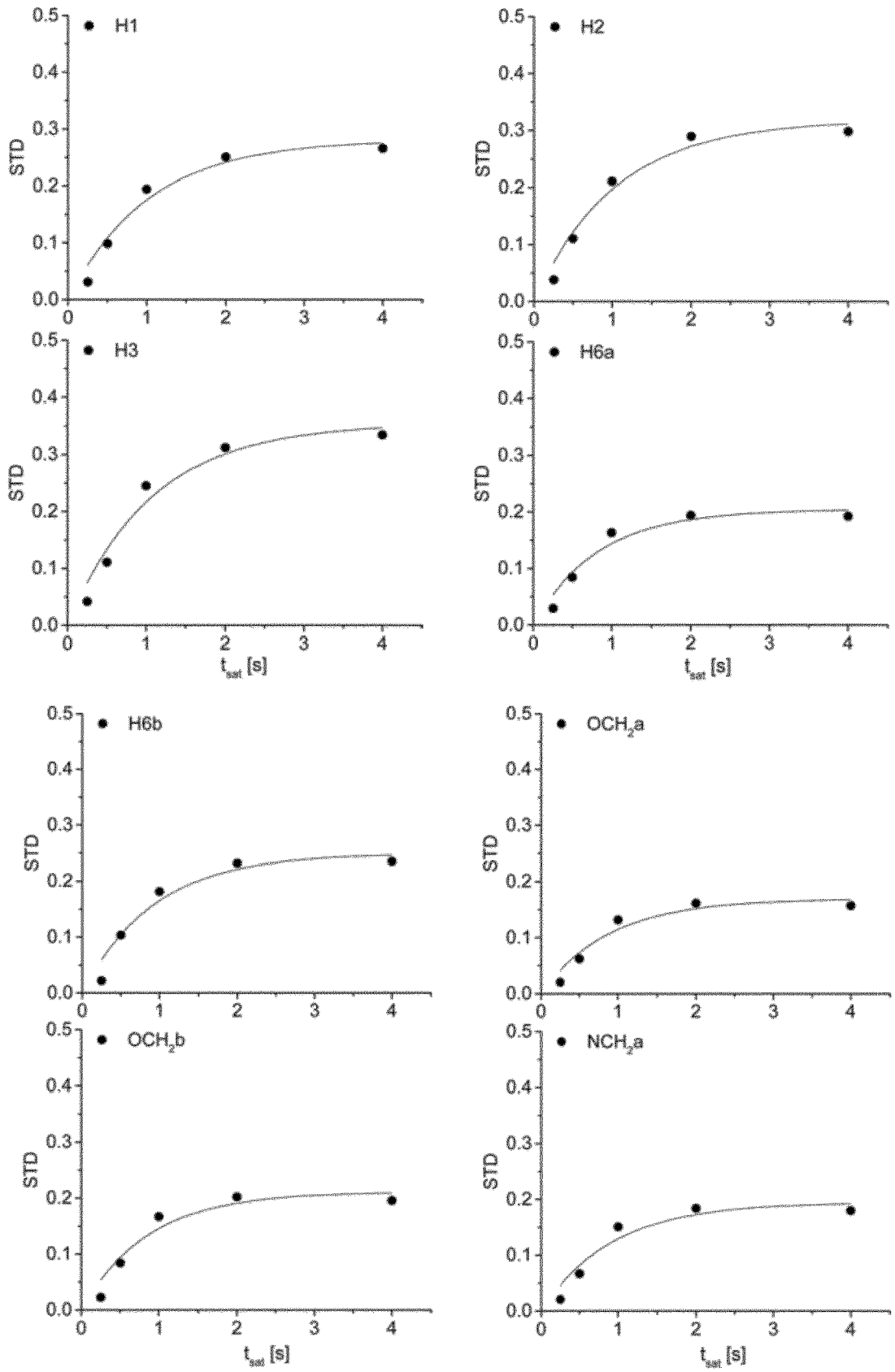
FIG. 35 shows the STD NMR build-up curves for GlcNS analog 16. Equation 5 was fitted to STD values to calculate STD'$_0$ values for the determination of the binding epitope of 16.
Figures 2, 35:
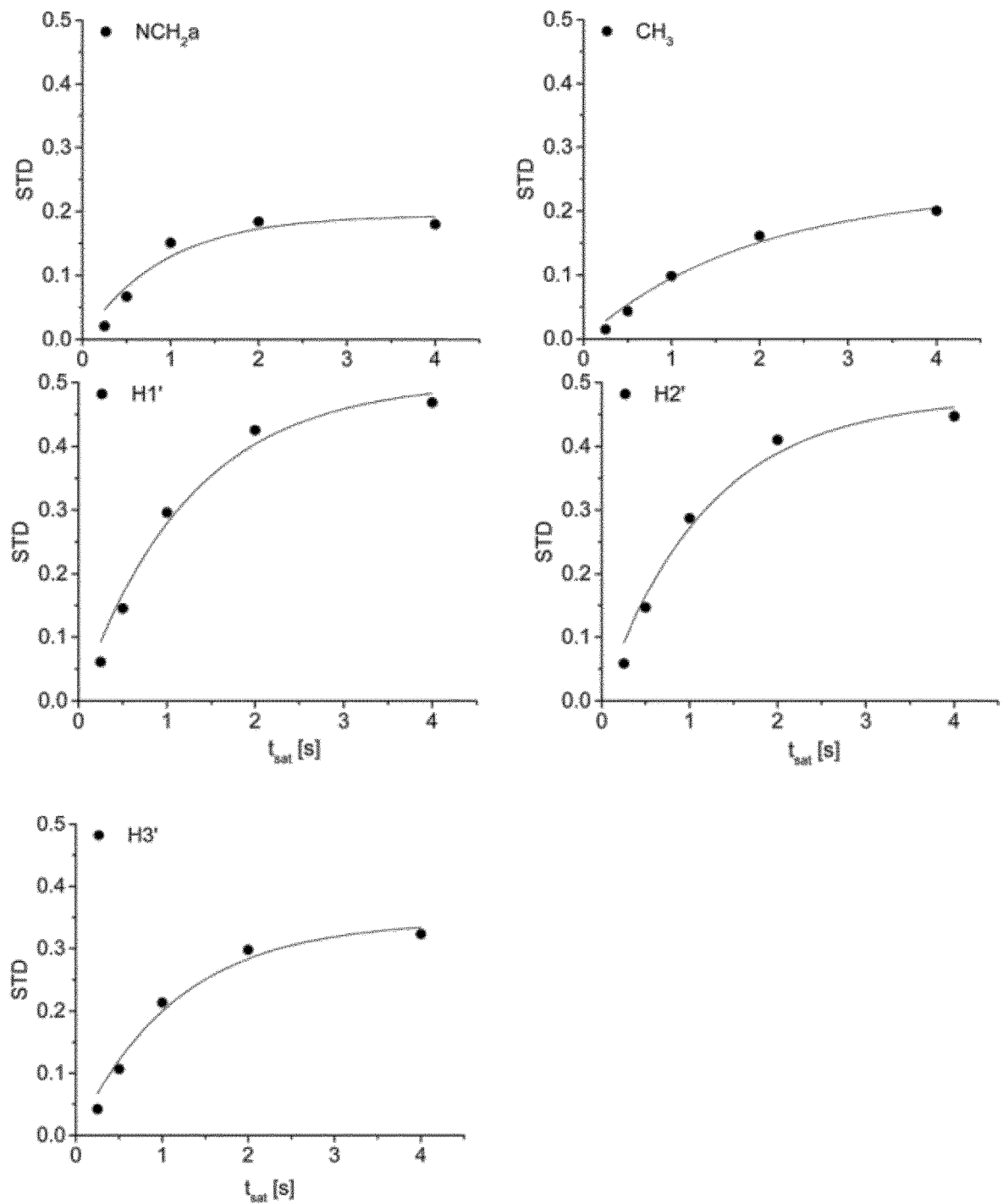
Figure 36:
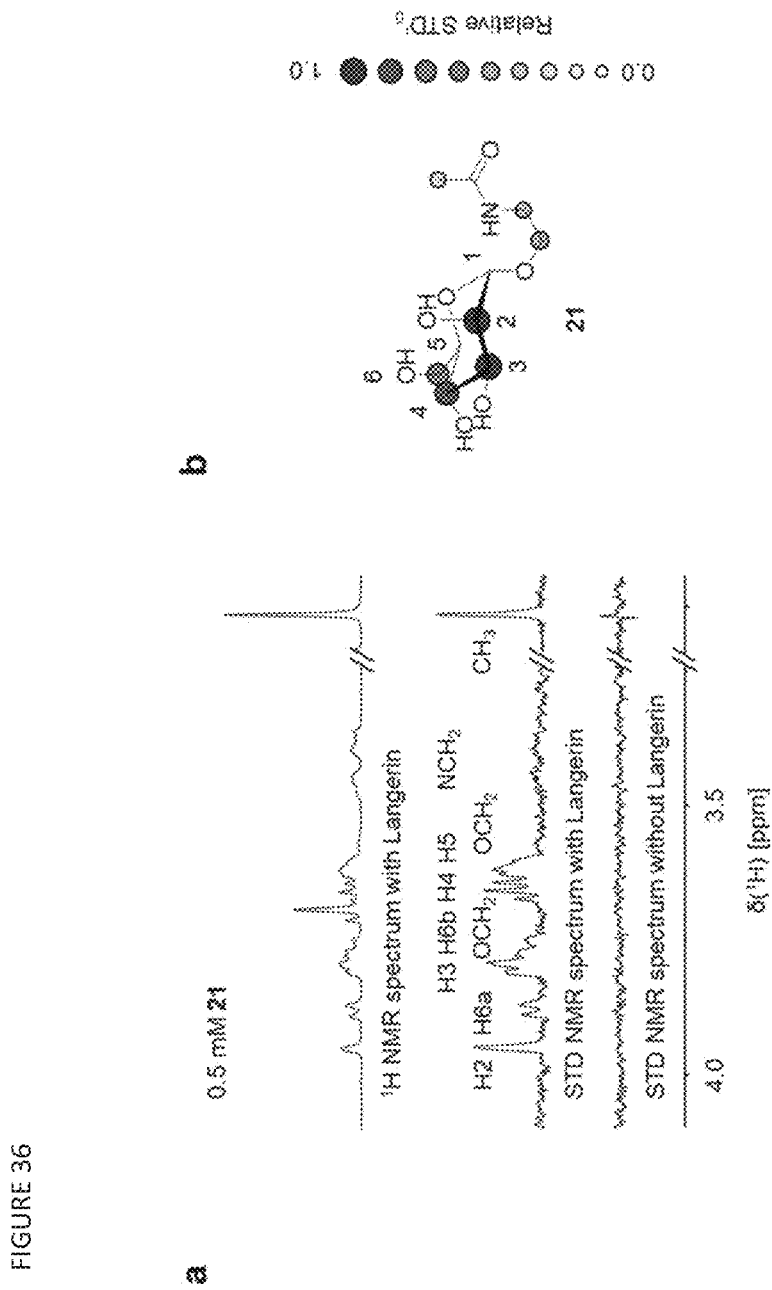
FIG. 36 shows the STD NMR epitope mapping for Man analog 21.
Figures 1, 37:
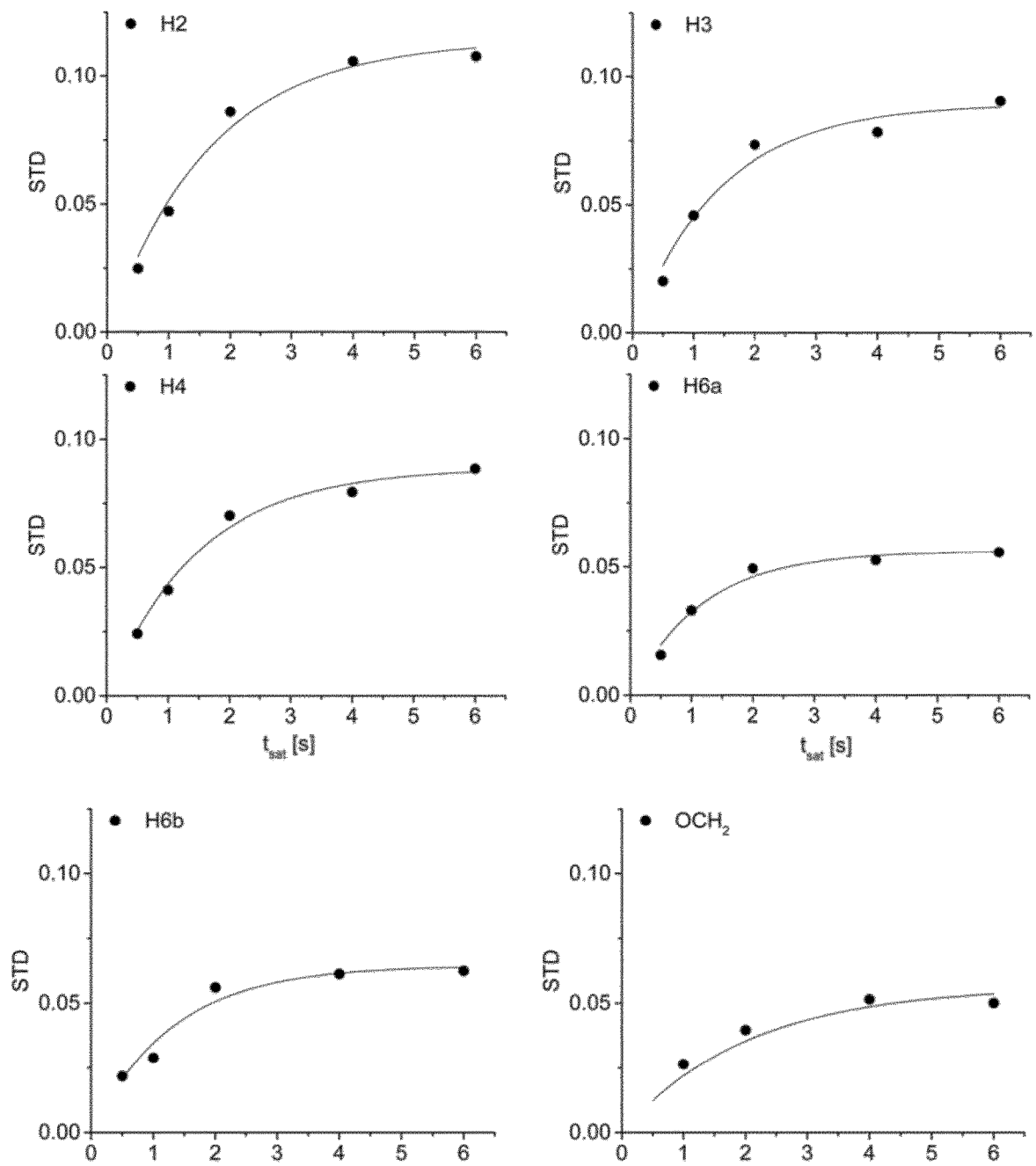
FIG. 37 shows the STD NMR build-up curves for Man analog 21. Equation 5 was fitted to STD values to calculate STD'$_0$ values for the determination of the binding epitope of 21.

To complement the protein-observed NMR experiments and to investigate the orientation of the acetylated ethylamino linker, STD NMR epitope mapping with 16 and 21 (see FIG. 27 (A)) was conducted. The binding epitope of 16 was dominated by uniformly high STD effects for the phenyl ring and thus supports a model in which favorable secondary interactions are formed between this substituent and the Langerin surface (FIG. 28 (D) and FIG. 35). The acetylated ethylamino linker did, by contrast, display uniformly low STD effects indicating a solvent exposed orientation and validating the developed conjugation strategy for GlcNS analogs. Similarly, the ethylamino linker of 21 received decreased STD effects compared to the Man scaffold (FIGS. 36 and 37).

Figure 38:
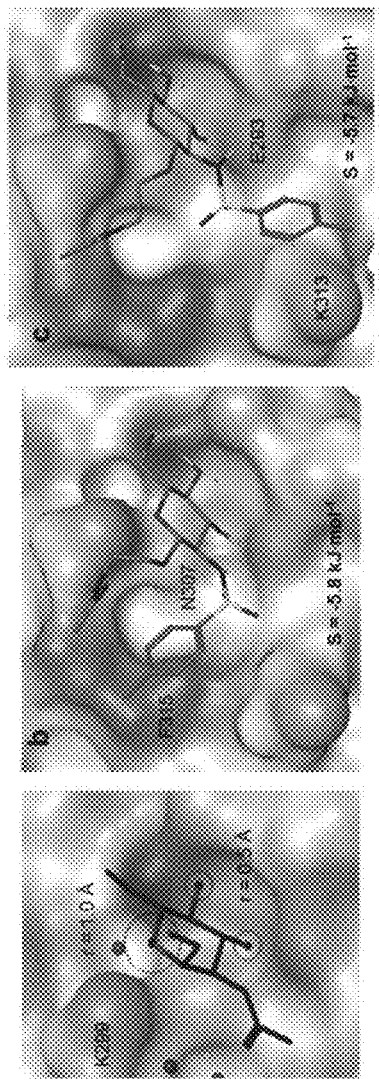
FIG. 38 shows the Molecular docking for GlcNS analog 16.

Finally, molecular docking was performed utilizing the X-ray structure of the Langerin complex with GlcNAc (see FIG. 28 (E) and FIG. 38) (Feinberg, H. et al. Common Polymorphisms in Human Langerin Change Specificity for Glycan Ligands. J Biol Chem, 288, 36762-71 (2013)). Generated docking poses were evaluated in the context of the NMR experiments and representative poses were selected to visualize the formation of potential secondary interactions. Indeed, orienting the phenyl ring towards F315 resulted in the formation of π-π interactions. This orientation also coincided with the formation of a weak hydrogen bond between the sulfonamide linker and N307. Both interactions explain the pronounced CSP values observed for residues that are associated with F315 and N307 including I250, Y251, N297 and K299. Furthermore, the phenyl ring received high STD effects indicating the formation of secondary interaction and high proximity to the Langerin surface. Conversely, the acetylated ethylamino linker displayed high solvent exposure and no conserved secondary interactions for the majority of docking poses. This observation was in accordance with the low STD effects and thus validated the developed conjugation strategy for GlcNS analogs. Overall, a binding mode for 16 is proposed that displays a conserved orientation of the Glc scaffold, consistent with both STD and $^{15}$N HSQC NMR experiments. The affinity increase can be rationalized by the formation of π-π interactions between the phenyl substituent and F315 as well as a hydrogen bond between the sulfonamide linker and N297.

Example 23

Application of a Lipid-Based Plate-Based Enzyme-Linked Lectin Assay (ELLA)

Monosaccharide analogs 15 or 20 (see FIG. 27 (A)) were utilized to synthesize glycolipids 22 and 23, respectively (see FIG. 27 (E)). Their affinity for Langerin was evaluated in a plate-based enzyme-linked lectin assay (ELLA). While a dose-dependent interaction could be demonstrated for 22, no interaction was detected for the immobilization of 23. This validates the determined affinity increase of model ligand 16 (see FIG. 27 (A)) over the Man-based reference molecule 21. Then targeted liposomes labeled with Alexa Fluor (AF) 647 with a diameter d of 160±60 nm were prepared that were stable over several months when stored at 4° C. in PBS. $^1$H NMR experiments were employed to probe the accessibility of targeting ligand 15 on the surface of the liposomes. Herein two states were observed for the resonances corresponding to H1' and H2' of the phenyl ring. Both states displayed linewidths vas smaller than 30 Hz, suggesting residual flexibility due to the presentation of the targeting ligand on an extended polyethylene glycol linker. The alternative state potentially corresponds to targeting ligands oriented towards the lumen of the liposomes. In summary, 15 is likely presented favorably on the surface of the liposomes to enable interactions with Langerin, further validating the developed conjugation strategy.

The invention claimed is:

1. A method of targeting and delivering a cargo to Langerin$^+$ cells, comprising:

contacting a Langerin$^+$ cell with a composition comprising:

a vehicle capable of specifically binding to a Langerin$^+$ cell, said vehicle comprising (a) at least one carrier and (b) at least one conjugate of the general formula (I)

(I)

wherein (i) R is independently selected from the group consisting of substituted or non-substituted alkyl, alkenyl, alkynyl, cycloalkyl, $C_1$-$C_8$ alkyl cycloalkyl, aryl, $C_1$-$C_8$ alkyl aryl, heteroaryl, $C_1$-$C_8$ alkyl heteroaryl, biaryl and $C_1$-$C_8$ alkyl biaryl, wherein, when substituted, the substituents are independently selected from the group consisting of —N($R^a$)($R^b$), —O$R^a$, —S$R^a$, —C(O)$R^a$, —C(O)O$R^a$, —C(O)N($R^a$)($R^b$), —N($R^a$)C(O)$R^b$, —N($R^a$)S(O)$_2R^b$, —OS(O)$_2R^a$, halogen, —$NO_2$, —CN, —NC, —$N_3$, —NCO, —OCN, —NCS, —SCN, substituted or non-substituted alkyl, alkenyl, alkynyl, aryl and heteroaryl, wherein $R^a$ and $R^b$ are independently selected from the group consisting of hydrogen, substituted or non-substituted $C_{1-8}$ alkyl, $C_{2-8}$ alkenyl, $C_{2-8}$ alkynyl, $C_{3-6}$ cycloalkyl, aryl-$C_{1-5}$ alkyl, heteroaryl-$C_{1-5}$ alkyl, aryl, heteroaryl;

(ii) R' is independently selected from the group consisting of

—O$R^a$, and —NHS(O)$_2R^a$, wherein $R^a$ is defined as above;

(iii) A-D-B-L is a linker group binding the glucose derivative of formula (I) covalently to the carrier or to a part of the carrier; and a cargo, thereby delivering the cargo to the Langerin$^+$ cell.

2. The method of claim 1, wherein R is a substituted or non-substituted phenyl.

3. The method of claim 2, wherein the substituted or non-substituted phenyl is a substituted phenyl that is mono-, di- or trisubstituted, and substituents of the phenyl are independently selected from the group consisting of:

—NH₂, —OH, —OCH₃, —C(O)CH₃, C(O)NH₂, —C(O)NHCH₃, —CH₂OH—NHC(O)CH₃, —F, —Cl, —Br, —NO₂, —CN, C₁-C₄ alkyl, naphtyl and phenyl.
4. The method of claim 3, wherein said conjugate is a conjugate of one of the following formulas (I-1) to (I-15):
(I-1)
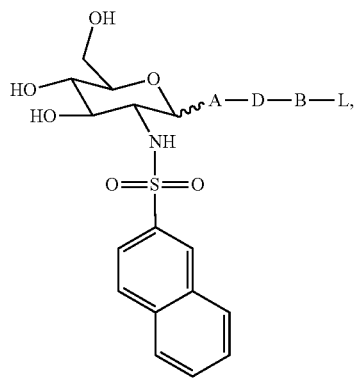
(I-2)
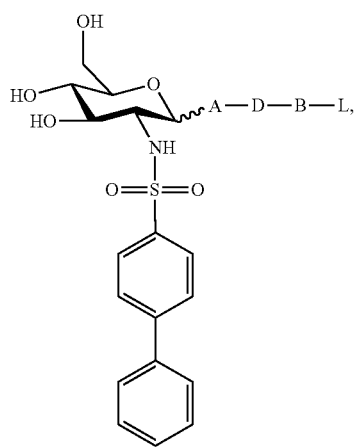
(I-3)
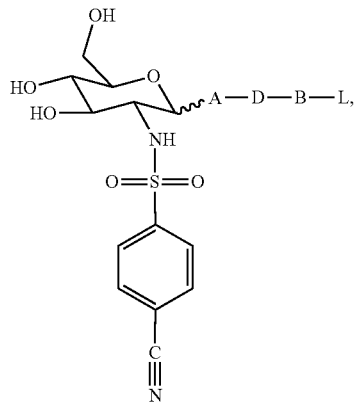
(I-4)
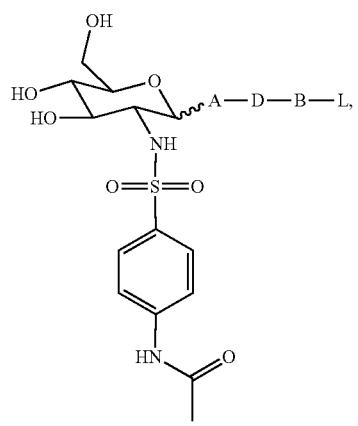
(I-5)
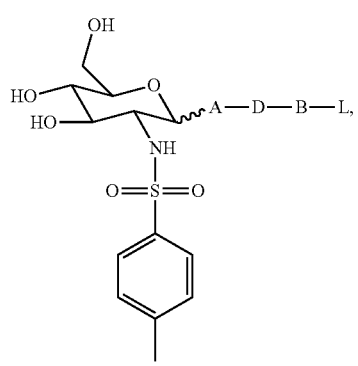
(I-6)
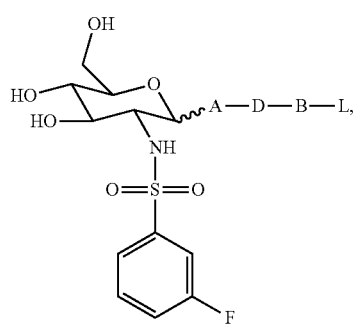
(I-7)
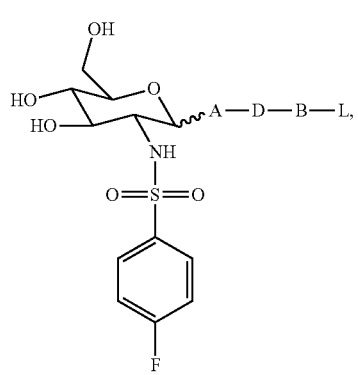

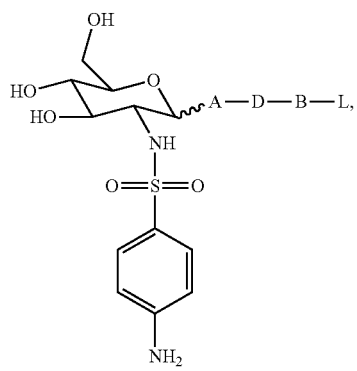
(I-8)
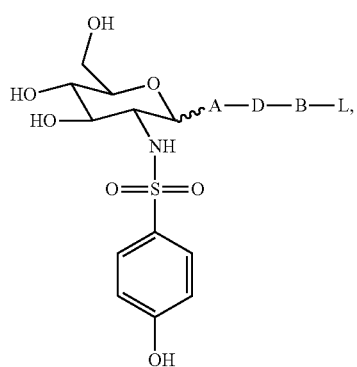
(I-9)
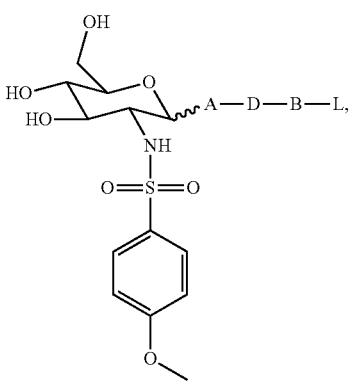
(I-10)
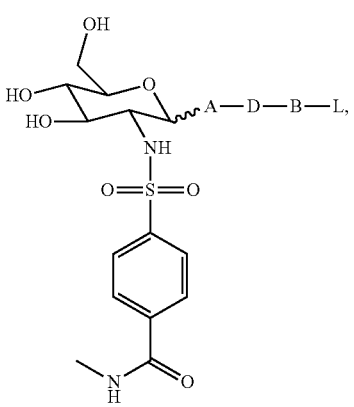
(I-11)
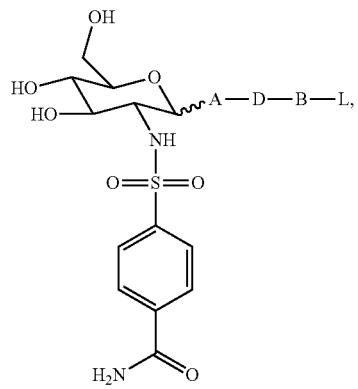
(I-12)
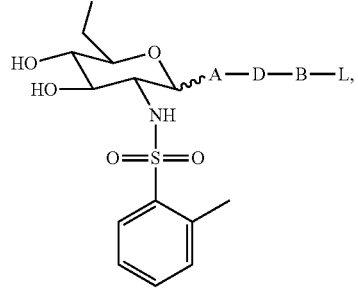
(I-13)
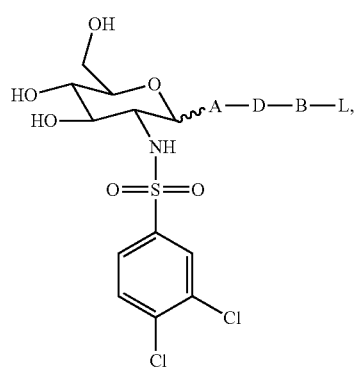
(I-14)
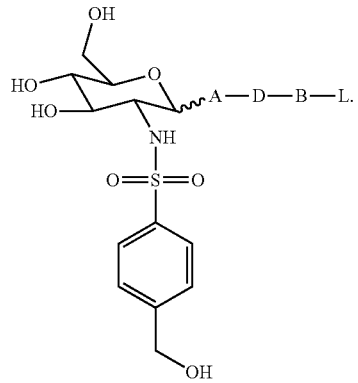
(I-15)
5. The method of claim 1, wherein said A-D-B-L linker group is a group consisting of a spacer A-D-B and a linker L, and wherein said linker L is a linker of the following general formula (L-1)

185

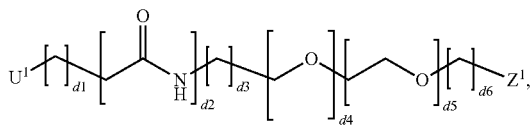

(L-1)

wherein
$U^1$ is a group connected via B with the spacer D, wherein U is selected from the group consisting of, —CH$_2$—, —CH=CH—, or —C≡C—;
$Z^1$ is a moiety binding the linker to the carrier selected from the group consisting of —O—, —S—, —N($R^d$)—, —C($R^d$)($R^e$)—, —$R^d$C=C$R^e$—, —C(O)—, —C(O)O—, —OC(O)—, —C(O)S—, —C(O)N($R^d$)—, —N($R^d$)C(O)—, —N($R^d$)C(O)N($R^e$)—, —N($R^d$)C(S)N($R^e$)—, —N($R^d$)C(O)O—, —OC(O)N($R^d$)—, -cyclohexene-, -triazoles-, —NHS(O)$_2$—, —S(O)$_2$—, —OP(O)(H)O—, or —OP(O)(OH)O—;
wherein $R^d$ and $R^e$ are independently selected from the group consisting of hydrogen, substituted or non-substituted C$_{1-32}$ alkyl, C$_{2-32}$ alkenyl, C$_{3-8}$ cycloalkyl, aryl, C$_1$-C$_8$ alkyl aryl, heteroaryl, C$_1$-C$_8$ alkyl heteroaryl; and
d1 to d5 is each an integer from 0 to 50, d6 an integer from 1 to 50.

6. The method of claim 5, wherein said at least one carrier is a soft particle selected from the group consisting of a liposome, a niosome, a micelle, a hydrophilic deformable phospholipid vesicle, and a transferosome and wherein the conjugate is directly bound via $Z^1$ to one part of the soft particle, wherein said one part of the soft particle is a lipid, a modified lipid, a phospholipid, 1,2-Distearoyl-sn-glycero-3-phosphoethanolamine (DSPE), a membrane lipid, or a modified phosphatidylcholine.

7. The method of claim 6, wherein the conjugate is bound to one part of a soft particle carrier resulting in the following structure (II):

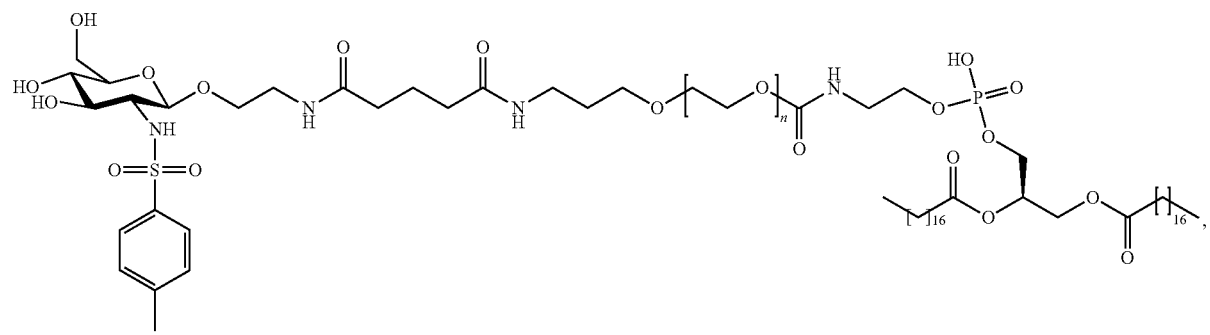

(II)

wherein n is an integer from 0 to 150.

8. The method of claim 1, wherein said carrier comprises, or is associated to the cargo.

9. The method of claim 8, wherein said cargo is located within the carrier, is linked to the outside of the carrier, and/or is integrated into a mono- or bilayer structure of the carrier.

10. The method of claim 1, wherein said cargo is a small molecule, a peptide, a protein, a cytotoxic substance, a nucleic acid, a pigment, a dye, a metal, a radionuclide, a virus, a modified virus, a viral vector, an inoculant, a plasmid, and/or a multicomponent system; or is a pharmaceutically active compound or an immunologically active compound; or wherein said cargo comprises, essentially consists of or consists of (i) a cancer antigen or epitope or comprises a cancer antigen or epitope, (ii) an autoimmune disease antigen or epitope or comprises an autoimmune disease antigen or epitope, (iii) a bacterial antigen or comprises a bacterial antigen or epitope, (iv) a viral antigen or comprises a viral antigen or epitope, (v) a parasitic antigen or comprises a parasitic antigen or epitope, or (vi) an allergen, or an epitope of an allergen, or comprises an allergen or an epitope of an allergen.

11. A pharmaceutical composition comprising:
a vehicle comprising (a) at least one carrier and (b) at least one conjugate of the general formula (I)

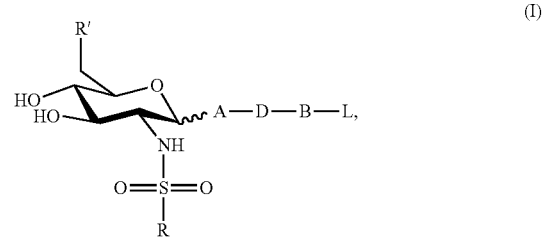

(I)

wherein
(i) R is independently selected from the group consisting of
substituted or non-substituted alkyl, alkenyl, alkynyl, cycloalkyl, C$_1$-C$_8$ alkyl cycloalkyl, aryl, C$_1$-C$_8$ alkyl aryl, heteroaryl, C$_1$-C$_8$ alkyl heteroaryl, biaryl and C$_1$-C$_8$ alkyl biaryl,
wherein, when substituted, the substituents are independently selected from the group consisting of
—N($R^a$)($R^b$), —O$R^a$, —S$R^a$, —C(O)$R^a$, —C(O)O$R^a$, —C(O)N($R^a$)($R^b$), —N($R^a$)C(O)$R^b$, —N($R^a$)S(O)$_2R^b$, —OS(O)$_2R^a$, halogen, —NO$_2$, —CN, —NC, —N$_3$, —NCO, —OCN, —NCS, —SCN, substituted or non-substituted alkyl, alkenyl, alkynyl, aryl and heteroaryl,
wherein $R^a$ and $R^b$ are independently selected from the group consisting of hydrogen, substituted or non-substituted C$_{1-8}$ alkyl, C$_{2-8}$ alkenyl, C$_{2-8}$ alkynyl, C$_{3-6}$ cycloalkyl, aryl-C$_{1-5}$ alkyl, heteroaryl-C$_{1-5}$ alkyl, aryl, heteroaryl;

(ii) R' is independently selected from the group consisting of
—OR$^a$, and —NHS(O)$_2$R$_a$,
wherein R$^a$ is defined as above;
(iii) A-D-B-L is a linker group binding the glucose derivative of formula (I) covalently to the carrier or to a part of the carrier;
a cargo,
wherein the carrier comprises or is associated to a pharmaceutically active cargo, and
a pharmaceutically acceptable carrier substance or a pharmaceutical adjuvant.

12. The method of claim 1, for use in the treatment or prevention of cancer, an autoimmune disease, a bacterial infection, a viral infection, a parasitic infection or a graft-vs. host disease, a local or systemic inflammation, allergy, or for hyposensitization.

13. The pharmaceutical composition of claim 11, wherein the carrier comprises or is associated to a pharmaceutically active cargo.

14. A medical kit comprising the pharmaceutical composition of claim 11, wherein the carrier comprises or is associated to a pharmaceutically active cargo and optionally a leaflet with instructions.

15. The pharmaceutical composition of claim 11, wherein the carrier comprises or is associated to an inoculant cargo.

16. The pharmaceutical composition of claim 11, further comprising a pharmaceutical adjuvant.

17. The pharmaceutical composition of claim 11, wherein the cargo comprises: an immunogen; a cancer antigen or epitope; an autoimmune disease antigen or epitope; a bacterial antigen or epitope; a viral antigen or epitope; a parasitic antigen or epitope, an allergen or an epitope of an allergen; a DNA; an RNA; a gene-editing tool; an adjuvant; a TLR agonist; an immunostimulant; a toxin; a lipid; or a small molecule drug.

18. The method of claim 6, wherein the soft particle is a hydrophilic deformable phospholipid vesicle.

19. The method of claim 6, wherein the soft particle is a transferosome.

20. The method of claim 10, wherein the multicomponent system is a CRISPR/Cas system.

21. The method of claim 10, wherein the immunologically active compound is an inhibitor of apoptosis.

22. The pharmaceutical composition of claim 17, wherein the gene editing tool is CRISPR/Cas9.

\* \* \* \* \*

UNITED STATES PATENT AND TRADEMARK OFFICE
CERTIFICATE OF CORRECTION

PATENT NO. : 12,290,535 B2
APPLICATION NO. : 16/963107
DATED : May 6, 2025
INVENTOR(S) : Christoph Rademacher et al.

Page 1 of 1

It is certified that error appears in the above-identified patent and that said Letters Patent is hereby corrected as shown below:

On the Title Page

Column 2, item (56), Other Publications, Line 6, Delete "Glycomimetric" and insert -- Glycomimetic --

Column 2, item (56), Other Publications, Line 9, Delete "thioglucaoside" and insert -- thioglucoside --

Column 2, item (56), Other Publications, Line 13, Delete "acetyglycoasminyltransferases" and insert -- acetylglucosaminyltransferases --

Column 2, item (56), Other Publications, Line 14, Delete "galactosyltrasnferases"," and insert -- galactosyltransferase", --

In the Claims

Column 181, Line 3, Claim 3, Delete "naphtyl" and insert -- naphthyl --

Column 185, Line 12, Claim 5, Delete "U" and insert -- $U^1$ --

Column 186, Line 41, Claim 11, Delete "--C(O)N($R^a$) ($R^b$)," and insert -- --C(O)N($R^a$)($R^b$), --

Column 187, Line 3, Claim 11, Delete "--NHS(O)$_2$R$_a$," and insert -- --NHS(O)$_2$R$^a$, --

Signed and Sealed this
Twenty-second Day of July, 2025

Coke Morgan Stewart
*Acting Director of the United States Patent and Trademark Office*

SEQUENCE LISTING

```
<160> NUMBER OF SEQ ID NOS: 82

<210> SEQ ID NO 1
<211> LENGTH: 328
<212> TYPE: PRT
<213> ORGANISM: Homo sapiens

<400> SEQUENCE: 1

Met Thr Val Glu Lys Glu Ala Pro Asp Ala His Phe Thr Val Asp Lys
1               5                   10                  15

Gln Asn Ile Ser Leu Trp Pro Arg Glu Pro Pro Pro Lys Ser Gly Pro
            20                  25                  30

Ser Leu Val Pro Gly Lys Thr Pro Thr Val Arg Ala Ala Leu Ile Cys
        35                  40                  45

Leu Thr Leu Val Leu Val Ala Ser Val Leu Leu Gln Ala Val Leu Tyr
    50                  55                  60

Pro Arg Phe Met Gly Thr Ile Ser Asp Val Lys Thr Asn Val Gln Leu
65                  70                  75                  80

Leu Lys Gly Arg Val Asp Asn Ile Ser Thr Leu Asp Ser Glu Ile Lys
                85                  90                  95

Lys Asn Ser Asp Gly Met Glu Ala Ala Gly Val Gln Ile Gln Met Val
            100                 105                 110

Asn Glu Ser Leu Gly Tyr Val Arg Ser Gln Phe Leu Lys Leu Lys Thr
        115                 120                 125

Ser Val Glu Lys Ala Asn Ala Gln Ile Gln Ile Leu Thr Arg Ser Trp
    130                 135                 140

Glu Glu Val Ser Thr Leu Asn Ala Gln Ile Pro Glu Leu Lys Ser Asp
145                 150                 155                 160

Leu Glu Lys Ala Ser Ala Leu Asn Thr Lys Ile Arg Ala Leu Gln Gly
                165                 170                 175

Ser Leu Glu Asn Met Ser Lys Leu Leu Lys Arg Gln Asn Asp Ile Leu
            180                 185                 190

Gln Val Val Ser Gln Gly Trp Lys Tyr Phe Lys Gly Asn Phe Tyr Tyr
        195                 200                 205

Phe Ser Leu Ile Pro Lys Thr Trp Tyr Ser Ala Glu Gln Phe Cys Val
    210                 215                 220
```

```
Ser Arg Asn Ser His Leu Thr Ser Val Thr Ser Glu Ser Glu Gln Glu
225                 230                 235                 240

Phe Leu Tyr Lys Thr Ala Gly Gly Leu Ile Tyr Trp Ile Gly Leu Thr
            245                 250                 255

Lys Ala Gly Met Glu Gly Asp Trp Ser Trp Val Asp Asp Thr Pro Phe
        260                 265                 270

Asn Lys Val Gln Ser Val Arg Phe Trp Ile Pro Gly Glu Pro Asn Asn
    275                 280                 285

Ala Gly Asn Asn Glu His Cys Gly Asn Ile Lys Ala Pro Ser Leu Gln
290                 295                 300

Ala Trp Asn Asp Ala Pro Cys Asp Lys Thr Phe Leu Phe Ile Cys Lys
305                 310                 315                 320

Arg Pro Tyr Val Pro Ser Glu Pro
                325
```

<210> SEQ ID NO 2
<211> LENGTH: 987
<212> TYPE: DNA
<213> ORGANISM: Homo sapiens

<400> SEQUENCE: 2

```
atgactgtgg agaaggaggc ccctgatgcg cacttcactg tggacaaaca gaacatctcc      60
ctctggcccc gagagcctcc tcccaagtcc ggtccatctc tggtcccggg gaaaacaccc     120
acagtccgtg ctgcattaat ctgcctgacg ctggtcctgg tcgcctccgt cctgctgcag     180
gccgtccttt atccccggtt tatgggcacc atatcagatg taaagaccaa tgtccagttg     240
ctgaaaggtc gtgtggacaa catcagcacc ctggattctg aaattaaaaa gaatagtgac     300
ggcatggagg cagctggcgt tcagatccag atggtgaatg agagcctggg ttatgtgcgt     360
tctcagttcc tgaagttaaa aaccagtgtg agaaggcca acgcacagat ccagatctta     420
acaagaagtt gggaagaagt cagtacctta aatgcccaaa tcccagagtt aaaaagtgat     480
ttggagaaag ccagtgcttt aaatacaaag atccgggcac tccagggcag cttggagaat     540
atgagcaagt gctcaaacg acaaaatgat attctacagg tggtttctca aggctggaag     600
tacttcaagg ggaacttcta ttactttttct ctcattccaa agacctggta gtgccgag      660
cagttctgtg tgtccaggaa ttcacacctg acctcggtga cctcagagag tgagcaggag     720
tttctgtata aaacagcggg gggactcatc tactggattg cctgactaa agcagggatg      780
gaagggact ggtcctgggt ggatgacacg ccattcaaca aggtccaaag tgtgaggttc      840
tggattccag gtgagcccaa caatgctggg aacaatgaac actgtggcaa tataaaggct     900
ccctcacttc aggcctggaa tgatgcccca tgtgacaaaa cgtttctttt catttgtaag     960
cgaccctatg tcccatcaga accgtga                                         987
```

<210> SEQ ID NO 3
<211> LENGTH: 328
<212> TYPE: PRT
<213> ORGANISM: Homo sapiens

<400> SEQUENCE: 3

```
Met Thr Val Glu Lys Glu Ala Pro Asp Ala His Phe Thr Val Asp Lys
1               5                   10                  15

Gln Asn Ile Ser Leu Trp Pro Arg Glu Pro Pro Lys Ser Gly Pro
            20                  25                  30

Ser Leu Val Pro Gly Lys Thr Pro Thr Val Arg Ala Ala Leu Ile Cys
```

```
                35                  40                  45
Leu Thr Leu Val Leu Val Ala Ser Val Leu Gln Ala Val Leu Tyr
 50                  55                  60

Pro Arg Phe Met Gly Thr Ile Ser Asp Val Lys Thr Asn Val Gln Leu
 65                  70                  75                  80

Leu Lys Gly Arg Val Asp Asn Ile Ser Thr Leu Asp Ser Glu Ile Lys
                 85                  90                  95

Lys Asn Ser Asp Gly Met Glu Ala Ala Gly Val Gln Ile Gln Met Val
                100                 105                 110

Asn Glu Ser Leu Gly Tyr Val Arg Ser Gln Phe Leu Lys Leu Lys Thr
                115                 120                 125

Ser Val Glu Lys Ala Asn Ala Gln Ile Gln Ile Leu Thr Arg Ser Trp
130                 135                 140

Glu Glu Val Ser Thr Leu Asn Ala Gln Ile Pro Glu Leu Lys Ser Asp
145                 150                 155                 160

Leu Glu Lys Ala Ser Ala Leu Asn Thr Lys Ile Arg Ala Leu Gln Gly
                165                 170                 175

Ser Leu Glu Asn Met Ser Lys Leu Leu Lys Arg Gln Asn Asp Ile Leu
                180                 185                 190

Gln Val Val Ser Gln Gly Trp Lys Tyr Phe Lys Gly Asn Phe Tyr Tyr
                195                 200                 205

Phe Ser Leu Ile Pro Lys Thr Trp Tyr Ser Ala Glu Gln Phe Cys Val
210                 215                 220

Ser Arg Asn Ser His Leu Thr Ser Val Thr Ser Glu Ser Glu Gln Glu
225                 230                 235                 240

Phe Leu Tyr Lys Thr Ala Gly Gly Leu Ile Tyr Trp Ile Gly Leu Thr
                245                 250                 255

Lys Ala Gly Met Glu Gly Asp Trp Ser Trp Val Asp Asp Thr Pro Phe
                260                 265                 270

Asn Lys Val Gln Ser Ala Arg Phe Trp Ile Pro Gly Glu Pro Asn Asn
                275                 280                 285

Ala Gly Asn Asn Glu His Cys Gly Asn Ile Lys Ala Pro Ser Leu Gln
                290                 295                 300

Ala Trp Asn Asp Ala Pro Cys Asp Lys Thr Phe Leu Phe Ile Cys Lys
305                 310                 315                 320

Arg Pro Tyr Val Pro Ser Glu Pro
                325

<210> SEQ ID NO 4
<211> LENGTH: 987
<212> TYPE: DNA
<213> ORGANISM: Homo sapiens

<400> SEQUENCE: 4
atgactgtgg agaaggaggc ccctgatgcg cacttcactg tggacaaaca gaacatctcc      60
ctctggcccc gagagcctcc tcccaagtcc ggtccatctc tggtcccggg gaaaacaccc     120
acagtccgtg ctgcattaat ctgcctgacg ctggtcctgg tcgcctccgt cctgctgcag     180
gccgtccttt atccccggtt tatgggcacc atatcagatg taaagaccaa tgtccagttg     240
ctgaaaggtc gtgtggacaa catcagcacc ctggattctg aaattaaaaa gaatagtgac     300
ggcatggagg cagctggcgt tcagatccag atggtgaatg agagcctggg ttatgtgcgt     360
tctcagttcc tgaagttaaa aaccagtgtg gagaaggcca acgcacagat ccagatctta     420
acaagaagtt gggaagaagt cagtacctta aatgcccaaa tcccagagtt aaaaagtgat     480
```

```
ttggagaaag ccagtgcttt aaatacaaag atccgggcac tccagggcag cttggagaat    540
atgagcaagt tgctcaaacg acaaaatgat attctacagg tggtttctca aggctggaag    600
tacttcaagg ggaacttcta ttactttttct ctcattccaa agacctggta tagtgccgag    660
cagttctgtg tgtccaggaa ttcacacctg acctcggtga cctcagagag tgagcaggag    720
tttctgtata aacagcggg gggactcatc tactggattg gcctgactaa agcagggatg    780 gaagggact ggtcctgggt ggatgacacg ccattcaaca aggtccaaag tgcgaggttc    840
tggattccag gtgagcccaa caatgctggg aacaatgaac actgtggcaa tataaaggct    900
ccctcacttc aggcctggaa tgatgccca tgtgacaaaa cgtttctttt catttgtaag    960
cgaccctatg tcccatcaga accgtga                                      987
```

```
<210> SEQ ID NO 5
<211> LENGTH: 328
<212> TYPE: PRT
<213> ORGANISM: Homo sapiens

<400> SEQUENCE: 5
```

Met Thr Val Glu Lys Glu Ala Pro Asp Ala His Phe Thr Val Asp Lys
1               5                   10                  15

Gln Asn Ile Ser Leu Trp Pro Arg Glu Pro Pro Lys Ser Gly Pro
            20                  25                  30

Ser Leu Val Pro Gly Lys Thr Pro Thr Val Arg Ala Ala Leu Ile Cys
        35                  40                  45

Leu Thr Leu Val Leu Val Ala Ser Val Leu Gln Ala Val Leu Tyr
50                  55                  60

Pro Arg Phe Met Gly Thr Ile Ser Asp Val Lys Thr Asn Val Gln Leu
65              70                  75                  80

Leu Lys Gly Arg Val Asp Asn Ile Ser Thr Leu Asp Ser Glu Ile Lys
                85                  90                  95

Lys Asn Ser Asp Gly Met Glu Ala Ala Gly Val Gln Ile Gln Met Val
            100                 105                 110

Asn Glu Ser Leu Gly Tyr Val Arg Ser Gln Phe Leu Lys Leu Lys Thr
        115                 120                 125

Ser Val Glu Lys Ala Asn Ala Gln Ile Gln Ile Leu Thr Arg Ser Trp
    130                 135                 140

Glu Glu Val Ser Thr Leu Asn Ala Gln Ile Pro Glu Leu Lys Ser Asp
145                 150                 155                 160

Leu Glu Lys Ala Ser Ala Leu Asn Thr Lys Ile Arg Ala Leu Gln Gly
                165                 170                 175

Ser Leu Glu Asn Met Ser Lys Leu Leu Lys Arg Gln Asn Asp Ile Leu
            180                 185                 190

Gln Val Val Ser Gln Gly Trp Lys Tyr Phe Lys Gly Asn Phe Tyr Tyr
        195                 200                 205

Phe Ser Leu Ile Pro Lys Thr Trp Tyr Ser Ala Glu Gln Phe Cys Val
    210                 215                 220

Ser Arg Asn Ser His Leu Thr Ser Val Thr Ser Glu Ser Glu Gln Glu
225                 230                 235                 240

Phe Leu Tyr Lys Thr Ala Gly Gly Leu Ile Tyr Trp Ile Gly Leu Thr
                245                 250                 255

Lys Ala Gly Met Glu Gly Asp Trp Ser Trp Val Asp Asp Thr Pro Phe
            260                 265                 270

Asn Lys Val Gln Ser Ala Arg Phe Trp Ile Pro Gly Glu Pro Asn Asp

```
            275                 280                 285
Ala Gly Asn Asn Glu His Cys Gly Asn Ile Lys Ala Pro Ser Leu Gln
        290                 295                 300

Ala Trp Asn Asp Ala Pro Cys Asp Lys Thr Phe Leu Phe Ile Cys Lys
305                 310                 315                 320

Arg Pro Tyr Val Pro Ser Glu Pro
                325

<210> SEQ ID NO 6
<211> LENGTH: 987
<212> TYPE: DNA
<213> ORGANISM: Homo sapiens

<400> SEQUENCE: 6
atgactgtgg agaaggaggc ccctgatgcg cacttcactg tggacaaaca gaacatctcc      60
ctctggcccc gagagcctcc tcccaagtcc ggtccatctc tggtcccggg aaaacaccc     120 acagtccgtg ctgcattaat ctgcctgacg ctggtcctgg tcgcctccgt cctgctgcag    180
gccgtccttt atccccggtt tatgggcacc atatcagatg taaagaccaa tgtccagttg    240
ctgaaaggtc gtgtggacaa catcagcacc ctggattctg aaattaaaaa gaatagtgac    300
ggcatggagg cagctggcgt tcagatccag atggtgaatg agagcctggg ttatgtgcgt    360
tctcagttcc tgaagttaaa aaccagtgtg gagaaggcca acgcacagat ccagatctta    420
acaagaagtt gggaagaagt cagtacctta aatgcccaaa tcccagagtt aaaaagtgat    480
ttggagaaag ccagtgcttt aaatacaaag atccgggcac tccagggcag cttggagaat    540
atgagcaagt tgctcaaacg acaaaatgat attctacagg tggtttctca aggctggaag    600
tacttcaagg ggaacttcta ttactttttct ctcattccaa agacctggta tagtgccgag    660
cagttctgtg tgtccaggaa ttcacacctg acctcggtga cctcagagag tgagcaggag    720
tttctgtata aaacagcggg gggactcatc tactggattg gcctgactaa agcagggatg    780
gaaggggact ggtcctgggt ggatgacacg ccattcaaca aggtccaaag tgcgaggttc    840
tggattccag gtgagcccaa cgatgctggg aacaatgaac actgtggcaa tataaaggct    900
ccctcacttc aggcctggaa tgatgcccca tgtgacaaaa cgtttctttt catttgtaag    960
cgaccctatg tcccatcaga accgtga                                        987

<210> SEQ ID NO 7
<211> LENGTH: 328
<212> TYPE: PRT
<213> ORGANISM: Homo sapiens

<400> SEQUENCE: 7

Met Thr Val Glu Lys Glu Ala Pro Asp Ala His Phe Thr Val Asp Lys
1               5                   10                  15

Gln Asn Ile Ser Leu Trp Pro Arg Glu Pro Pro Lys Ser Gly Pro
                20                  25                  30

Ser Leu Val Pro Gly Lys Thr Pro Thr Val Arg Ala Ala Leu Ile Cys
                35                  40                  45

Leu Thr Leu Val Leu Val Ala Ser Val Leu Gln Ala Val Leu Tyr
        50                  55                  60

Pro Arg Phe Met Gly Thr Ile Ser Asp Val Lys Thr Asn Val Gln Leu
65                  70                  75                  80

Leu Lys Gly Arg Val Asp Asn Ile Ser Thr Leu Asp Ser Glu Ile Lys
                85                  90                  95
```

Lys Asn Ser Asp Gly Met Glu Ala Ala Gly Val Gln Ile Gln Met Val
            100                 105                 110

Asn Glu Ser Leu Gly Tyr Val Arg Ser Gln Phe Leu Lys Leu Lys Thr
        115                 120                 125

Ser Val Glu Lys Ala Asn Ala Gln Ile Gln Ile Leu Thr Arg Ser Trp
130                 135                 140

Glu Glu Val Ser Thr Leu Asn Ala Gln Ile Pro Glu Leu Lys Ser Asp
145                 150                 155                 160

Leu Glu Lys Ala Ser Ala Leu Asn Thr Lys Ile Arg Ala Leu Gln Gly
                165                 170                 175

Ser Leu Glu Asn Met Ser Lys Leu Leu Lys Arg Gln Asn Asp Ile Leu
            180                 185                 190

Gln Val Val Ser Gln Gly Trp Lys Tyr Phe Lys Gly Asn Phe Tyr Tyr
        195                 200                 205

Phe Ser Leu Ile Pro Lys Thr Trp Tyr Ser Ala Glu Gln Phe Cys Val
210                 215                 220

Ser Arg Asn Ser His Leu Thr Ser Val Thr Ser Glu Ser Glu Gln Glu
225                 230                 235                 240

Phe Leu Tyr Lys Thr Ala Gly Gly Leu Ile Tyr Trp Ile Gly Leu Thr
                245                 250                 255

Lys Ala Gly Met Glu Gly Asp Trp Ser Trp Val Asp Asp Thr Pro Phe
            260                 265                 270

Asn Lys Val Gln Ser Ala Arg Phe Trp Ile Pro Gly Glu Pro Asn Asn
        275                 280                 285

Ala Gly Asn Asn Glu His Cys Gly Asn Ile Lys Ala Pro Ser Leu Gln
290                 295                 300

Ala Trp Asn Asp Ala Pro Cys Asp Ile Thr Phe Leu Phe Ile Cys Lys
305                 310                 315                 320

Arg Pro Tyr Val Pro Ser Glu Pro
                325

```
<210> SEQ ID NO 8
<211> LENGTH: 987
<212> TYPE: DNA
<213> ORGANISM: Homo sapiens

<400> SEQUENCE: 8
atgactgtgg agaaggaggc ccctgatgcg cacttcactg tggacaaaca gaacatctcc      60
ctctggcccc gagagcctcc tcccaagtcc ggtccatctc tggtcccggg gaaaacaccc     120
acagtccgtg ctgcattaat ctgcctgacg ctggtcctgg tcgcctccgt cctgctgcag     180
gccgtccttt atccccggtt tatgggcacc atatcagatg taaagaccaa tgtccagttg     240
ctgaaaggtc gtgtggacaa catcagcacc ctggattctg aaattaaaaa gaatagtgac     300
ggcatggagg cagctggcgt tcagatccag atggtgaatg agagcctggg ttatgtgcgt     360
tctcagttcc tgaagttaaa aaccagtgtg gagaaggcca acgcacagat ccagatctta     420
acaagaagtt gggaagaagt cagtaccttt aatgcccaaa tcccagagtt aaaaagtgat     480
ttggagaaag ccagtgcttt aaatacaaag atccgggcac tccagggcag cttggagaat     540
atgagcaagt tgctcaaacg acaaaatgat attctacagg tggtttctca aggctggaag     600
tacttcaagg ggaacttcta ttactttttct ctcattccaa agacctggta tagtgccgag     660
cagttctgtg tgtccaggaa ttcacacctg acctcggtga cctcagagag tgagcaggag     720
tttctgtata aacagcgggg gggactcatc tactggattg gcctgactaa agcagggatg     780
```

```
gaagggggact ggtcctgggt ggatgacacg ccattcaaca aggtccaaag tgcgaggttc      840
tggattccag gtgagcccaa caatgctggg aacaatgaac actgtggcaa tataaaggct      900
ccctcacttc aggcctggaa tgatgcccca tgtgacataa cgtttctttt catttgtaag      960
cgaccctatg tcccatcaga accgtga                                          987
```

<210> SEQ ID NO 9
<211> LENGTH: 328
<212> TYPE: PRT
<213> ORGANISM: Homo sapiens

<400> SEQUENCE: 9

```
Met Thr Val Glu Lys Glu Ala Pro Asp Ala His Phe Thr Val Asp Lys
1               5                   10                  15

Gln Asn Ile Ser Leu Trp Pro Arg Glu Pro Pro Lys Ser Gly Pro
            20                  25                  30

Ser Leu Val Pro Gly Lys Thr Pro Thr Val Arg Ala Ala Leu Ile Cys
        35                  40                  45

Leu Thr Leu Val Leu Val Ala Ser Val Leu Leu Gln Ala Val Leu Tyr
    50                  55                  60

Pro Arg Phe Met Gly Thr Ile Ser Asp Val Lys Thr Asn Val Gln Leu
65              70                  75                  80

Leu Lys Gly Arg Val Asp Asn Ile Ser Thr Leu Asp Ser Glu Ile Lys
                85                  90                  95

Lys Asn Ser Asp Gly Met Glu Ala Ala Gly Val Gln Ile Gln Met Val
            100                 105                 110

Asn Glu Ser Leu Gly Tyr Val Arg Ser Gln Phe Leu Lys Leu Lys Thr
        115                 120                 125

Ser Val Glu Lys Ala Asn Ala Gln Ile Gln Ile Leu Thr Arg Ser Trp
    130                 135                 140

Glu Glu Val Ser Thr Leu Asn Ala Gln Ile Pro Glu Leu Lys Ser Asp
145                 150                 155                 160

Leu Glu Lys Ala Ser Ala Leu Asn Thr Lys Ile Arg Ala Leu Gln Gly
                165                 170                 175

Ser Leu Glu Asn Met Ser Lys Leu Leu Lys Arg Gln Asn Asp Ile Leu
            180                 185                 190

Gln Val Val Ser Gln Gly Trp Lys Tyr Phe Lys Gly Asn Phe Tyr Tyr
        195                 200                 205

Phe Ser Leu Ile Pro Lys Thr Trp Tyr Ser Ala Glu Gln Phe Cys Val
    210                 215                 220

Ser Arg Asn Ser His Leu Thr Ser Val Thr Ser Glu Ser Glu Gln Glu
225                 230                 235                 240

Phe Leu Tyr Lys Thr Ala Gly Gly Leu Ile Tyr Trp Ile Gly Leu Thr
                245                 250                 255

Lys Ala Gly Met Glu Gly Asp Trp Ser Trp Val Asp Asp Thr Pro Phe
            260                 265                 270

Asn Lys Val Gln Ser Ala Arg Phe Trp Ile Pro Gly Glu Pro Asn Asp
        275                 280                 285

Ala Gly Asn Asn Glu His Cys Gly Asn Ile Lys Ala Pro Ser Leu Gln
    290                 295                 300

Ala Trp Asn Asp Ala Pro Cys Asp Ile Thr Phe Leu Phe Ile Cys Lys
305                 310                 315                 320

Arg Pro Tyr Val Pro Ser Glu Pro
                325
```

<210> SEQ ID NO 10
<211> LENGTH: 987
<212> TYPE: DNA
<213> ORGANISM: Homo sapiens

<400> SEQUENCE: 10

```
atgactgtgg agaaggaggc ccctgatgcg cacttcactg tggacaaaca gaacatctcc      60
ctctggcccc gagagcctcc tcccaagtcc ggtccatctc tggtcccggg gaaaacaccc     120
acagtccgtg ctgcattaat ctgcctgacg ctggtcctgg tcgcctccgt cctgctgcag     180
gccgtccttt atccccggtt tatgggcacc atatcagatg taaagaccaa tgtccagttg     240
ctgaaaggtc gtgtggacaa catcagcacc ctggattctg aaattaaaaa gaatagtgac     300
ggcatggagg cagctggcgt tcagatccag atggtgaatg agagcctggg ttatgtgcgt     360
tctcagttcc tgaagttaaa accagtgtg gagaaggcca acgcacagat ccagatctta     420
acaagaagtt gggaagaagt cagtaccta atgcccaaa tcccagagtt aaaaagtgat     480
ttggagaaag ccagtgcttt aaatacaaag atccgggcac tccagggcag cttggagaat     540
atgagcaagt tgctcaaacg acaaaatgat attctacagg tggtttctca aggctggaag     600
tacttcaagg ggaacttcta ttactttttct ctcattccaa agacctggta tagtgccgag     660
cagttctgtg tgtccaggaa ttcacacctg acctcggtga cctcagagag tgagcaggag     720
tttctgtata aaacagcggg gggactcatc tactggattg gctgactaa agcagggatg     780
gaaggggact ggtcctgggt ggatgacacg ccattcaaca aggtccaaag tgcgaggttc     840
tggattccag gtgagcccaa cgatgctggg aacaatgaac actgtggcaa tataaaggct     900
ccctcacttc aggcctggaa tgatgcccca tgtgacataa cgtttctttt catttgtaag     960
cgaccctatg tcccatcaga accgtga                                          987
```

<210> SEQ ID NO 11
<211> LENGTH: 404
<212> TYPE: PRT
<213> ORGANISM: Homo sapiens

<400> SEQUENCE: 11

Met Ser Asp Ser Lys Glu Pro Arg Leu Gln Gln Leu Gly Leu Leu Glu
1               5                   10                  15

Glu Glu Gln Leu Arg Gly Leu Gly Phe Arg Gln Thr Arg Gly Tyr Lys
            20                  25                  30

Ser Leu Ala Gly Cys Leu Gly His Gly Pro Leu Val Leu Gln Leu Leu
        35                  40                  45

Ser Phe Thr Leu Leu Ala Gly Leu Leu Val Gln Val Ser Lys Val Pro
    50                  55                  60

Ser Ser Ile Ser Gln Glu Gln Ser Arg Gln Asp Ala Ile Tyr Gln Asn
65                  70                  75                  80

Leu Thr Gln Leu Lys Ala Ala Val Gly Glu Leu Ser Glu Lys Ser Lys
                85                  90                  95

Leu Gln Glu Ile Tyr Gln Glu Leu Thr Gln Leu Lys Ala Ala Val Gly
            100                 105                 110

Glu Leu Pro Glu Lys Ser Lys Leu Gln Glu Ile Tyr Gln Glu Leu Thr
        115                 120                 125

Arg Leu Lys Ala Ala Val Gly Glu Leu Pro Glu Lys Ser Lys Leu Gln
    130                 135                 140

Glu Ile Tyr Gln Glu Leu Thr Trp Leu Lys Ala Ala Val Gly Glu Leu
145                 150                 155                 160

```
Pro Glu Lys Ser Lys Met Gln Glu Ile Tyr Gln Glu Leu Thr Arg Leu
            165                 170                 175
Lys Ala Ala Val Gly Glu Leu Pro Glu Lys Ser Lys Gln Gln Glu Ile
        180                 185                 190
Tyr Gln Glu Leu Thr Arg Leu Lys Ala Ala Val Gly Glu Leu Pro Glu
    195                 200                 205
Lys Ser Lys Gln Gln Glu Ile Tyr Gln Glu Leu Thr Arg Leu Lys Ala
210                 215                 220
Ala Val Gly Glu Leu Pro Glu Lys Ser Lys Gln Gln Glu Ile Tyr Gln
225                 230                 235                 240
Glu Leu Thr Gln Leu Lys Ala Ala Val Glu Arg Leu Cys His Pro Cys
            245                 250                 255
Pro Trp Glu Trp Thr Phe Phe Gln Gly Asn Cys Tyr Phe Met Ser Asn
        260                 265                 270
Ser Gln Arg Asn Trp His Asp Ser Ile Thr Ala Cys Lys Glu Val Gly
    275                 280                 285
Ala Gln Leu Val Val Ile Lys Ser Ala Glu Glu Gln Asn Phe Leu Gln
290                 295                 300
Leu Gln Ser Ser Arg Ser Asn Arg Phe Thr Trp Met Gly Leu Ser Asp
305                 310                 315                 320
Leu Asn Gln Glu Gly Thr Trp Gln Trp Val Asp Gly Ser Pro Leu Leu
            325                 330                 335
Pro Ser Phe Lys Gln Tyr Trp Asn Arg Gly Glu Pro Asn Asn Val Gly
        340                 345                 350
Glu Glu Asp Cys Ala Glu Phe Ser Gly Asn Gly Trp Asn Asp Asp Lys
    355                 360                 365
Cys Asn Leu Ala Lys Phe Trp Ile Cys Lys Lys Ser Ala Ala Ser Cys
370                 375                 380
Ser Arg Asp Glu Glu Gln Phe Leu Ser Pro Ala Pro Ala Thr Pro Asn
385                 390                 395                 400
Pro Pro Pro Ala

<210> SEQ ID NO 12
<211> LENGTH: 1215
<212> TYPE: DNA
<213> ORGANISM: Homo sapiens

<400> SEQUENCE: 12
atgagtgact ccaaggaacc aagactgcag cagctgggcc tcctggagga ggaacagctg      60
agaggccttg gattccgaca gactcgagga tacaagagct tagcagggtg tcttggccat     120
ggtcccctgg tgctgcaact cctctccttc acgctcttgg ctgggctcct tgtccaagtg     180
tccaaggtcc ccagctccat aagtcaggaa caatccaggc aagacgcgat ctaccagaac     240
ctgacccagc ttaaagctgc agtgggtgag ctctcagaga atccaagctg caggagatc      300
taccaggagc tgacccagct gaaggctgca gtgggtgagc ttccagagaa atctaagctg     360
caggagatct accaggagct gacccggctg aaggctgcag tgggtgagct tccagagaaa     420
tctaagctgc aggagatcta ccaggagctg acctggctga aggctgcagt gggtgagctt     480
ccagagaaat ctaagatgca ggagatctac caggagctga ctcggctgaa ggctgcagtg     540
ggtgagcttc agagaaatc taagcagcag gagatctacc aggagctgac ccggctgaag     600
gctgcagtgg gtgagcttcc agagaaatct aagcagcagg agatctacca ggagctgacc     660
cggctgaagg ctgcagtggg tgagcttcca gagaaatcta agcagcagga gatctaccag     720
```

```
gagctgaccc agctgaaggc tgcagtggaa cgcctgtgcc acccctgtcc ctgggaatgg      780
acattcttcc aaggaaactg ttacttcatg tctaactccc agcggaactg gcacgactcc      840
atcaccgcct gcaaagaagt gggggcccag ctcgtcgtaa tcaaaagtgc tgaggagcag      900
aacttcctac agctgcagtc ttccagaagt aaccgcttca cctggatggg actttcagat      960
ctaaatcagg aaggcacgtg gcaatgggtg gacggctcac ctctgttgcc cagcttcaag     1020
cagtattgga acagaggaga gcccaacaac gttggggagg aagactgcgc ggaatttagt     1080
ggcaatggct ggaacgacga caaatgtaat cttgccaaat tctggatctg caaaaagtcc     1140
gcagcctcct gctccaggga tgaagaacag tttctttctc cagcccctgc accccaaac     1200 ccccctcctg cgtag                                                      1215
```

<210> SEQ ID NO 13
<211> LENGTH: 331
<212> TYPE: PRT
<213> ORGANISM: Mus musculus

<400> SEQUENCE: 13

```
Met Pro Glu Ala Glu Met Lys Glu Ala Pro Glu Ala His Phe Thr
1               5                   10                  15

Val Asp Lys Gln Asn Ile Ser Leu Trp Pro Arg Glu Pro Pro Lys
                20                  25                  30

Gln Asp Leu Ser Pro Val Leu Arg Lys Pro Leu Cys Ile Cys Val Ala
            35                  40                  45

Phe Thr Cys Leu Ala Leu Val Leu Val Thr Ser Ile Val Leu Gln Ala
50                  55                  60

Val Phe Tyr Pro Arg Leu Met Gly Lys Ile Leu Asp Val Lys Ser Asp
65                  70                  75                  80

Ala Gln Met Leu Lys Gly Arg Val Asp Asn Ile Ser Thr Leu Gly Ser
                85                  90                  95

Asp Leu Lys Thr Glu Arg Gly Arg Val Asp Ala Glu Val Gln Met
            100                 105                 110

Gln Ile Val Asn Thr Thr Leu Lys Arg Val Arg Ser Gln Ile Leu Ser
            115                 120                 125

Leu Glu Thr Ser Met Lys Ile Ala Asn Asp Gln Leu Gln Ile Leu Thr
        130                 135                 140

Met Ser Trp Gly Glu Val Asp Ser Leu Ser Ala Lys Ile Pro Glu Leu
145                 150                 155                 160

Lys Arg Asp Leu Asp Lys Ala Ser Ala Leu Asn Thr Lys Val Gln Gly
                165                 170                 175

Leu Gln Asn Ser Leu Glu Asn Val Asn Lys Leu Leu Lys Gln Gln Ser
            180                 185                 190

Asp Ile Leu Glu Met Val Ala Arg Gly Trp Lys Tyr Phe Ser Gly Asn
        195                 200                 205

Phe Tyr Tyr Phe Ser Arg Thr Pro Lys Thr Trp Tyr Ser Ala Glu Gln
210                 215                 220

Phe Cys Ile Ser Arg Lys Ala His Leu Thr Ser Val Ser Ser Glu Ser
225                 230                 235                 240

Glu Gln Lys Phe Leu Tyr Lys Ala Ala Asp Gly Ile Pro His Trp Ile
                245                 250                 255

Gly Leu Thr Lys Ala Gly Ser Glu Gly Asp Trp Tyr Trp Val Asp Gln
            260                 265                 270

Thr Ser Phe Asn Lys Glu Gln Ser Arg Arg Phe Trp Ile Pro Gly Glu
```

```
              275                 280                 285
Pro Asn Asn Ala Gly Asn Asn Glu His Cys Ala Asn Ile Arg Val Ser
    290                 295                 300

Ala Leu Lys Cys Trp Asn Asp Gly Pro Cys Asp Asn Thr Phe Leu Phe
305                 310                 315                 320

Ile Cys Lys Arg Pro Tyr Val Gln Thr Thr Glu
                325                 330

<210> SEQ ID NO 14
<211> LENGTH: 996
<212> TYPE: DNA
<213> ORGANISM: Mus musculus

<400> SEQUENCE: 14
atgccagagg cagagatgaa ggaggaggct cccgaagcgc acttcacagt ggacaaacag      60
aacatctctc tctggcctcg agagcctcct cccaagcaag atctgtctcc agttctgagg     120
aaacctctct gtatctgcgt ggccttcacc tgcctggcat tggtgctggt cacctccatt     180
gtgcttcagg ctgttttcta tcctaggttg atgggcaaaa tattggatgt gaagagtgat     240
gcccagatgt tgaaaggtcg tgtggacaac atcagcaccc tgggttctga tcttaagact     300
gaaagaggtc gtgtggacga tgctgaggtt cagatgcaga tagtgaacac caccctcaag     360
agggtgcgtt ctcagatcct gtctttggaa accagcatga agatagccaa tgatcagctc     420
cagatattaa caatgagctg gggagaggtt gacagtctca gtgccaaaat cccagaactg     480
aaaagagatc tggataaagc cagcgccttg aacacaaagg tccaaggact acagaacagc     540
ttggagaatg tcaacaagct gctcaaacaa cagagtgaca ttctggagat ggtggctcga     600
ggctggaagt atttctcggg gaacttctat tactttttcac gcaccccaaa gacctggtac     660
agcgcagagc agttctgtat ttctagaaaa gctcacctga cctcagtgtc ctcagaatcg     720
gaacaaaagt ttctctacaa ggcagcagat ggaattccac actggattgg acttaccaaa     780
gcagggagcg aaggggactg gtactgggtg accagacatt cattcaacaa ggagcaaagt     840
aggaggttct ggattccagg tgaacccaac aacgcaggga acaacgagca ctgtgccaat     900
atcagggtgt ctgccctgaa gtgctggaac gatggtccct gtgacaatac atttctttc     960 atctgcaaga ggccctacgt ccaaacaact gaatga                               996

<210> SEQ ID NO 15
<211> LENGTH: 244
<212> TYPE: PRT
<213> ORGANISM: Mus musculus

<400> SEQUENCE: 15

Met Lys Tyr His Ser His Ile Glu Asn Leu Asp Glu Asp Gly Tyr Thr
1               5                   10                  15

Gln Leu Asp Phe Ser Thr Gln Asp Ile His Lys Arg Pro Arg Gly Ser
                20                  25                  30

Glu Lys Gly Ser Arg Ala Pro Ser Pro Trp Arg Pro Ile Ala Val
            35                  40                  45

Gly Leu Gly Ile Leu Cys Phe Val Val Val Val Ala Ala Val Leu
        50                  55                  60

Gly Ala Leu Ala Phe Trp Arg His Asn Ser Gly Arg Asn Pro Glu Glu
65                  70                  75                  80

Lys Asp Asn Phe Leu Ser Arg Asn Lys Glu Asn His Lys Pro Thr Glu
                85                  90                  95
```

```
Ser Ser Leu Asp Glu Lys Val Ala Pro Ser Lys Ala Ser Gln Thr Thr
            100                 105                 110

Gly Gly Phe Ser Gln Ser Cys Leu Pro Asn Trp Ile Met His Gly Lys
        115                 120                 125

Ser Cys Tyr Leu Phe Ser Phe Ser Gly Asn Ser Trp Tyr Gly Ser Lys
    130                 135                 140

Arg His Cys Ser Gln Leu Gly Ala His Leu Leu Lys Ile Asp Asn Ser
145                 150                 155                 160

Lys Glu Phe Glu Phe Ile Glu Ser Gln Thr Ser Ser His Arg Ile Asn
                165                 170                 175

Ala Phe Trp Ile Gly Leu Ser Arg Asn Gln Ser Glu Gly Pro Trp Phe
            180                 185                 190

Trp Glu Asp Gly Ser Ala Phe Phe Pro Asn Ser Phe Gln Val Arg Asn
        195                 200                 205

Thr Val Pro Gln Glu Ser Leu Leu His Asn Cys Val Trp Ile His Gly
    210                 215                 220

Ser Glu Val Tyr Asn Gln Ile Cys Asn Thr Ser Ser Tyr Ser Ile Cys
225                 230                 235                 240

Glu Lys Glu Leu

<210> SEQ ID NO 16
<211> LENGTH: 735
<212> TYPE: DNA
<213> ORGANISM: Mus musculus

<400> SEQUENCE: 16
atgaaatatc actctcatat agagaatctg gatgaagatg gatatactca attagacttc    60
agcactcaag acatccataa aaggcccagg ggatcagaga aaggaagccg ggctccatct   120
tcaccttgga ggcccattgc agtgggttta ggaatcctgt gctttgtggt agtagtggtt   180
gctgcagtgc tgggtgccct agcattttgg cgacacaatt cagggagaaa tccagaggag   240
aaagacaact tcctatcaag aaataaagag aaccacaagc ccacagaatc atctttagat   300
gagaaggtgg ctcccctcca ggcatcccaa actacaggag ttttttctca gtcttgcctt   360
cctaattgga tcatgcatgg gaagagctgt tacctattta gcttctcagg aaattcctgg   420
tatggaagta agagacactg ctcccagcta ggtgctcatc tactgaagat agacaactca   480
aaagaatttg agttcattga agccaaaaca tcgtctcacc gtattaatgc attttggata   540
ggcctttccc gcaatcagag tgaagggcca tggttctggg aggatggatc agcattcttc   600
cccaactcgt ttcaagtcag aaatacagtt ccccaggaaa gcttactgca caattgtgta   660
tggattcatg gatcagaggt ctacaaccaa atctgcaata cttcttcata cagtatctgt   720
gagaaggaac tgtaa                                                    735

<210> SEQ ID NO 17
<211> LENGTH: 44
<212> TYPE: DNA
<213> ORGANISM: Artificial Sequence
<220> FEATURE:
<223> OTHER INFORMATION: hLangerin Primer Forward

<400> SEQUENCE: 17
ctggctagcg tttaaactta agcatgactg tggagaagga ggcc                     44

<210> SEQ ID NO 18
<211> LENGTH: 34
<212> TYPE: DNA
```

<213> ORGANISM: Artificial Sequence
<220> FEATURE:
<223> OTHER INFORMATION: hLangerin Primer Reverse

<400> SEQUENCE: 18
ctagactcga gcggcctcac ggttctgatg ggac                            34

<210> SEQ ID NO 19
<211> LENGTH: 21
<212> TYPE: DNA
<213> ORGANISM: Artificial Sequence
<220> FEATURE:
<223> OTHER INFORMATION: Backbone plasmid Primer Forward

<400> SEQUENCE: 19
gcttaagttt aaacgctagc c                                          21

<210> SEQ ID NO 20
<211> LENGTH: 18
<212> TYPE: DNA
<213> ORGANISM: Artificial Sequence
<220> FEATURE:
<223> OTHER INFORMATION: Backbone plasmid Primer Reverse

<400> SEQUENCE: 20
ggccgctcga gtctagag                                              18

<210> SEQ ID NO 21
<211> LENGTH: 44
<212> TYPE: DNA
<213> ORGANISM: Artificial Sequence
<220> FEATURE:
<223> OTHER INFORMATION: hLangerin pcDNA 5 Primer Forward

<400> SEQUENCE: 21
ctggctagcg tttaaactta agcatgactg tggagaagga ggcc                 44

<210> SEQ ID NO 22
<211> LENGTH: 35
<212> TYPE: DNA
<213> ORGANISM: Artificial Sequence
<220> FEATURE:
<223> OTHER INFORMATION: hLangerin pcDNA 5 Primer Reverse

<400> SEQUENCE: 22
gtgatggtga tgatgactca cggttctgat gggac                           35

<210> SEQ ID NO 23
<211> LENGTH: 21
<212> TYPE: DNA
<213> ORGANISM: Artificial Sequence
<220> FEATURE:
<223> OTHER INFORMATION: Backbone plasmid pcDNA5 Primer Forward

<400> SEQUENCE: 23
gcttaagttt aaacgctagc c                                          21

<210> SEQ ID NO 24
<211> LENGTH: 18
<212> TYPE: DNA
<213> ORGANISM: Artificial Sequence
<220> FEATURE:
<223> OTHER INFORMATION: Backbone plasmid pcDNA5 Primer Reverse

<400> SEQUENCE: 24
gtcatcatca ccatcacc                                              18

<210> SEQ ID NO 25
<211> LENGTH: 22
<212> TYPE: DNA
<213> ORGANISM: Artificial Sequence
<220> FEATURE:
<223> OTHER INFORMATION: hLangerin RP172 Primer Forward

<400> SEQUENCE: 25
ctggctagcg tttaaactta ag                                              22

<210> SEQ ID NO 26
<211> LENGTH: 20
<212> TYPE: DNA
<213> ORGANISM: Artificial Sequence
<220> FEATURE:
<223> OTHER INFORMATION: hLangerin RP172 Primer Reverse

<400> SEQUENCE: 26
caatggtgat ggtgatgatg                                                 20

<210> SEQ ID NO 27
<211> LENGTH: 47
<212> TYPE: DNA
<213> ORGANISM: Artificial Sequence
<220> FEATURE:
<223> OTHER INFORMATION: Backbone plasmid RP172 Forward

<400> SEQUENCE: 27
gagctagcag tattaattaa ccaccctggc tagcgtttaa acttaag                   47

<210> SEQ ID NO 28
<211> LENGTH: 40
<212> TYPE: DNA
<213> ORGANISM: Artificial Sequence
<220> FEATURE:
<223> OTHER INFORMATION: Backbone plasmid RP172 Reverse

<400> SEQUENCE: 28
gtaccggtta ggatgcatgc caatggtgat ggtgatgatg                           40

<210> SEQ ID NO 29
<211> LENGTH: 855
<212> TYPE: DNA
<213> ORGANISM: Artificial Sequence
<220> FEATURE:
<223> OTHER INFORMATION: Codon optimized sequence for Langerin with
    StreptagII and TEV

<400> SEQUENCE: 29
atggcacgct tcatgggcac gattagcgat gttaaaacca atgttcaact gctgaaaggc     60
cgtgtggaca atatctcgac cctggatagt gaaattaaga aaaacagcga tggcatggaa    120
gcggccggtg tccagatcca aatggtgaat gaatcactgg ttatgtccg ttcgcagttt     180 ctgaaactga aaccagtgt tgaaaaagca acgctcaga ttcaaatcct gacccgctca      240
tgggaagaag tgtcgacgct gaatgcccag attccggaac tgaaaagcga tctggaaaaa    300
gcgtctgccc tgaacacgaa atccgtgca ctgcagggca gcctggaaaa catgtctaaa    360
ctgctgaaac gccaaaatga cattctgcag gtggttagcc aaggctggaa atacttcaag    420
ggtaacttct actacttcag tctgatcccg aaaacctggt actccgccga acagtttttgc    480 gtgagtcgta actcccatct gaccagcgtt acgagcgaat ctgaacaaga atttctgtat    540
aaaaccgctg gcggtctgat ttactggatc ggtctgacga aagcgggcat ggaggtgat    600

```
tggtcatggg ttgatgacac cccgtttaat aaagtccagt cggcgcgttt ctggattccg    660
ggcgaaccga acaatgccgg taacaatgaa cactgtggca acatcaaagc accgagcctg    720
caggcatgga atgatgctcc gtgcgacaaa acgtttctgt tcatttgtaa acgcccgtac    780
gttccgtctg aaccgggatc cgaaaatctg tacttccaag gttcggcgtg gtcccatccg    840
cagtttgaaa aataa                                                     855
```

```
<210> SEQ ID NO 30
<211> LENGTH: 40
<212> TYPE: DNA
<213> ORGANISM: Artificial Sequence
<220> FEATURE:
<223> OTHER INFORMATION: Truncated Langerin extracellular domain (ECD)
      Primer Forward

<400> SEQUENCE: 30
ggtggtcata tggcctcgac gctgaatgcc cagattccgg                           40

<210> SEQ ID NO 31
<211> LENGTH: 33
<212> TYPE: DNA
<213> ORGANISM: Artificial Sequence
<220> FEATURE:
<223> OTHER INFORMATION: Truncated Langerin extracellular domain (ECD)
      Primer Reverse

<400> SEQUENCE: 31
accaccaagc ttttattttt caaactgcgg atg                                  33

<210> SEQ ID NO 32
<211> LENGTH: 42
<212> TYPE: DNA
<213> ORGANISM: Artificial Sequence
<220> FEATURE:
<223> OTHER INFORMATION: Langerin carbohydrate recognition domain (CRD)
      Primer Forward

<400> SEQUENCE: 32
ggtggtcata tggcccaggt ggttagccaa ggctggaaat ac                        42

<210> SEQ ID NO 33
<211> LENGTH: 33
<212> TYPE: DNA
<213> ORGANISM: Artificial Sequence
<220> FEATURE:
<223> OTHER INFORMATION: Langerin carbohydrate recognition domain (CRD)
      Primer Reverse

<400> SEQUENCE: 33
accaccaagc ttttattttt caaactgcgg atg                                  33

<210> SEQ ID NO 34
<211> LENGTH: 43
<212> TYPE: DNA
<213> ORGANISM: Artificial Sequence
<220> FEATURE:
<223> OTHER INFORMATION: hLangerin Backbone SNP Forward

<400> SEQUENCE: 34
gagctagcag tattaattaa ccaccatgac tgtggagaag gag                       43

<210> SEQ ID NO 35
<211> LENGTH: 92
<212> TYPE: DNA
```

<213> ORGANISM: Artificial Sequence
<220> FEATURE:
<223> OTHER INFORMATION: hLangerin-FLAG Backbone SNP Reverse

<400> SEQUENCE: 35
acgtttcttt tcatttgtaa gcgaccctat gtcccatcag aaccggacta caaagacgat      60
gacgacaagt gagcatgcat cctaaccggt ac                                    92

<210> SEQ ID NO 36
<211> LENGTH: 38
<212> TYPE: DNA
<213> ORGANISM: Artificial Sequence
<220> FEATURE:
<223> OTHER INFORMATION: N288D Primer Forward

<400> SEQUENCE: 36
ccaggtgagc ccaacgatgc tgggaacaat gaacactg                              38

<210> SEQ ID NO 37
<211> LENGTH: 38
<212> TYPE: DNA
<213> ORGANISM: Artificial Sequence
<220> FEATURE:
<223> OTHER INFORMATION: N288D Primer Reverse

<400> SEQUENCE: 37
cattgttccc agcatcgttg ggctcacctg gaatccag                              38

<210> SEQ ID NO 38
<211> LENGTH: 93
<212> TYPE: DNA
<213> ORGANISM: Artificial Sequence
<220> FEATURE:
<223> OTHER INFORMATION: K313I Primer Reverse

<400> SEQUENCE: 38
gtaccggtta ggatgcatgc tcacggttct gatgggacat agggtcgctt acaaatgaaa      60
agaaacgtta tgtcacatgg ggcatcattc cag                                   93

<210> SEQ ID NO 39
<211> LENGTH: 43
<212> TYPE: DNA
<213> ORGANISM: Artificial Sequence
<220> FEATURE:
<223> OTHER INFORMATION: K313 Primer Forward

<400> SEQUENCE: 39
gagctagcag tattaattaa ccaccatgac tgtggagaag gag                        43

<210> SEQ ID NO 40
<211> LENGTH: 46
<212> TYPE: DNA
<213> ORGANISM: Artificial Sequence
<220> FEATURE:
<223> OTHER INFORMATION: DC-SIGN Primer Forward

<400> SEQUENCE: 40
ctggctagcg tttaaactta agcatgagtg actccaagga accaag                     46

<210> SEQ ID NO 41
<211> LENGTH: 31
<212> TYPE: DNA
<213> ORGANISM: Artificial Sequence
<220> FEATURE:
<223> OTHER INFORMATION: DC-SIGN Primer Reverse -continued

```
<400> SEQUENCE: 41
ctagactcga gcggccctac gcaggagggg g                                            31

<210> SEQ ID NO 42
<211> LENGTH: 21
<212> TYPE: DNA
<213> ORGANISM: Artificial Sequence
<220> FEATURE:
<223> OTHER INFORMATION: DC-SIGN Backbone plasmid Primer Forward

<400> SEQUENCE: 42
gcttaagttt aaacgctagc c                                                       21

<210> SEQ ID NO 43
<211> LENGTH: 18
<212> TYPE: DNA
<213> ORGANISM: Artificial Sequence
<220> FEATURE:
<223> OTHER INFORMATION: DC-SIGN Backbone plasmid Primer Reverse

<400> SEQUENCE: 43
ggccgctcga gtctagag                                                           18

<210> SEQ ID NO 44
<211> LENGTH: 46
<212> TYPE: DNA
<213> ORGANISM: Artificial Sequence
<220> FEATURE:
<223> OTHER INFORMATION: DC-SIGN pcDNA5 Primer Forward

<400> SEQUENCE: 44
ctggctagcg tttaaactta agcatgagtg actccaagga accaag                            46

<210> SEQ ID NO 45
<211> LENGTH: 35
<212> TYPE: DNA
<213> ORGANISM: Artificial Sequence
<220> FEATURE:
<223> OTHER INFORMATION: DC-SIGN pcDNA5 Primer Reverse

<400> SEQUENCE: 45
gtgatggtga tgatgaccta cgcaggaggg gggtt                                        35

<210> SEQ ID NO 46
<211> LENGTH: 21
<212> TYPE: DNA
<213> ORGANISM: Artificial Sequence
<220> FEATURE:
<223> OTHER INFORMATION: DC-SIGN pcDNA5 Backbone plasmid Primer Forward

<400> SEQUENCE: 46
gcttaagttt aaacgctagc c                                                       21

<210> SEQ ID NO 47
<211> LENGTH: 18
<212> TYPE: DNA
<213> ORGANISM: Artificial Sequence
<220> FEATURE:
<223> OTHER INFORMATION: DC-SIGN pcDNA5 Backbone plasmid Primer Reverse

<400> SEQUENCE: 47
gtcatcatca ccatcacc                                                           18

<210> SEQ ID NO 48
```

<211> LENGTH: 22
<212> TYPE: DNA
<213> ORGANISM: Artificial Sequence
<220> FEATURE:
<223> OTHER INFORMATION: DC-SIGN RP172 Primer Forward

<400> SEQUENCE: 48
ctggctagcg tttaaactta ag                                          22

<210> SEQ ID NO 49
<211> LENGTH: 20
<212> TYPE: DNA
<213> ORGANISM: Artificial Sequence
<220> FEATURE:
<223> OTHER INFORMATION: DC-SIGN RP172 Primer Reverse

<400> SEQUENCE: 49
caatggtgat ggtgatgatg                                             20

<210> SEQ ID NO 50
<211> LENGTH: 47
<212> TYPE: DNA
<213> ORGANISM: Artificial Sequence
<220> FEATURE:
<223> OTHER INFORMATION: DC-SIGN RP172 Backbone plasmid Primer Forward

<400> SEQUENCE: 50
gagctagcag tattaattaa ccaccctggc tagcgtttaa acttaag                47

<210> SEQ ID NO 51
<211> LENGTH: 40
<212> TYPE: DNA
<213> ORGANISM: Artificial Sequence
<220> FEATURE:
<223> OTHER INFORMATION: DC-SIGN RP172 Backbone plasmid Primer Reverse

<400> SEQUENCE: 51
gtaccggtta ggatgcatgc caatggtgat ggtgatgatg                       40

<210> SEQ ID NO 52
<211> LENGTH: 1331
<212> TYPE: DNA
<213> ORGANISM: Artificial Sequence
<220> FEATURE:
<223> OTHER INFORMATION: Codon optimized sequence of DC-SIGN containing
      a StreptagII and TEV site

<400> SEQUENCE: 52
gaattcgtac aagaaagctg ggtctagatg agcgatagca agaaccgcg tctgcaacag    60 ctgggcctgc tggaagagga acagctgcgt ggtctgggtt tcgtcagac ccgtggttat   120 aaaagcctgg caggttgtct gggtcatggt ccgctggttc tgcaactgct gagctttacc   180
ctgctggcag gtctgctggt tcaggttagc aaagttccga gcagcattag ccaagaacag   240
agccgtcagg atgcaattta tcagaatctg acacagctga agcagcagt tggtgaactg   300 agcgaaaaaa gcaaactgca agaaatctat caagagctga cccaactgaa agctgccgtg   360
ggcgaactgc cggaaaaatc aaaactgcaa gagatttacc aagaactgac acgtctgaaa   420
gctgcggtag tgagctgcc tgagaaaagt aaactgcaag atctatca agaactgacg   480 tggctgaaag ccgctgtcgg agaactgcca gagaaaagca aatgcaaga atttaccaa   540 gagctgactc gcctgaaagc agctgttggg gagctgccgg aaaaaagcaa acaacaagag   600
atttatcaag agctgacccg tctgaaagcc gcagtcggcg aactgcctga aaatctaaa   660

```
caacaagaaa tctaccaaga actgacgcgt ctgaaagcag ccgttggaga actgccagaa      720
aaaagtaaac agcaagagat ctaccaagag ctgactcagc tgaaagccgc agttgaacgt      780
ctgtgtcatc cgtgtccgtg ggaatggacc ttttttcagg gtaattgcta tttcatgagc      840
aatagccagc gtaattggca tgatagcatt accgcatgta aagaagttgg cgcacagctg      900
gttgtgatta aagcgcaga gaacagaat tcctgcaac tgcaaagcag tcgtagcaat      960
cgttttacct ggatgggtct gagcgatctg aatcaagagg gcacctggca gtgggttgat     1020
ggtagtccgc tgctgccgag ctttaaacag tattggaatc gtggtgaacc gaataatgtt     1080
ggtgaagaag attgcgcaga atttagcggt aatggttgga atgatgataa atgcaacctg     1140
gccaaattct ggatctgtaa aaaaagtgca gcaagctgta gccgtgatga gaacagtttt     1200
ctgagtccgg caccggcaac cccgaatccg cctccggcaa caggtgaaaa tctgtatttt     1260
cagggcacag gttggagcca tccgcagttt gaaaaatgat aaactagtag cctgcttttt     1320
tgtacctgca g                                                          1331
```

<210> SEQ ID NO 53
<211> LENGTH: 83
<212> TYPE: DNA
<213> ORGANISM: Artificial Sequence
<220> FEATURE:
<223> OTHER INFORMATION: DC-SIGN extracellular domain (ECD) - Primer
      Forward

<400> SEQUENCE: 53

```
gccgcctcta gagagtaata cgactcacta tagggactag agaaagagga gaaaactaga      60
tggccaaagt tccgagcagc att                                             83
```

<210> SEQ ID NO 54
<211> LENGTH: 35
<212> TYPE: DNA
<213> ORGANISM: Artificial Sequence
<220> FEATURE:
<223> OTHER INFORMATION: DC-SIGN extracellular domain (ECD) - Primer
      Reverse

<400> SEQUENCE: 54

```
ggcggcctgc aggtacaaaa aagcaggcta ctagt                                35
```

<210> SEQ ID NO 55
<211> LENGTH: 85
<212> TYPE: DNA
<213> ORGANISM: Artificial Sequence
<220> FEATURE:
<223> OTHER INFORMATION: DC-SIGN carbohydrate recognition domain (CRD) -
      Primer Forward

<400> SEQUENCE: 55

```
ccgcctctag aggagtaata cgactcacta tagggactag agaaagagga gaaaactaga      60
tggctgaacg tctgtgtcat ccgtg                                           85
```

<210> SEQ ID NO 56
<211> LENGTH: 35
<212> TYPE: DNA
<213> ORGANISM: Artificial Sequence
<220> FEATURE:
<223> OTHER INFORMATION: DC-SIGN carbohydrate recognition domain (CRD) -
      Primer Reverse

<400> SEQUENCE: 56

```
ggcggcctgc aggtacaaaa aagcaggcta ctagt                                35
```

<210> SEQ ID NO 57
<211> LENGTH: 44
<212> TYPE: DNA
<213> ORGANISM: Artificial Sequence
<220> FEATURE:
<223> OTHER INFORMATION: mLangerin Primer Forward

<400> SEQUENCE: 57
ctggctagcg tttaaactta agcatgccag aggcagagat gaag          44

<210> SEQ ID NO 58
<211> LENGTH: 35
<212> TYPE: DNA
<213> ORGANISM: Artificial Sequence
<220> FEATURE:
<223> OTHER INFORMATION: mLangerin Primer Reverse

<400> SEQUENCE: 58
ctagactcga gcggcctcat tcagttgttt ggacg          35

<210> SEQ ID NO 59
<211> LENGTH: 21
<212> TYPE: DNA
<213> ORGANISM: Artificial Sequence
<220> FEATURE:
<223> OTHER INFORMATION: mLangerin Backbone plasmid Primer Forward

<400> SEQUENCE: 59
gcttaagttt aaacgctagc c          21

<210> SEQ ID NO 60
<211> LENGTH: 18
<212> TYPE: DNA
<213> ORGANISM: Artificial Sequence
<220> FEATURE:
<223> OTHER INFORMATION: mLangerin Backbone plasmid Primer Reverse

<400> SEQUENCE: 60
ggccgctcga gtctagag          18

<210> SEQ ID NO 61
<211> LENGTH: 44
<212> TYPE: DNA
<213> ORGANISM: Artificial Sequence
<220> FEATURE:
<223> OTHER INFORMATION: mLangerin pcDNA5 Primer Forward

<400> SEQUENCE: 61
ctggctagcg tttaaactta agcatgccag aggcagagat gaag          44

<210> SEQ ID NO 62
<211> LENGTH: 36
<212> TYPE: DNA
<213> ORGANISM: Artificial Sequence
<220> FEATURE:
<223> OTHER INFORMATION: mLangerin pcDNA5 Primer Reverse

<400> SEQUENCE: 62
gtgatggtga tgatgactca ttcagttgtt tggacg          36

<210> SEQ ID NO 63
<211> LENGTH: 21
<212> TYPE: DNA
<213> ORGANISM: Artificial Sequence
<220> FEATURE:

<223> OTHER INFORMATION: mLangerin pcDNA5 Backbone plasmid Primer
      Forward

<400> SEQUENCE: 63
gcttaagttt aaacgctagc c                                              21

<210> SEQ ID NO 64
<211> LENGTH: 18
<212> TYPE: DNA
<213> ORGANISM: Artificial Sequence
<220> FEATURE:
<223> OTHER INFORMATION: mLangerin pcDNA5 Backbone plasmid Primer
      Forward

<400> SEQUENCE: 64
gtcatcatca ccatcacc                                                  18

<210> SEQ ID NO 65
<211> LENGTH: 22
<212> TYPE: DNA
<213> ORGANISM: Artificial Sequence
<220> FEATURE:
<223> OTHER INFORMATION: mLangerin RP172 Primer Forward

<400> SEQUENCE: 65
ctggctagcg tttaaactta ag                                             22

<210> SEQ ID NO 66
<211> LENGTH: 20
<212> TYPE: DNA
<213> ORGANISM: Artificial Sequence
<220> FEATURE:
<223> OTHER INFORMATION: mLangerin RP172 Primer Reverse

<400> SEQUENCE: 66
caatggtgat ggtgatgatg                                                20

<210> SEQ ID NO 67
<211> LENGTH: 47
<212> TYPE: DNA
<213> ORGANISM: Artificial Sequence
<220> FEATURE:
<223> OTHER INFORMATION: mLangerin RP172 Backbone plasmid Primer Forward

<400> SEQUENCE: 67
gagctagcag tattaattaa ccaccctggc tagcgtttaa acttaag                  47

<210> SEQ ID NO 68
<211> LENGTH: 40
<212> TYPE: DNA
<213> ORGANISM: Artificial Sequence
<220> FEATURE:
<223> OTHER INFORMATION: mLangerin RP172 Backbone plasmid Primer Reverse

<400> SEQUENCE: 68
gtaccggtta ggatgcatgc caatggtgat ggtgatgatg                          40

<210> SEQ ID NO 69
<211> LENGTH: 46
<212> TYPE: DNA
<213> ORGANISM: Artificial Sequence
<220> FEATURE:
<223> OTHER INFORMATION: mDectin-1 Primer Forward

<400> SEQUENCE: 69
tagcgtttaa acttaagcat gaaatatcac tctcatatag agaatc                   46

<210> SEQ ID NO 70
<211> LENGTH: 38
<212> TYPE: DNA
<213> ORGANISM: Artificial Sequence
<220> FEATURE:
<223> OTHER INFORMATION: mDectin-1 Primer Reverse

<400> SEQUENCE: 70
tagactcgag cggccttaca gttccttctc acagatac        38

<210> SEQ ID NO 71
<211> LENGTH: 21
<212> TYPE: DNA
<213> ORGANISM: Artificial Sequence
<220> FEATURE:
<223> OTHER INFORMATION: mDectin-1 Backbone plasmid Primer Forward

<400> SEQUENCE: 71
gcttaagttt aaacgctagc c        21

<210> SEQ ID NO 72
<211> LENGTH: 18
<212> TYPE: DNA
<213> ORGANISM: Artificial Sequence
<220> FEATURE:
<223> OTHER INFORMATION: mDectin-1 Backbone plasmid Primer Reverse

<400> SEQUENCE: 72
ggccgctcga gtctagag        18

<210> SEQ ID NO 73
<211> LENGTH: 46
<212> TYPE: DNA
<213> ORGANISM: Artificial Sequence
<220> FEATURE:
<223> OTHER INFORMATION: mDectin-1 pcDNA5 Primer Forward

<400> SEQUENCE: 73
tagcgtttaa acttaagcat gaaatatcac tctcatatag agaatc        46

<210> SEQ ID NO 74
<211> LENGTH: 40
<212> TYPE: DNA
<213> ORGANISM: Artificial Sequence
<220> FEATURE:
<223> OTHER INFORMATION: mDectin-1 pcDNA5 Primer Reverse

<400> SEQUENCE: 74
gtgatggtga tgatgactta cagttccttc tcacagatac        40

<210> SEQ ID NO 75
<211> LENGTH: 21
<212> TYPE: DNA
<213> ORGANISM: Artificial Sequence
<220> FEATURE:
<223> OTHER INFORMATION: mDectin-1 pcDNA5 Backbone plasmid Forward

<400> SEQUENCE: 75
gcttaagttt aaacgctagc c        21

<210> SEQ ID NO 76
<211> LENGTH: 18
<212> TYPE: DNA
<213> ORGANISM: Artificial Sequence
<220> FEATURE:

-continued

<223> OTHER INFORMATION: mDectin-1 pcDNA5 Backbone plasmid Reverse

<400> SEQUENCE: 76
gtcatcatca ccatcacc                                                      18

<210> SEQ ID NO 77
<211> LENGTH: 22
<212> TYPE: DNA
<213> ORGANISM: Artificial Sequence
<220> FEATURE:
<223> OTHER INFORMATION: mDectin-1 RP172 Primer Forward

<400> SEQUENCE: 77
ctggctagcg tttaaactta ag                                                 22

<210> SEQ ID NO 78
<211> LENGTH: 20
<212> TYPE: DNA
<213> ORGANISM: Artificial Sequence
<220> FEATURE:
<223> OTHER INFORMATION: mDectin-1 RP172 Primer Reverse

<400> SEQUENCE: 78
caatggtgat ggtgatgatg                                                    20

<210> SEQ ID NO 79
<211> LENGTH: 47
<212> TYPE: DNA
<213> ORGANISM: Artificial Sequence
<220> FEATURE:
<223> OTHER INFORMATION: mDectin-1 RP172 Backbone plasmid Primer Forward

<400> SEQUENCE: 79
gagctagcag tattaattaa ccaccctggc tagcgtttaa acttaag                      47

<210> SEQ ID NO 80
<211> LENGTH: 40
<212> TYPE: DNA
<213> ORGANISM: Artificial Sequence
<220> FEATURE:
<223> OTHER INFORMATION: mDectin-1 RP172 Backbone plasmid Primer Reverse

<400> SEQUENCE: 80
gtaccggtta ggatgcatgc caatggtgat ggtgatgatg                              40

<210> SEQ ID NO 81
<211> LENGTH: 19
<212> TYPE: PRT
<213> ORGANISM: Artificial Sequence
<220> FEATURE:
<223> OTHER INFORMATION: Amphipathic peptide for carrier

<400> SEQUENCE: 81

Val Leu Thr Thr Gly Leu Pro Ala Leu Ile Ser Trp Ile Lys Arg Lys
1               5                   10                  15

Arg Gln Gln

<210> SEQ ID NO 82
<211> LENGTH: 240
<212> TYPE: PRT
<213> ORGANISM: Artificial Sequence
<220> FEATURE:
<223> OTHER INFORMATION: modified GFP

<400> SEQUENCE: 82

-continued

```
Met Val Ser Lys Gly Glu Glu Leu Phe Thr Gly Val Val Pro Ile Leu
1               5                   10                  15
Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80
Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110
Val Lys Phe Glu Gly Asp Thr Leu Val Asn Arg Ile Glu Leu Lys Gly
        115                 120                 125
Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160
Gly Ile Lys Val Asn Phe Lys Ile Arg His Asn Ile Glu Asp Gly Ser
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ala
225                 230                 235                 240
```